(12) United States Patent
Kudo et al.

(10) Patent No.: US 7,910,579 B2
(45) Date of Patent: Mar. 22, 2011

(54) BENZOXAZOLE DERIVATIVES

(75) Inventors: Yukitsuka Kudo, Sendai (JP); Syozo Furumoto, Sendai (JP); Nobuyuki Okamura, Sendai (JP)

(73) Assignee: Tohoku University, Sendai-shi, Miyagi (JP)

( * ) Notice: Subject to any disclaimer, the term of this patent is extended or adjusted under 35 U.S.C. 154(b) by 0 days.

(21) Appl. No.: 12/520,752

(22) PCT Filed: Jul. 4, 2007

(86) PCT No.: PCT/JP2007/063350
§ 371 (c)(1),
(2), (4) Date: Jun. 22, 2009

(87) PCT Pub. No.: WO2008/078424
PCT Pub. Date: Mar. 7, 2008

(65) Prior Publication Data
US 2010/0021385 A1  Jan. 28, 2010

(30) Foreign Application Priority Data
Dec. 25, 2006 (WO) ................. PCT/JP2006/325804

(51) Int. Cl.
| | |
|---|---|
| A61K 31/541 | (2006.01) |
| A61K 31/5377 | (2006.01) |
| A61K 31/4523 | (2006.01) |
| A61K 31/427 | (2006.01) |
| A61K 31/423 | (2006.01) |
| C07D 417/14 | (2006.01) |
| C07D 413/14 | (2006.01) |
| C07D 277/20 | (2006.01) |
| C07D 263/30 | (2006.01) |

(52) U.S. Cl. .................. 514/222.2; 514/233.8; 514/321; 514/365; 514/375; 544/62; 544/133; 544/143; 546/198; 548/202; 548/217

(58) Field of Classification Search ................ 514/222.2, 514/233.8, 321, 365, 375; 544/62, 133, 143; 546/198; 548/202, 217
See application file for complete search history.

(56) References Cited

U.S. PATENT DOCUMENTS

| | | |
|---|---|---|
| 5,374,512 A | 12/1994 | Heki et al. |
| 2003/0003396 A1 | 1/2003 | Berneth et al. |
| 2003/0138374 A1 | 7/2003 | Kudo et al. |
| 2005/0009865 A1 | 1/2005 | Kudo et al. |
| 2005/0260126 A1 | 11/2005 | Kudo et al. |
| 2006/0018825 A1 | 1/2006 | Kudo et al. |

FOREIGN PATENT DOCUMENTS

| | | |
|---|---|---|
| EP | 1 967 517 A1 | 9/2008 |
| JP | 2000-344684 | 12/2000 |
| JP | 2000-344685 | 12/2000 |
| JP | 2002-275099 | 9/2002 |
| JP | 04 067659 | 3/2004 |
| WO | WO 96/34853 | 11/1996 |
| WO | WO 97 26919 A2 | 7/1997 |
| WO | WO 98/47969 | 10/1998 |
| WO | WO 01/70699 A1 | 9/2001 |
| WO | WO 02 080150 A2 | 10/2002 |
| WO | WO 03/018070 A1 | 3/2003 |
| WO | WO 03/106439 A1 | 12/2003 |
| WO | WO 2005/016384 A1 | 2/2005 |

OTHER PUBLICATIONS

Morissette et al. Advanced Drug Delivery Reviews 2004, 56, 275-300.*
Vippagunta et al., abstract, Vippagunta, Sudha R. "Crystalline Solids." Advanced Drug Delivery Reviews 48(2001): 3-26.*
Office Action in U.S. Appl. No. 12/097,842, mailed Feb. 22, 2010.
Morissette et al., "High-throughput crystallization: polymorphs, salts, co-crystals and solvates of pharmaceutical solids," Advanced Drug Delivery Reviews, vol. 56, pp. 275-300 (2004).
Vippagunta et al., "Crystalline Solids," Advanced Drug Delivery Reviews, vol. 48, pp. 3-26 (2001).
International Search Report PCT/JP2007/063350 dated Aug. 7, 2007.
International Preliminary Report on Patentability; and Written Opinion of the International Searching Authority Application No. PCT/JP2007/063350 dated Jun. 30, 2009.
Koichi Ishiguro et al., "Phosphorylated Tau in Human Cerebrospinal Fluid is a Diagnostic Marker for Alzheimer's Disease", *Neuroscience Letters*, 1999, pp. 91-94, vol. 270.
Nobuo Itoh et al., "Large-Scale, Multicenter Study of Cerebrospinal Fluid Tau Protein Phosphorylated at Serine 199 for the Antemortem Diagnosis of Alzheimer's Disease", *Ann. Neurol*, 2001, pp. 150-156, vol. 50.
Claude M. Wischik et al., "Neurobiology of Alzheimer's Disease", Oxford University, Press, 2001, pp. 103-206.
H. Braak et al., "Neuropathological Staging of Alzheimer-Related Changes", *Acta Neuropathol*, 1991, pp. 239-259, vol. 82.
B. Yankner et al., "Neurotoxicity of a Fragment of the Amyloid Precursor Associated with Alzheimer's Disease", *Science*, 1989, pp. 417-420, vol. 245.
H. Le Vine, "Thioflavine T Interaction with Synthetic Alzheimer's Disease {beta}-amyloid peptides: Detection of Amyloid Aggregation in Solution", *Protein Science*, 1993, pp. 404-410, vol. 2.
H. Puchtler et al., "Application of Thiazole Dyes to Amyloid Under Conditions of Direct Cotton Dyeing: Correlation of Histochemical and Chemical Data", *Histochemistry*, 1983, pp. 431-445, vol. 77.
Holde Puchtler et al., "On the Binding of Congo Red by Amyloid", *Journal of Histochemistry and Cytochemistry*, 1961, pp. 355-364, vol. 10.

(Continued)

*Primary Examiner* — Yong Chu
*Assistant Examiner* — Samantha L Shterengarts
(74) *Attorney, Agent, or Firm* — Nixon Peabody LLP; Jeffrey L. Costellia

(57) ABSTRACT

It is intended to provide a benzoxazole derivative or a pharmaceutically acceptable salt or solvate thereof which is useful in the early diagnosis of a conformation disease; a composition or a kit containing the same for diagnosing a conformation disease; a medical composition for treating and/or preventing a conformation disease; and so on.

29 Claims, 25 Drawing Sheets

OTHER PUBLICATIONS

Ishikawa, K., et al., Styrylbenzoazole derivatives for imaging of prion plaques and treatment of transmissible spongiform encephalopathies, Journal of Neurochemistry, 2006, pp. 198-205, vol. 99.

Okamura, N., et al., Styrylbenzoxazole Derivatives for In Vivo Imaging of Amyloid Plaques in the Brain, The Journal of Neuroscience, Mar. 10, 2004, pp. 2535-2541, vol. 24.

Okamura, N., et al., Quinoline and Bezimidazole Derivatives: Candidate Probes In Vivo Imaging of Tau Pathology in Alzheimer's Disease, The Journal of Neuroscience., Nov. 23, 2005, pp. 10857-10862, vol. 25.

Shimadzu, H., et al., Novel probes for imaging amyloid-$\beta$:F-18 and C-11 labeling of 2-(4-aminostyryl) benzoxazole derivatives, Journal of Labelled Compounds and Radiopharmaceuticals, 2004, pp. 181-190, vol. 47.

Stetinova, J., et al., 2-(Benzoxazole-2-yl)-3-Heteroarylprop-2-enenitrile, Chem Papers, 1997, pp. 390-394, vol. 51 (6b) Compound IIc, IId.

International Search Report PCT/JP2006/325804 dated Mar. 20, 2007.

International Preliminary Report on Patentability; and Written Opinion of the International Searching Authority Application No. PCT/JP2006/325804 dated Jul. 1, 2008.

Extended European Search Report in European Application No. 07768120.3, issued Jun. 1, 2010.

Office Action in pending U.S. Appl. No. 12/097,842, mailed Aug. 18, 2010.

* cited by examiner

[Fig. 1]
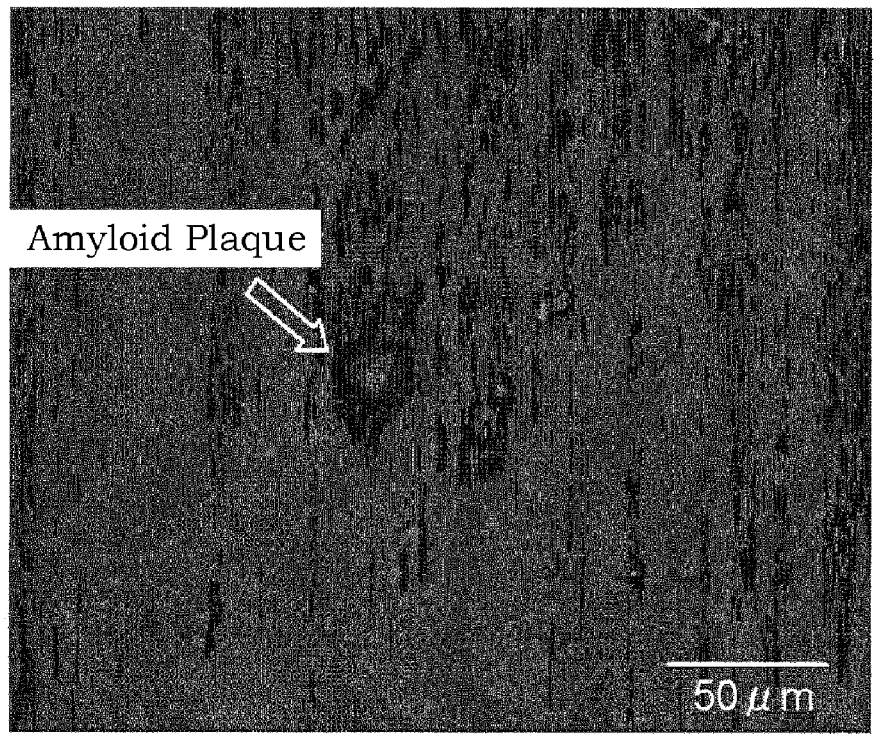
[Fig. 2]
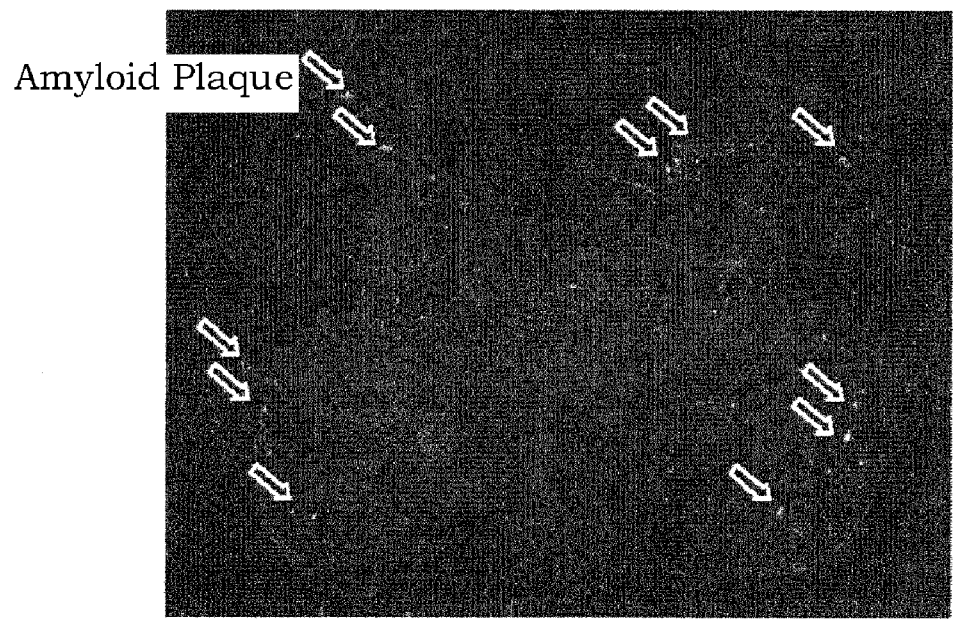

[Fig. 3]
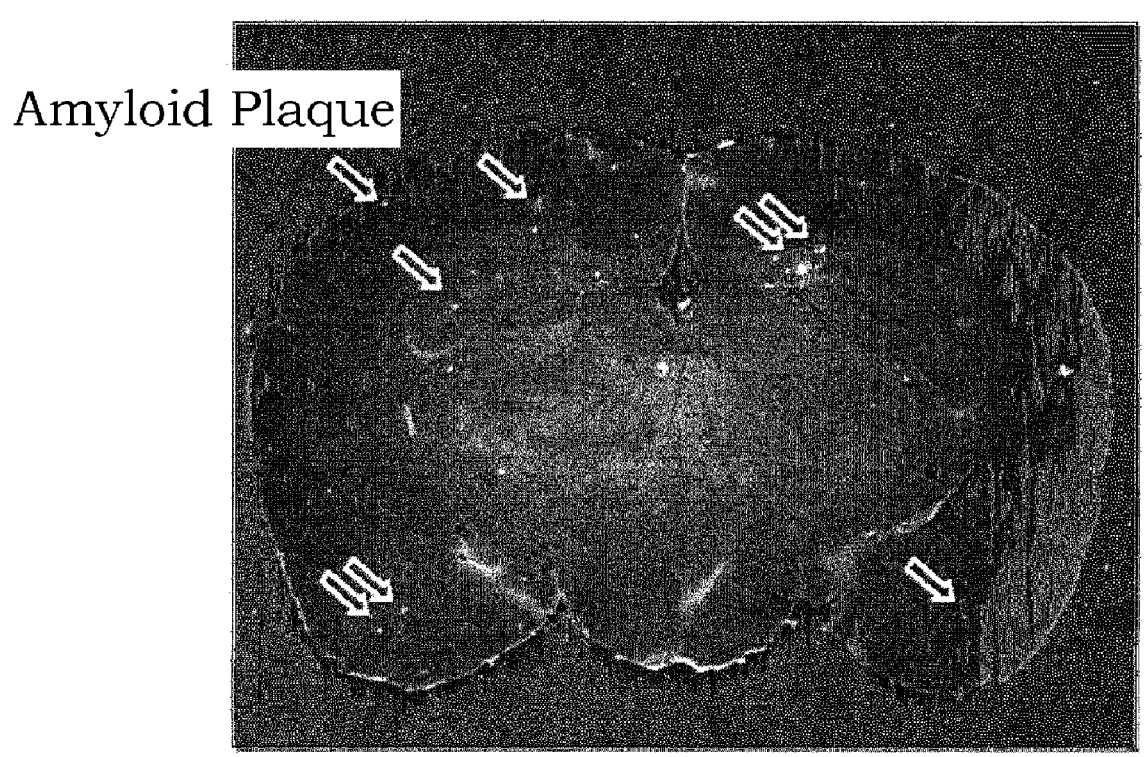

[Fig. 4]
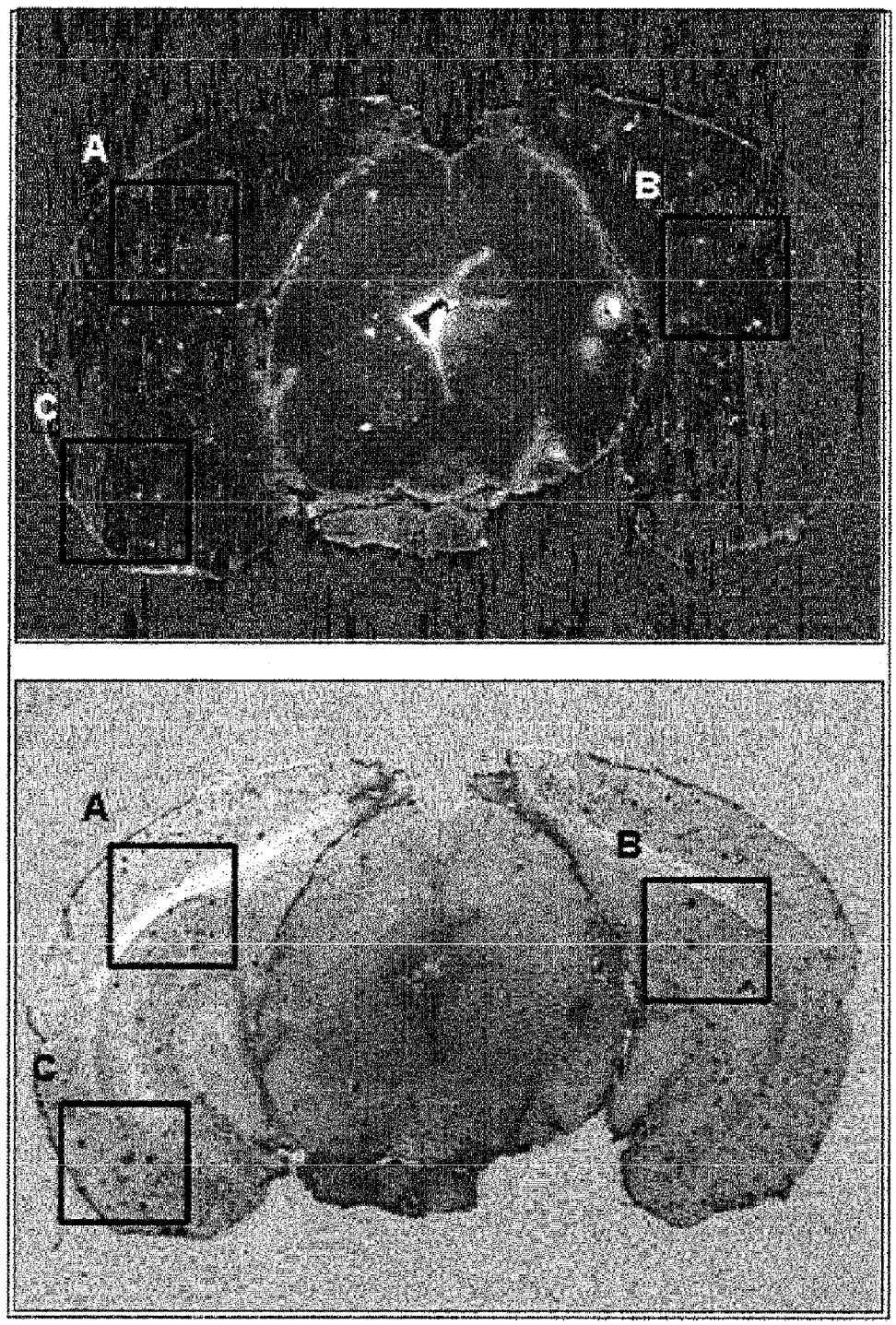

[Fig. 5]
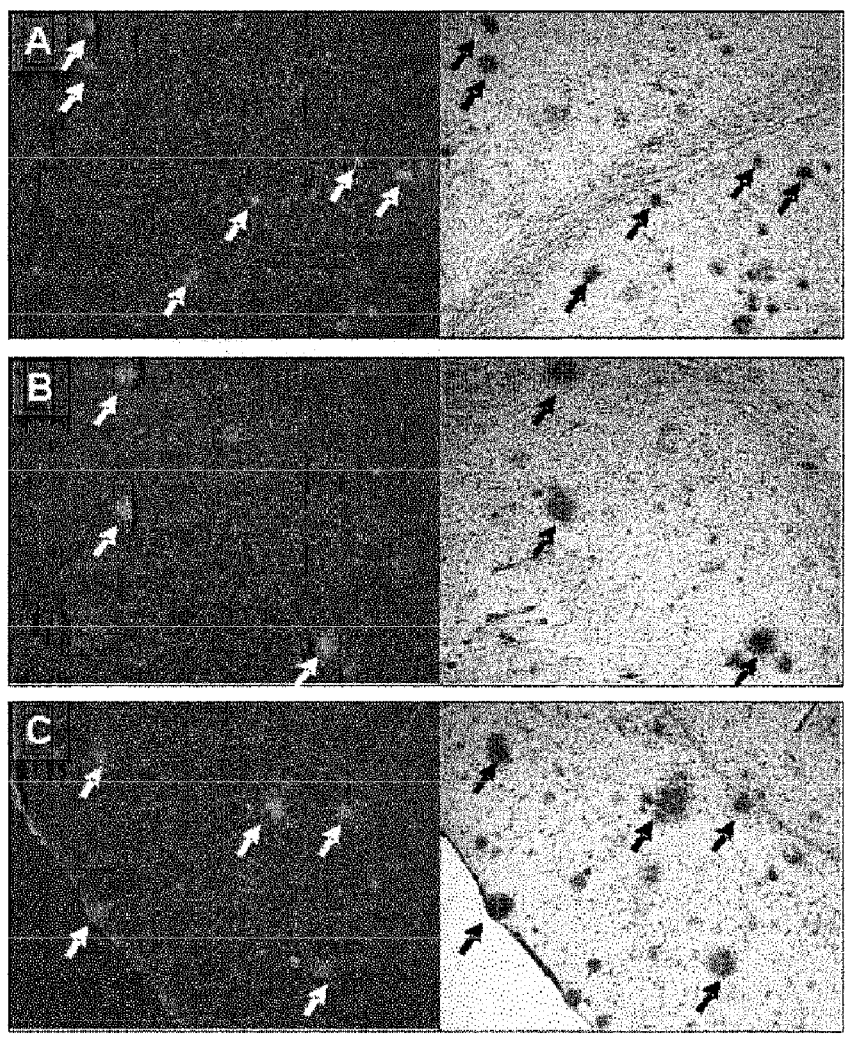

[Fig. 6]
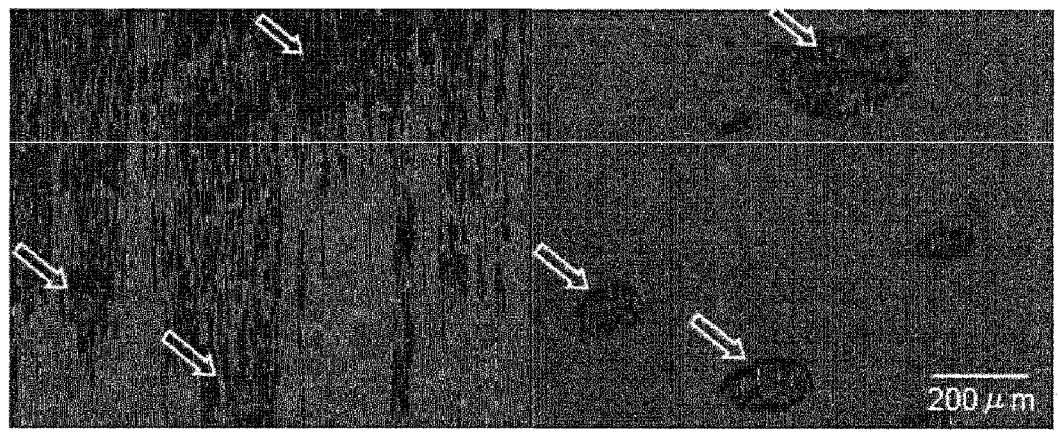
THK-097 Staining      Anti-A Antibody Staining
[Fig. 7]
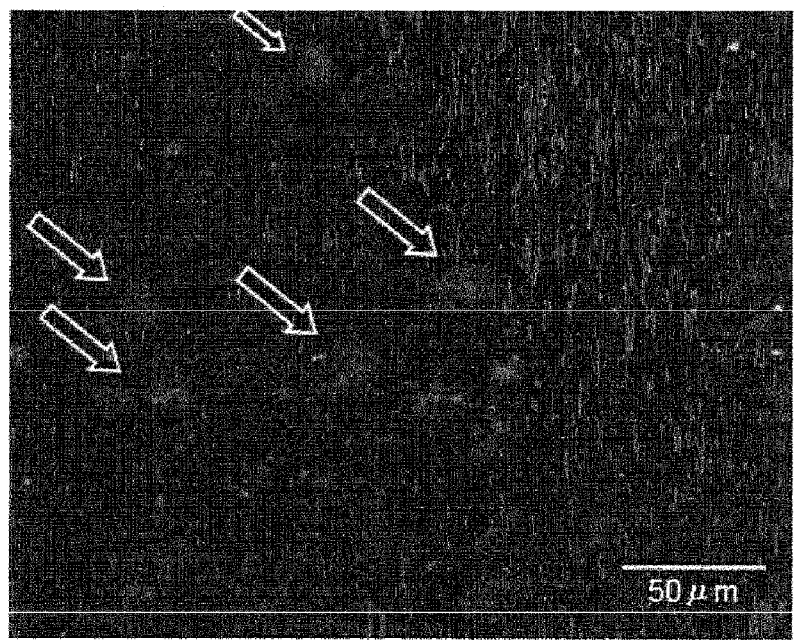
THK-184 Staining

[Fig. 8]
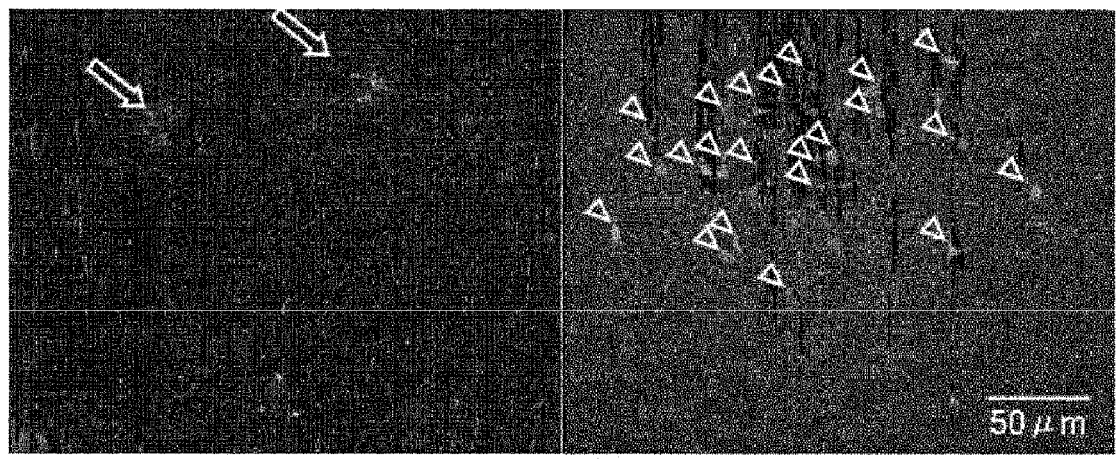
THK-185 Staining
[Fig. 9]
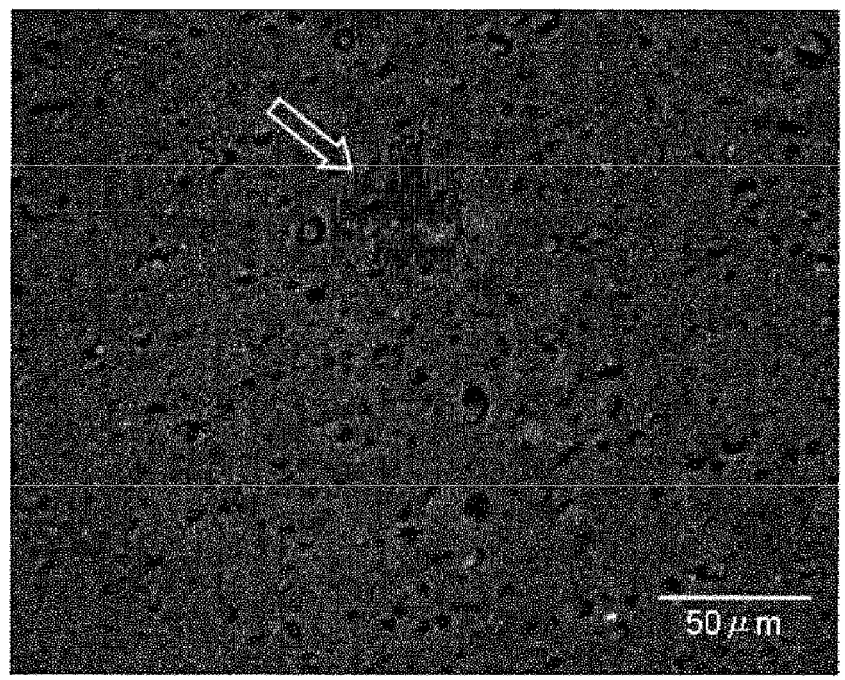
THK-203 Staining

[Fig. 10]
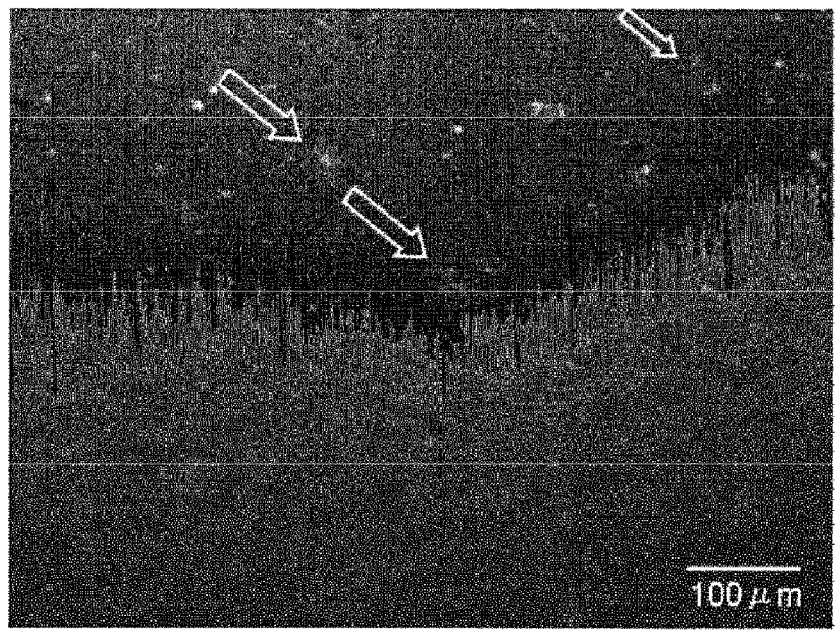
THK-207 Staining
[Fig. 11]
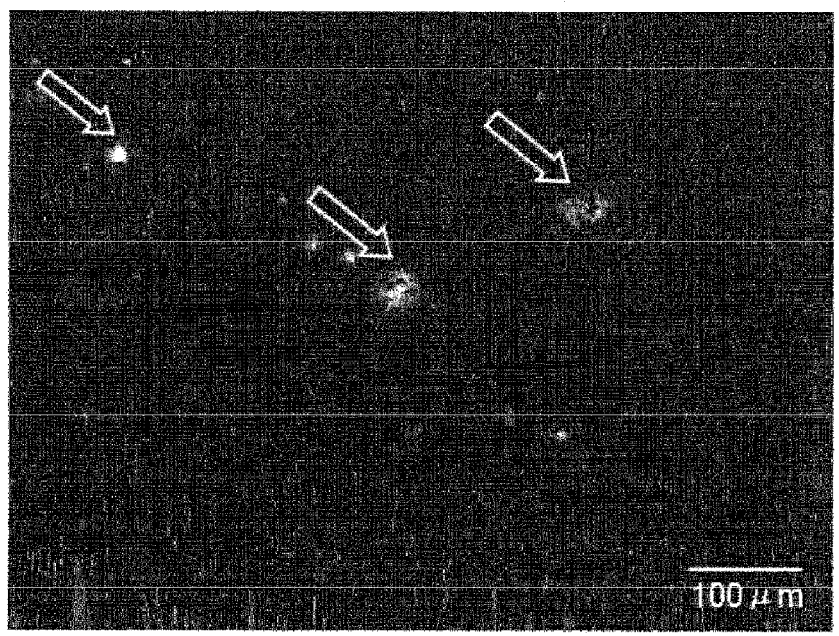
THK-248 Staining

[Fig. 12]
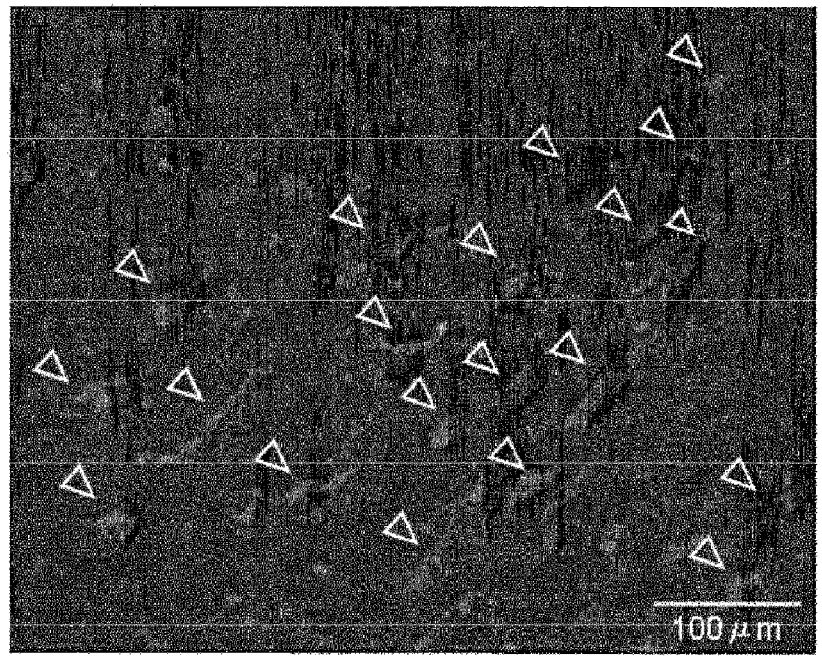
THK-254 Staining
[Fig. 13]
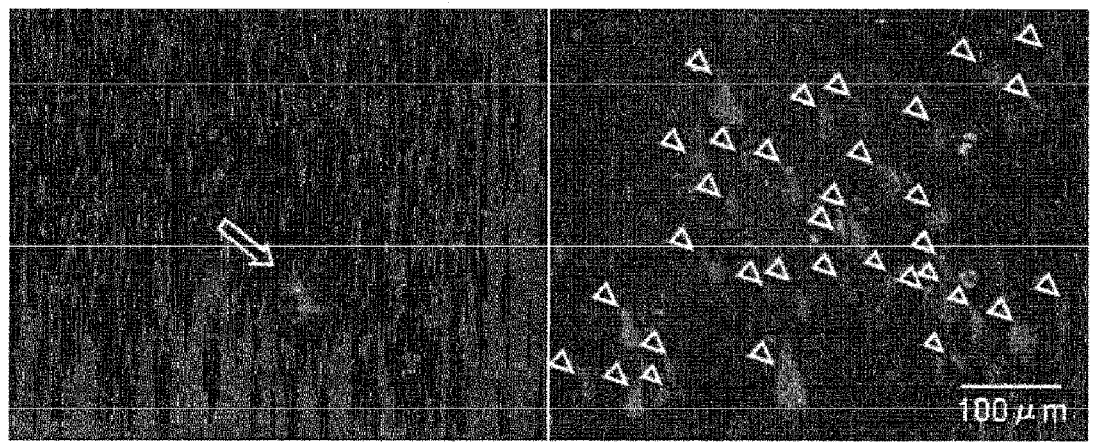
THK-258 Staining

[Fig. 14]
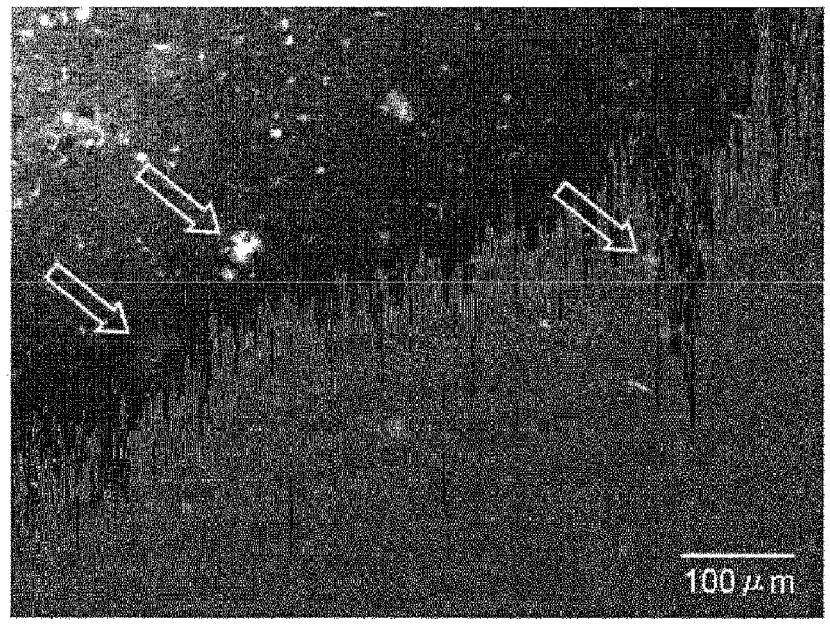
THK-262 Staining
[Fig. 15]
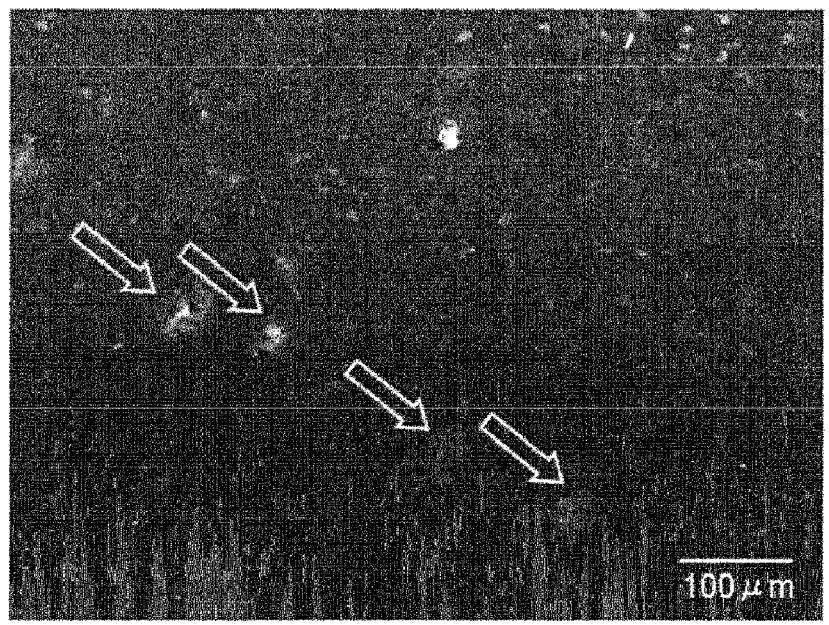
THK-276 Staining

[Fig. 16]
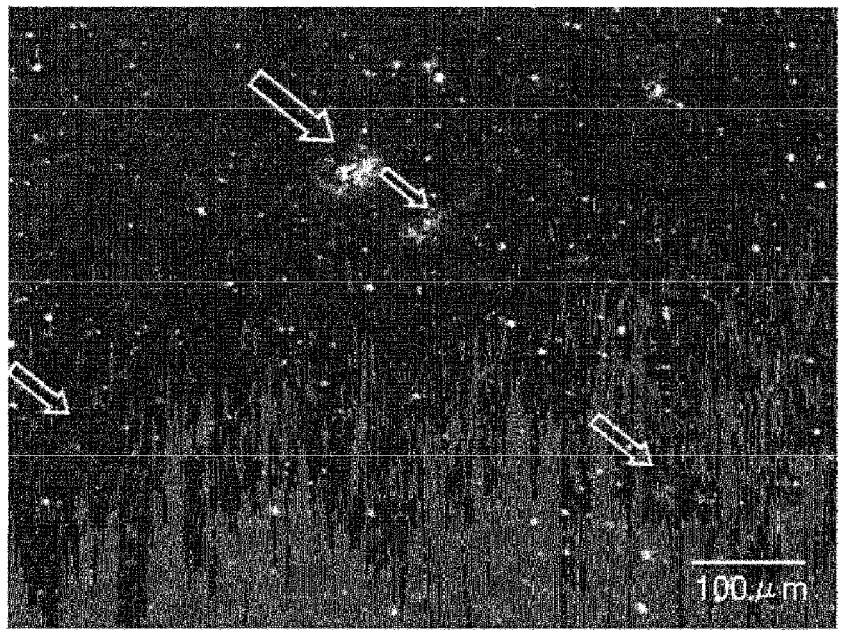
THK-281 Staining
[Fig. 17]
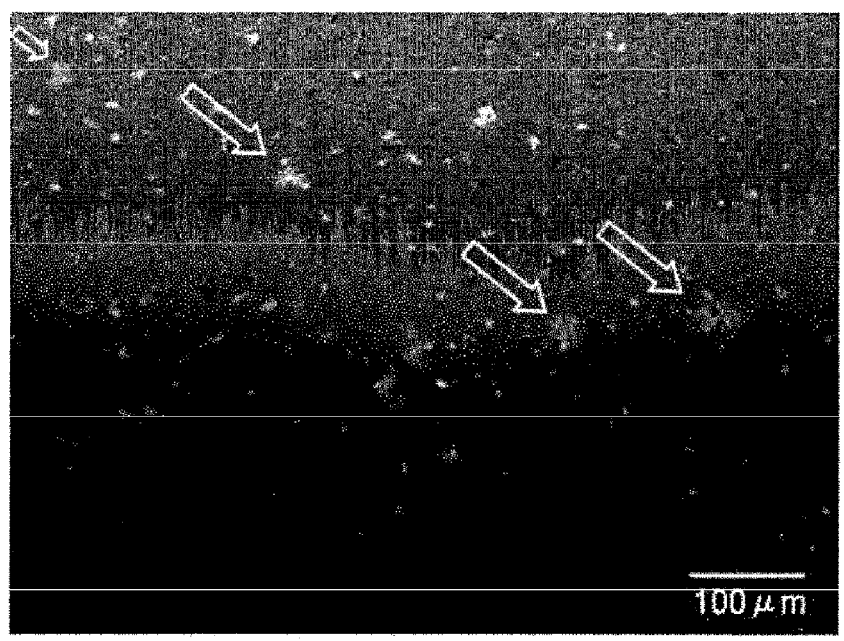
THK-308 Staining

[Fig. 18]
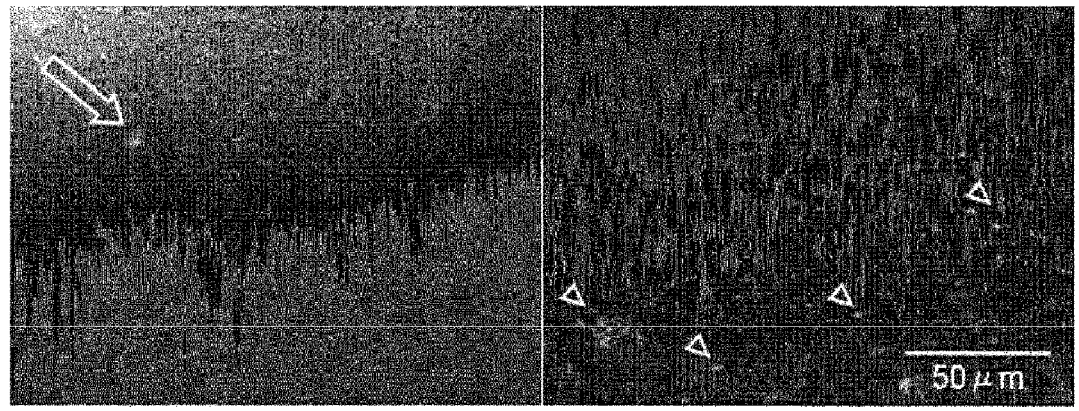
THK-317 Staining
[Fig. 19]
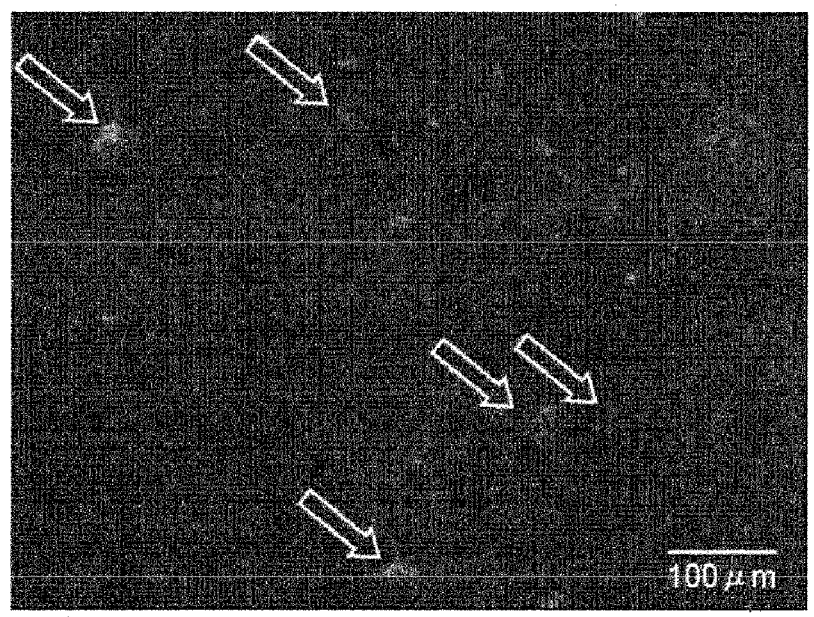
THK-383 Staining

[Fig. 20]
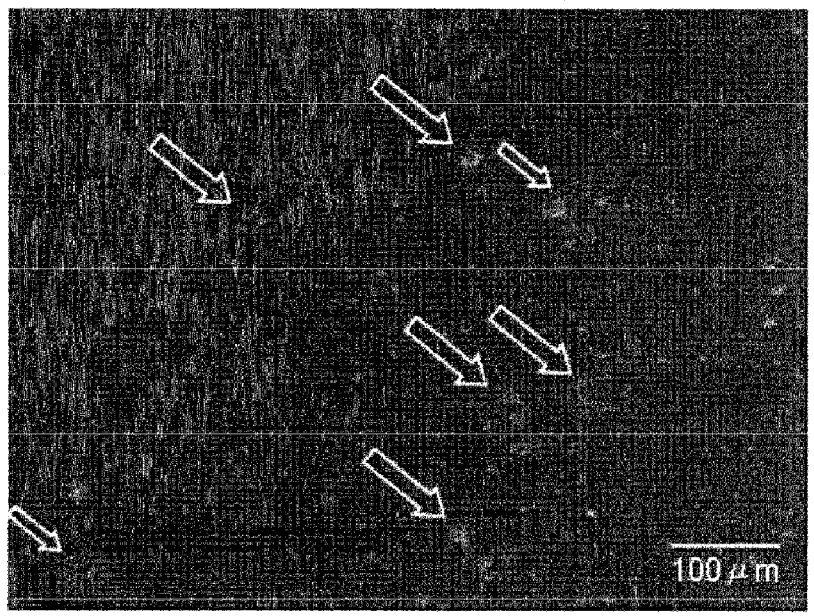
THK-385 Staining
[Fig. 21]
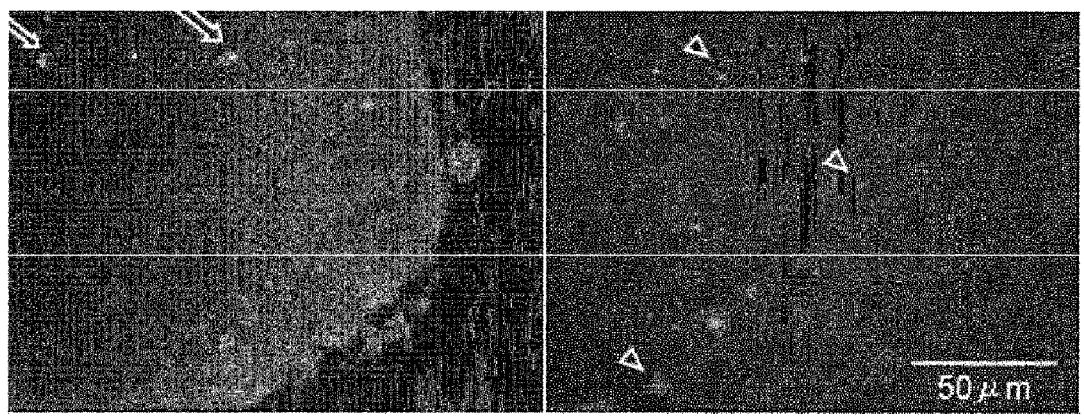
THK-386 Staining

[Fig. 22]
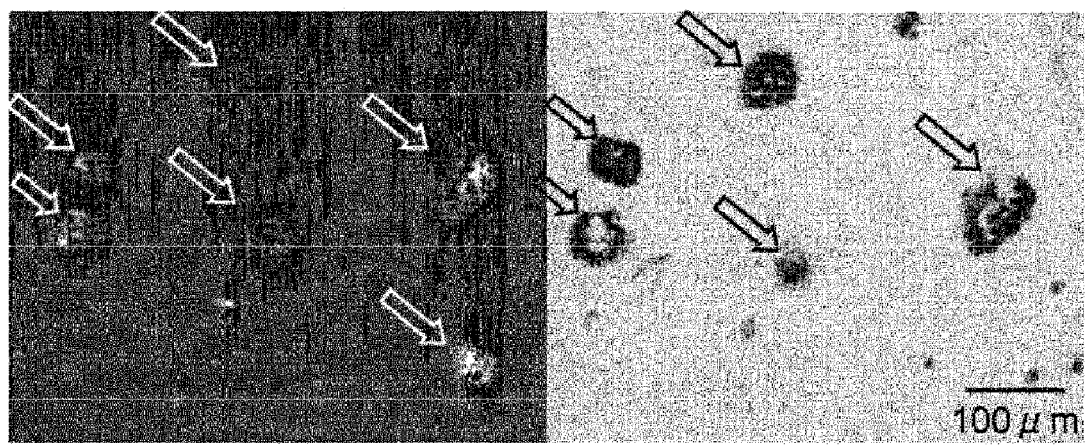
THK-525 Staining     Anti-A Antibody Staining
[Fig. 23]
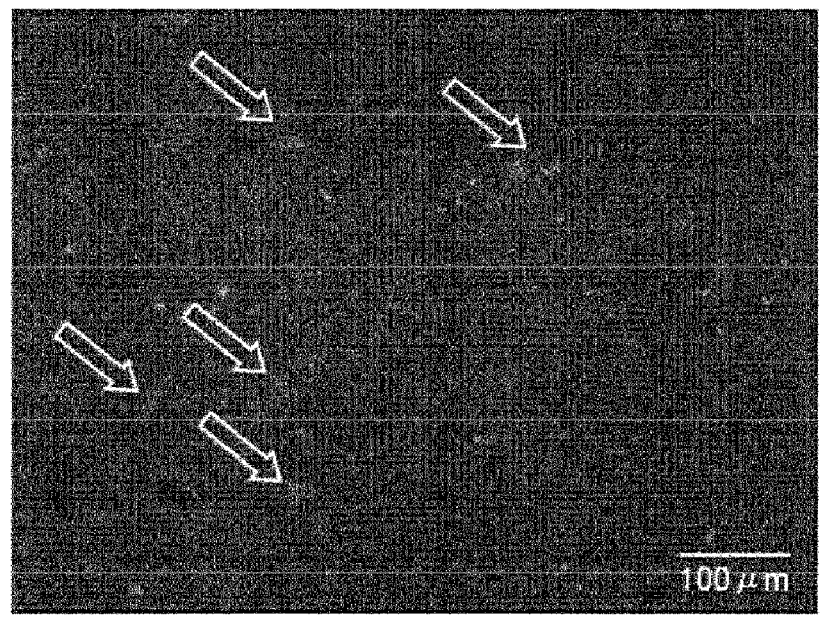
THK-556 Staining

[Fig. 24]
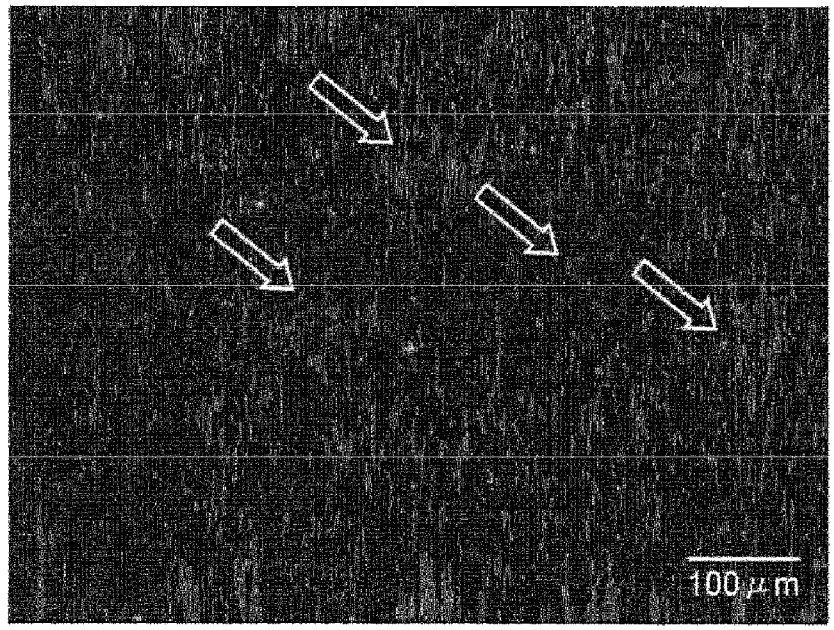
THK-558 Staining
[Fig. 25]
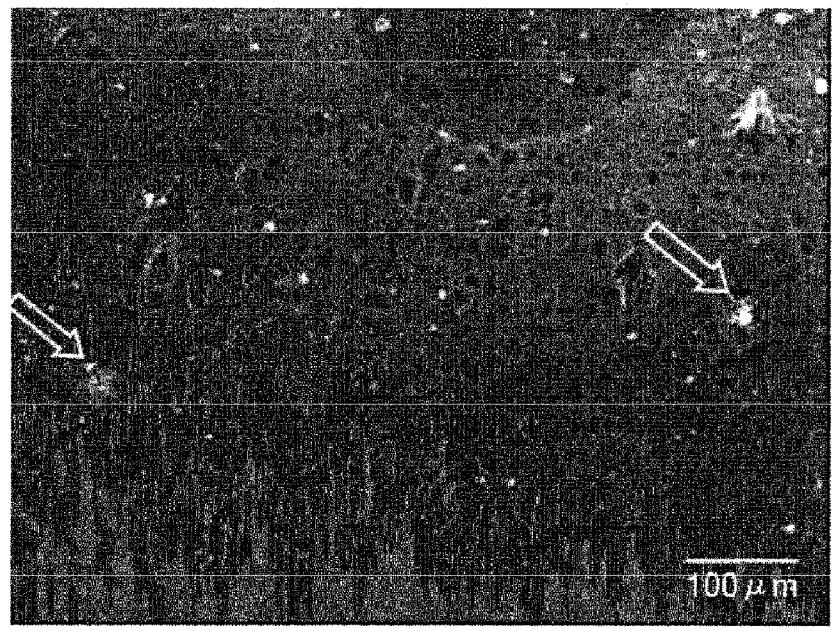
THK-559 Staining

[Fig. 26]
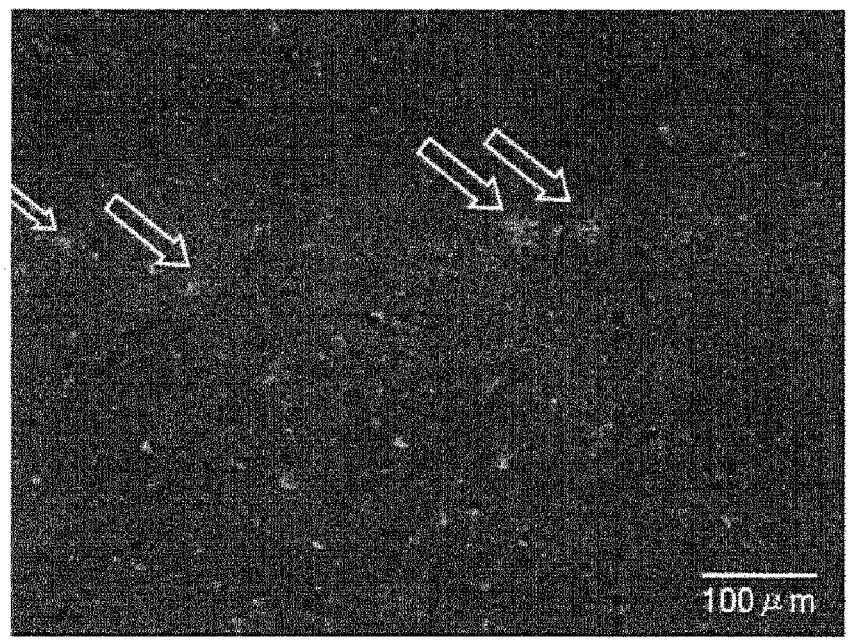
THK-561 Staining
[Fig. 27]
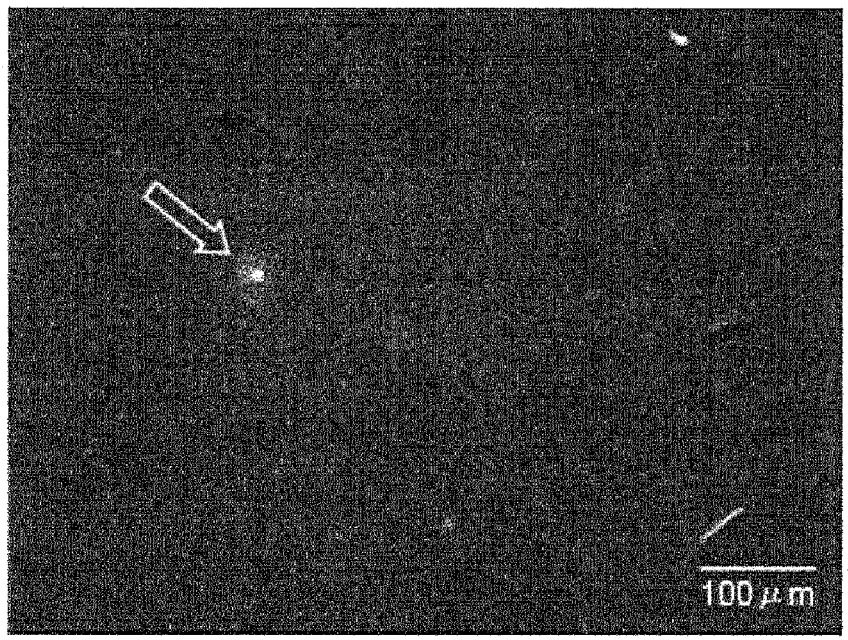
THK-562 Staining

[Fig. 28]
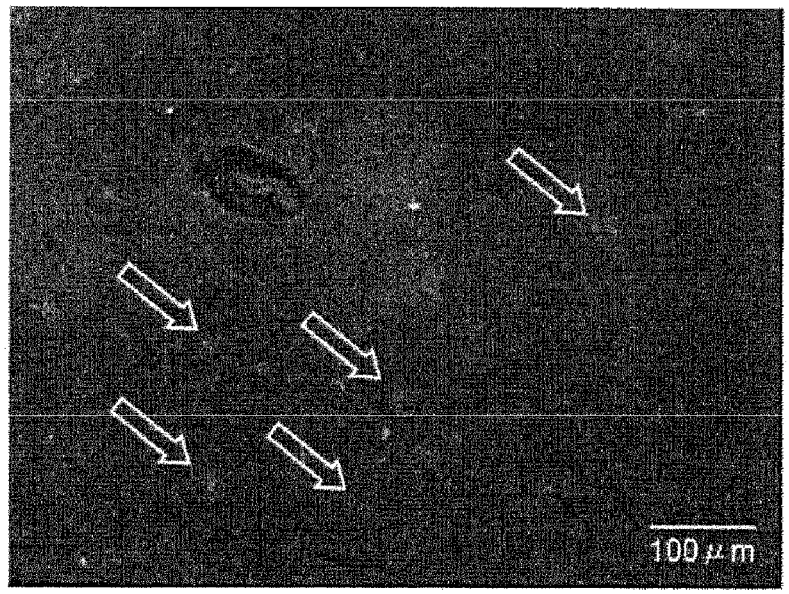
THK-563 Staining
[Fig. 29]
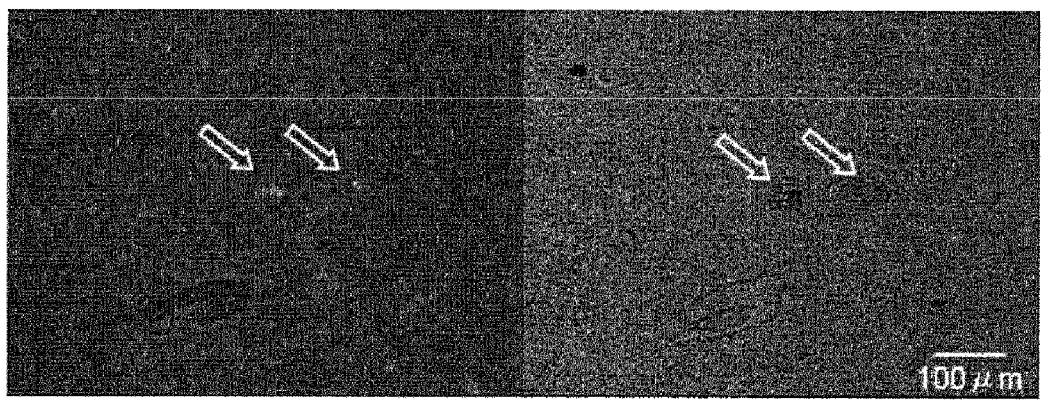
THK-565 Staining         Anti-A Antibody Staining

[Fig. 30]
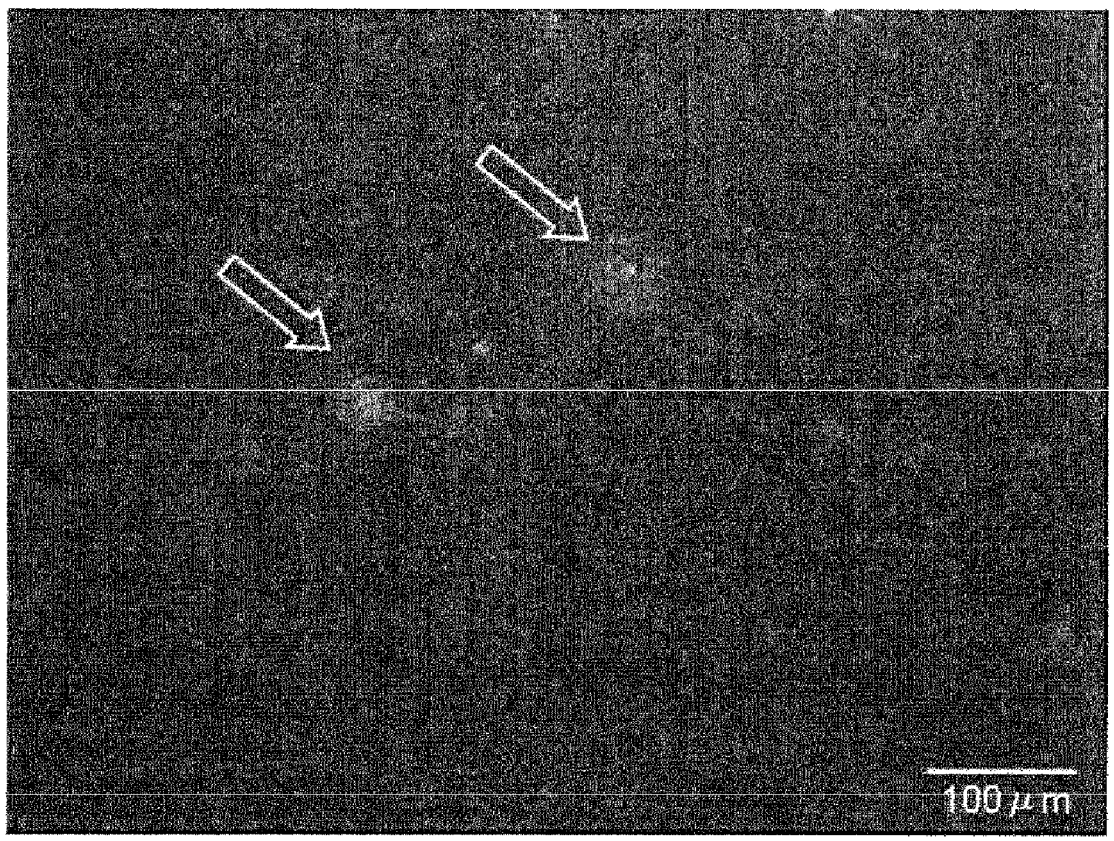
THK-585 Staining

[Fig. 31]
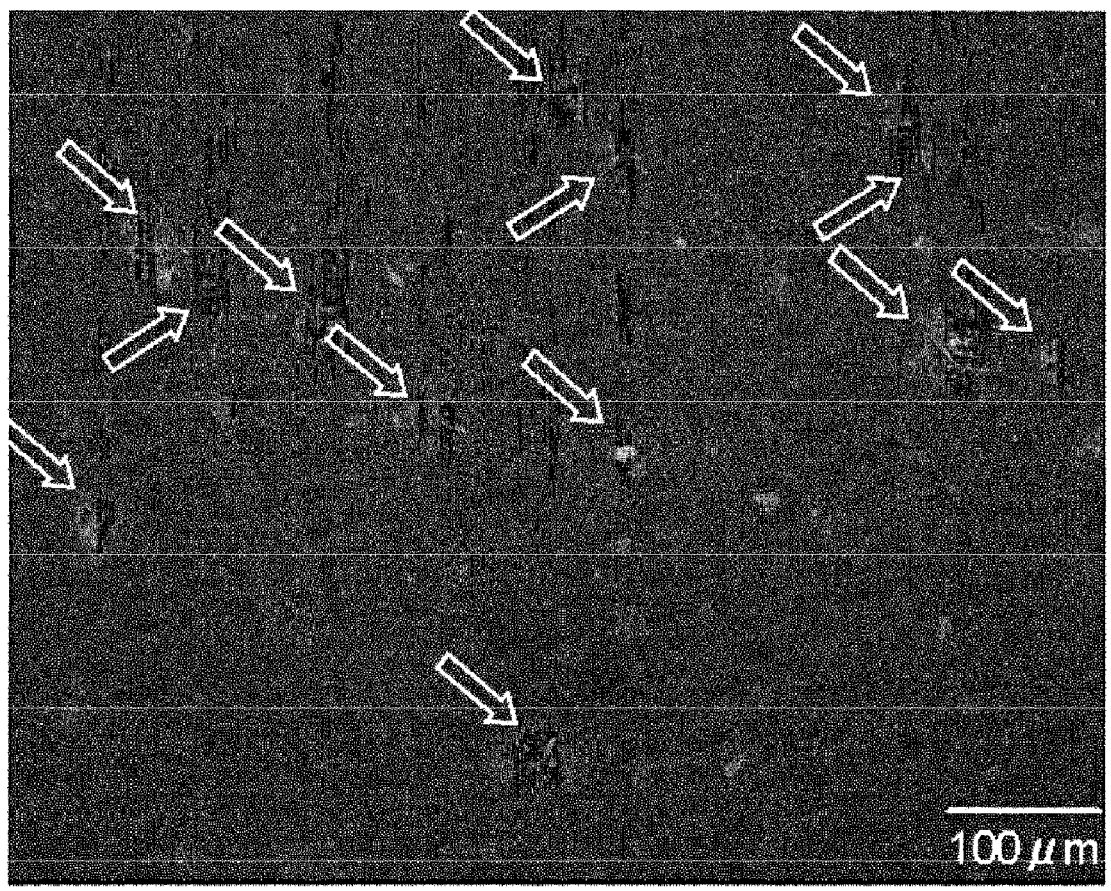
THK-702 Staining

[Fig. 32]
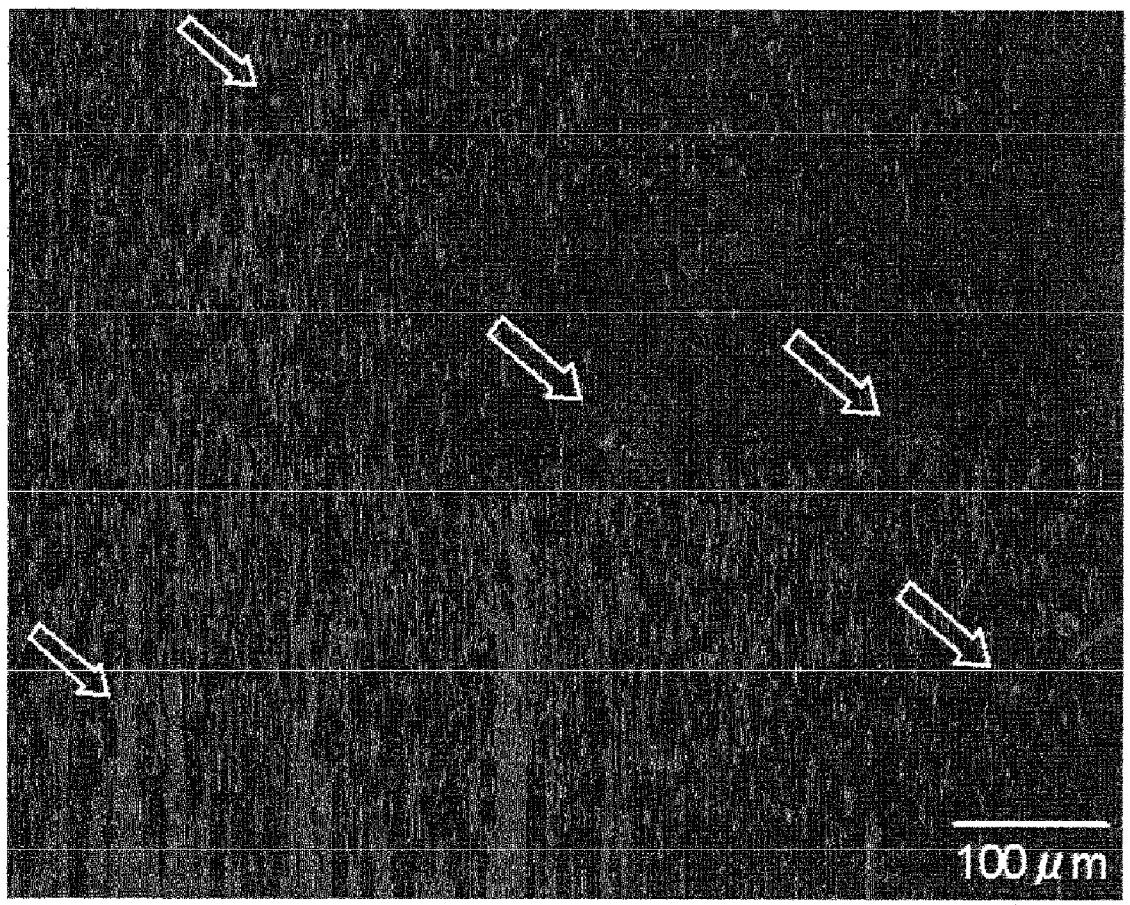
THK-708 Staining

[Fig. 33]
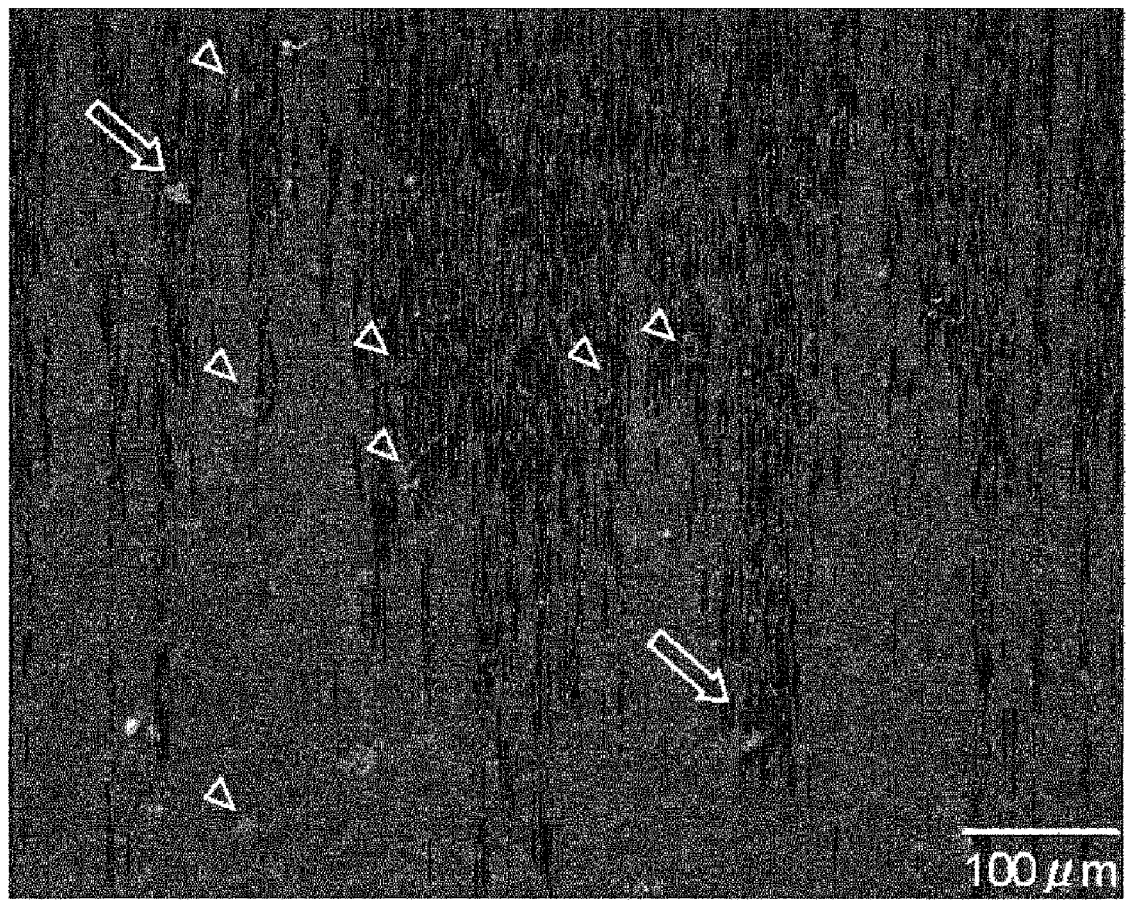
THK-727 Staining

[Fig. 34]
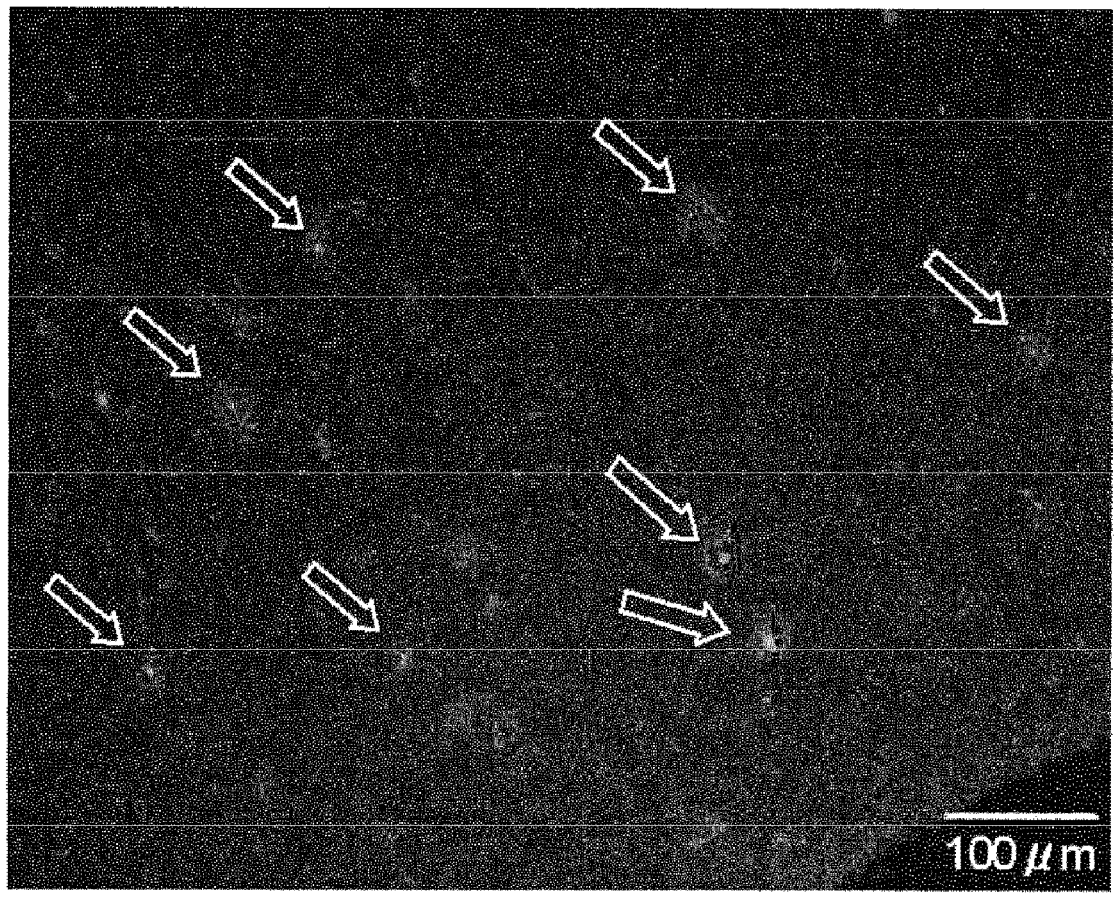
THK-752 Staining

[Fig. 35]
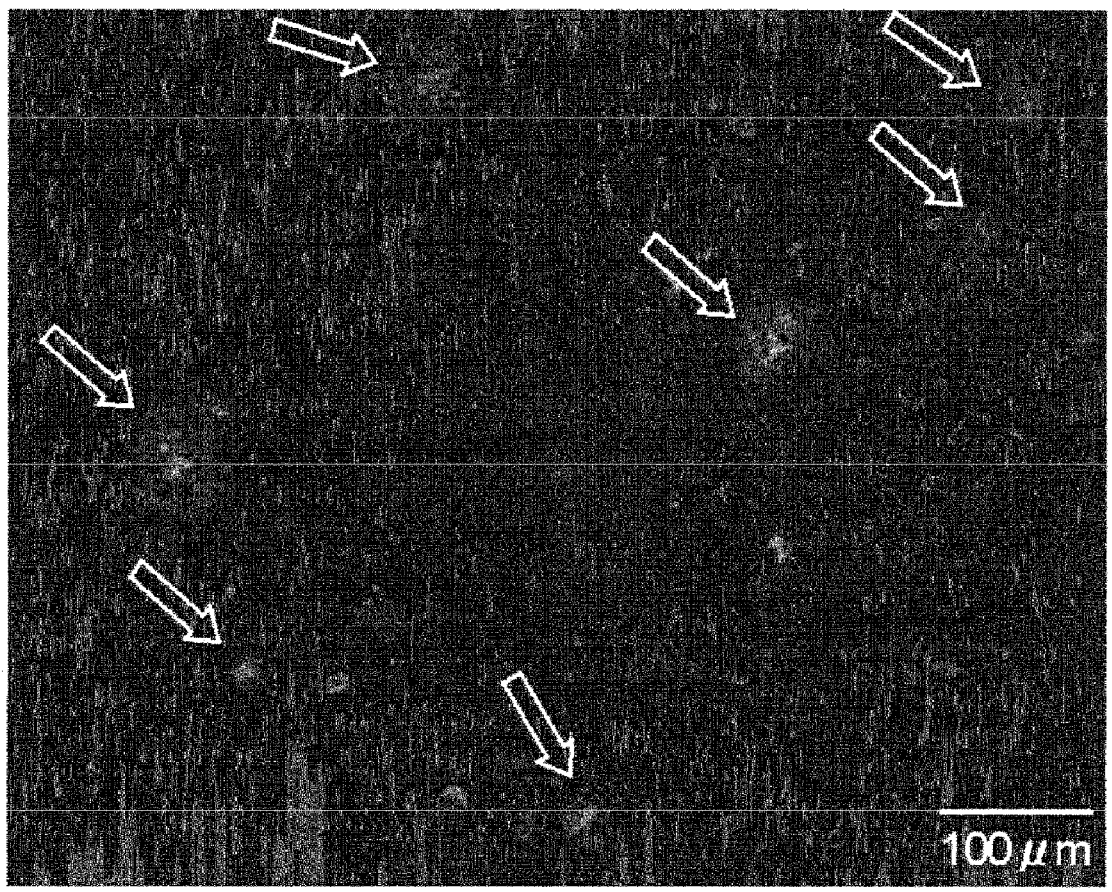
THK-761 Staining

[Fig. 36]
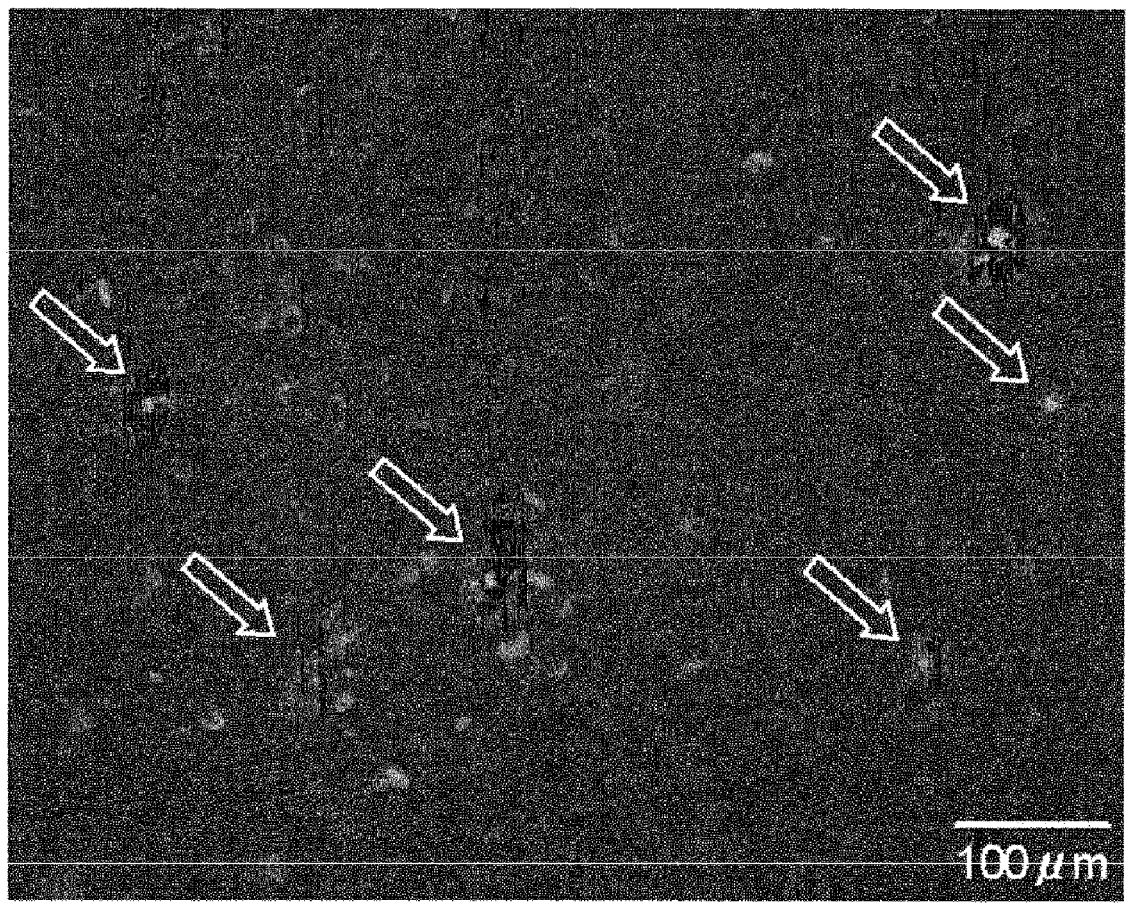
THK-763 Staining

[Fig. 37]
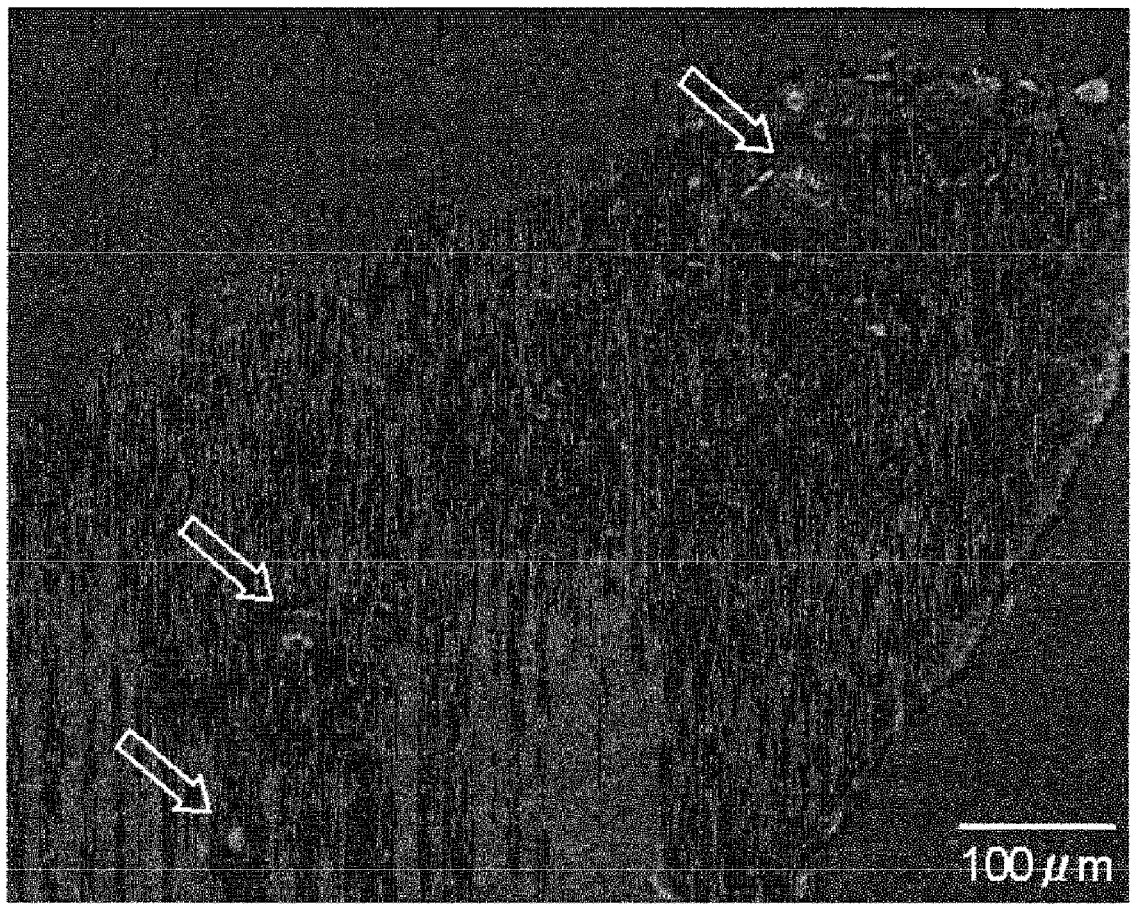
THK-766 Staining

[Fig. 38]
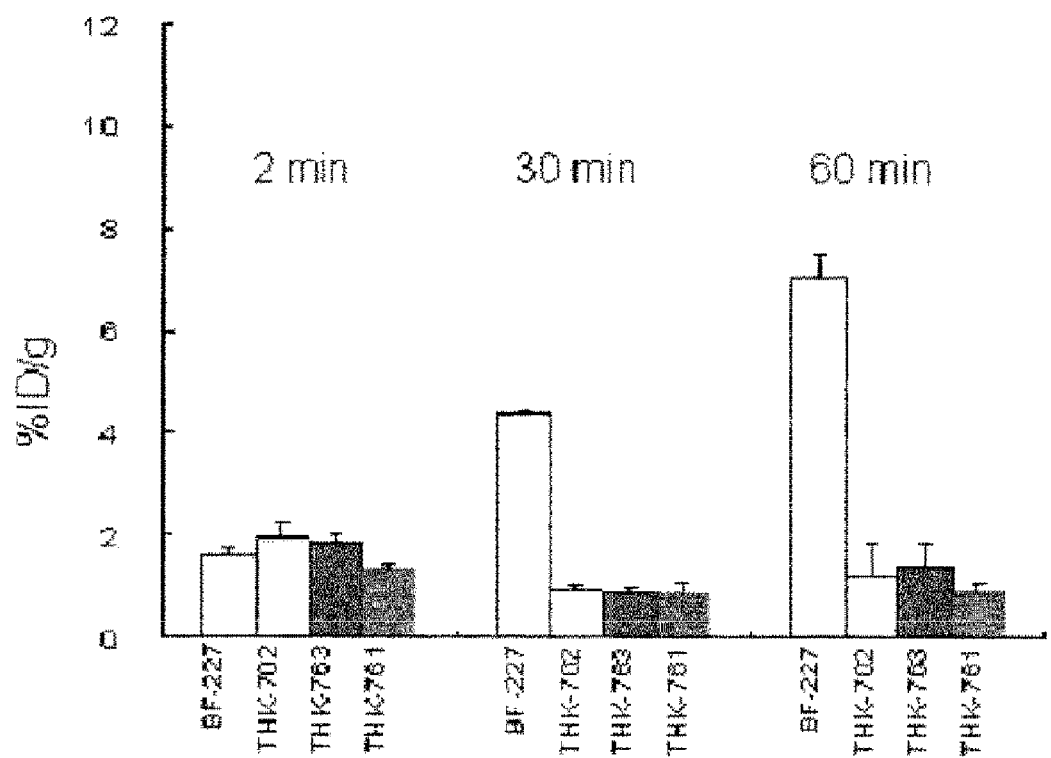

BENZOXAZOLE DERIVATIVES

TECHNICAL FIELD

The present invention relates to a diagnostic probe for conformation disease, in particular to an imaging diagnostic probe, and in detail, to a probe labeled with a positron emitter, and to a composition for imaging diagnosis that comprises the probe. Further, the invention relates to a pharmaceutical composition, for example, for detection/staining of amyloid β protein and neurofibrillary tangle in a brain material, and for example, for detection/staining of senile plaque in the brain of Alzheimer disease patients, and for prevention and/or treatment of conformation disease. The invention also relates to a composition for diagnosis of conformation disease that comprises the above-mentioned probe compound.

BACKGROUND ART

Disorders with deposition of a β sheet structure-having protein that is intrinsic to conformation disease include various diseases characterized by deposition of insoluble fibrillary protein in various organs and tissues of a body. These diseases include Alzheimer disease, prion disease, Lewy body disease, Parkinson disease, Huntington disease, spinobulbar muscular atrophy, dentatorubral-pallidoluysian atrophy, spinocerebellar ataxia, Machado-Joseph disease, amyophic lateral sclerosis (ALS), Down syndrome, Pick disease, FTDP-17 (frontotemporal dementia and parkinsonism linked to chromosome 17), LNTD (limbic neurofibrillary tangle dementia), sudanophilic leukodystrophy, amyloidosis, etc.

Of those, Alzheimer disease (AD) is at present considered as one of most incurable diseases, and accurate early diagnosis is desired for it. Alzheimer disease is a disease characterized by progressive dementia occurring essentially in the presenile stage to the senile stage. From the pathological viewpoint, the disease is characterized by entire cerebral involution, extreme denaturation and omission of neurons and appearance of neurofibrillary tangle and senile plaque. It is known that the most significant risk factor of dementia such as typically Alzheimer disease is aging. Accordingly, the increase in the number of the case patients with the increase in the senile population is remarkable especially in Japan, America and European countries that are in aging society, and the medical cost for the disease has brought about a crisis of the medical system in these countries.

In our country, the number of Alzheimer disease patients is estimated at about 1,000,000, and with the increase in the senile population in future, the number of the patients will surely increase. The cost for one Alzheimer disease patient inclusive of care expense will be from 1,000,000 yens to 3,000,000 yens/year, and therefore, our country would have already paid a social economic cost of from 1,000,000,000,000 yens to 3,000,000,000,000 yens. Medical treatment of Alzheimer disease before the actual development of the symptom of the disease or in the stage thereof as early as possible could bring about a great medical economic effect, and it is now a global common sense.

At present, various methods are known for diagnosis of Alzheimer disease. In our country, generally employed is a method of quantitatively detecting the reduction in the cognitive function of an individual that may have suffered from Alzheimer disease, such as a Hasegawa method, ADAS, MMSE or the like; but rarely and secondarily employed is an imaging diagnostic method (e.g., MRI, CT). However, these diagnostic methods are unsatisfactory for deciding the disease, and the decisive diagnosis requires biopsy of the brain during the lifetime and histopathologic examination of the brain after death. Despite of energetic studies made for it, no one could make any significant progress in diagnosis of Alzheimer disease. As a result of many studies, it has become known that neurodegeneration characteristic of Alzheimer disease may begin much before the development of the first clinical symptom of the disease (in a long case, it is before about 40 years). In addition, it is known that, when the family or the clinicians around the patient of the disease have noticed the first clinical symptom of the disease, then the intracerebral pathologic image of the patient has already advanced to an irreparable state. In consideration of the progressive characteristic of the disease symptom and of the significant increase in the number of the disease patients, the necessity and the meaning of accurate early stage diagnosis of Alzheimer disease is extremely great.

The histopathologic image of Alzheimer disease is characterized by two typical cardinal signs. They are senile plaque and neurofibrillary tangle. The essential constitutive component of the former is a β sheet structure-having amyloid β (Aβ) protein; and that of the latter is an overphosphorylated amyloid β protein. The decisive diagnosis of Alzheimer disease is based on the expression of these pathologic characteristics in a patient's brain.

Amyloid β protein is characteristic of conformation disease that includes Alzheimer disease, and the two have close relation to each other. Accordingly, detection of a β sheet structure-having amyloid β protein as a marker in a body, especially in a brain is one important method for diagnosis of conformation disease, especially Alzheimer disease. Searches for substances capable of specifically binding to intracorporeal, especially intracerebral amyloid β protein to stain it have heretofore been made for the purpose of diagnosis of a disease with amyloid deposition such as typically Alzheimer disease. As such substances, known are Congo red (see Non-Patent Reference 1), Thioflavin S (see Non-Patent Reference 2), Thioflavin T (Non-Patent Reference 3) and Crysamine G and its derivatives (see Patent Reference 1 and Patent Reference 2). However, these have a lot of problems in point of their binding specificity to amyloid β protein, blood-brain barrier permeability, solubility and toxicity. We, the present inventors have found out various compounds characterized by high specificity to amyloid β protein, great blood-brain barrier permeability and solubility and less toxicity (see Patent Reference 3, Patent Reference 4, Patent Reference 5, Patent Reference 6 and Patent Reference 7).

A disease is known, which is caused by an intracerebral protein itself having a β sheet structure. It is considered that, in Alzheimer disease, amyloid β protein and tau protein may have a β sheet structure and the proteins themselves may be a cause of the disease or a part of the cause of the disease. Yankner, et al. reported for the first time that, when amyloid β protein is made to have a β sheet structure, then it exhibits neuron toxicity (see Non-Patent Reference 4). After that, many replication studies for it have been made, and have confirmed that the β sheet structure-having amyloid β protein has neuron toxicity. In that manner, the β sheet structure-having amyloid β protein and tau protein have neuron toxicity, and therefore, it may be suggested that a compound capable of inhibiting the cytotoxicity could be a remedial drug for a disease, of which the cause or a part of the cause is the β sheet structure-having protein itself, or that is, conformation disease such as Alzheimer disease. At present, however, the development of such a remedial drug could not bring about a sufficient result.

Accordingly, the necessity is increasing for a compound having high specificity to amyloid β protein for diagnosis of conformation disease such as typically Alzheimer disease, for a staining agent specific to amyloid β protein, and for treatment and prevention of conformation disease.

Another histopathologic cardinal sign of Alzheimer disease comprises neurofibrillary tangle and its essential constitutive component, overphosphorylated tau protein, hut in general, it is considered that these may be expressed later than amyloid β protein. However, it is considered that neurofibrillary tangle may well correlate to the degree of dementia as compared with amyloid β protein (see Non-Patent Reference 5 and Non-Patent Reference 6).

Apart from Alzheimer disease, disorders characterized by the cardinal sign of intracerebral deposition tau protein (tauopathy) are Pick disease and progressive supranuclear palsy (PSP). Conformation disease also includes these diseases.

To that effect, tau protein is characteristic of the disease with deposition of tau protein that includes Alzheimer disease, and it has close relation to the disease. Accordingly, the detection of intracorporeal, especially intracerebral β sheet structure-having tau protein as a marker is one important method for diagnosis of diseases with tau deposition, especially Alzheimer disease.

A method for quantitatively determining the tau level in a body, especially in a cerebrospinal fluid for the purpose of diagnosis of tau deposition-associated diseases such as typically Alzheimer disease has been reported by a few groups (see Non-Patent Reference 7 and Non-Patent Reference 8). However, any probe for in-vivo noninvasive quantitative determination of tau is not known at all in the world.

Accordingly, a necessity is increasing for a compound having high specificity to neurofibrillary tangle, for diagnosis and treatment of a disease of which the cause or a part of the cause is neurofibrillary tangle such as typically Alzheimer disease or for staining neurofibrillary tangle.

Compounds with high specificity for amyloid-beta proteins and neurofibrillary tangle have been reported (see patent document 8, patent document 9, patent document 10, and patent document 11). When these compounds are used in-vivo, in particular, in the body of a human patient, it is preferable that the compounds provide extremely low or no mutagenicity. Alternatively, it is preferable that the compounds have extremely little or no bone accumulation. Consequently, search of compounds which provide extremely low or no mutagenicity and/or have extremely little or no bone accumulation, and which can be used as conformation disease diagnosis probe is necessary.

Patent Reference 1: PCT/US96/05918
Patent Reference 2: PCT/US98/07889
Patent Reference 3: Japanese Patent Application 2000-080082
Patent Reference 4: Japanese Patent Application 2000-080083
Patent Reference 5: Japanese Patent Application 2001-076075
Patent Reference 6: PCT/JP01/02204
Patent Reference 7: PCT/JP01/02205
Patent Reference 8: PCT/JP03/07183
Patent Reference 9: PCT/JP03/15269
Patent Reference 10: PCT/JP03/15229
Patent Reference 11: PCT/JP2004/01546
Non-Patent Reference 1: Puchtler et al., Journal of Histochemistry and Cytochemistry, Vol. 10, p. 35, 1962
Non-Patent Reference 2: Puchtler et al., Journal of Histochemistry and Cytochemistry, Vol. 77, p. 431, 1983
Non-Patent Reference 3: Le Vine, Protein Science, Vol. 2, pp. 404-410, 1993
Non-Patent Reference 4: Yankner et al., Science, Vol. 245, pp. 417-420, 1989
Non-Patent Reference 5: Braak H. and Braak E., Acta Neuropathol., Vol. 82, pp. 239-259, 1991
Non-Patent Reference 6: Wischik en al., Neurobiology of Alzheimer's Disease, pp. 103-206, Oxford University Press, Oxford, 2001
Non-Patent Reference 7: Ishiguro et al., Neurosc-ylett., Vol. 270, pp. 81-84, 1999
Non-Patent Reference 8: Itoh en al., Ann. Neurol., Vol. 50, pp. 150-156, 2001

DISCLOSURE OF INVENTION

Problems to be Solved by the Invention

In view of the above-mentioned conditions, the present invention provides a substance which has high specificity for amyloid-beta proteins and/or neurofibrillary tangle, has high brain migration, and provides low or no mutagenicity, and/or has extremely little or no bone accumulation, and which can be used for conformation disease diagnostic probe. In addition, the present invention provides such labeled substance used for conformation disease diagnostic imaging probe as well as such diagnostic imaging diagnostic compositions and kits that include a probe, too. Furthermore, the present invention provides detection and/or staining method of amyloid-beta proteins and neurofibrillary tangle in the brain material, kits for that purpose, as well as pharmaceutical compositions for prevention and/or treatment of conformation disease. In addition, the present invention provides compounds useful for early diagnosis of conformation diseases and diagnostic imaging compositions that contain the compounds, too.

Means for Solving the Problems

The present inventors have intensively studied to solve the above-mentioned problems, and as a result, found that a compound (provided that the compounds are excluded wherein $R^3$ is a —O— lower alkyl group substituted with only halogen atom, and $R^1$ and $R^2$ are each independently denotes hydrogen atom or lower alkyl group), pharmaceutically acceptable salt or solvate thereof represented by formula (I):

[Formula 1]

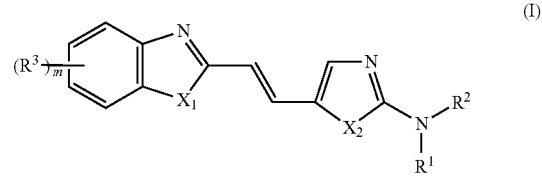

[wherein
$R^1$ and $R^2$ are independently hydrogen atom, lower alkyl group, or cycloalkyl group respectively, or 3- to 8-membered nitrogen-containing aliphatic ring formed together by $R^1$, $R^2$ and a nitrogen atom bonded thereto, together (carbon atoms which constitute the nitrogen-containing aliphatic ring may be substituted with nitrogen atom, sulfur atom or oxygen atom, and when the carbon atom is substituted with nitrogen atom, the nitrogen atom may be substituted lower alkyl group), $X_1$ and $X_2$ are each independently nitrogen atom, sulfur atom, or oxygen atom, $R^3$ is —O— lower alkyl group (the alkyl group is optionally substituted with halogen atom, and may be substituted with hydroxy group), and m is an integer of 1 to 3]

is able to be used as a diagnostic probe for conformation disease which has high specificity to beta-amyloid proteins and/or neurofibrillary tangle, and high brain migration, and extremely low or no mutagenicity, and achieved the present invention.

In particular, the compound of the present invention with a morpholino group on one terminal provides extremely low mutagenicity or is free of mutagenicity as shown in an example. It is one of the characteristics of the present invention to include such a compound group with low or no mutagenicity.

A compound with an —O— lower alkyl group (the alkyl group may be optionally substituted halogen atom, and furthermore may be optionally substituted hydroxy group) on the other terminal frequently provides low or extremely low bone accumulation. It is another characteristic of the present invention to include such a compound with low or extremely low bone accumulation.

The present invention provides a compound, pharmaceutically acceptable salt or solvate thereof with higher safety as compared to conventional amyloid PET probe, by having a group with a morpholino group on one terminal and/or a group represented by —O— lower alkyl group (the alkyl group may be optionally substituted halogen atom, and may be optionally substituted hydroxy group) on the other terminal, of the compounds represented by formula (I).

Accordingly, the compounds of the invention are extremely highly safe. Since the compounds of the invention stain amyloid β protein specifically and sharply, they may enable accurate early stage diagnosis of especially Alzheimer disease and Down syndrome. Further, the compounds of the invention have high brain permeability, or that is, high blood-brain barrier permeability. Having these characteristics, using the compound of the invention enables in-vivo no invasive early stage diagnosis especially in human patients.

As a drug for a PET probe to aid diagnosis of amyloid, for example, in WO2004/035522, a large number of benzoxazol derivatives are disclosed. However, in the specifications, no compound whose one terminal is morpholino is disclosed, and no compound the other terminal of which is an —O— lower alkyl group (the alkyl group may be optionally substituted with halogen atom, and furthermore may be optionally substituted with hydroxy group) is disclosed, either.

EFFECT OF THE INVENTION

The present invention provides a compound with extremely high safety, which has remarkably high specificity for beta-amyloid proteins and/or neurofibrillary tangle, and high blood-brain barrier permeability, low or no mutagenicity. In addition, the present invention provides a compound with extremely high safety, which has remarkably high specificity for beta-amyloid proteins and/or neurofibrillary tangle, and high blood-brain barrier permeability, low or practically no bone accumulation. Consequently, it is possible to diagnose, treatment and/or prevention conformation diseases by the use of the compound of the present invention. In addition, according to the present invention, diagnostic imaging of conformation diseases, in particular, diagnostic imaging by the use of PET may be possible. Consequently, the present invention enables accurate early diagnosis, effective treatment, and prevention of conformation diseases.

BRIEF DESCRIPTION OF DRAWINGS

FIG. 1 is a fluorescence microscopy image (ex vivo in intravenous administration of THK-097 (0.2 mg/kg) to a Tg mouse (Tg2576) with amyloid β protein deposition.

FIG. 2 is a fluorescence microscopy image (ex-vivo) in intravenous administration of THK-525 (4 mg/kg) to a Tg mouse (Tg2576) with amyloid β protein deposition. The white space arrow indicates amyloid β protein.

FIG. 3 is a fluorescence microscopy image (ex-vivo) in intravenous administration of THK-727 (4 mg/kg) to a Tg mouse (APPswe2576/Tau JPL3) with amyloid β protein deposition. The white space arrow indicates amyloid β protein.

FIG. 4 is a fluorescence microscopy image in intravenous administration of THK-702 (4 mg/kg) to a Tg mouse (Tg2576) with amyloid β protein deposition (upper panel); and an anti-amyloid (Aβ) antibody-stained image of the same section (lower panel).

FIG. 5 shows enlarged microscope images of FIG. 4. A, B and C correspond to A, B and C of FIG. 4, respectively. The white and black arrows indicate amyloid β protein.

FIG. 6 is a THK-097 (left panel)-stained image and an anti-amyloid β (Aβ) antibody-stained image (right panel: adjacent section to that of left panel) in a brain section of an Alzheimer disease patient. The white space arrow indicates amyloid β protein.

FIG. 7 is a THK-184-stained image in a brain section of an Alzheimer disease patient. The white space arrow indicates amyloid β protein.

FIG. 8 is a THK-185-stained image in a brain section of an Alzheimer disease patient. The white space arrow indicates amyloid β protein; and the white space arrow head indicates neurofibrillary tangle.

FIG. 9 is a THK-203-stained image in a brain section of an Alzheimer disease patient. The white space arrow indicates amyloid β protein.

FIG. 10 is a THK-207-stained image in a brain section of an Alzheimer disease patient. The white space arrow indicates amyloid β protein.

FIG. 11 is a THK-248-stained image in a brain section of an Alzheimer disease patient. The white space arrow indicates amyloid β protein.

FIG. 12 is a THK-254-stained image in a brain section of an Alzheimer disease patient. The white space arrow head indicates neurofibrillary tangle.

FIG. 13 is a THK-258-stained image in a brain section of an Alzheimer disease patient. The white space arrow Indicates amyloid β protein; and the white space arrow head indicates neurofibrillary tangle.

FIG. 14 is a THK-262-stained image in a brain section of an Alzheimer disease patient. The white space arrow indicates amyloid β protein.

FIG. 15 is a THK-276-stained image in a brain section of an Alzheimer disease patient. The white space arrow indicates amyloid β protein.

FIG. 16 is a THK-281-stained image in a brain section or an Alzheimer disease patient. The white space arrow indicates amyloid β protein.

FIG. 17 is a THK-308-stained image in a brain section of an Alzheimer disease patient. The white space arrow indicates amyloid β protein.

FIG. 18 is a THK-317-stained image in a brain section of an Alzheimer disease patient. The white space arrow indicates amyloid β protein; and the white space arrow head indicates neurofibrillary tangle.

FIG. 19 is a THK-383-stained image in a brain section of an Alzheimer disease patient. The white space arrow indicates amyloid β protein.

FIG. 20 is a THK-385-stained image in a brain section of an Alzheimer disease patient. The white space arrow indicates amyloid β protein.

FIG. 21 is a THK-386-stained image in a brain section of an Alzheimer disease patient. The white space arrow indicates amyloid β protein; and the white space arrow head indicates neurofibrillary tangle.

FIG. 22 is a THK-525 (left panel)-stained image and an anti-amyloid β (Aβ) antibody-stained image (right panel: adjacent section to that of left panel) in a brain section of an Alzheimer disease patient. The white space arrow indicates amyloid β protein.

FIG. 23 is a THK-556-stained image in a brain section of an Alzheimer disease patient. The white space arrow indicates amyloid β protein.

FIG. 24 is a THK-558-stained image in a brain section of an Alzheimer disease patient. The white space arrow indicates amyloid β protein.

FIG. 25 is a THK-559-stained image in a brain section of an Alzheimer disease patient. The white space arrow indicates amyloid β protein.

FIG. 26 is a THK-561-stained image in a brain section of an Alzheimer disease patient. The white space arrow indicates amyloid β protein.

FIG. 27 is a THK-562-stained image in a brain section of an Alzheimer disease patient. The white space arrow indicates amyloid β protein.

FIG. 28 is a THK-563-stained image in a brain section of an Alzheimer disease patient. The white space arrow indicates amyloid β protein.

FIG. 29 is a THK-565 (left panel)-stained image and an anti-amyloid β (Aβ) antibody-stained image (right panel: adjacent section to that of left panel) in a brain section of an Alzheimer disease patient. The white space arrow indicates amyloid β protein.

FIG. 30 is a THK-585-stained image in a brain section of an Alzheimer disease patient. The white space arrow indicates amyloid β protein.

FIG. 31 is a THK-702-stained image in a brain section of an Alzheimer disease patient. The white space arrow indicates amyloid β protein.

FIG. 32 is a THK-708-stained image in a brain section of an Alzheimer disease patient. The white space arrow indicates amyloid β protein.

FIG. 33 is a THK-727-stained image in a brain section of an Alzheimer disease patient. The white space arrow indicates amyloid β protein; and the white space arrow head indicates neurofibrillary tangle.

FIG. 34 is a THK-752-stained image in a brain section of an Alzheimer disease patient. The white space arrow indicates amyloid β protein.

FIG. 35 is a THK-761-stained image in a brain section of an Alzheimer disease patient. The white space arrow indicates amyloid β protein.

FIG. 36 is a THK-763-stained image in a brain section of an Alzheimer disease patient. The white space arrow indicates amyloid β protein.

FIG. 37 is a THK-766-stained image in a brain section of an Alzheimer disease patient. The white space arrow indicates amyloid β protein.

FIG. 38 is bone accumulation of $^{18}$F-labeled THK-702, THK-763, THK-761, and BF-227 in mice after 2 minutes, 30 minutes, and 60 minutes.

BEST MODE FOR CARRYING OUT THE INVENTION

The compounds of the present invention are ones represented by the formulae (I), (I') to (VI) described below or salts and solvates thereof. In the present specification, "the compounds of the present invention" or "the compounds according to the present invention" include, as long as not otherwise mentioned, the compounds of the formulae (I), (I') to (VI), as well as salts and solvates thereof.

In the present specification, "lower alkyl group" means alkyl groups having the straight chain or branch composed of 1 to 6 carbons, specifically includes methyl group, ethyl group, propyl group, isopropyl group, butyl group, Isobutyl group, sec-butyl group, tert-butyl group, pentyl group, isoamyl group, neopentyl group, Isopentyl group, 1,1-dimethyl propyl group, 1-methyl-butyl group, 2-methyl-butyl group, 1,2-dimethyle-propyl group, hexyl group, isohexyl group, 1-methyl-pentyl group, 2-methyl-pentyl group, 3-methyl-pentyl group, 1,1-dimethyl-butyl group, 1,2-dimethyl-butyl group, 2,2-dimethyl-butyl group, 1,3-dimethyl-butyl group, 2,3-dimethyl-butyl group, 3,3-dimethyl-butyl group, 1-ethyl-butyl group, 2-ethyl-butyl group, 1,2,2-trimethyl-propyl group, and 1-ethyl-2-methyl-propyl group and the like.

In the present specification, "cycloalkyl group" means cycloalkyl groups having 3 to 7 carbons specifically includes, for example, cyclopropyl group, cyclobutyl group, cyclopentyl group, cyclohexyl group, and cycloheptyl group.

In the present specification, "halogen atom" means a fluorine atom, a chlorine atom, a bromine atom, and an iodine atom.

In the present specification, "amyloid beta protein", "amyloid β protein", "Aβ protein", "amyloid beta", "amyloid β", and "Aβ" are synonymous terms.

If the double bond exists between two rings in the compounds of the present invention, there may be both cis-isomer and trans-isomer.

If asymmetric carbon atoms exist in the compounds of the present invention, the mixture of the isomer, and their individual isomer are also included in the compounds of the present invention.

For example, if one asymmetric carbon atom exists in the compounds of the present invention, each of optically active compounds is separately synthesized, or each enantiomer can be separated by column chromatography.

When enantiomer is separated by column chromatography, the column used includes, for example, CHIRALPAK AD (DAICEL).

The solvent to be used can be the solvent ordinarily used to separate isomer, chloroform, acetinitrile, acetic ether, methanol, ethanol, acetone, hexane, water or the like alone or combination of these 2 or more solvents.

In order to furthermore specifically disclose the compound expressed by the formula (I) of the present invention,

[Formula 2]

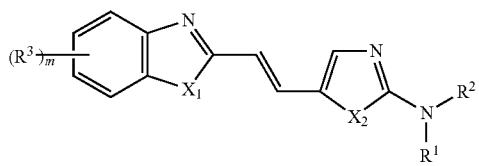

[In the formula, each variable is the same as that described above], each type of variable used in formula (I) is exemplified.

$R^1$ and $R^2$ express each dependently a hydrogen atom, a lower alkyl group, or a cycloalkyl group, or $R^1$, $R^2$, and a nitrogen atom bound to them each other together form a three- to eight-membered aliphatic ring with nitrogen atom(s) (carbon atoms constituting said aliphatic ring with nitrogen atom(s) may be substituted by a nitrogen atom, a sulfur atom or an oxygen atom, and if a carbon atom is substituted by a nitrogen atom, said nitrogen atom may be substituted by a lower alkyl group).

"Lower alkyl group" expressed by $R^1$ and $R^2$ means the same as the lower alkyl group defined above. In particular, a methyl group, an ethyl group, and a propyl group are preferable, and an ethyl group is more preferable.

"Cycloalkyl group" expressed by $R^1$ and $R^2$ means the same as the cycloalkyl group defined above.

A three- to eight-membered aliphatic ring with nitrogen atoms formed by $R^1$, $R^2$, and a nitrogen atom bound to them each other together (a carbon atom comprising said aliphatic ring with nitrogen atoms may be substituted by a nitrogen atom, a sulfur atom or an oxygen atom, and if a carbon atom is substituted by a nitrogen atom, said nitrogen atom may be substituted by a lower alkyl group) specifically includes, for example, groups expressed by

[Formula 3]

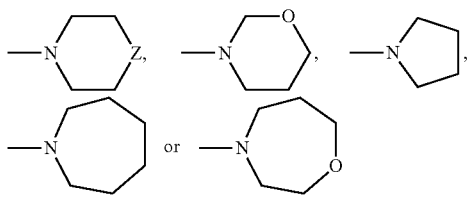

[In the formula, Z represents O, S, $CH_2$ or $NR^e$, and $R^e$ represents a hydrogen, or a $C_{1-4}$ alkyl group] or the like. Among them, a morpholino group is preferable.

As groups expressed by

[Formula 4]

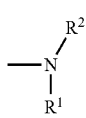

[In the formula, each variable is the same as that described above], a dimethylamino group, a methylamino group, and a morpholino group are preferable, and a dimethylamino group or a morpholino group is more preferable.

$X_1$ represents a nitrogen atom, a sulfur atom, or an oxygen atom, and among these, an oxygen atom is preferable.

$X_2$ represents a nitrogen atom, a sulfur atom, or an oxygen atom, and among these, a sulfur atom is preferable.

m represents an integral number from 1 to 3, and among these, m=1 is preferable.

$R^3$ represents a —O— lower alkyl group (said alkyl group is substituted by a halogen atom, and furthermore, it may be substituted by a hydroxy group). Among these, a —O— lower alkyl group substituted by a halogen atom or a —O— lower alkyl group substituted by a halogen atom and a hydroxy group, are preferable, and groups expressed by

[Formula 5]

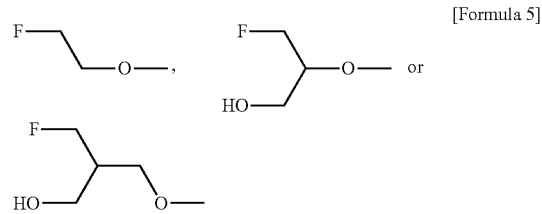

are more preferable.

Among the compounds of the present invention, pharmaceutically acceptable salts and solvates thereof, the compound expressed by formula (I), and pharmaceutically acceptable salts and solvates thereof are preferable.

Among the compounds of the present invention, pharmaceutically acceptable salts and solvates thereof, the case that the group expressed by

[Formula 6]

In the formula (I) is a morpholino group, or $R^3$ in the formula (I) is the compound expressed by

[Formula 7]

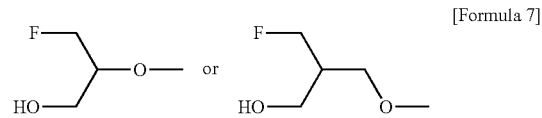

or pharmaceutically acceptable salts or solvates thereof is preferable.

The compound where the group expressed by

[Formula 8]

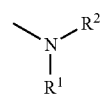

in the formula (I)

has a morpholino group showed extremely low mutagenicity or no mutagenicity as shown in examples.

Additionally, the compound where $R^3$ in the formula (I) has a group expressed by

[Formula 9]

F—\—O—
HO—/ showed hardly or extremely low bone accumulation as shown in examples.

Furthermore, as shown in examples, these compounds, and pharmaceutically acceptable salts or solvates thereof have high specificity against Aβ, have low toxicity, and show high transfer into the brain. In addition, after a predetermined period, most of drugs promptly disappear from the brain.

Accordingly, the compounds of the invention can be used a safe probe for imaging diagnosis of conformation disease.

The present invention also provides the compound to be used as the precursor to synthesize the compound expressed by formula (I). Those skilled in the art can easily design said precursor from the target compounds of the present invention, and perform the synthesis thereof. Alternatively, said precursor can be obtained by modifying the compounds available in the market.

Said precursor includes the compounds (provided that the compounds are excluded wherein $R^3$ is the —O— lower alkyl group substituted by the halogen atom alone, and $R^1$ and $R^2$ are each independently hydrogen atom or a lower alkyl group), for example, expressed by formula (I'):

[Formula 10]

(I')

[wherein, $R^1$ and $R^2$ are each independently a hydrogen atom, a lower alkyl group, or a cycloalkyl group, or $R^1$, $R^2$, and a nitrogen atom bound thereto together form a three- to eight-membered aliphatic ring with nitrogen atom(s) (carbon atoms constituting said aliphatic ring with nitrogen atoms may be substituted by a nitrogen atom, a sulfur atom or an oxygen atom, and if a carbon atom is substituted by a nitrogen atom, said nitrogen atom may be substituted by a lower alkyl group), $X_1$ and $X_2$ are dependently a nitrogen atom, a sulfur atom, or an oxygen atom, respectively, $R^4$ is a —O— lower alkyl group (said alkyl group is substituted by a tosyl group and further, may be substituted by a hydroxy group), and m is an integral number from 1 to 3] or pharmaceutically acceptable salts or solvates thereof.

$R^1$, $R^2$, $X_1$, and $X_2$ in the formula (I') are the same as those in the formula (I).

Among $R^4$, group expressed by

[Formula 11]

TsO—\—O—,  TsO—\—O— or
      /              /
                 HO—

TsO—\—O—
     /
HO—/ is preferable.

The second embodiment is a compound of a formula (II):

[Formula 12]

[wherein G represents furan, thiophen, pyrrole, pyridine, benzofuran, benzothiophen, benzoxazole, benzothiazole, benzimidazole or indol ring;

the ring may be substituted with halogen, OH, COOH, $SO_3H$, $NO_2$, SH, $NR^fR^g$, $C_{1-6}$ alkyl, O—$C_{1-6}$ alkyl, CN or C=O;

$R_7$ represents hydrogen, halogen, OH, COOH, $SO_3H$, $NO_2$, SH, $NR^fR^g$, $C_{1-6}$ alkyl, O—$C_{1-6}$ alkyl, CN or C=O;

$R_8$ represents hydrogen, halogen, OH, COOH, $SO_3H$, $NO_2$, SH, $NR^fR^g$, $C_{1-6}$ alkyl, O—$C_{1-6}$ alkyl, CN, C=O, pyrrolidine ring, or

[Formula 13]

—N⟨ ⟩$Z^{II}$;

$R^f$ and $R^g$ each independently represent hydrogen or $C_{1-4}$ alkyl;

p indicates an integer of from 1 to 4;

$Z^{II}$ represents O, $CH_2$, N—$R^{e'}$;

$R^{e'}$ represents hydrogen or $C_{1-4}$ alkyl;

the alkyl may be substituted with halogen], or its salt or solvate.

Preferred substituents in the compounds of formula (II) are mentioned below.

Preferably, G is furan, thiophen, pyrrole, pyridine, benzofuran, benzothiophene or indole ring.

The ring may be substituted with $C_{1-6}$ alkyl or O—$C_{1-6}$ alkyl.

Preferably, $R_7$ is hydrogen.

Preferably, $R_8$ is hydrogen or $NR^fR^g$ or

[Formula 14]

—N⟨ ⟩$Z^{II}$

Preferably, $Z^{II}$ is O.

Preferably, $R^f$ and $R^g$ are independently hydrogen or methyl.

p is an integer of from 1 to 4.

The alkyl may be substituted with halogen.

Of the compounds of formula (II), those wherein $R_8$ is a morpholine ring are more preferred, as they have little or no mutagenicity. Such compounds of formula (II) include THK-383, THK-384, THK-385, THK-386 and THK-387. The compounds of formula (II) having high specificity to amyloid β are those such as THK-258, THK-262, THK-383, THK-385 and THK-386. Accordingly, the compounds of formula (II) having high specificity to amyloid β and having little or no mutagenicity are those such as THK-383, THK-385 and THK-386.

The third embodiment is a compound of a formula (III):

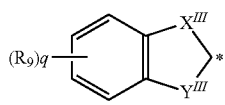

[Formula 15]

[wherein
$X^{III}$ and $Y^{III}$ each independently represent $CH_2$ or C=O;
$R^9$ represents hydrogen, halogen, OH, COOH, $SO_3H$, $NO_2$, SH, $NR^hR^i$, $C_{1-6}$ alkyl, O—$C_{1-6}$ alkyl, CN or C=O;
$R^h$ and $R^i$ each independently represent hydrogen or $C_{1-4}$ alkyl;
At *, the following part bonds to the formula:

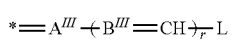

[Formula 16]

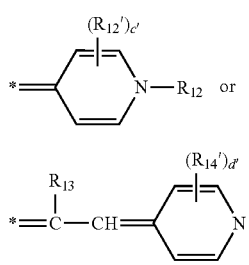

[Formula 17]

[Formula 18]

L represents

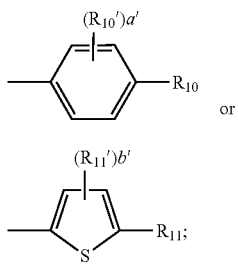

[Formula 19]

[Formula 20]

$A^{III}$ and $B^{III}$ each independently represent CH or N;
$R_{10}$, $R_{11}$, $R_{12}$ and $R_{14}$ each independently represent hydrogen, halogen, OH, COOH, $SO_3H$, $NO_2$, SH, $NR^jR^{ii}$, $C_{1-6}$ alkyl, O—$C_{1-6}$ alkyl, CN, C=O, pyrrolidine ring, or

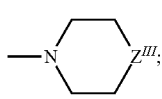

[Formula 21]

$R_{13}$ represents hydrogen, halogen or $C_{1-4}$ alkyl;
$R_{10}{}'$, $R_{11}{}'$, $R_{12}{}'$ and $R_{14}{}'$ each independently represent hydrogen, halogen or $C_{1-4}$ alkyl;

r indicates an integer of from 0 to 2;
a' indicates an integer of from 1 to 4;
b' indicates an integer of 1 or 2;
c' indicates an integer of from 1 to 4;
d' indicates an integer of from 1 to 4;
$Z^{III}$ represents O, $CH_2$ or N—$R^{e''}$;
$R^{e''}$ represents hydrogen or $C_{1-4}$ alkyl;
the alkyl may be substituted with halogen;
the configuration around the double bond that bonds two ring parts may be, if possible, any of cis-form or trans-form], or its salt or solvate.

Preferred substituents in the compounds of formula (III) are mentioned below.

Preferably, one or both of $X^{III}$ and $Y^{III}$ are C=O.
Preferably, $R^9$ is hydrogen.
At *, the following part bonds to the formula:

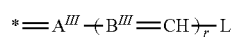

[Formula 22]

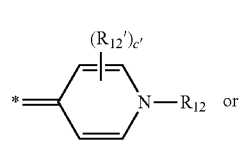

[Formula 23]

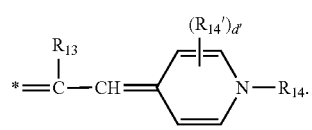

[Formula 24]

L is

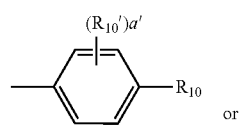

[Formula 25]

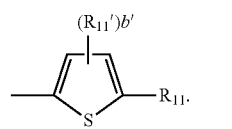

[Formula 26]

Preferably, $A^{III}$ and $B^{III}$ are CH.
Preferably, $R_{10}$, $R_{11}$, $R_{12}$ and $R_{14}$ are independently hydrogen, $C_{1-6}$ alkyl, or morpholine ring.
Preferably, $R_{13}$ is hydrogen or methyl.
Preferably, $R_{10}{}'$, $R_{11}{}'$, $R_{12}{}'$ and $R_{14}{}'$ are independently hydrogen or $C_{1-4}$ alkyl.
Preferably, r is an integer of 0 or 1.
When the substituent is not hydrogen, preferred a', b', c' and d' are independently an integer of 1 or 2.
The alkyl may be substituted with halogen.
If possible, the configuration around the double bond that bonds two ring parts may be any of cis-form or trans-form.

Of the compounds of formula (III), those wherein $R_{10}$, $R_{11}$, $R_{12}$ or $R_{14}$ is a morpholine are more preferred as they have little or no mutagenicity. The compounds of formula (III) having high specificity to amyloid β are those such as THK-184 and THK-248.

The fourth embodiment is a compound of a formula (IV):

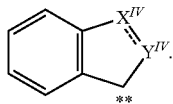

[Formula 27]

[wherein
$X^{IV}$ represents N or $NR^{IV}$;
$NR^{IV}$ represents hydrogen or $C_{1-4}$ alkyl;
$Y^{IV}$ represents CH or C=O;
the dotted line means an optionally-existing single bond;
at **, the following part bonds to the formula:

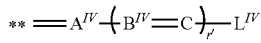

[Formula 28]

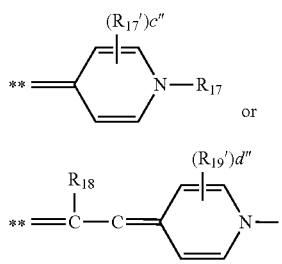

[Formula 29]

or

[Formula 30]

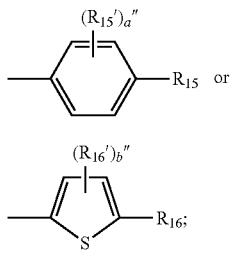

$L^{IV}$ represents

[Formula 31]

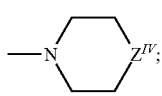

or

[Formula 32]

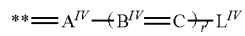

$A^{IV}$ and $B^{IV}$ each independently represent CH, CCH$_3$ or N;
$R_{15}$, $R_{16}$, $R_{17}$ and $R_{19}$ each independently represent hydrogen, halogen, OH, COOH, SO$_3$H, NO$_2$, SH, $NR^jR^k$, $C_{1-6}$ alkyl, O—CO$_{1-6}$ alkyl, CN, C=O, pyrrolidine ring or

[Formula 33]

—N⟨  ⟩$Z^{IV}$;

$R^j$ and $R^k$ each independently represent hydrogen or $C_{1-4}$ alkyl;
$R_{18}$ represents hydrogen, halogen or $C_{1-4}$ alkyl;
$R_{15}'$, $R_{16}'$, $R_{17}'$ and $R_{19}'$ each independently represent hydrogen, halogen or $C_{1-4}$ alkyl;
r' indicates an integer of from 0 to 2;
a" Indicates an integer of from 1 to 4;
b" indicates an integer of 1 or 2;
c" indicates an integer of from 1 to 4;
d" indicates an integer of from 1 to 4;
$Z^{IV}$ represents O, CH$_2$ or N—$R^{e'''}$;
$R^{e'''}$ represents hydrogen or $C_{1-4}$ alkyl;
the alkyl may be substituted with halogen;
the configuration around the double bond that bonds two ring parts may be, if possible, any of cis-form or trans-form], or its salt or solvate.

Preferred substituents in the compounds of formula (IV) are mentioned below.
Preferably, $X^{IV}$ is N, NH or NCH$_3$.
Preferably, $Y^{IV}$ is CH or C=O.
The dotted line means an optionally-existing single bond.
At **, the following part bonds to the formula:

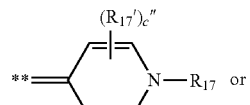

[Formula 34]

[Formula 35]

or

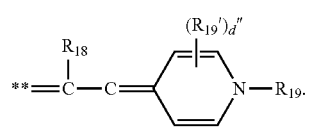

[Formula 36]

$L^{IV}$ is

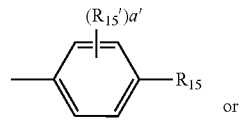

[Formula 37]

or

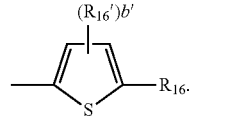

[Formula 38]

Preferably, $A^{IV}$ and $B^{IV}$ are independently CH or N.
$R_{15}$, $R_{16}$, $R_{17}$ and $R_{19}$ each are hydrogen, NH$_2$, N(CH$_3$)$_2$ or morpholine ring.
Preferably, $R_{18}$ is hydrogen.
Preferably, $R_{15}'$, $R_{16}'$, $R_{17}'$ and $R_{19}'$ each are hydrogen or $C_{1-4}$ alkali.
Preferably, r' is 1.
a" is an integer of from 1 to 4.
b" is an integer of 1 or 2.
c" is an integer of from 1 to 4.
d" is an integer of from 1 to 4.
$Z^{IV}$ is O, CH$_2$ or N—$R^{e'''}$.
$R^{e'''}$ is hydrogen or $C_{1-4}$ alkyl.
The above alkyl may be substituted with halogen.
If possible, the configuration around the double bond that bonds two ring parts may be any of cis-form or trans-form.
Of the compounds of formula (IV), those wherein $R_{15}$, $R_{16}$, $R_{17}$ or $R_{19}$ is a morpholine ring are more preferred as they have little or no mutagenicity. Such compounds of formula (IV) are those such as THK-276, THK-277 and THK-308. The compounds of formula (IV) having high specificity to amyloid β are those such as THK-185, THK-254, THK-276 and THK-308. Accordingly, the compounds of formula (IV)

having high specificity to amyloid β and having little or no mutagenicity are those such as THK-276 and THK-308.

The fifth embodiment is a compound of a formula (V):

[Formula 39]

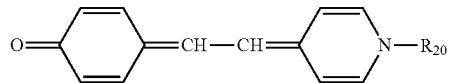

[wherein $R_{20}$ represents hydrogen, $C_{1-4}$ alkyl, pyrrolidine ring or

[Formula 40]

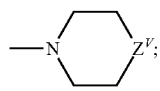

$Z^V$ represents O, $CH_2$ or N—$R^{eV}$;
$R^{eV}$ represents hydrogen or $C_{1-4}$ alkyl], or its salt or solvate.

Preferred substituents of the compounds of formula (V) are mentioned below.

Preferably, $R_{20}$ is hydrogen, methyl or morpholine ring. The compounds where $R_{20}$ is a morpholine ring are more preferred, as having little or no mutagenicity. The compounds of formula (V) having high specificity to amyloid β are THK-317, etc.

The sixth embodiment is a compound of a formula (VI):

[Formula 41]

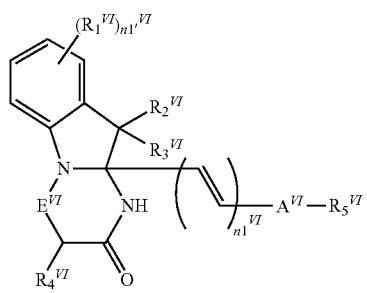

[wherein
$R_1^{VI}$ represents hydrogen, $C_{1-6}$ alkyl, halogen or $C_{1-6}$ alkyl-halogen;
$R_2^{VI}$ and $R_3^{VI}$ each independently represent hydrogen or $C_{1-6}$ alkyl;
$R_4^{VI}$ represents hydrogen or $C_{1-6}$ alkyl;
$E^{VI}$ represents $CH_2$, or is absent;
$A^{VI}$ represents a 5-membered or 6-membered ring, having the following structure:

[Formula 42]

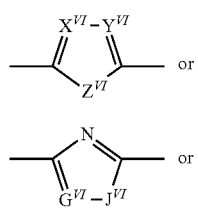
or

[Formual 43]

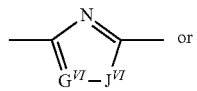
or

[Formula 44]

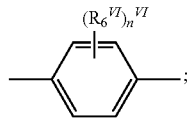
;

$X^{VI}$ and $Y^{VI}$ each independently represent N or CH;
$Z^{VI}$ represents O, S, $CH_2$ or N—$C_pH_{2p+1}$;
$G^{VI}$ represents N or CH;
$J^{VI}$ represents O, S, $CH_2$ or N—$C_qH_{2q+1}$;
$R_5^{VI}$ represents hydrogen, $C_{1-6}$ alkyl, pyrrole, pyrazole, imidazole, triazole or $NR_I^{VI}R_{II}^{VI}$;
$R_6^{VI}$ represents hydrogen, $C_{1-6}$ alkyl or halogen;
$R_I^{VI}$ and $R_{II}^{VI}$ each independently represent hydrogen or $C_{1-6}$ alkyl, or taken together, they form a pyrrolidine ring, a morpholine ring, a piperidine ring, or a piperazine ring in which the hydrogen atom may be substituted with $C_{1-3}$ alkyl;
$n_1^{VI}$ indicates an integer of from 1 to 4;
$n_{1'}^{VI}$ indicates an integer of from 1 to 4;
$n^{VI}$ indicates an integer of from 1 to 4;
$p^{VI}$ indicates an integer of from 1 to 4;
$q^{VI}$ indicates an integer of from 1 to 4; in the above formula, the configuration around the double bond that bonds two ring parts is a trans-form, but this configuration may be any of cis-form or trans-form], or its salt or solvate.

Preferred substituents of the compounds of formula (VI) are mentioned below.

Preferably, $R_1^{VI}$ is hydrogen, $C_{1-3}$ alkyl, fluorine, chlorine or bromine.
Preferably, $R_2^{IV}$ and $R_3^{VI}$ are methyl.
Preferably, $R_4^{IV}$ is hydrogen.
Preferably, $E^{VI}$ is $CH_2$ or is absent.

$A^{VI}$ is a 5-membered or 6-membered ring, having the following structure:

[Formula 45]

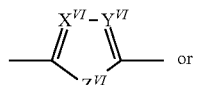
or

[Formula 46]

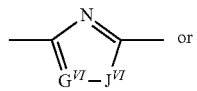
or

[Formula 47]

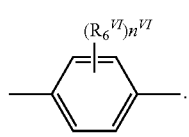
.

$X^{VI}$ and $Y^{VI}$ are independently N or CH.
Preferably, $Z^{VI}$ is S.
$G^{VI}$ is N or CH.
Preferably, $J^{VI}$ is O, S or $CH_2$.
Preferably, $R_5^{VI}$ is hydrogen, $N(CH_3)_2$ or morpholine ring.
Preferably, all $R_6^{VI}$'s are hydrogen.
Preferably, $n_6^{VI}$ is an integer of 1 or 2.

The configuration around the double bond that bonds two ring parts may be any of cis-form or trans-form.

Of the compounds of formula (VI), those wherein $R_5^{VI}$ is a morpholine ring are more preferred, as having little or no mutagenicity. Such compounds of formula (VI) include THK-330, THK-336, THK-533, THK-651, THK-652, THK-653 and THK-655. The compounds of formula (VI) having high specificity to amyloid β are those such as THK-556, THK-558, THK-559, THK-561, THK-562, THK-563, THK-565 and THK-585.

Examples of the compounds of formula (I) and (I') are shown in the following table.

TABLE 1-1

| | Structure | |
|---|---|---|
| THK-525 | 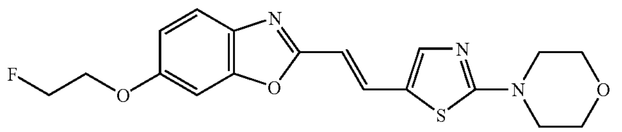 | 6-(2-fluoro-ethoxy)-2-[2-(2-morpholin-4-yl-thiazol-5-yl)-vinyl]-benzoxazole |
| THK-727 | 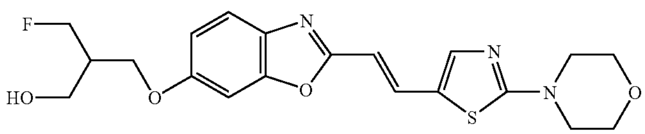 | 2-fluoromethyl-3-[2-[2-(2-morpholin-4-yl-thiazol-5-yl)-vinyl]-benzoxazol-6-yloxy]-propan-1-ol |
| THK-702 | 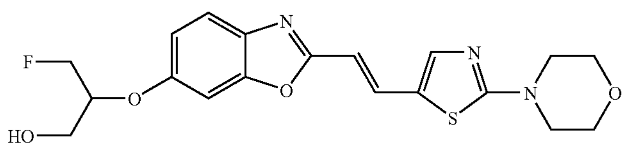 | (E)-2-[2-(2-morpholinothiazol-5-yl)ethenyl]-6-[(1-fluoromethyl-2-hydroxy)ethoxy]-benzoxazole |

TABLE 1-2

| | Structure | |
|---|---|---|
| THK-763 | 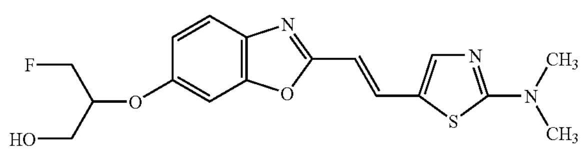 | (E)-6-[(1-fluoromethyl-2-hydroxy)ethoxy]-2-[2-[2-dimethylamino-thiazol-5-yl]ethenyl]benzoxazole |
| THK-761 | 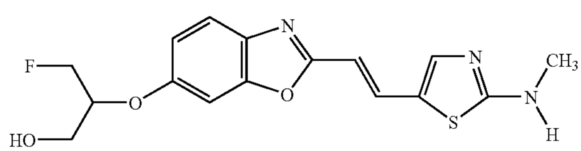 | (E)-6-[(1-fluoromethyl-2-hydroxy)ethoxy]-2-[2-[2-methylaminothiazol-5-yl]ethenyl]-benzoxazole |
| THK-711 | 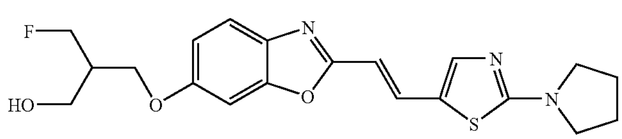 | (E)-6-[(2-fluoromethyl-3-hydroxy)propoxy]-2-[2-(2-piperidinothiazol-5-yl)ethenyl]-benzoxazole |
| THK-713 | 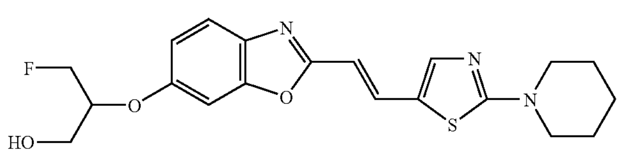 | (E)-6-[(1-fluoromethyl-2-hydroxy)ethoxy]-2-[2-(2-piperidinoxazol-5-yl)ethenyl]-benzoxazole |
| THK-707 | 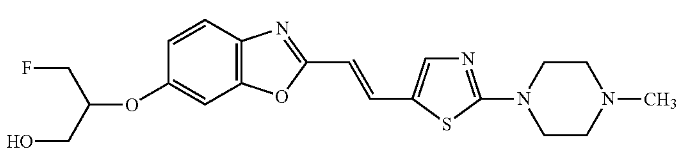 | (E)-6-[(1-fluoromethyl-2-hydroxy)ethoxy]-2-[2-[2-(4-methylpiperazin-1-yl)thiazol-5-yl]ethenyl]benzoxazole |

TABLE 1-3

| | Structure | |
|---|---|---|
| THK-708 | 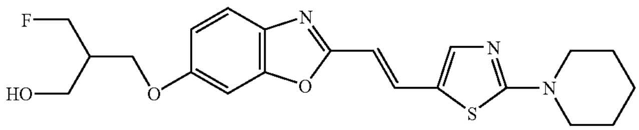 | (E)-6-[(2-fluoromethyl-3-hydroxy)propoxy]-2-[2-[2-(pyrrolidin-1-yl)thiazol-5-yl]ethenyl]-benzoxazole |
| THK-752 | 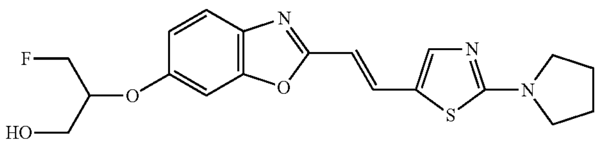 | (E)-6-[(1-fluoromethyl-2-hydroxy)ethoxy]-2-[2-[2-(pyrrolidin-1-yl)-thiazol-5-yl]ethenyl]benzoxazole |
| THK-757 | 0.1H$_2$O | (E)-6-[(1-fluoromethyl-2-hydroxy)ethoxy]-2-[2-[2-([1,3]oxadinan-3-yl)-thiazol-5-yl]ethenyl]benzoxazole |
| THK-765 | 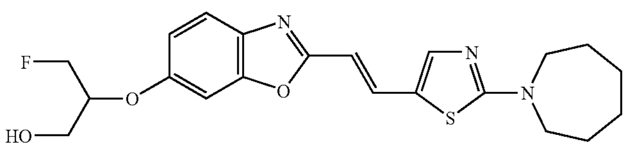 | (E)-6-[(1-fluoromethyl-2-hydroxy)ethoxy]-2-[2-[2-(homopiperidin-1-yl)thiazol-5-yl]ethenyl]benzoxazole |
| THK-766 | 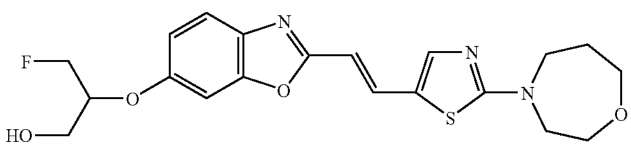 | (E)-6-[(1-fluoromethyl-2-hydroxy)ethoxy]-2-[2-[2-homomorpholinothiazol-5-yl)ethenyl]benzoxazole |

TABLE 1-4

| | Structure | |
|---|---|---|
| THK-767 | 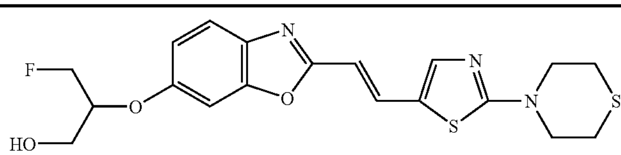 | (E)-6-[(1-fluoromethyl-2-hydroxy)ethoxy]-2-[2-(2-thiomorpholinothiazol-5-yl)ethenyl]benzoxazole |

TABLE 1-5

| | Structure | |
|---|---|---|
| THK-575 | 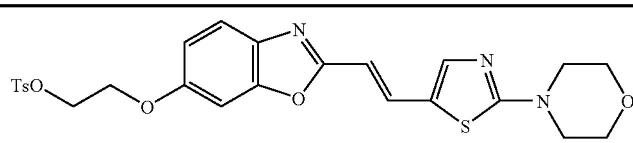 | Toluene-4-sulfonic acid 2-[2-[2-(2-morpholin-4-yl-thiazol-5-yl)-vinyl-benzoxazol-6-yloxy]-ethyl toluene-4-sulfonate |
| THK-726 | •0.15AcOEt | (E)-6-[(3-hydroxy-2-tosyloxymethyl)propoxy]-2-[2-(2-morpholinothiazol-5-yl)ethenyl]-benzoxazole |

TABLE 1-5-continued

| | Structure | |
|---|---|---|
| THK-703 | 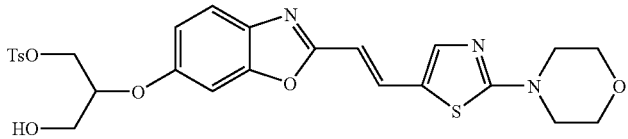 ·0.14AcOEt | (E)-6-[(2-hydroxy-1-tosyloxymethyl)-ethoxy]-2-[2-(2-morpholinothiazol-5-yl)-ethenyl]-benzoxazole |
| THK-762 | 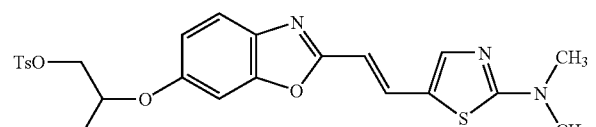 | (E)-6-[(2-hydroxy-1-tolyloxymethyl)ethoxy]-2-[2-[2-dimethylamino-thiazol-5-yl]ethenyl]benzoxazole |

TABLE 1-6

| | Structure | |
|---|---|---|
| THK-760 | 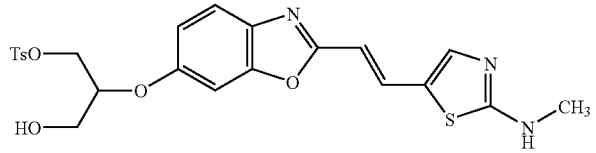 | (E)-6-[(2-hydroxy-1-tosyloxymethyl)ethoxy]-2-[2-[2-methylaminothiazol-5-yl]ethenyl]benzoxazole |
| THK-710 | 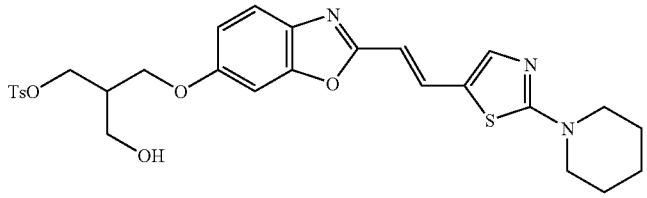 | (E)-6-[(3-hydroxy-2-tosyloxymethyl)propoxy]-2-[2-(2-piperidinothiazole-5-yl)ethenyl]benzoxazole |
| THK-712 | 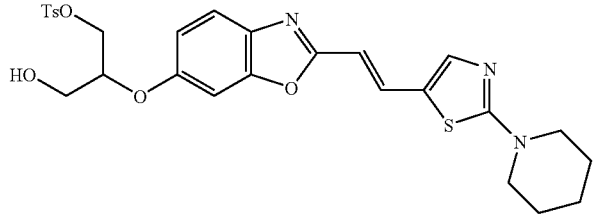 | (E)-6-[(2-hydroxy-1-tosyloxymethyl)ethoxy]-2-[2-(2-piperidinothiazole-5-yl)ethenyl]benzoxazole |
| THK-751 | 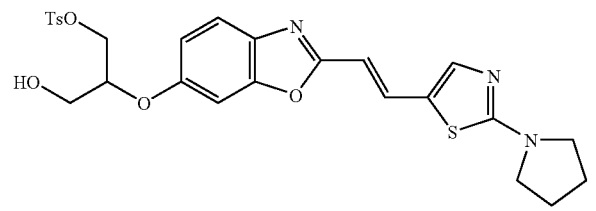 | (E)-6-[(1-hydroxymethyl-2-tosyloxy)ethoxy]-2-[2-[2-(pyrrolidin-1-yl)-thiazole-5-yl]ethenyl]benzoxazole |

TABLE 1-7

| | Structure | |
|---|---|---|
| THK-683 | 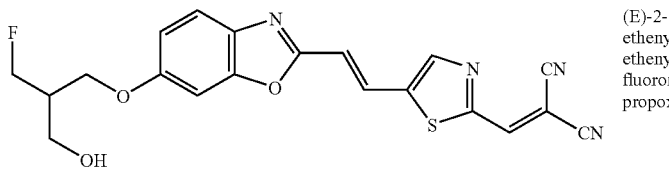 | (E)-2-[2-(2,2-dicyano-ethenylthiazol-5-yl)ethenyl]-6-[(2-fluoromethyl-3-hydoxy)propoxy]benzoxazole |

TABLE 1-7-continued

| | Structure | |
|---|---|---|
| THK-774 | 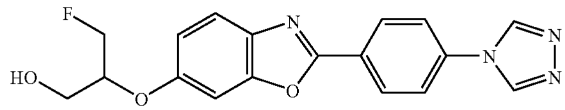 | (E)-6-[(1-fluoromethyl-2-hydroxy)ethoxy]-2-[4-(1,2,4-triazol-4-yl)phenyl]benzoxazole |
| THK-775 | 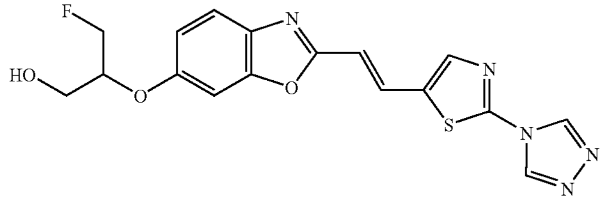 | (E)-6-[(1-fluoromethyl-2-hydroxy)ethoxy]-2-[2-[2-(1,2,4-triazole-4-yl)-thiazole-5-yl)ethenyl]benzoxazole |

Examples of the compounds of formula (II) are shown in the following table.

TABLE 1-8

| | Structure | |
|---|---|---|
| THK-255 | 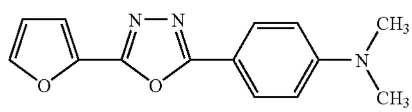 | [4-(5-furan-2-yl-[1,3,4]oxadiazol-2-yl)-phenyl]-dimethyl-amine |
| THK-256 | 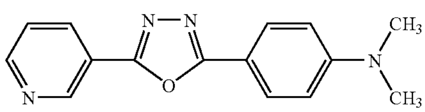 | dimethyl-[4-(5-pyridin-3-yl-[1,3,4]oxadiazol-2-yl)-phenyl]-amine |
| THK-257 | 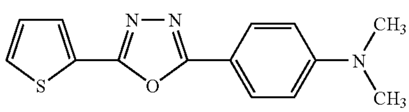 | dimethyl-[4-(5-thiophen-2-yl-[1,3,4]oxadiazol-2-yl)-phenyl]-amine |
| THK-258 | 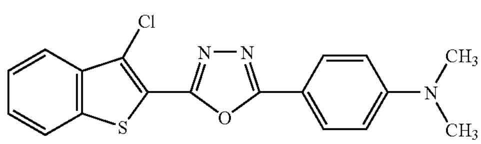 | [4-[5-(3-chloro-benzo[b]thiophen-2-yl)-[1,3,4]oxadiazol-2-yl]-phenyl]-dimethylamine |
| THK-262 | 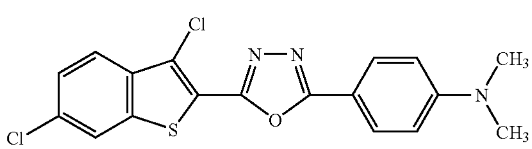 | [4-[5-(3,6-dichloro-benzo[b]thiophen-2-yl)-[1,3,4]oxadiazol-2-yl]-phenyl]-dimethylamine |
| THK-383 | 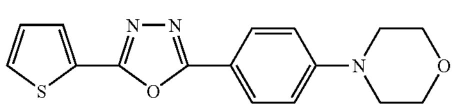 | 4-[4-(5-thiophen-2-yl-[1,3,4]oxadiazol-2-yl)-phenyl]-morpholine |
| THK-384 | 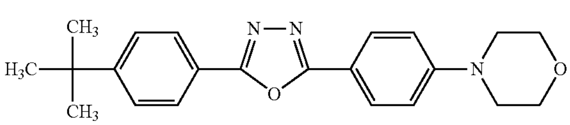 | 4-[4-[5-(4-tert-butyl-phenyl)-[1,3,4]oxadiazol-2-yl]-phenyl]-morpholine |
| THK-385 | 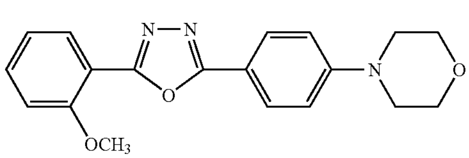 | 4-[4-(5-o-tolyl-[1,3,4]oxazin-2-yl)-phenyl]-morpholine |

TABLE 1-8-continued

| | Structure | |
|---|---|---|
| THK-386 | 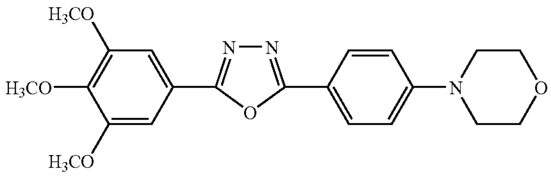 | 4-{4-[5-(3,4,5-trimethyl-phenyl)-[1,3,4]oxadiazol-2-yl]-phenyl}morpholine |
| THK-387 | 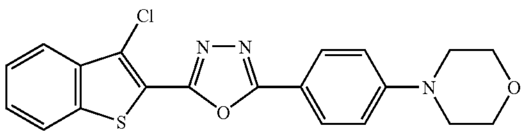 | 4-[4-[5-(3-chloro-benzo[b]thiophen-2-yl)-[1,3,4]oxadiazol-2-yl]-phenyl]-morpholine |

Examples of the compounds of formula (III) are shown in the following table.

TABLE 1-9

| | Structure | |
|---|---|---|
| THK-156 | 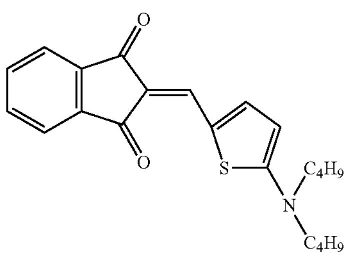 | 2-(5-dibutylamino-thiophen-2-ylmethylene)-indane-1,3-dione |
| THK-184 | 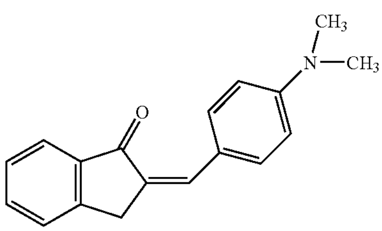 | 2-(4-dibutylamino-benzylidene)-indan-1-one |
| THK-248 | 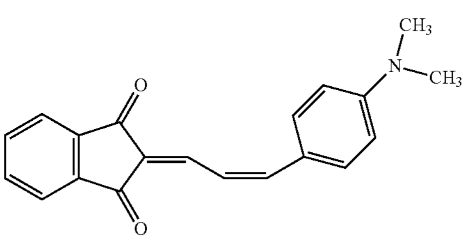 | 2-[3-(4-dimethylamino-phenyl)-allylidene]-indane-1,3-dione |
| THK-253 | 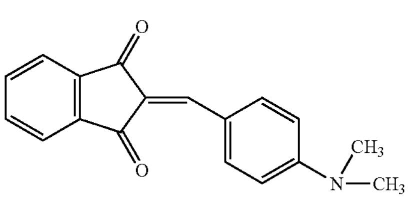 | 2-(4-dimethylamino-benzylidene)-indane-1,3-dione |

TABLE 1-9-continued

| | Structure | |
|---|---|---|
| THK-287 | 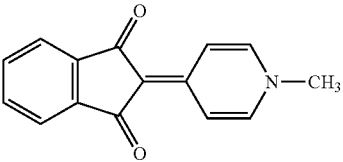 | 2-(1-methyl-1H-pyridin-4-ylidene)-indane-1,3-dione |
| THK-532 | 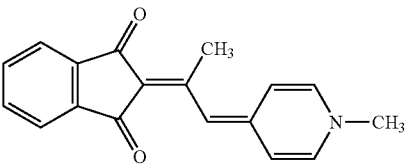 | 2-[1-methyl-2-(1-methyl-1H-pyridin-4-ylidene)-ethylidene]-indane-1,3-dione |

Examples of the compounds of formula (IV) are shown in the following table.

TABLE 1-10

| | Structure | |
|---|---|---|
| THK-185 | 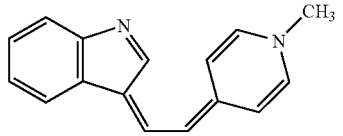 | 3-[2-(1-methyl-1H-pyridin-4-ylidene)-ethylidene]-3H-indole |
| THK-186 | 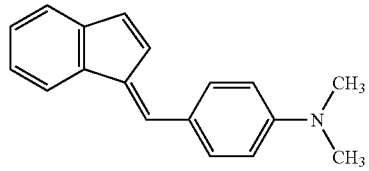 | (4-indene-1-ylidenemethyl-phenyl)-dimethyl-amine |
| THK-209 | 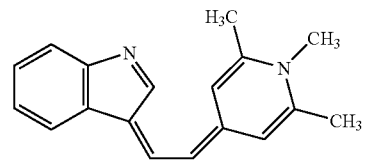 | 3-[2-(1,2,6-trimethyl-1H-pyridin-4-ylidene)-ethylidene]-3H-indole |
| THK-254 | 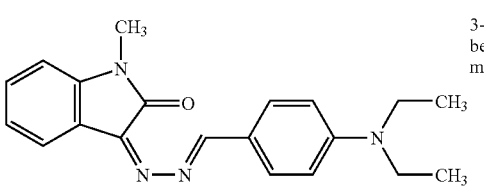 | 3-[(4-dimethylamino-benzylidene)-hydrazono]-1-methyl-1,3-dihydroindol-2-one |
| THK-276 | 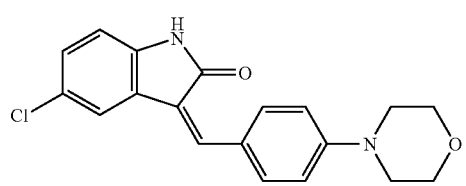 | 5-chloro-3-(4-morpholin-4-yl-benzylidene)-1,3-dihydroindol-2-one |
| THK-277 | 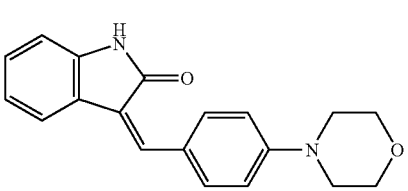 | 3-(4-morpholin-4-yl-benzylidene)-1,3-dihydroindol-2-one |

TABLE 1-10-continued

| | Structure | |
|---|---|---|
| THK-308 | 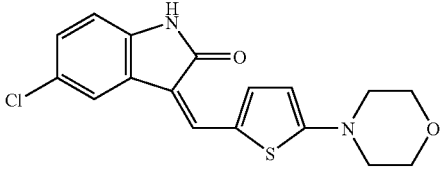 | 5-chloro-3-(5-morpholin-4-yl-thiophen-2-ylmethylene)-1,3-dihydroindol-2-one |

Example of the compounds of formula (V) are shown in the following table.

TABLE 1-11

| | Structure | |
|---|---|---|
| THK-317 | 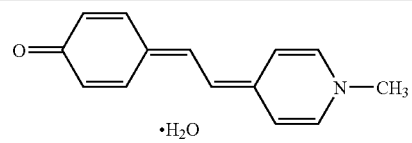 | 4-[2-(1-methyl-1H-pyridin-4-ylidene)-ethylidene]-cyclohexa-2,5-dienone |

Examples of the compounds of formula (VI) are shown in the following table.

TABLE 1-12

| | Structure | |
|---|---|---|
| THK-330 | 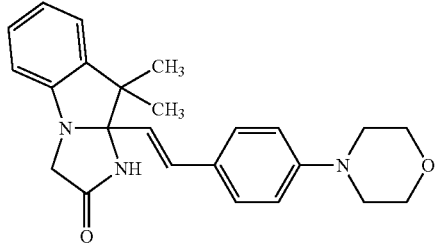 | 9,9-dimethyl-9a-[2-(4-morpholin-4-yl-phenyl)-vinyl-9,9a-dihydro-1H-imidazol[1,2-a]indol-2-one |
| THK-336 | 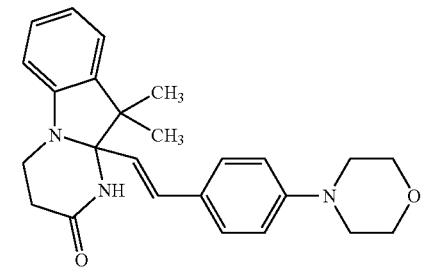 | 10,10-dimethyl-10a-2-(4-morpholin-4-yl-phenyl)-vinyl]-3,4,10,10a-tetrahydro-1H-pyrimidol[1,2-a]indol-2-one |
| THK-533 | 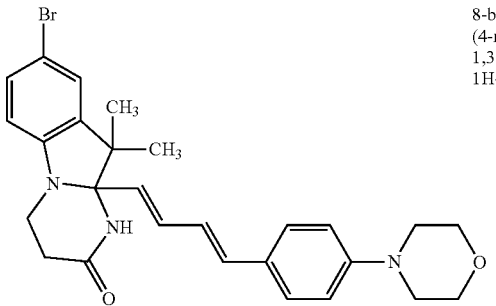 | 8-bromo-10,10-dimethyl-10a-[4-(4-morpholin-4-yl-phenyl)-buta-1,3-dienyl]-3,4,10,10a-tetrahydro-1H-pyrimido[1,2-a]indol-2-one |

TABLE 1-12-continued

| | Structure | |
|---|---|---|
| THK-556 | 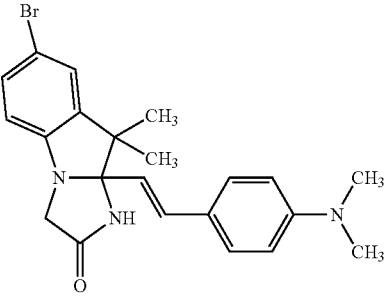 | 7-bromo-9a-[2-(4-dimethyl-amino-phenyl)-vinyl]-9,9-dimethyl-9,9a-dihydro-1H-imidazo[1,2-a]indol-2-one |
| THK-558 | 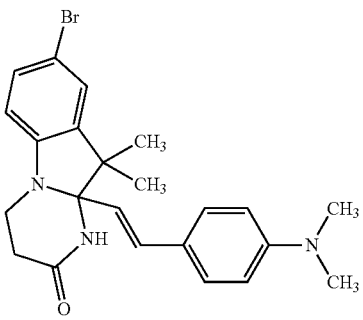 | 8-bromo-10a-[2-(4-dimethyl-amino-phenyl)-vinyl]-10,10-dimethyl 1-3,4,10,10a-tetrahydro-1H-pyrimido[1,2-a]indol-2-one |

Among the compounds of the present invention, pharmaceutically acceptable salts, solvates thereof, the compounds expressed by formula (I) or pharmaceutically acceptable salts or solvates thereof is preferable.

Additionally, compounds expressed by the formula (I') that is the precursor of the compound of the formula (I), pharmaceutically acceptable salts or solvates thereof is also preferable.

Accordingly, the invention provides the following:

(1) A compound represented by formula (I), pharmaceutically acceptable salt or solvate thereof:

(2) The compound, pharmaceutically acceptable salt or solvate thereof according to (1), wherein $X_1$ is an oxygen atom.

(3) The compound, pharmaceutically acceptable salt or solvate thereof according to (1), wherein $X_1$ is an oxygen atom, and X2 is a sulfur atom.

(4) The compound, pharmaceutically acceptable salt or solvate thereof according to (1), wherein $R^3$ is —O— lower alkyl group substituted with hydroxy group and halogen atom.

(5) The compound, pharmaceutically acceptable salt or solvate thereof according to (1), wherein the group in formula (I) represented by:

[Formula 48]

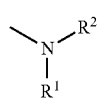

[wherein each variable has the foregoing meaning] is a morpholino group or dimethylamino group.

(6) The compound, pharmaceutically acceptable salt or solvate thereof according to (1), wherein $R^3$ is a group represented by:

[Formula 49]

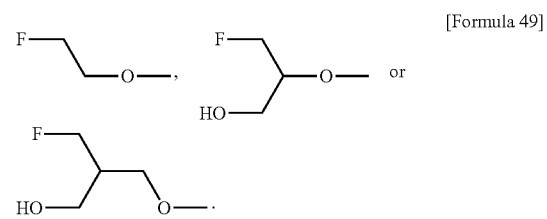

(7) The compound, pharmaceutically acceptable salt or solvate thereof according to (1), wherein the compound represented by formula (I) is selected from the group consisting of:

6-(2-fluoro-etoxy)-2-[2-(2-morpholin-4-yl-thiazole-5-yl)-vinyl]benzoxazol;

toluene-4-sulfonic acid 2-[2-[2-(2-morpholin-4-yl-thiazole-5-yl)-vinyl-benzoxazol-6-yloxy]ethyl ester;

2-fluoromethyl-3-[2-[2-(2-morpholin-4-yl-thiazole-5-yl)-vinyl]benzoxazol-6-yloxy]-propane-1-ole;

(E)-2-[2-(2-morpholinothiazole-5-yl)ethenyl]-6-[(1-fluoromethyl-2-hydroxy)ethoxy]benzoxazol;

(E)-6-[(1-fluoromethyl-2-hydroxy)ethoxy]-2-[2-[2-methylaminothiazole-5-yl]ethenyl]benzoxazol;

(E)-6-[(1-fluoromethyl-2-hydroxy)ethoxy]-2-[2-[2-dimethylamino-thiazole-5-yl]ethenyl]benzoxazol;

(E)-6-[(2-fluoromethyl-3-hydroxy)propoxy]-2-[2-(2-piperidinothiazole-5-yl]ethenyl]benzoxazol;

(E)-6-[(1-fluoromethyl-2-hydroxy)ethoxy]-2-[2-(2-piperidinothiazole-5-yl)ethenyl]benzoxazol;

(E)-6-[(1-fluoromethyl-2-hydroxy)ethoxy]-2-[2-(4-methylpiperidine-1-yl)thiazole-5-yl)ethenyl]benzoxazol;

(E)-6-[(2-fluoromethyl-3-hydroxy)propoxy]-2-[2-[2-(pyrrolidine-1-yl]thiazole-5-yl)ethenyl]]benzoxazol;

(E)-6-[(1-fluoromethyl-2-hydroxy)ethoxy]-2-[2-[2-(pyrrolidine-1-yl)-thiazole-5-yl]ethenyl]benzoxazol;

(E)-6-[(1-fluoromethyl-2-hydroxy)ethoxy]-2-[2-[2-([1,3]
oxazine-3-yl)-thiazole-5-yl)ethenyl]benzoxazol;
(E)-6-[(1-fluoromethyl-2-hydroxy)ethoxy]-2-[2-[2-homopi-
peridine-1-yl)-thiazole-5-yl)ethenyl]benzoxazol;
(E)-6-[(1-fluoromethyl-2-hydroxy)ethoxy]-2-[2-(2-homo-
morpholinothiazole-5-yl)ethenyl]benzoxazol; and
(E)-6-[(1-fluoromethyl-2-hydroxy)ethoxy]-2-[2-(2-thio-
morpholinothiazole-5-yl)ethenyl]benzoxazol.

(8) The compound, pharmaceutically acceptable salt or solvate thereof according to any one of (1) to (7), which is labeled.

(9) The compound, pharmaceutically acceptable salt or solvate thereof according to (8), which is labeled with a radionuclide.

(10) The compound, pharmaceutically acceptable salt or solvate thereof according to (9), wherein the radionuclide is a gamma-ray emitting radionuclide.

(11) The compound, pharmaceutically acceptable salt or solvate thereof according to (8), wherein the label is a positron emitter.

(12) The compound, pharmaceutically acceptable salt or solvate thereof according to (11), wherein the positron emitter is selected from the group consisting of $^{11}C$, $^{13}N$, $^{15}O$, $^{18}F$, $^{35m}Cl$, $^{76}Br$, $^{45}Ti$, $^{48}V$, $^{60}Cu$, $^{61}Cu$, $^{62}Cu$, $^{66}Ga$, $^{89}Zr$, $^{94m}Tc$ and $^{124}I$.

(13) The compound, pharmaceutically acceptable salt or solvate thereof according to (11), wherein the positron emitter is $^{11}C$ or $^{18}F$.

(14) A pharmaceutical composition containing the compound, pharmaceutically acceptable salt or solvate thereof according to any one of claims (1) to (13).

(15) A pharmaceutical composition containing the compound, pharmaceutically acceptable salt or solvate thereof according to any one of claims (1) to (13) and a solubilizing agent.

(16) The pharmaceutical composition according to claim (15) wherein the solubilizing agent is selected from the group consisting of polysolvate 80, polyethylene glycol, ethanol, and propylene glycol.

(17) The pharmaceutical composition according to any one of (14) to (16), wherein the pharmaceutical composition is an injection drug.

(18) A composition for diagnosis of conformation diseases containing the compound, pharmaceutically acceptable salt or solvate thereof according to any one of (1) to (13).

(19) A pharmaceutical composition to treat and/or prevent conformation diseases containing the compound, pharmaceutically acceptable salt or solvate thereof according to any one of (1) to (13).

(20) A kit for diagnosis of conformation diseases, containing the compound, pharmaceutically acceptable salt or solvate thereof according to any one of (1) to (13) as a essential component.

(21) A composition or kit for detecting or staining proteins with beta sheet structure or neurofibrillary tangle, containing the compound, pharmaceutically acceptable salt or solvate thereof according to any one or (1) to (13) as a essential component.

(22) The kit according to (20) or (21), wherein the kit is intended for diagnostic imaging.

(23) A method for treatment and/or prevention of a conformation disease in a subject, which comprises administering the compound, pharmaceutically acceptable salt or solvate thereof according to any one of (1) to (13) to the subject.

(24) A method for diagnosis of a conformation disease in a subject, which comprises administering the compound, pharmaceutically acceptable salt or solvate thereof according to any one of (1) to (13) to the subject.

(25) A use of the compound, pharmaceutically acceptable salt or solvate thereof according to any one of (1) to (13) for producing a composition or kit for aid of diagnosis of a conformation disease in a subject.

(26) A use of the compound, pharmaceutically acceptable salt or solvate thereof according to any one of (1) to (13) for producing a pharmaceutical composition for treatment and/or prevention of a conformation disease in a subject.

(27) A method of detecting or staining proteins with beta sheet structure in a sample or neurofibrillary tangle, which comprises using the compound, pharmaceutically acceptable salt or solvate thereof according to any one of (1) to (13) to stain the sample.

(28) A use of the compound, pharmaceutically acceptable salt or solvate thereof according to any one of (1) to (13) for producing a composition or a kit for detecting or staining a protein with beta sheet structure in a sample or neurofibrillary tangle.

(29) The composition or the kit according to (21), the method according to (27), or the use of (28) wherein the compound is 6-(2-fluoro-etoxy)-2-[2-(2-morpholin-4-yl-thiazole-5-yl)-vinyl]benzoxazol; 2-fluoromethyl-3-[2-[2-(2-morpholin-4-yl-thiazole-5-yl)-vinyl]benzoxazol-6-yloxy]-propane-1-ole; (E)-2-[2-(2-morpholinothiazole-5-yl) ethenyl]-6-[(1-fluoromethyl-2-hydroxy)ethoxy]benzoxazol; or (E)-6-[(1-fluoromethyl-2-hydroxy)ethoxy]-2-[2-[2-dimethylamino-thiazole-5-yl]ethenyl]benzoxazol.

(30) A compound, pharmaceutically acceptable salt or solvate thereof represented by formula (I')

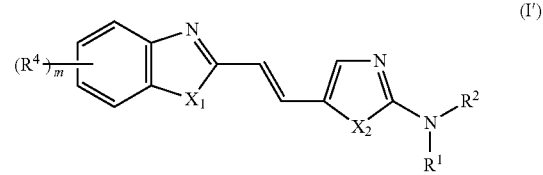

[wherein $R^1$ and $R^2$ are independently hydrogen atom, lower alkyl group respectively, or cycloalkyl group, or 3- to 8-membered nitrogen-containing aliphatic ring formed by $R^1$, $R^2$ and a nitrogen atom bonded thereto, together (carbon atoms which constitute the nitrogen-containing aliphatic ring may be substituted with nitrogen atom, sulfur atom or oxygen atom, and when the carbon atom is substituted nitrogen atom, the nitrogen atom may be substituted with lower alkyl group), $X_1$ and $X_2$ are each independently nitrogen atom, sulfur atom, or oxygen atom, $R^4$ is —O— lower alkyl group (the alkyl group may be substituted with tosyl group, and furthermore may be substituted with hydroxy group), and m is an integer of 1 to 3]

provided that the compounds are excluded wherein $R^3$ is a —O— lower alkyl group substituted with only halogen atom, and $R^1$ and $R^2$ are each independently denotes hydrogen atom or lower alkyl group.

(31) The compound according to (30), wherein $R^4$ is a group represented by:

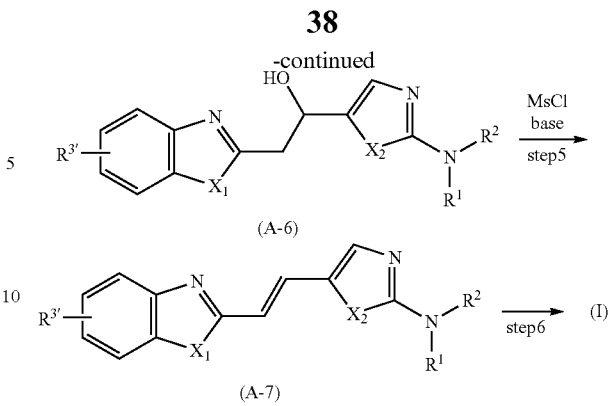

[wherein, X represents a halogen atom, and R a dimethylamino group a morpholino group, or the like. $R^{3'}$ means $R^3$, or if $R^3$ has a hydroxy group, it means $R^3$ where the hydroxy group is protected. Ms represents a mesyl (methanesulfonyl) group, and other variable means the same as described above]

(Step 1)

The present step is the method to produce the compound (A-2) by reacting the compound (A-1) with an amino compound (B-1).

As X in (A-1), a bromine atom is preferable.

The amount of compound (B-1) to be used is generally 1 equivalent to solvent amount relative to the compound (A-1).

The reaction time in the present step is generally 1 to 24 hours, and preferably 1 to 10 hours.

The reaction temperature in the present step is generally 50 to 200° C. and preferably 80 to 150° C.

Reaction solvents in the present step include a solvent amount of (B-1), dimethylformamide or the like.

The compound (A-2) thus obtained can be adopted to the next step with isolation and purification by well-known separation and purification means such as concentration, vacuum concentration, crystallization, solvent extraction, reprecipitation, or chromatography, or without isolation and purification.

As the compound (A-2), the publicly known compound can be used, or it is possible to synthesize by the method ordinarily employed in the field of organic chemistry, or the method pursuant thereto using the publicly known compound as the material.

(Step 2)

The present step is the method to produce the compound (A-3) by reacting the compound (A-2) with the compound (B-2) in the presence of base.

The bases to be used include, for example, sodium hydroxide, butyllithium, lithium di-isopropylamide (LDA), and the like. Among these, lithium di-isopropylamide is preferable. Lithium di-isopropylamide can be used by preparing from butyllithium and di-isopropylamine as necessary.

The amount of base to be used is generally 0.5 to 10 equivalents, preferably 1 to 3 equivalents relative to the compound (A-2).

Reaction temperature is generally −78 to 50° C., preferably −78° C. to room temperature.

Reaction time is generally 0.1 to 24 hours, preferably 0.1 to 6 hours.

Any reaction solvents which do not inhibit the reaction, without any limitation, can include, for example, N,N-dimethylformamide (DMF), tetrahydrofuran (THF), 1-methylimidazolidinone, and the like.

The compound (A-3) thus obtained can be isolated and purified by the known separation and purification means such

[Formula 50]

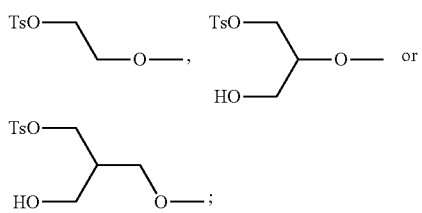

(32) The compound according to (30), wherein the compound represented by formula (I') is toluene-4-sulfonic acid 2-[2-[2-(2-morpholin-4-yl-thiazole-5-yl)-vinyl-benzoxazol-6-yloxy-3-ethyl ester;

(E)-6-[(3-hydroxy-2-tosyloxymethyl)propoxy]-2-[2-(2-morpholinothiazole-5-yl)ethenyl]benzoxazol;

(E)-6-[2-hydroxy-1-tosyloxymethyl)ethoxy]-2-[2-[2-dimethylamino-thiazole-5-yl]ethenyl]benzoxazol;

(E)-6-[(2-hydroxy-1-tosyloxymethyl)ethoxy]-2-[2-[2-methylaminothiazole-5-yl]ethenyl]benzoxazol;

(E)-6-[(3-hydroxy-2-tosyloxymethyl)propoxy]-2-[2-(2-piperidinothiazole-5-yl)ethenyl]benzoxazol;

(E)-6-[(2-hydroxy-1-tosyloxymethyl)ethoxy]-2-[2-(2-piperidinothiazole-5-yl)ethenyl]benzoxazol; or (E)-6-[(1-hydroxymethyl-2-tosyloxy)ethoxy]-2-[2-[2-(pyrrolidine-1-yl)-thiazole-5-yl]ethenyl]benzoxazol.

Then, methods for production of the compounds according to the present invention is explained. The compounds expressed by the formula (I) or the formula (I') can be produced by, for example, the following methods.

[Formula 51]

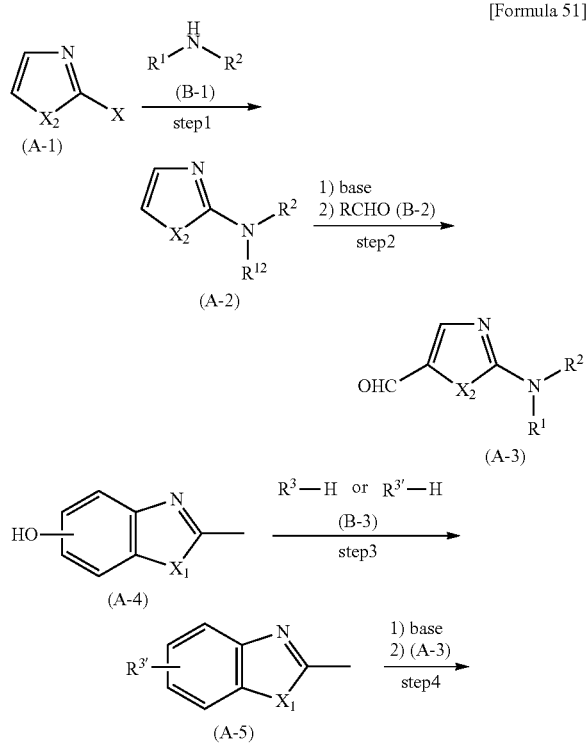

as concentration, vacuum concentration, solvent extraction, crystallization, reprecipitation, chromatography, or the like, or submitted to the next step without isolation and purification.

(Step 3)

The present step is the method to produce the compound (A-5) by reacting the compound (A-4) with the compound (B-3). The reaction in the present step is so-called Mitsunobu reaction, and it can be conducted by the method described in the literatures (For example, Mitsunobu. O, The use of diethyl-azodicarboxylate and triphenylphosphine in synthesis and transformation of natural products, Synthesis, Vol. 1, 1984. pp 1-28), or the method pursuant thereto, or the method combining these with common procedure.

As the compound (A-4), the publicly known one can be used, or it is possible to synthesize by the method ordinarily employed in the field of organic chemistry, or the method pursuant thereto using the publicly known compound as the material.

The amount of compound (B-3) to be used is generally 0.5 to 10 equivalents, preferably 1 to 5 equivalents relative to the compound (A-4).

The phosphine compound to be used in the present step includes, for example, triphenylphosphine, triethylphosphine, and the like.

The amount of phosphine compound to be used is generally 1 to 10 equivalents, preferably 1 to 5 equivalents relative to the compound (A-4).

Azo compound to be used includes, for example, diethyl-azo-dicarboxylate, diisopropyl-azo-dicarboxylate, and the like.

The amount of azo compound to be used is generally 0.5 to 10 equivalents, preferably 1 to 5 equivalents relative to the compound (A-4).

Reaction time is generally 1 to 48 hours, preferably 1 to 24 hours.

Reaction temperature is generally 0° C. to reflux temperature of the reaction solvent, preferably 0 to 50° C.

In the present step, any reaction solvents which do not Inhibit the reaction, without any limitation, can include, for example, tetrahydrofuran (THF), toluene, and the like.

The compound (A-5) thus obtained can be isolated and purified by the known separation and purification means such as concentration, vacuum concentration, crystallization, solvent extraction, reprecipitation, chromatography, or the like, or submitted to the next step without isolation and refinement.

(Step 4)

The present step is the method to produce the compound (A-6) by reacting the compound (A-5) with the compound (A-3) in the presence of a base.

The amount of a base to be used is generally 0.5 to 10 equivalents, preferably 1 to 5 equivalents relative to the compound (A-5).

The compound to be used includes, for example, lithium-diisopropylamide (LDA) and the like.

Reaction temperature is generally −78 to 50° C., preferably −78° C. to room temperature.

Reaction time is generally 0.1 to 24 hours, preferably 0.1 to 6 hours.

Any reaction solvents which do not inhibit the reaction, without any limitation, can include, for example, tetrahydrofuran (THF) and the like.

The compound (A-6) thus obtained can be isolated and purified by the known separation and purification means such as concentration, vacuum concentration, crystallization, solvent extraction, reprecipitation, chromatography, or the like, or submitted to the next step without isolation and purification.

(Step 5)

The present step is the method to produce the compound (A-7) by reacting the compound (A-6) with MsCl in the presence of a base.

The amount of a base to be used is generally 1 to 10 equivalents, preferably 1 to 5 equivalents relative to the compound (A-6).

Bases to be used include, for example, triethylamine, diisopropylamine and the like.

The amount of MsCl to be used is generally 1 to 10 equivalents, preferably 1 to 5 equivalents relative to the compound (A-6).

Reaction temperature is generally 0 to 50° C., preferably 0° C. to room temperature.

Reaction time is generally 0.1 to 48 hours, preferably 0.1 to 24 hours.

Any reaction solvents which do not inhibit the reaction, without any limitation, can include, for example, dichloromethane, tetrahydrofuran, dimethylformamide, and the like.

The compound (A-7) thus obtained can be isolated and purified by the known separation and purification means such as concentration, vacuum concentration, crystallization, solvent extraction, reprecipitation, chromatography, or the like, or submitted to the next step without isolation and purification.

If $R^3$ in the compound (A-7) does not possess a protective group of a hydroxy group, the compound (A-7) corresponds to the compound (I) according to the present invention, If $R^3$ in the compound (A-7) possesses a protective group of a hydroxy group, it is possible to produce the compound (I) according to the present invention by conducting the next step 6.

(Step 6)

The present step is the method to produce the compound (I) according to the present invention by removing a protective group of a hydroxy group of $R^3$ in the compound (A-7).

Introduction of the protective group of hydroxy group of $R^3$ and removal thereof can be conducted by the method described in the literatures (Protective Groups in Organic Synthesis, T. W. Green, 2nd edition, John Wiley & Sons, 1991, and the like), or the method pursuant thereto, or the method combining these with common procedure.

The compound (I) according to the present invention thus obtained can be isolated and purification by the known separation and refinement means such as concentration, vacuum concentration, crystallization, solvent extraction, reprecipitation, chromatography, or the like.

If either of $R^1$ or $R^2$ of the compound (B-1) to be used in the step 1 is a hydrogen atom, it is possible to remove a protective group of said amino group, if necessary, by introducing a protective group to an amino group of the compound (B-1). Introduction of a protective group of said amino group and removal thereof can be conducted by the method described in the literatures (Protective Groups in Organic Synthesis, T. W. Green, 2nd edition, John Wiley & Sons, 1991, and the like), or the method pursuant thereto, or the method combining these with common procedure.

The compound represented by the above described formula (A-7) can be also produced, for example, by the following method.

[Formula 52]

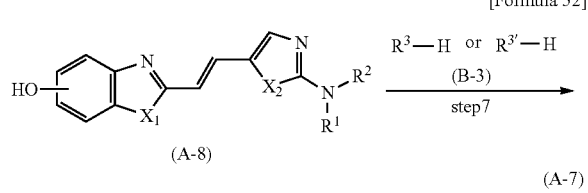

(Step 7)

The present step is the method to produce the compound (A-7) by reacting the compound (A-8) with the compound (B-3). The reaction in the present step is so-called Mitsunobu reaction, and it can be conducted by the method similar to that of above mentioned step 3, or the method pursuant thereto, or the method combining these with common procedure.

The compound (A-7) thus obtained can be isolated and purified by the known separation and purification means such as concentration, vacuum concentration, crystallization, solvent extraction, reprecipitation, chromatography, or the like, or submitted to the next step without isolation and purification.

The compound (A-8) used in the above mentioned step 7 can be produced, for example, by the following method.

[Formula 53]

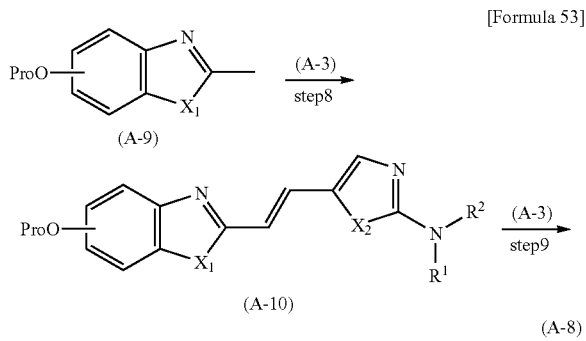

[wherein, Pro represents a protective group of a hydroxy group, and other variables are the same as described above]

(Step 8)

The present step is the method to produce the compound (A-10) by reacting the compound (A-9) with the compound (A-3) in the presence of a base.

Bases to be used include, for example, NaOH and the like.

The amount of a base to be used is generally 1 to 50 equivalents, preferably 1 to 20 equivalents relative to the compound (A-9).

Reaction temperature is generally 0 to 50° C., preferably 0° C. to room temperature.

Reaction time is generally 1 to 100 hours, preferably 1 to 30 hours.

Any reaction solvents which do not inhibit the reaction, without any limitation, include, for example, DMSO, methanol, ethanol or mixture solvent of these with water and the like.

The compound (A-10) thus obtained can be isolated and purified by the known separation and purification means such as concentration, vacuum concentration, crystallization, solvent extraction, reprecipitation, chromatography, or the like, or submitted to the next step without isolation and purification.

(Step 9)

The present step is the method to produce the compound (A-8) by removing the protective group of a hydroxyl group which the compound (A-10) possesses. Removal protective group of a hydroxyl group can be conducted by the method described in above described Protective Groups in Organic Synthesis, T. W. Green, 2nd edition, John Wiley & Sons, 1991, and the like, or the method pursuant thereto, or the method combining these with common procedure.

The compound (A-8) thus obtained can be isolated and purified by the known separation and purification means such as concentration, vacuum concentration, crystallization, solvent extraction, reprecipitation, chromatography, or the like.

The compound (I-2) of the present invention

[Formula 54]

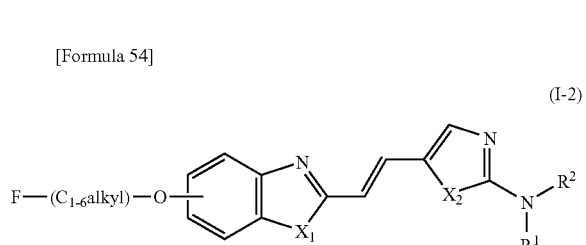

[wherein, $C_{1-6}$ alkyl represents a straight or branched alkyl group with 1 to 6 carbons, and other variables are the same as above mentioned]

can be produced, for example, using the compound represented by the following formula (A-11).

[Formula 55]

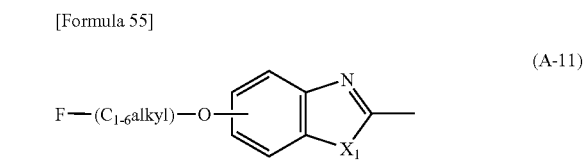

[wherein, each variable is the same as that mentioned above]

[Formula 56]

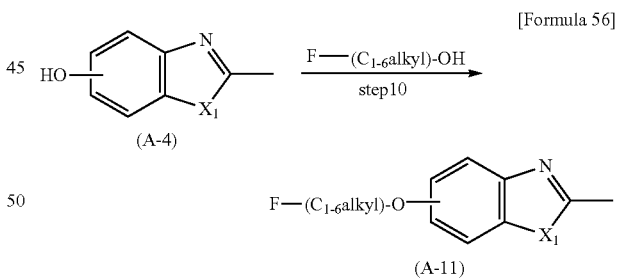

(Step 10)

The present step is the method to produce the compound (A-11) by reacting the compound (A-4) with the compound (B-4).

The reaction in the present step can be conducted by the method similar to that of above mentioned step 3, or the method pursuant thereto, or the method combining these with common procedure.

The amount of the compound (B-4) to be used is generally 0.5 to 10 equivalents, preferably 1 to 5 equivalents relative to the compound (A-4).

The compound (A-11) thus obtained can be isolated and purified by the known separation and purification means such as concentration, vacuum concentration, crystallization, solvent extraction, reprecipitation, chromatography, or the like.

The compound (I-2) included in the formula (I) can be produced by the method similar to that of above mentioned steps 4, 5, 6, the method pursuant thereto, or the method combining these with common procedure using the above mentioned compound (A-11).

The compound represented by the formula (I-3) included in the formula (I) according to the present invention,

[Formula 57]

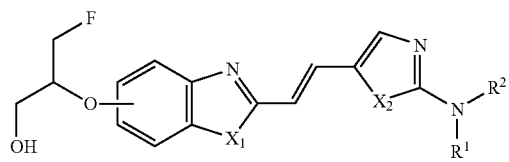
(I-3)

[wherein, each variable is the same as that mentioned above] can be synthesized, for example, from the compound (A-17) produced by the following method.

[Formula 58]

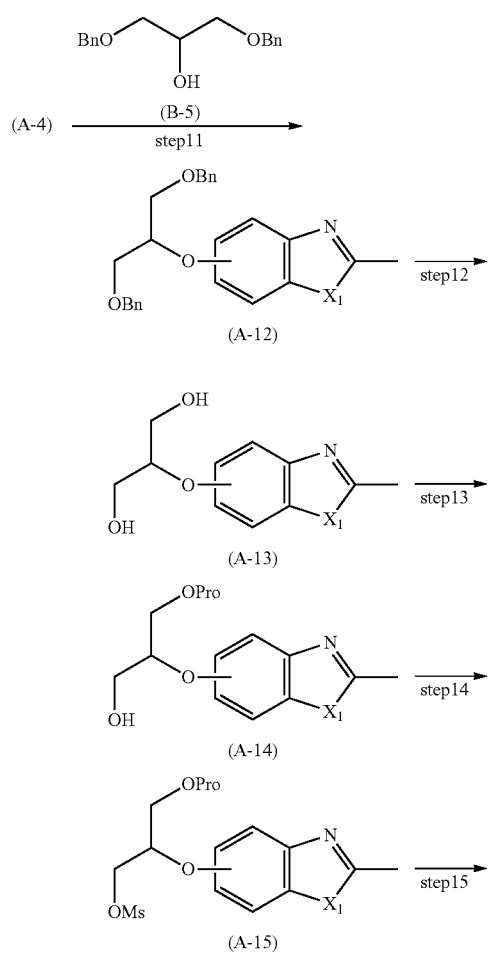

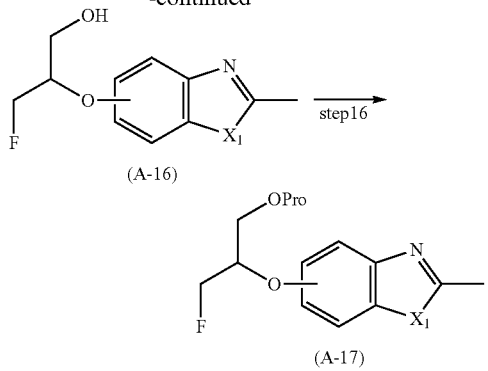

[wherein, Pro represents a protective group of a hydroxy group, Bn represents a benzyl group, and each variable is the same as above mentioned]

(Step 11)

The present step is the method to produce the compound (A-12) by reacting the compound (A-4) with the compound (B-5). The reaction in the present step is so-called Mitsunobu reaction, and it can be conducted by the method similar to that in the above mentioned step 3 or 7, the method pursuant thereto, or the method combining these with common procedure.

The amount of compound (B-5) to be used is generally 0.5 to 10 equivalents, preferably 1 to 5 equivalents relative to the compound (A-4).

The compound (B-5) can be the compound available in the market, or can be produced by the method well known for those skilled in the art, the method pursuant to this, or the method connecting these with common procedure.

The compound (A-12) thus obtained can be isolated and purified by the known separation and purification means such as concentration, vacuum concentration, crystallization, solvent extraction, reprecipitation, chromatography, or the like, or submitted to the next step without isolation and purification.

(Step 12)

The present step is the method to produce the compound (A-13) by removing the protective group of hydroxy group which the compound (A-12) possesses.

Removal of a protective group of a hydroxy group can be conducted by the method described in above described Protective Groups in Organic Synthesis, T. W. Green, 2nd edition, John Wiley & Sons, 1991, and the like, or the method pursuant thereto, or the method combining these with common procedure. For example, if Bn (benzyl) group is used as a protective group of a hydroxy group, it is possible to remove said protective group by using Pd—C in a hydrogen atmosphere.

The compound (A-13) thus obtained can be isolated and purified by the known separation and purification means such as concentration, vacuum concentration, crystallization, solvent extraction, reprecipitation, chromatography, or the like, or submitted to the next step without isolation and purification.

(Step 13)

The present step is the method to produce the compound (A-14) by protecting one of two hydroxy groups of the compound (A-13).

Introduction of the protective group in the present step can be conducted by the method described in above mentioned Protective Groups in Organic Synthesis, T. W. Green, 2nd edition, John Wiley & Sons, 1991, and the like, or the method pursuant thereto, or the method combining these with common procedure. The protective group includes, for example, TBS (tert-butyl-dimethyl-silyl) group and the like.

The compound (A-14) thus obtained can be isolated and purified by the known separation and purification means such as concentration, vacuum concentration, crystallization, solvent extraction, reprecipitation, chromatography, or the like, or submitted to the next step without isolation and purification.

(Step 14)

The present step is the method to produce the compound (A-15) by reacting the compound (A-14) with MsCl in the presence of a base.

The base to be used includes, for example, triethylamine, diisopropylamin and the like.

The amount of base to be used is generally 1 to 10 equivalents, preferably 1 to 5 equivalents relative to the compound (A-4).

The amount of MsCl to be used is generally 1 to 10 equivalents, preferably 1 to 5 equivalents relative to the compound (A-14).

Reaction temperature is 0° C. to room temperature.

Reaction time is 0.1 to 10 hours, preferably 0.1 to 5 hours.

Any reaction solvents which do not inhibit the reaction, without any limitation, can include, for example, dichloromethane, dimethylformamide, tetrahydrofuran and the like.

The compound (A-15) thus obtained can be isolated and purified by the known separation and purification means such as concentration, vacuum concentration, crystallization, solvent extraction, reprecipitation, chromatography, or the like, or submitted to the next step without isolation and purification.

(Step 15)

The present step is the method to produce the compound (A-16) by introducing a fluorine atom to the compound (A-15) and removing a TBS group that is the protective group of a hydroxy group.

Introduction of a fluorine atom, and removal of a TBS group can be conducted using TBAF (tetrabutylammonium fluoride).

The amount of TBAF to be used is generally 1 to 50 equivalents, preferably 1 to 20 equivalents relative to the compound (A-15).

Reaction temperature is generally 0-50° C., preferably 0° C. to room temperature.

Reaction time is 1 to 48 hours, preferably 1 to 24 hours.

Any reaction solvents which do not inhibit the reaction, without any limitation, can include, for example, tetrahydrofuran, dichloromethane, dimethylformamide and the like.

The compound (A-16) thus obtained can be isolated and purified by the known separation and purification means such as concentration, vacuum concentration, crystallization, solvent extraction, reprecipitation, chromatography, or the like, or submitted to the next step without isolation and purification.

(Step 16)

The present step is the method to produce the compound (A-17) by introducing a protective group to a hydroxy group which the compound (A-16) possesses.

Introduction of a protective group of a hydroxy group can be conducted by the method described in above mentioned Protective Groups in Organic Synthesis, T. W. Green, 2nd edition, John Wiley & Sons, 1991, and the like, or the method pursuant thereto, or the method combining these with common procedure.

The compound (A-17) thus obtained can be isolated and refined by the publicly known separation and refinement means such as concentration, vacuum concentration, crystallization, solvent extraction, reprecipitation, chromatography, or the like.

The compound (I-3) according to the present invention can be produced by the method similar to that in above steps 4, 5, 6, the method pursuant thereto, or the method combining these with common procedure using the compound (A-17) as the raw material.

The compound represented by the formula (I-3) according to the present invention

[Formula 59]

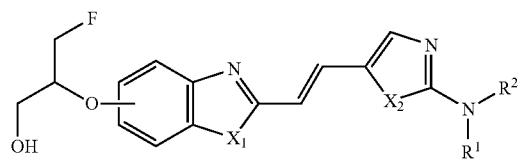

(I-3)

[wherein, each variable is the same as that mentioned above] or the compound represented by the formula (I'-1):

[Formula 60]

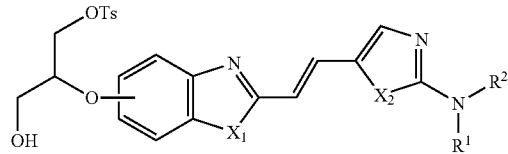

(I'-1)

[In the formula, Ts represents tosyl (p-toluenesulfon group) and other variable is the same as that mentioned above] can be also produced, for example, by the following method.

[Formula 61]

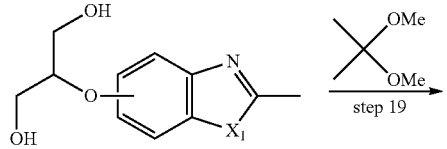

(A-13)

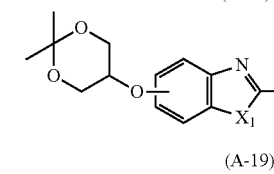

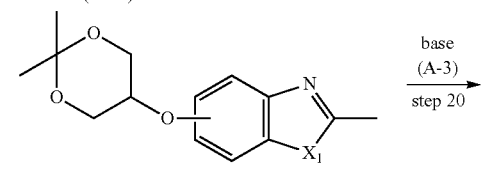

(A-19)

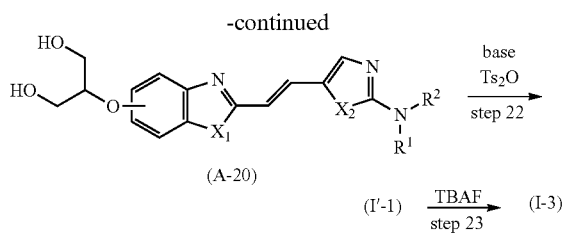

(A-20)

(I'-1) $\xrightarrow[\text{step 23}]{\text{TBAF}}$ (I-3)

[wherein, each variable is the same as that mentioned above]

(Step 19)

The present step is the method to produce the compound (A-18) by reacting the compound (A-13) with 2,2-dimethoxypropane. The reaction in the present step can be conducted by the method described in above mentioned Protective Groups in Organic Synthesis, T. W. Green, 2nd edition, John Wiley & Sons, 1991, and the like, or the method pursuant thereto, or the method combining these with common procedure.

The compound (A-18) thus obtained can be isolated and purified by the known separation and purification means such as concentration, vacuum concentration, crystallization, solvent extraction, reprecipitation, chromatography, or the like, or submitted to the next step without isolation and purification.

(Step 20)

The present step is the method to produce the compound (A-19) by reacting the compound (A-18) with the compound (A-3) in the presence of a base. The reaction in the present step can be conducted by the method similar to that in the above step 8, the method pursuant thereto, or the method combining these with common procedure.

The compound (A-18) thus obtained can be isolated and purified by the known separation and purification means such as concentration, vacuum concentration, crystallization, solvent extraction, reprecipitation, chromatography, or the like, or submitted to the next step without isolation and purification.

(Step 21)

The present step is the method to produce the compound (A-20) by removing the protective group of diol which the compound (A-19) possesses.

The reaction in the present step can be conducted by the method described in above mentioned Protective Groups in Organic Synthesis, T. W. Green, 2nd edition, John Wiley & Sons, 1991, and the like, or the method pursuant thereto, or the method combining these with common procedure.

The compound (A-20) thus obtained can be isolated and purified by the known separation and purification means such as concentration, vacuum concentration, crystallization, solvent extraction, reprecipitation, chromatography, or the like, or submitted to the next step without isolation and purification.

(Step 22)

The present step is the method to produce the compound (I'-1) according to the present invention by reacting the compound (A-20) with p-toluenesulfonic anhydride in the presence of a base.

A base to be used includes, for example, triethylamine, diisopropylethylamin and the like.

Applying a catalyst quantity of dimethylaminopyridine may be also applied to the reaction system.

The amount of a base to be used is generally 1 to 10 equivalents, preferably 1 to 5 equivalents relative to the compound (A-20).

The amount of p-toluenesulfonic acid used is generally 0.5 to 1 equivalents relative to the compound (A-20).

Reaction temperature is generally room temperature to boiling point temperature of the solvent, preferably 50 to 80° C.

Reaction time is generally 1 to 48 hours, preferably 1 to 24 hours.

Any reaction solvents which do not inhibit the reaction, without any limitation, can include, for example, dimethoxyethane, dimethylformamide and the like.

The compound (I'-1) thus obtained can be isolated and purified by the known separation and purification means such as concentration, vacuum concentration, crystallization, solvent extraction, reprecipitation, chromatography, or the like, or submitted to the next step without isolation and purification.

(Step 23)

The present step is the method to produce the compound (I-3) according to the present invention by reacting the compound (I'-1) with TBAF.

The reaction in the present step can be conducted by the method similar to that of above mentioned step 15, or the method pursuant thereto, or the method combining these with common procedure.

The compound (I-3) thus obtained can be isolated and purified by the known separation and refinement means such as concentration, vacuum concentration, crystallization, solvent extraction, reprecipitation, chromatography, or the like.

The compound that is represented by the formula (I'-2) according to the present invention

[Formula 62]

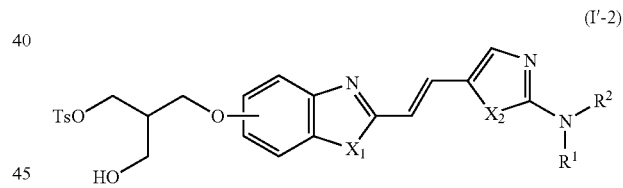

[wherein, each variable is the same as that mentioned above] can be also produced, for example, by the following method.

[Formula 63]

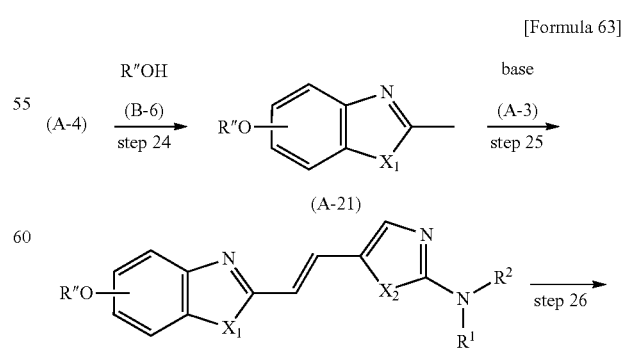

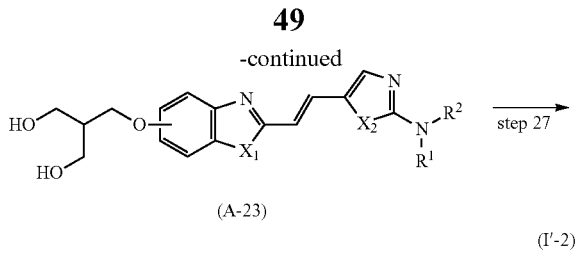

(A-23)

(I'-2)

[wherein, R"OH means

[Formula 64]

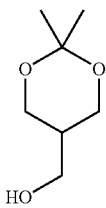

and each variable is the same as that mentioned above]

(Step 24)

The present step is the method to produce the compound (A-21) by reacting the compound (A-4) with the compound (B-6).

The reaction in the present step is so-called Mitsunobu reaction and can be conducted by the method similar to that of above mentioned step 3, the method pursuant thereto, or the method combining these with common procedure.

The compound (A-21) thus obtained can be isolated and purified by the known separation and purification means such as concentration, vacuum concentration, crystallization, solvent extraction, reprecipitation, chromatography, or the like, or submitted to the next step without isolation and purification.

(Step 25)

The present step is the method to produce the compound (A-22) by reacting the compound (A-21) with the compound (A-3) in the presence of a base.

The present step can be conducted by the method similar to that in the above steps 8, 20, the method pursuant thereto, or the method combining these with common procedure.

The compound (A-22) thus obtained can be isolated and purified by the known separation and purification means such as concentration, vacuum concentration, crystallization, solvent extraction, reprecipitation, chromatography, or the like, or submitted to the next step without isolation and purification.

(Step 26)

The present step is the method to produce the compound (A-23) by stepping the compound (A-22) with acid.

The reaction in the present step can be conducted by the method described in above described Protective Groups in Organic Synthesis, T. W. Green, 2nd edition, John Wiley & Sons, 1991, and the like, the method pursuant thereto, or the method combining these with common procedure.

The compound (A-23) thus obtained can be isolated and purified by the known separation and purification means such as concentration, vacuum concentration, crystallization, solvent extraction, reprecipitation, chromatography, or the like, or submitted to the next step without isolation and purification.

(Step 27)

The present step is the method to produce the compound (I'-2) according to the present invention by reacting the compound (A-23) with p-toluenesulfonic anhydride in the presence of a base, and can be conducted by the method similar to that in the above mentioned step 22, or the method pursuant thereto, or the method combining these with common procedure.

The compound (I'-2) thus obtained can be isolated and purified by the known separation and purification means such as concentration, vacuum concentration, crystallization, solvent extraction, reprecipitation, chromatography, or the like.

The compound represented by the formula (I-4) according to the present invention

[Formula 65]

(I-4)

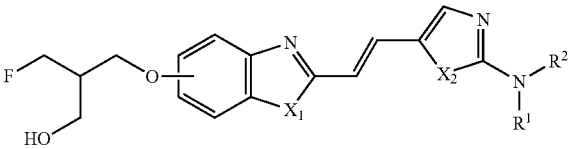

[wherein, each variable is the same as that mentioned above] can be also produced, for example, by reacting the above mentioned (I'-2) with TBAF, and said reaction can be conducted by the method similar to that in the above mentioned step 23, the method pursuant thereto, or the method combining these with common procedure.

(I'-1) can be also produced by the method similar to that in the above mentioned steps 24, 25, 26, and 27, the method pursuant thereto, or the method combining these with common procedure using 2-phenyl-1,3-dioxane-5-ol in place of 2,2-dimethyl-1,3-dioxane-5-methanol used in the above mentioned step 24.

If hydrochloride of amino compound is used in producing the compound (I) or the compound (I') according to the present invention, a base may be coexisted in the reaction system.

Salts of the compounds of the present invention are also included in the present invention. Said salts can be produced by the conventional procedure using the compounds represented by the formula (I) or (I') provided by the present invention.

Specifically, if the compounds represented by the above formula (I) or (I') possess, for example, a basic group derived from an amino group, a pyridyl group and the like within said molecule, it is possible to transform said compound into a corresponding salt by processing it with acid.

Said acid salts include, for example, halogenated hydroacid salts such as hydrochloride, hydrofluoric acid salt, hydrobromic acid salt, hydriodic acid salt; inorganic acid salts such as nitrate, perchlorate, sulfate, phosphate, carbonate; lower alkyl sulfonic acid salts such as methansulfonic acid salt, trifluoromethansulfonic acid salt, ethansulfonic acid salt; aryl sulfonic acid salts such as benzenesulfonic acid salt, p-toluensulfonic acid salt; organic acid salts such as fumarate, succinate, citrate, tartrate, oxalate, maleate; and organic acid salts of amino acid such as glutamate, and aspartate.

If the compounds of the present invention possess an acidic group, for example, a carboxyl group or the like in said group, it is possible to convert said compound into a pharmaceutically acceptable corresponding salt by processing said compound with base. Said basic salts include, for example, alkali metal salts such as sodium, potassium; alkali-earth metal salts such as calcium, magnesium; and salts by organic base such as, ammonium salt guanidine, triethylamine, and dicyclohexylamine.

The preparation method of the compounds of the formulae (I) and (I') of the present invention, and salts thereof are explained above, and the compounds of the formulae (II) to (VI) of the present invention and salts thereof can be also easily prepared by those skilled in the art.

Furthermore, compounds of the present invention may exist as any hydrate or solvate of free compounds or salts thereof.

In the diagnosis for protein conformation diseases, it is possible to employ the compounds of the present invention as the probe without labeling. For example, it is may be examined whether there is a part to be stained by contacting the compounds of the present invention with the biopsy specimen. However, the labeled compounds of the present invention generally used as the diagnostic probe for protein conformation diseases. The labels may include fluorescent material, affinity substance, enzyme substrate, and radiation nuclide. In image diagnosis for protein conformation diseases, generally the probe labeled with radiation nuclides are used. It is possible to label the compounds of the present invention with a variety of radiation nuclides by the well known method in said field. For example, $^{3}H$, $^{14}C$, $^{35}S$, and $^{131}I$ are conventionally used radiation nuclides, and in many cases, used in vitro. The general requirements needed for the imaging diagnostic probe and detection means thereof include a possibility of conducting image diagnosis in vivo, less damage to patients (in particular, non invasive), high detection sensitivity, and an appropriate length of half life (time to prepare the labeling probe, and diagnosis time are appropriate). Therefore, recently, positron emission tomography (PET) utilizing gamma ray having high detection sensitivity and substance transmissivity or Single Photon Emission Computed Tomography (SPECT) by use of radiation nuclides have been used. Among these, PET is preferable because it can detect 2 gamma rays that are emitted to the opposite direction from the positron emitting nuclides by a pair of detectors using the coincidence method, and provides information more excellent in resolution or quantitation. For SPECT, it is possible to label the compounds of the present invention with gamma ray emitting nuclides such as $^{99m}Tc$, $^{111}In$, $^{67}Ga$, $^{201}Tl$, $^{123}I$, and $^{133}Xe$. $^{99m}Tc$ and $^{123}I$ are comparatively frequently used for SPECT. For PET, the compounds of the present invention can be labeled with positron emitting nuclides such as $^{11}C$, $^{13}N$, $^{15}O$, $^{18}F$, $^{62}Cu$, $^{68}Ga$, and $^{76}Br$. Among positron emitting nuclides, $^{11}C$, $^{13}N$, $^{15}O$, and $^{18}F$ are preferable, and $^{19}F$ is particularly preferable in terms of appropriateness of half life and easiness for labeling. With regard to the labeling position of radiation nuclides including positron emitting nuclides, or gamma ray emitting nuclides in the compounds of the present invention, any position is allowed, but preferable labeling position is an alkyl group and/or a phenyl ring of the compound. The compounds of the present invention labeled like this are also included in the present invention. For example, if the compounds of the present invention is labeled with $^{18}F$, any group of the side-chain may be labeled with $^{18}F$ or hydrogen on the ring may be substituted with $^{18}F$. For example, the hydrogen contained in any of alkyl substituent may be substituted with $^{18}F$. If the compounds of the present invention is labeled with $^{11}C$, the carbon contained in any of alkyl substituent of the side-chain may be substituted with $^{11}C$. Although self-evident to those skilled in the art, m of $^{99m}Tc$ represents isomer in the metastable state.

The nuclides used in the compounds of the present invention may be produced by apparatus that are referred to as cyclotron or generator. Those skilled in the art could select the production method and the apparatus suitable to the nuclide to be produced. Using the nuclide thus produced, the compounds of the invention may be labeled.

Methods for producing compounds labeled with such radionuclides are well known in this technical field. Typical methods are a chemical synthesis method, an isotope transfer method and a biosynthesis method. The chemical synthesis method has been used widely from the past, and this does not substantially differ from an ordinary chemical synthesis method except that a radioactive starting substance is used in the former. According to this method, various nuclides are introduced into compounds. The isotope transfer method comprises transferring $^{3}H$, $^{35}S$ or $^{125}I$ in a simple-structured compound into a compound having a complicated structure, thereby giving a compound having a complicated structure and labeled with the nuclide. The biosynthesis method comprises giving a $^{14}C$ or $^{35}S$-labeled compound to cells such as those of microorganisms, thereby producing a metabolite that has the nuclide.

Regarding the labeling position, the synthetic scheme may be planned in accordance with the object, like in ordinary synthesis, whereby the labeling substance may be introduced into the desired position. Those skilled in the art well know the planning.

On the other hand, for example, when a positron emitter having a relatively short half life, such as $^{11}C$, $^{13}N$, $^{15}O$ or $^{18}F$ is used, then a desired nuclide may be obtained in a (ultra) small-size cyclotron installed in an institution such as hospital, thereafter a desired compound may be labeled with it at the desired position thereof according to the above-mentioned method, and it may be directly used for diagnosis, examination or treatment.

According to the methods known to those skilled in the art, the compounds of the invention may be labeled with a desired nuclide by introducing the nuclide to them at the desired position thereof.

The labeled compound of the invention may be administered to a subject either locally or systemically. The administration route includes subcutaneous, intraabdominal, intravenous, intra-arterial or intraspinal injection or infusion; and it may be selected depending on the factors such as the type of the disease, the nuclide used, the compound used, the condition of the subject and the examination site. After the probe of the invention has been administered and after a sufficient period of time has passed for binding the compound to amyloid β protein and disintegrating it, the examination site may be inspected according to means of PET or SPECT. These means may be suitably selected depending on the factors such as the type of the disease, the nuclide used, the compound used, the condition of the subject and the examination site.

The dose of the radionuclide-labeled compound of the invention varies depending on the type of the disease, the nuclide used, the compound used, the age of the subject, the physical condition, the sex, the degree of the disease and the examination site thereof. In particular, special attention should be paid to the dose equivalent to be applied to the subject. For example, the radioactivity of the compound of the invention labeled with a positron emitter such as $^{11}C$, $^{13}N$, $^{15}O$ or $^{18}F$ is within a scope of generally from 3.7 megabecquerels to 3.7 gigabecquerels, preferably from 18 megabecquerels to 740 megabecquerels.

The compounds of the present invention, or salts or solvates thereof are appropriate as treatment method, diagnosis method, compositions for treatment or diagnosis, kit for diagnosis of protein conformation diseases, as well as for the use to produce these compositions and kits, and other use, but the compounds exemplified in the explanation above regarding the compounds of the formulae (I)-(VI) or salts or solvates thereof are preferable, and the compound of the formula (I) or salts or solvates thereof are particularly preferable. Among the compounds of the present invention, those having a morpholino group, particularly a morpholino group as the terminal group have no or extremely low mutagenicity, thus appropriate for administration to human body. Among compounds of the present invention, those having

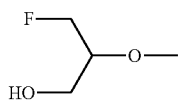

[Formula 66]

as $R^3$ in the formula (I) has extremely low or little bone accumulation, thus appropriate for administration to the human body.

The invention provides a composition for imaging diagnosis of conformation disease, which comprises the compound of the invention. The composition of the invention comprises the compound of the invention and a medically-acceptable carrier. Preferably, the compound of the invention in the composition is labeled. There are known various labeling methods as mentioned above, but for in-vivo imaging diagnosis application, the compound is preferably labeled with a radionuclide (especially for PET, positron emitter such as $^{11}C$, $^{13}N$, $^{15}O$, $^{16}F$). Regarding its form, the composition of the invention is preferably an injectable or infusible one in view of its object. Accordingly, the medically-acceptable carrier is preferably liquid, for example, a water-based solvent such as potassium phosphate buffer, physiological saline water, Ringer solution, distilled water, or a non-aqueous solvent such as polyethylene glycol, vegetable oil and fat, ethanol, glycerin, dimethyl sulfoxide, propylene glycol, to which, however, the invention should not be limited. The blend ratio of the carrier and the compound of the invention may be suitably determined depending on the application site and the detection means, and in general, it may be from 100,000/1 to 2/1, preferably from 10,000/1 to 10/1. The composition of the invention may contain any known microbicide (e.g., antibiotic), local anesthetic (e.g., procaine hydrochloride, dibucaine hydrochloride), buffer (e.g., tris-HCl buffer, Hepes buffer), osmoregulator (e.g., glucose, sorbitol, sodium chloride).

The invention further provides a kit for imaging diagnosis of conformation disease, which comprises the compound of the invention as the indispensable constitutive ingredient thereof. In general, the kit comprises the components such as a compound of the invention, a solvent for dissolving it, a buffer, an osmoregulator, a microbicide and a local anesthetic, which are individually packaged or are partly combined and packaged together, and are packed in one container. The compound of the invention may be unlabeled or labeled. When the compound is unlabeled, it may be labeled before use according to the ordinary method described in the above. If desired, the compound of the invention may be provided as a solid such as a freeze-dried powder; or it may be provided as a solution prepared by dissolving it in a suitable solvent. The solvent may be the same as that for the carrier for the composition of the invention mentioned hereinabove. The other components such as buffer, osmoregulator, microbicide and local anesthetic may also be the same as those for use in the composition of the invention mentioned in the above. Various types of containers may be suitably selected and used. The containers may have a shape suitable for labeling of the compounds of the invention, or may be formed of a light-shielding material depending on the properties of the compounds. For example, the containers may have a shape of vials or syringes capable of facilitating administration to patients. The kit may comprise appliances necessary for diagnosis, such as syringe, fusion set, as well as appliances for use in PET or SPECT apparatus. In general, an instruction booklet is attached to the kit.

Since the compounds of the invention may specifically bind to amyloid β protein, they may be used for detection and quantification of amyloid β protein in a sample by bringing the compound into in-vitro contact with a sample, while unlabeled or after labeled. For example, the compounds of the invention may be used for amyloid β protein staining of a sample in microscopy, for colorimetry of amyloid β protein in a sample, or for quantification of amyloid β protein with a scintillation counter. Preparing the sample for microscopy and staining it with the compound of the invention may be attained by any ordinary method known to those skilled in the art.

As mentioned hereinabove, the compounds of the invention have high specificity to amyloid β protein. Accordingly, the compounds of the invention are useful, for example, for studies of amyloid β protein deposition-related disorders or for diagnosis thereof while alive or after death. For example, the compounds may be useful as a staining agent for seline plaque in the brain of an Alzheimer disease patient. Staining a sample, such as a brain section with the compound of the invention may be attained by any ordinary method known to those skilled in the art.

As mentioned above, among the compounds of the present invention, those particularly having a morpholino group as the terminal group have no or extremely low mutagenicity, and among the compounds of the present invention, those having

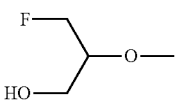

[Formula 67]

as $R^3$ in the formula (I) has extremely low or little bone accumulation. Therefore, the compounds of the present invention are not only the extremely safe diagnosis probe for protein conformation diseases but also have a high safety if used as the therapeutic drug or preventive preparation mentioned below.

Accordingly, the invention relates to a composition for staining amyloid β protein in a sample, which comprises the compound or its medically-acceptable salt or solvate of the invention, and to a kit for staining amyloid β protein in a sample, which comprises, as the indispensable constitutive component thereof, the compound or its medically-acceptable salt or solvate of the invention. Further, the invention relates to a method for staining amyloid β protein in a sample, which comprises using the compound or its medically-acceptable salt or solvate of the invention. The sample suitable to staining is a brain section.

As mentioned above, it is known that β sheet structure-having amyloid β protein exhibits neuron toxicity. The compounds of the invention may specifically bind to β sheet structure-having amyloid β protein, and therefore they may inhibit its neuron toxicity. Accordingly, the compounds of the invention may be a remedial or preventive agent for a conformation disease such as Alzheimer disease, of which the cause or a part of the cause is that protein having a β sheet structure.

Accordingly, the invention provides the following:

A method for treatment and/or prevention of amyloid β protein deposition-related diseases, which comprises administering a compound of formula (I) or its salt or solvate;

A method for diagnosis of amyloid β protein deposition-related diseases, which comprises using a compound of formula (I) or its salt or solvate; and Use of the compound of formula (I) or its salt or solvate for production of a composition or kit for treatment, prevention or diagnosis of amyloid β protein deposition-related diseases.

Not specifically defined, the form of such a pharmaceutical composition is preferably a liquid preparation, more preferably that for injection. The injection may be directly injected into a brains or the pharmaceutical composition may be administered through intravenous injection or infusion since the compound of the invention has high blood-brain barrier permeability as in Example 3. The liquid preparation may be produced in any method known in the art. For producing a solution-type preparation, for example, a compound of the invention may be dissolved in a suitable carrier, injection water, physiological saline water or Ringer solution, then sterilized through a filter, and thereafter it may be filled in suitable containers such as vials or ampoules. As the case may be, the solution preparation may be freeze-dried, and may be restored to its solution with a suitable carrier just before use. A suspension-type preparation may be produced, for example, by sterilizing a compound of the invention through exposure to ethylene oxide, and then suspending it in a sterilized liquid carrier.

If those drug compositions are used as liquid prescription, in particular, prescription for injection, benzoxazole derivative of the present invention added with solubilizing agent can be used as injectable solution.

Said solubilizing agents to be used include nonionic surfactant, cationic surfactant, amphoteric surfactant. Among these, Polysorbate 80, polyethylene glycol, ethanol, or propylene glycol are preferable, and Polysorbate 80 is more preferable.

The dose of the compound of the invention to a human subject in the above-mentioned therapeutic method, preventive method and use may vary depending on the condition of a patient, the sex, the age and the body weight thereof, but in general, the dose thereof to an adult having a body weight of 70 kg may be from 0.1 mg to 1 g a day, preferably from 1 mg to 100 mg, more preferably from 5 mg to 50 mg. After a patient is treated at the dose for a predetermined period of time, the dose may be increased or decreased depending on the therapeutical result.

The compounds or their salts or solvates of the invention may be used as a diagnostic probe for conformation disease, preferably as an imaging diagnostic probe that is labeled with a radiation emitter. Further, the compounds of the invention are effective for treatment and/or prevention of conformation disease.

Accordingly, the invention relates to the following:

A compound or its salt or solvate of the invention for use as an imaging diagnostic probe for a is conformation disease;

An imaging diagnostic composition or kit for a conformation disease that comprises a compound or its salt or solvate of the invention;

A pharmaceutical composition for prevention and/or treatment of a conformation disease, comprising the compound or its medically-acceptable salt or solvate of the invention and a medically-acceptable carrier;

A method for diagnosis of a conformation disease, characterized by using a compound or its medically-acceptable salt or solvate of the invention;

Use of the compound or its medically-acceptable salt or solvate of the invention for diagnosis of a conformation disease;

A method for prevention and/or treatment of a conformation disease, characterized by administering a compound or its medically-acceptable salt or solvate of the invention to a subject;

Use of the compound or its medically-acceptable salt or solvate of the invention for prevention and/or treatment of a conformation disease; and Use of the compound of the invention in production of a pharmaceutical composition for prevention and/or treatment of a conformation disease.

The dose of the compound of the invention to a human subject in the above-mentioned therapeutical method and preventive method may be as mentioned in the above.

Among the compounds of the present invention, some kinds of them recognize the change in neurofibrils, thus they can be used as the detection probe for the change in neurofibrils or staining agent for the change in neurofibrils. Therefore, the present invention relates to the use of the compounds of the present invention, or salts or solvates thereof as the detection probe for the change in neurofibrils, in particular, as the image detection probe. The preferable compounds of the present invention as the staining agent for the change in neurofibrils include THK-185, THK-258, THK-317, THK-702, THK-761, THK-727, and THK-763.

Accordingly, the invention provides the following:

A composition for detecting or staining neurofibrillary tangier which comprises a compound or its salt or solvate of the invention;

A kit for detecting or staining neurofibrillary tangle, which comprises a compound or its salt or solvate of the invention;

A method for detecting or staining neurofibrillary tangle, which comprises using a compound or its salt or solvate of the invention; and Use of the compound or its salt or solvate of the invention for producing a composition for detecting or staining neurofibrillary tangle.

For preparing the sample for detection and staining neurofibrillary tangle therein and the method for staining as mentioned above, any ordinary method known to those skilled in the art may be applied.

Examples are shown below, and the present invention is more detailed and specifically explained. However, the present invention is not limited at all by examples.

EXAMPLE 1

Synthesis of the Compounds of the Present Invention

The synthesis example of the compounds of the present invention is shown below.

For silica gel column chromatography of the embodiment, silica gel BW300 of Fuji Silysia Chemical Ltd. was used. For basic silica gel column chromatography using silica gel combined with an amino group, Chromatorex NH-DM 1020 of Fuji Silysia Chemical Ltd. was used.

$^1$H-NMR was measured using UNITY INOVA500 (500 MHz) of VARIAN, JNM-LA400 (400 MHz) of JEOL Ltd., and Gemini 2000 (300 MHz) tetramethylsilane of VARIAN as the reference material, and all the δ values were measured in ppm.

Mass spectra were conducted by Atmospheric pressure chemical ionization (APCI) using LCQ-Advantage of ThermoQuest, or SSQ-7000C of FinniganMAT.

Infrared spectra were conducted using Paragon1000 FT-IR of Perkin-Elmer, and for measurement of melting point, B-545 of BUCHI was used.

NMR abbreviations are spelled out as below.
s: singlet
d: doublet
dd: double-doublet
ddd: double double-doublet
t: triplet
dt: double triplet
q: quartet
m: multiplet
br: broad
J: coupling constant
Hz: Hertz
CDCl₃: deuterated chloroform
DMSO-d₆: deuterated dimethyl sulfoxide THK-525 (6-(20-fluoro-ethoxy)-2-[2-(2-morpholine-4-yl-thiazole-5-yl)-vinyl]benzoxazole: Production of 7 and 2

[Formula 68]

Production of 2

Morpholine solution (18.7 ml) of 1 (7.19 g, 43.84 mmol) was stirred at 120° C. for 9 hours. The reaction solution was allowed to stand to cool down and filtered to remove the insolubles, and the filtrate was evaporated to dryness under reduced pressure. The residue was purified by silica gel column chromatography (solvent: n-hexane/ethyl acetate=5/1), to obtain 2 (7.46 g, 100%) of oily light yellow substance.

IR (Neat) 2854, 1524 cm⁻¹, APCI-MS m/z 171 [M+H]⁺

Production of 3

To tetrahydrofuran solution (100 ml) of di-isopropylamine (7.41 ml, 52.58 mmol), 1.58 M n-butyllithium/n-hexane solution (33.3 ml, 52.58 mmol) was dropped at −60° C. or below in argon atmosphere while stirring, and then, the mixture was slowly warmed up to 0° C. Then, tetrahydrofuran solution (10 ml) of 2 (7.46 g, 43.82 mmol) was dropped at −70° C. or below, and the mixture was stirred at −78° C. for 1 hr. Then, dimethylformamide (5.08 ml, 65.73 mmol) was added all at once at the same temperature, and the mixture was stirred for 30 min at the same temperature. The reaction mixture was added water, and extracted with ethyl acetate. The extract was washed with water, dried, and evaporated to dryness under reduced pressure, and the residue was recrystallized with ethyl acetate/n-hexane, to obtain 3 (7.54 g, 87%) of oily light yellow crystal.

mp 164~165° C., IR (Nujol) 1650 cm⁻¹
APCI-MS m/z 199 [M+H]⁺

Production of 5

To tetrahydrofuran solution (30 ml) of 4 (0.95 g, 6.37 mmol), 2-fluoroethanol (0.82 ml, 14.01 mmol) and triphenylphosphine (3.67 g, 14.01 mmol) were added, and diisopropyl azodicarboxylate (2.76 ml, 14.01 mmol) was dropped while ice-cooling with shaking, and the mixture was stirred at room temperature for 16 hours. The reaction mixture was evaporated to dryness under reduced pressure, and the residue was purified by silica gel column chromatography (solvent: n-hexane/ethyl acetate=1/1), to obtain 5 (0.82 g, 66%) of oily light yellow substance.

IR (Neat) 1726, 1632, 1618 cm⁻
APCI-MS m/z 196 [M+H]⁺

Production of 6

To tetrahydrofuran solution (40 ml) of di-isopropylamine (0.88 ml, 6.23 mmol), 1.54 M n-butyllithium/n-hexane solution (4.04 ml, 6.23 mmol) was dropped at −60° C. or below while shaking in argon atmosphere, and then, the mixture was slowly warmed up to 0° C. Then, tetrahydrofuran solution (10 ml) of 5 (0.81 g, 4.15 mmol) was dropped at −70° C. or below, and the mixture was stirred at −78° C. for 1 hr. Then, tetrahydrofuran solution (50 ml) of 3 (1.23 g, 6.23 mmol) was added all at once at the same temperature, and the mixture was stirred for 1 hr at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate=1/1 to ethyl acetate), to obtain 6 (1.40 g, 86%) of light yellow crystal.

mp 157.5~158.0° C., IR (Nujol) 3306, 1628, 1617 cm$^{-1}$

APCI-MS m/z 394 [M+m]$^+$

Production of 7

To dichloromethane solution (100 ml) of 6 (0.88 g, 2.24 mmol), triethylamine (1.25 ml, 8.95 mmol) was added, and methane sulfonyl chloride (0.35 ml, 4.47 mmol) was dropped while cooling in ice with shaking and stirred for 30 min at room temperature. The reaction mixture was added cold water, and extracted with ethyl acetate. The extract was washed with water, dried, and evaporated to dryness under reduced pressure, and the residue was recrystallized with ethyl acetate/n-hexane, to obtain 7 (0.49 g, 59%) of yellow crystal.

mp 174.5~175.2° C., $^1$H NMR (300 MHz, CDCl$_3$) δ 3.57 (4H, t, J=5.0 Hz), 3.83 (4H, t, J=5.0 Hz), 4.27 (2H, dt, J=27.8, 4.2 Hz), 4.79 (2H, dt, J=47.2, 4.2 Hz), 6.42 (1H, d, J=15.6 Hz), 6.94 (1H, dd, J=8.7, 2.2 Hz), 7.04 (1H, d, J=2.2 Hz), 7.36 (1H, s), 7.54 (1H, d, J=8.7 Hz), 7.68 (1H, d, J=15.6 Hz)

IR (Nujol) 1631 cm$^{-1}$, APCI-MS m/z 376[M+H]$^+$

THK-575 (toluene-4-sulfonic acid 2-[2-[2-(2-morpholine-4-yl-thiazole-5-yl)-vinyl-benzoxazole 6-yloxy]ethyl ester: Production of (12)

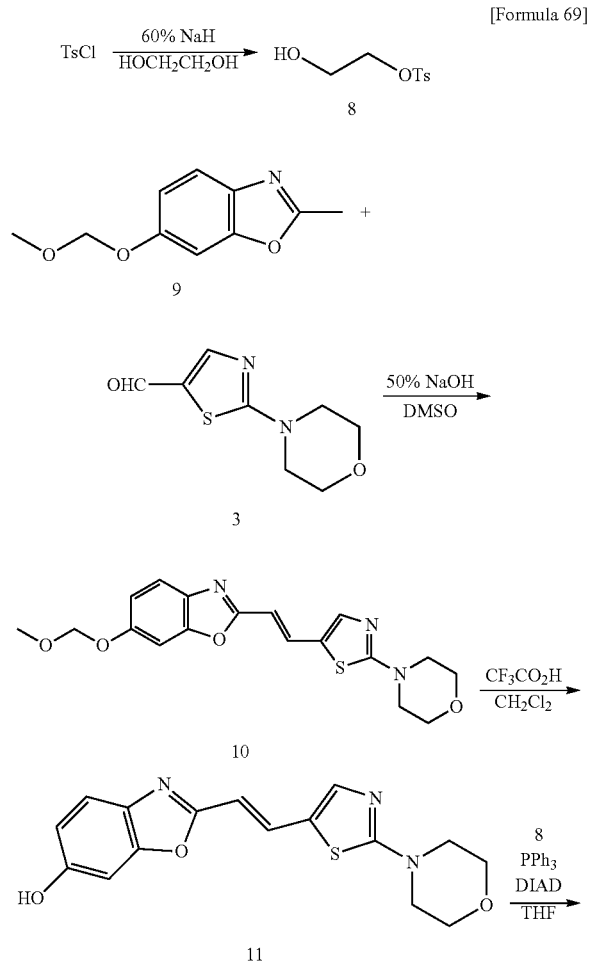

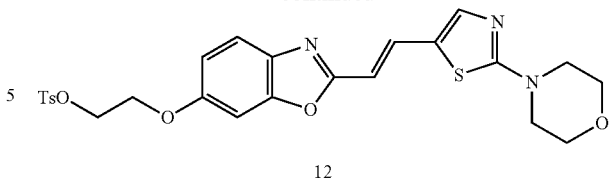

Production of 8

To ethylene glycol (130 mL), 60% sodium hydride (4.83 g, 120.6 mmol) was gradually added in argon atmosphere at room temperature with stirring, and stirred for 40 min, and toluene sulfonyl chloride (20.00 g, 104.9 mmol) was further added and stirred for 6 hours at the same temperature. Dichloromethane (100) was added to this reaction mixture, and stirred for 16 hours at room temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=5/1 to 1/1), to obtain 8 (7.30 g, 32%) of oily colorless substance.

Production of 10

Dimethyl sulfoxide solution (10 ml) of 9 (1.00 g, 5.18 mmol) and 3 (1.03 g, 5.18 mmol) was added 50% (w/w) sodium hydroxide solution (2.0 ml) at room temperature while stirring, and further stirred for 30 min. The reaction mixture was added water and filtered, and the filtrate was washed with water and dried to obtain 10 (1.55 g, 80%) of yellow crystal.

mp 156.0~156.6° C., IR (Nujol) 1631 cm$^{-1}$

APCI-MS m/z 374[M+H]$^+$

Production of 11

To dichlorometyane solution (25 ml) of 10 (1.55 g, 4.14 mmol), trifluoroacetic acid (17.5 ml) was dropped while ice-cooling with shaking, and stirred at room temperature for 40 min. The reaction mixture was added cold water, and potassium carbonate to adjust the pH to 10, and then extracted with ethyl acetate. The extract was washed with water, dried, and evaporated to dryness under reduced pressure, and the residue was recrystallized with ethyl acetate, to obtain 11 (1.04 g, 76%) of yellow crystal.

mp 233~234° C., IR (Nujol) 3491, 1631 cm$^{-1}$

APCI-MS m/z 330[M+H]$^+$

Production of 12

To tetrahydrofuran solution (20 ml) of 11 (0.50 g, 1.52 mmol), 8 (0.72 g, 3.34 mmol) and triphenylphosphine (0.88 g, 3.34 mmol) were added, and diisopropyl azodicarboxylate (0.66 ml, 3.34 mmol) was dropped while ice-cooling with shaking, and stirred at room temperature for 16 hours. The reaction mixture was evaporated to dryness under reduced pressure, and the residue was purified by silica gel column chromatography (solvent: toluene/ethyl acetate=2/1), and recrystallized with ethyl acetate, to obtain 12 (0.38 g, 48%) of orange crystal.

mp 168~169° C., $^1$H NMR (300 MHz, CDCl$_3$) δ 2.44 (3H, s), 3.55~3.62 (4H, m), 3.77~3.87 (4H, m), 4.11~4.22 (2H, m), 4.37~4.43 (2H, m), 6.38 (1H, d, J=15.7 Hz), 6.78 (1H, dd, J=8.7, 2.3 Hz), 6.90 (1H, d, J=2.3 Hz), 7.34 (2H, dd, J=7.6, 0.7 Hz), 7.37 (1H, s), 7.49 (1H, d, J=8.7 Hz), 7.67 (1H, d, J=15.7 Hz), 7.71~7.84 (2H, m)

IR (Nujol) 1633 cm$^{-1}$, APCI-MS m/z 528[M+H]$^+$

THK-727 (2-fluoromethyl-3-[2-[2-(2-morpholine-4-yl-thiazole-5-yl)-vinyl]benzoxazole 6-yloxy]-propane-1-ol: Production of (20)

[Formula 70]

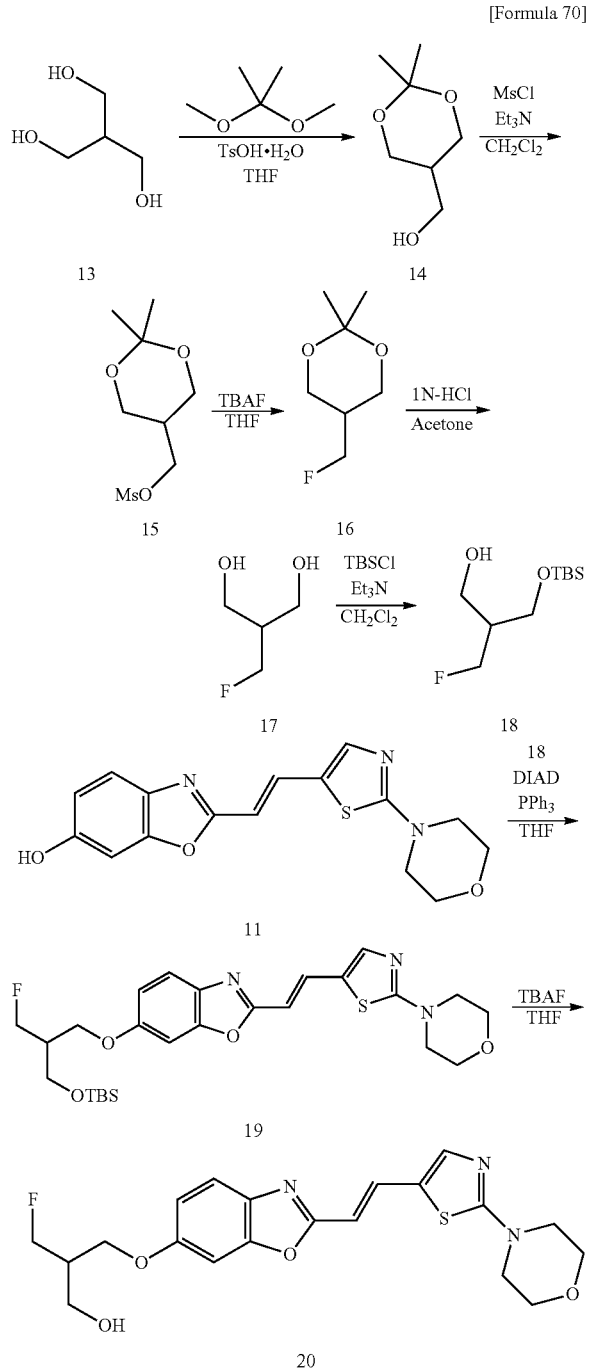

Production of 14

To tetrahydrofuran suspension (150 ml) of 13 (4.90 g, 46.17 mmol), acetone dimethyl acetal (6.56 ml, 53.54 mmol) and toluene sulfonic acid hydrate (0.26 g, 1.39 mmol) were added while shaking at room temperature, and stirred for 3 hours at room temperature. The reaction mixture was added triethylamine (3 ml), and evaporated to dryness under reduced pressure. The residue was purified by silica gel column chromatography (solvent: chloroform/methanol=10/1), to obtain 14 (6.38 g, 95%) of oily colorless substance.

APCI-MS m/z 147[M+H]$^+$

Production of 15

To dichloromethane solution (100 ml) of 14 (6.38 g, 43.64 mmol), triethylamine (9.08 ml, 65.47 mmol) was added, and methane sulfonyl chloride (3.69 ml, 48.01 mmol) was dropped while cooling in ice with shaking, and stirred for 30 min at the same temperature. The reaction mixture was added cold water, and extracted with ethyl acetate. The extract was washed with water, dried, and evaporated to dryness under reduced pressure, and the residue was purified by silica gel column chromatography (solvent: ethyl acetate/n-hexane=1/2), to obtain 15 (9.66 g, 99%) of oily light yellow substance.

APCI-MS m/z 225[M+H]$^+$

Production of 16

To tetrahydrofuran solution (100 ml) of 15 (9.66 g, 43.07 mmol), 1M tetrabutylammonium fluoride/tetrahydrofuran solution (260 ml, 260 mmol) was added while shaking at room temperature, and refluxed for 30 min. The reaction mixture was allowed to stand to cool down, added cold water, and extracted with ethyl acetate. The extract was washed with water, dried, and evaporated to dryness under reduced pressure, and the residue was purified by silica gel column chromatography (solvent: ethyl acetate/n-hexane 9/1), to obtain 16 (5.22 g, 82%) of oily light yellow substance.

APCI-MS m/z 149[M+H]$^+$

Production of 17

To acetone solution (100 ml) of 16 (5.22 g, 35.23 mmol), 1N hydrochloric acid (10 ml, 10 mmol) was added, and stirred for 2 hours at room temperature. The reaction mixture was evaporated to dryness under reduced pressure, and the residue was purified by silica gel column chromatography (solvent: ethyl acetate/n-hexane=4/1 to 1/1), to obtain 17 (3.16 g, 83%) of oily colorless substance.

APCI-MS m/z 126[M+NH4]$^+$

Production of 18

To dichloromethane solution (40 ml) of 17 (3.16 g, 29.23 mmol), triethylamine (10.19 ml, 73.08 mmol) was added, and t-butyl dimethylsilylchloride (4.41 g 29.23 mmol) was further added while ice-cooling with shaking, and stirred for 16 hours at room temperature. The reaction suspension was evaporated to dryness under reduced pressure, and the residue was suspended in ethyl acetate, and filtered. The filtrate was evaporated to dryness under reduced pressure, and the residue was purified by silica gel column chromatography (solvent: ethyl acetate/n-hexane 9/1), to obtain 18 (5.16 g, 79%) of oily colorless substance.

APCI-MS m/z 223[M+H]$^+$

Production of 19

To tetrahydrofuran suspension (40 ml) of 11 (0.55 g, 1.67 mmol), 18 (0.82 g, 3.67 mmol) and triphenylphosphine 10.96 g, 3.67 mmol) were added, and diisopropyl azodicarboxylate (0.72 ml, 3.67 mmol) was dropped while ice-cooling with shaking, and stirred at room temperature for 16 hours. The reaction mixture was evaporated to dryness under reduced pressure, and the residue was purified by silica gel column chromatography (solvent: ethyl acetate/n-hexane 4/1), to obtain 19 (0.67 g, 75%) of viscous yellow substance.

APCI-MS m/z: 534[M+H]$^+$

Production of 20

To dichloromethane solution (50 ml) of 19 (0.67 g, 1.26 mmol), 1M tetrabutylammonium fluoride/tetrahydrofuran solution (1.26 ml, 1.26 mmol) was dropped while ice cooling with shaking, and stirred for 40 min at room temperature. The reaction mixture was added cold water, and extracted with ethyl acetate. The extract was washed with water, dried, and evaporated to dryness under reduced pressure, and the residue was purified by silica gel column chromatography (solvent: ethyl acetate/n-hexane=4/1 to 1/1), and recrystallized with ethyl acetate/n-hexane, to obtain 20 (0.34 g, 65%) of yellow crystal.

mp 134~135° C., $^1$H NMR (300 MHz, CDCl$_3$) δ 2.38~2.53 (1H, m), 3.64 (4H, m), 3.85 (4H, m), 3.92 (2H, d, J=5.2 Hz), 4.16 (2H, d, J=5.5 Hz), 4.71 (2H, dd, J=47.2, 5.3 Hz), 6.42 (1H, d, J=15.8 Hz), 6.92 (1H, dd, J=8.8, 2.3 Hz), 7.04 (1H, d, J=2.3 Hz), 7.39 (1H, s), 7.54 (1H, d, J=8.8 Hz), 7.67 (1H, d, J=15.8 Hz)

IR (Nujol) 3324, 1634 cm$^{-1}$, APCI-MS m/z 420[M+H]$^+$

THK-702 ((E)-2-[2-(2-morpholinothiazole-5-yl)ethenyl]-6-[(1-fluoromethyl-2-hydroxy)ethoxy]benzoxazole): Production of (29)

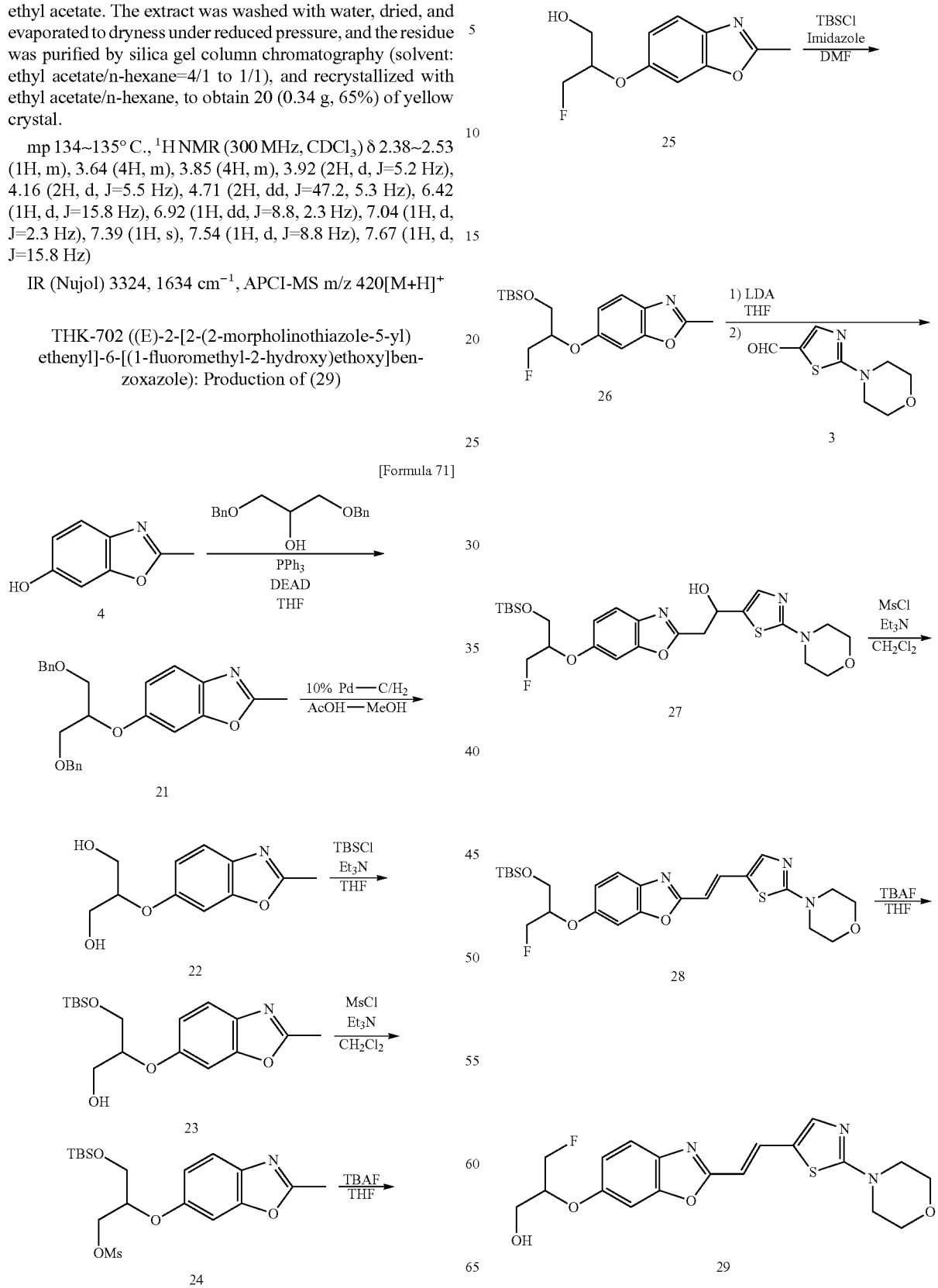

Production of 21

To tetrahydrofuran solution (50 ml) of 4 (3.00 g, 20.11 mmol), 1,3-dibenzyloxy-2-propanol (6.57 g, 24.14 mmol) and triphenylphosphine (6.33 g, 24.14 mmol) were added, and 40% diethyl azodicarboxylate/toluene solution (10.51 g, 24.14 mmol) was dropped while ice-cooling with shaking, and stirred at room temperature for 3 days. The reaction mixture was evaporated to dryness under reduced pressure, and the residue was suspended in isopropyl ether, and filtered, and the filtrate was evaporated to dryness under reduced pressure. The residue was purified by silica gel column chromatography (solvent: ethyl acetate/n-hexane=9/1), to obtain 21 (7.22 g, 89%) of oily colorless substance.

APCI-MS m/z 404[M+H]$^+$

Production of 22

To methanol/acetic acid solution (50/10 ml) of 21 (7.22 g, 17.89 mmol), 10% palladium-carbon (0.7 g) was added in argon atmosphere, and stirred in hydrogen atmosphere at normopressure and 50° C. for 24 hours. The palladium-carbon in reaction mixture was filterate, and the filtrate was evaporated to dryness under reduced pressure. The residue was diluted with ethyl acetate, washed with potassium carbonate solution, and with water, dried, and the solvent was evaporated to dryness under reduced pressure. The residue was purified by silica gel column chromatography (solvent: ethyl acetate/n-hexane=3/1 to 1/1), to obtain 22 (3.01 g, 75%) of red brown solid substance.

APCI-MS m/z 224[M+H]$^+$

Production of 23

To tetrahydrofuran solution (50 ml) of 22 (3.01 g, 13.48 mmol), triethylamine (4.70 ml, 33.71 mmol) was added, and t-butyl dimethylsilylchloride (2.03 g, 13.48 mmol) was further added at room temperature while stirring, and stirred for 2 days at room temperature. The reaction mixture was added water, and extracted with ethyl acetate. The extract was washed with water, dried, and evaporated to dryness under reduced pressure, and the residue was purified by silica gel column chromatography (solvent: ethyl acetate/n-hexane=9/1 to 1/1), to obtain 23 (2.00 g, 44%) of oily red substance.

APCI-MS m/z 338 [M+H]$^+$

Production of 24

To dichloromethane solution (20 ml) of 23 (2.00 g, 5.93 mmol), triethylamine (1.24 ml, 8.89 mmol) was added, and methane sulfonyl chloride (0.55 ml, 7.11 mmol) was dropped while cooling in ice with shaking, and stirred for 30 min at the same temperature. The reaction mixture was added cold water, and extracted with ethyl acetate. The extract was washed with water, dried, and evaporated to dryness under reduced pressure, and the residue was purified by silica gel column chromatography (solvent: ethyl acetate/n-hexane=2/1), to obtain 24 (2.46 g, 100%) of oily yellow substance.

APCI-MS m/z 416[M+H]$^+$

Production of 25

To 24 (2.46 g, 5.92 mmol), 1M tetrabutylammonium fluoride/tetrahydrofuran solution (23.7 ml, 23.7 mmol) was added, and stirred and 70° C. for 16 hours. The reaction mixture was allowed to stand to cool down, added cold water, and extracted with ethyl acetate. The extract was washed with water, dried, and evaporated to dryness under reduced pressure, and the residue was purified by silica gel column chromatography (solvent: ethyl acetate/n-hexane=9/1), to obtain 25 (0.89 g, 67%) of oily light yellow substance.

APCI-MS m/z 226 [M+H]$^+$

Production of 26

To dimethylformamide solution (10 ml) of 25 (0.75 g, 3.33 mmol), imidazole (0.27 g, 4.00 mmol) was added, and t-butyl dimethylsilylchloride (0.60 g 4.00 mmol) was further added while shaking at room temperature, and stirred for 16 hours at room temperature. The reaction mixture was added water, and extracted with ethyl acetate. The extract was washed, dried, and evaporated to dryness under reduced pressure, and the residue was purified by silica gel column chromatography (solvent: ethyl acetate/n-hexane=9/1 to 4/1), to obtain 26 (0.99 g, 88%) of oily colorless substance.

APCI-MS m/z 340[M+H]$^+$

Production of 27

To tetrahydrofuran solution (20 ml) of di-isopropylamine (0.62 ml, 4.37 mmol), 1.57 M n-butylithium/n-hexane solution (2.79 ml, 4.37 mmol) was dropped at −60° C. or below in argon atmosphere while stirring, and then, the mixture was slowly warmed up to 0° C. Then, tetrahydrofuran solution (10 ml) of 26 (0.99 g, 2.92 mmol) was dropped at −70° C. or below, and the mixture was stirred at −78° C. for 1 hr. Then, tetrahydrofuran solution (20 ml) of 3 (0.64 g, 3.21 mmol) was added all at once at the same temperature, and the mixture was stirred for 30 min at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate=1/1 to 1/2), to obtain 27 (1.26 g, 80%) of frothy yellow substance.

APCI-MS m/z 538[M+H]$^+$

Production of 28

To dichloromethane solution (20 ml) of 27 (1.26 g, 2.34 mmol), triethylamine (1.31 ml, 9.36 mmol) was added, and methane sulfonyl chloride (0.40 ml, 5.15 mmol) was dropped while cooling in ice with shaking, and stirred for 50 min at room temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=1/1), to obtain 28 (1.22 g, 100%) of oily yellow substance.

APCI-MS m/z 520[M+H]$^+$

Production of 29

To tetrahydrofuran solution (20 ml) of 28 (1.22 g, 2.35 mmol), 1M tetrabutylammonium fluoride/tetrahydrofuran solution (2.35 ml, 2.35 mmol) was added while shaking at room temperature, and refluxed for 30 min at room temperature. The reaction mixture was added water, and extracted with ethyl acetate. The extract was washed with water, dried, and evaporated to dryness under reduced pressure, and the residue was purified by silica gel column chromatography (solvent: ethyl acetate/n-hexane=1/1 to ethyl acetate) and recrystallized with ethyl acetate, to obtain 29 (0.44 g, 46×) of yellow crystal.

mp 152~153° C., $^1$H NMR (300 MHz, CDCl$_3$) δ 2.06 (t, J=5.3 Hz, D$_2$O, disappeared), 3.57 (4H, t, J=5.0 Hz), 3.83 (4H, t, J=5.0 Hz), 3.94 (2H, m), 4.50~4.57 (1H, m), 4.67 (1H, dd, J=46.8, 2.2 Hz), 4.69 (1H, dd, J=46.8, 2.3 Hz), 6.38 (1H, dd, J=15.8, 0.5 Hz), 6.98 (1H, dd, J=8.7, 2.3 Hz), 7.13 (1H, d, J=2.3 Hz), 7.37 (1H, t, J=0.6 Hz), 7.54 (1H, d, J=8.7 Hz), 7.69 (1H, dd, J=15.8, 0.8 Hz)

IR (Nujol) 3284, 1631 cm$^{-1}$, APCI-MS m/z 406[M+H]$^+$

THK-726 ((E)-6-[(3-hydroxy-2-tosyloxymethyl) propoxy]-2-[2-(2-morpholinothiazole-5-yl)ethenyl] benzoxazole: Production of (33)
[Formula 72]
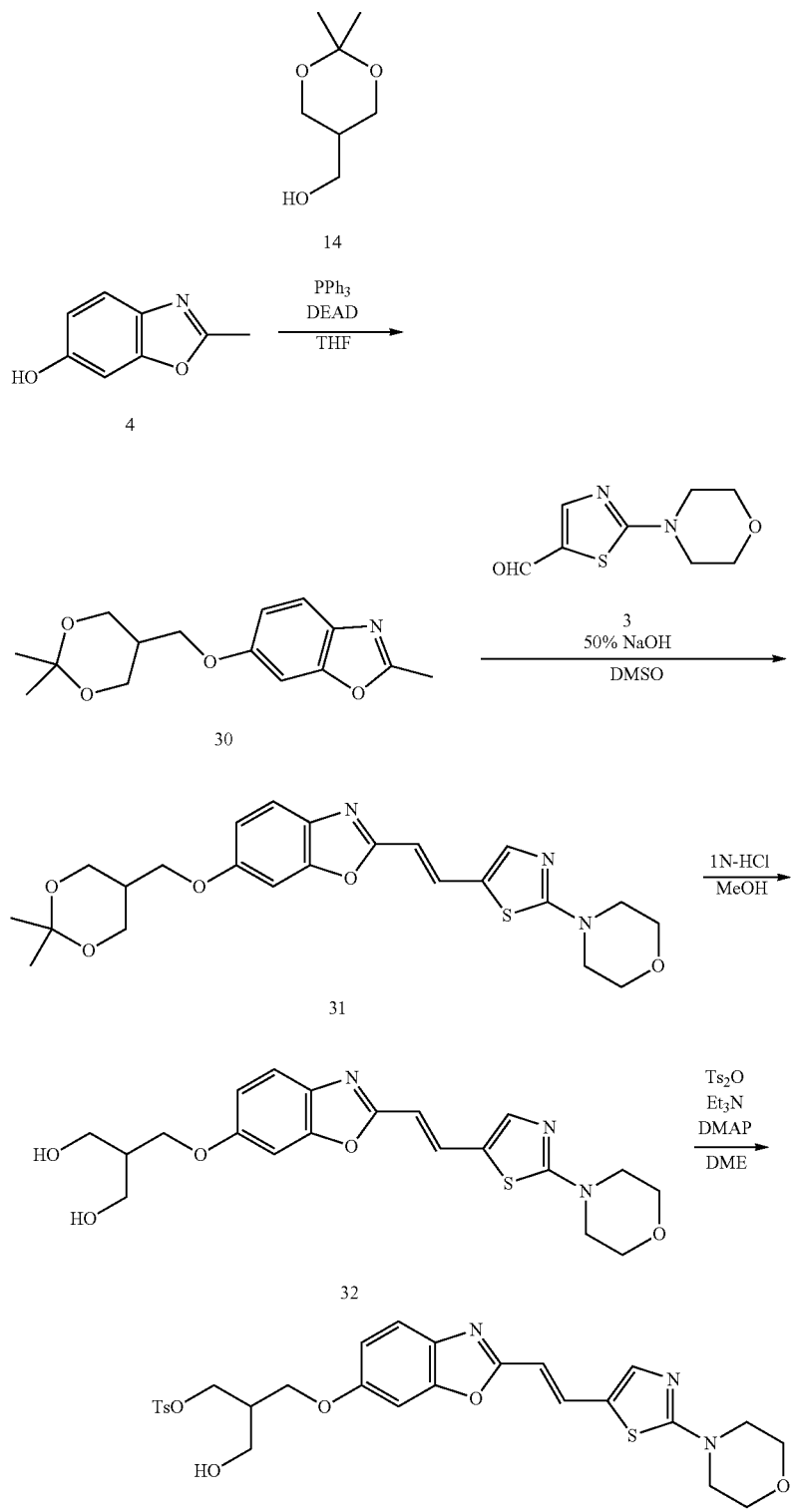

Production of 30

To tetrahydrofuran solution (40 ml) of 4 (1.74 g, 11.67 mmol), 14 (2.05 g, 14.00 mmol) and triphenylphosphine (3.68 g, 14.00 mmol) were added, and 40% diethyl azodicarboxylate/toluene solution (6.11 g, 14.00 mmol) was dropped while ice-cooling with shaking, and the mixture was stirred at room temperature for 3 days. The reaction mixture was evaporated to dryness under reduced pressure, and the residue was purified by silica gel column chromatography (solvent: ethyl acetate/n-hexane=4/1), to obtain 30 (2.80 g, 87%) of colorless solid substance.

APCI-MS m/z 278[M+H]$^+$

Production of 31

Dimethyl sulfoxide solution (20 ml) of 30 (2.06 g, 7.43 mmol) and 3 (1.47 g, 7.43 mmol) was added 50% (w/w) sodium hydroxide solution (2.8 ml) at room temperature while stirring, and stirred at room temperature for 1.5 hours. The reaction mixture was added water and filtered, and the filtrate was washed with water and dried, to obtain 31 (2.58 g, 76%) of yellow crystal.

mp 182.0~182.5° C., IR (Nujol) 1621 cm$^{-1}$
APCI-MS m/z 458[M+H]$^+$

Production of 32

To methanol suspension (40 ml) of 31 (2.58 g, 5.64 mmol), 1N hydrochloric acid (11.3 ml, 11.3 mmol) was added, and stirred for 1 hr at room temperature. The reaction mixture was evaporated to dryness under reduced pressure, and the residue was dissolved in water/ethyl acetate, and the pH was adjusted to 10 with potassium carbonate solution. The mixture was partitioned, and the organic layer was washed with water, dried, and evaporated to dryness under reduced pressure. The residue was recrystallized with ethyl acetate/n-hexane, to obtain 32 (2.35 g, 100%) of yellow crystal.

mp 162.0~163° C., APCI-MS m/z 418[M+H]$^+$

Production of 33

To ethylene glycol dimethyl ether suspension (220 ml) of 32 (1.85 g, 4.43 mmol), triethylamine (0.93 ml, 6.65 mmol), toluenesulfonate anhydride (1.45 g, 4.43 mmol), and dimethyl aminopyridine (0.054 g, 0.44 mmol) were added, and stirred at 70° C. for 16 hours. The reaction mixture was allowed to stand to cool down, diluted with ethyl acetate, washed with water, dried, and evaporated to dryness under reduced pressure. The residue was purified by silica gel column chromatography (solvent: ethyl acetate), and recrystallized with ethyl acetate, to obtain 33 (1.00 g, 39%) of yellow crystal.

mp 139~140° C., $^1$H NMR (300 MHz, CDCl$_3$) δ 1.84 (1H, t, J=5.6 Hz, D$_2$O, disappeared), 2.37 (3H, s), 2.43 (1H, m), 3.52~3.62 (4H, m), 3.78~3.87 (6H, m), 4.29 (2H, dd, J=5.2, 1.0 Hz), 6.38 (1H, dd, J=15.8, 0.6 Hz), 6.76 (1H, dd, J=8.8, 2.3 Hz), 6.90 (1H, d, J=2.3 Hz), 7.26 (2H, dd, J=8.6, 0.5 Hz), 7.37 (1H, t, J=0.6 Hz), 7.49 (1H, d, J=8.8 Hz), 7.68 (1H, dd, J=15.8, 0.8 Hz), 7.77 (2H, d, J=8.2 Hz)

IR (Nujol) 3490, 1633 cm$^{-1}$,
APCI-MS m/z 572 [M+H]$^+$

THK-703 [((E)-6-[(1-fluoromethyl-2-hydroxy)ethoxy]-2-[2-[2-methylaminothiazole-5-yl]ethenyl]benzoxazole: Production of (38)

[Formula 73]

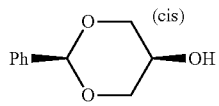

34

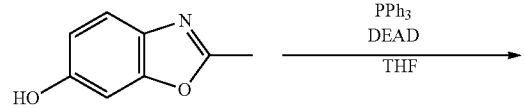

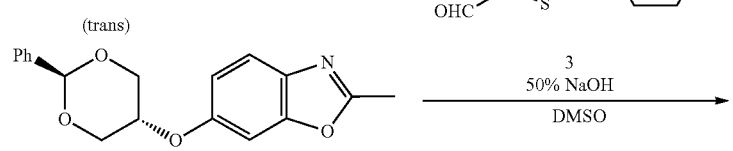

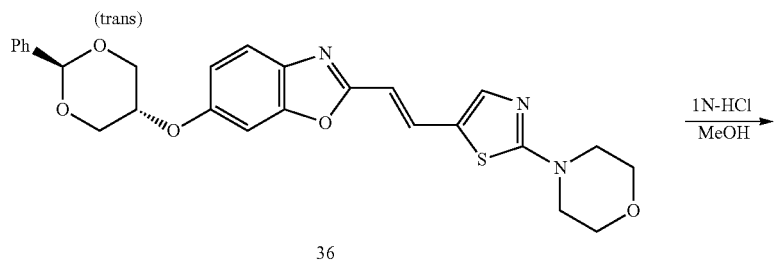

36

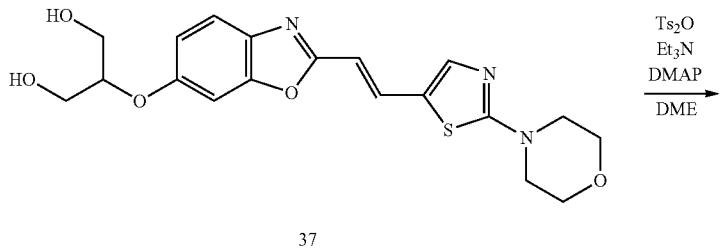

37

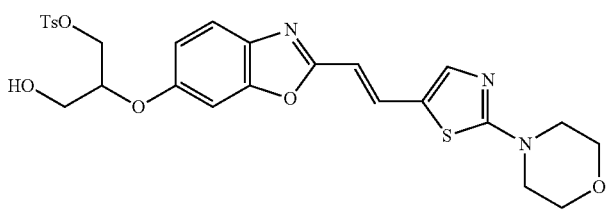

38

Production of 35

To tetrahydrofuran solution (30 ml) of 4 (1.00 g, 6.70 mmol), 34 (1.45 g, 8.05 mmol) and triphenylphosphine (2.11 g, 8.05 mmol) were added, and 40% diethyl azodicarboxylate/toluene solution (3.50 g, 8.05 mmol) was dropped while ice-cooling with shaking, and the mixture was stirred at room temperature for 4 days. Again, 34 (1.45 g, 8.05 mmol) and triphenylphosphine (2.11 g, 8.05 mmol) were added, and 40% diethyl azodicarboxylate/toluene solution (3.50 g, 8.05 mmol) was dropped while ice-cooling with shaking, and the mixture was stirred at room temperature for 1 day. The reaction mixture was evaporated to dryness under reduced pressure, and the residue was purified by silica gel column chromatography (solvent: ethyl acetate/n-hexane=4/1), to obtain 35 (1.71 g, 82%) of colorless solid substance.

APCI-MS m/z 312[M+H]$^+$

Production of 36

Dimethyl sulfoxide solution (8 ml) of 35 (0.80 g, 2.57 mmol) and 3 (0.51 g, 2.57 mmol) was added 50% (w/w) sodium hydroxide solution (0.96 ml) at room temperature while stirring, and stirred for 1 hr at room temperature. The reaction mixture was added water and filtered, and the filtrate was washed with water and dried. The resultant crude crystalline substance was recrystallized with ethyl acetate/n-hexane, to obtain 36 (0.74 g, 59%) of yellow crystal.

mp 202~203° C., IR (Nujol) 1637 cm$^{-1}$
APCI-MS m/z 492[M+H]$^+$

Production of 37

To methanol suspension (40 ml) of 36 (0.74 g, 1.51 mmol), 1N hydrochloric acid (3.01 ml, 3.01 mmol) was added, and stirred for 1 hr at 70° C. The reaction mixture was evaporated to dryness under reduced pressure, and the residue was heated in water (5 ml)/triethylamine (3 ml)/ethyl acetate to dissolve, purified by silica gel column chromatography (solvent: ethyl acetate), and recrystallized with ethyl acetate/n-hexane, to obtain 37 (0.52 g, 85%) of yellow crystal.

mp 172~174° C., APCI-MS m/z 404[M+H]$^+$

Production of 38

To ethylene glycol dimethyl ether suspension (200 ml) of 37 (1.37 g, 3.40 mmol), triethylamine toluene (0.71 ml, 5.10 mmol), toluenesulfonate anhydride (1.11 g, 3.40 mmol), and dimethyl aminopyridine (0.041 g, 0.34 mmol) were added, and stirred at 70° C. for 16 hours. The reaction mixture was allowed to stand to cool down, diluted with ethyl acetate, washed with water, dried, and evaporated to dryness under reduced pressure. The residue was purified by silica gel column chromatography (solvent: ethyl acetate), and recrystallized with ethyl acetate, to obtain 38 (0.42 g, 22%) of yellow crystal.

mp 184~185° C., $^1$H NMR (300 MHz, CDCl$_3$) δ 2.03 (t, J=6.4 Hz, D$_2$O, disappeared), 2.42 (3H, s), 3.55~3.63 (4H, m), 3.80~3.94 (6H, m), 4.28 (2H, d, J=4.9 Hz), 4.49~4.56 (1H, m), 6.38 (1H, dd, J=15.8, 0.6 Hz), 6.84 (1H, dd, J=8.8, 2.4 Hz), 7.00 (1H, d, J=2.4 Hz), 7.30 (2H, dd, J=8.6, 0.7 Hz), 7.37 (1H, t, J=0.7 Hz), 7.48 (1H, d, J=8.8 Hz), 7.69 (1H, dd, J=15.8, 0.6 Hz), 7.76 (2H, d, J=8.2 Hz)

IR (Nujol) 3320, 1733, 1632 cm$^{-1}$
APCI-MS m/z 558[M+H]$^+$

THK-762 ((E)-6-[(2-hydroxy-1-tosyloxymethyl)ethoxy]-2-[2-[2-dimethylaminothazole-5-yl]ethenyl]benzoxazole: Production of (44), and THK-763 ((E)-6-[(1-fluoromethyl-2-hydroxy)ethoxy-2-[2-[2-dimethylamino-thiazole-5-yl]ethenyl]benzoxazole: Production of (45)

[Formula 74]

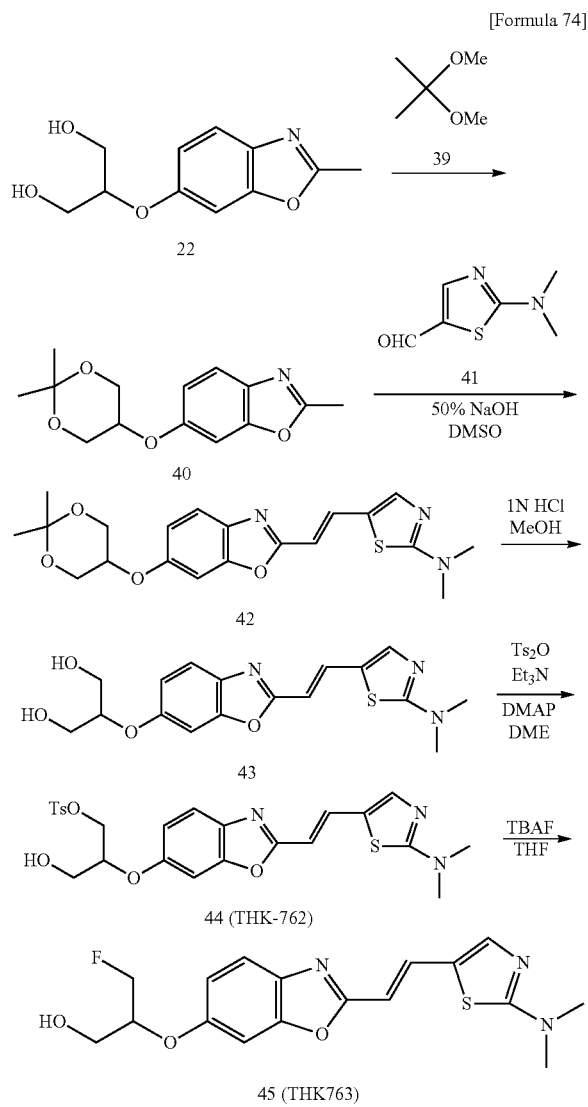

Production of 40

To toluene (100 ml), diol 22 (3.7 g, 16.57 mmol) was added, and 2,2-dimethoxy propane 39 (2.08 g, 20 mmol) and p-toluene sulfonic acid (100 mg) were further added and mixed, to react at 95° C. for 1 hr. After completion of the reaction, the mixture was diluted with ethyl acetate, and neutralized with saturated sodium bicarbonate solution. The organic layer was washed with saturated sodium chloride solution, and dried with anhydrous sodium sulfate. The solvent was evaporated to dryness, and the resultant crude product was solidified in hexane-diisopropyl ether, to obtain 40 (3.10, 71%) of colorless crystal.

mp 66-68° C.
IR (Nujol) 1621 cm$^{-1}$
APCI-MS m/z 264[M+H]$^+$
$^1$HNMR (CDCl$_3$) δ 1.460 (3H, s) 1.504 (3H, s) 2.60 (3H, s) 3.93 (2H, dd) 4.13 (2H, dd) 4.31-4.39 (1H, m) 6.91 (1H, dd, J=11.5 Hz, J=3.2 Hz) 7.03 (1H, d, J=3.2 Hz) 7.51 (1H, d, J=11.5 Hz)

Production of 42

To dimethyl sulfoxide solution (30 ml) of aldehyde 41 (2 g, 12.8 mmol) and benzoxazole derivative 40 (3.3 g, 12.8 mmol), 50% sodium hydroxide solution (5 ml) was dropped and stirred for 2 hours to react at room temperature. Yellow solid substance was precipitated out. The reaction solution was added 100 ml of water and stirred for 20 min. Then, the yellow solid substance was collected by filtering, washed with water, and dried under reduced pressure at 70° C., to obtain 42 (3.34 g, 65%).

mp 161~163° C.
IR (Nujol) 1635 cm$^{-1}$
APCI-MS m/z 402[M+H]$^+$

Production of 43

To methanol 120 ml, 42 (3.52 g, 8.89 mmol) was added, and 1 N hydrochloric acid (18 ml) was dropped at room temperature while stirring. The reaction mixture soon became homogeneous and clear. After reaction for 2 hours, the solvent was evaporated to dryness under reduced pressure, and the residue was dissolved in water. Upon alkalization of the solution with potassium carbonate solution, yellow precipitate was formed. The precipitate was filtered, washed with water, and dried under reduced pressure to obtain 43 (2.82 g, 87.5%).

mp 190~192° C.
IR (Nujol) 3236, 1629 cm$^{-1}$
APCI-MS m/z 362[M+H]$^+$

Production of 44

To anhydrous dimethoxyethane, (170 ml), diol 43 (3.0 g, 8.3 mmol) was added, and p-toluene sulfonic acid anhydride (2.71 g, 8.3 mmol) dimethyl aminopyrine (90 mg), and triethylamine (1.3 g) were further added and stirred, and heated in oil bath to react at 70 to 75° C. for 8 hours. The reaction mixture was allowed to stand to cool down, and filtered to remove the insolubles. The crude product obtained by condensing the filtrate was purified by silica gel column chromatography (solvent: n-hexane/ethyl acetate=1/2, 1/4, ethyl acetate, ethyl acetate/methanol=1/10), to obtain unreacted 43 (1.44 g, 48%) and 44 (1.64 g, 38%).

mp 201~202° C.
IR (Nujol) 3200, 1617 cm$^{-1}$
APCI-MS m/z: 516[M+H]$^+$
$^1$H-NMR (DMSO-d$_6$) δ 2.360 (3H, s) 3.131 (6H, s) 3.54-3.62 (2H, m) 4.18-4.33 (2H, m) 4.54 (1H, br) 5.06 (1H, t, J=5.5 Hz) 6.33 (1H, dd, J=15.7 Hz, J=0.54 Hz) 6.84 (1H, dd, J=8.8 Hz, 2.4 Hz) 7.187 (1H, d, J=2.4 Hz) 7.39 (2H, d) 7.48 (2H, d, J=8.8 Hz) 7.60 (1H, s) 7.72 (1H, d, J=8.3 Hz) 7.76 (1H, dd, J=–5.7 Hz, J=0.54 Hz)

Production of 45

Tosylate 44 (1.6 g, 3.1 mmol) was dissolved in tetrahydrofuran (15 ml), and 1M tetra-n-butylammonium fluoride/tetrahydrofuran solution (15 ml, 15 mmol) was further added while shaking, and refluxed for 2 hours under heating. Upon completion of the reaction, the reaction mixture was diluted with ethyl acetate, and washed with water. The organic layer was washed with saturated sodium chloride solution, and dried with magnesium sulfate anhydride. After evaporation of the solvent, the obtained crude product was purified by separating on silica gel column chromatography (solvent: n-hexane/acetone=5/4), to obtain 45 (660 mg). The product was recrystallized with ethyl acetate to obtain 45 (490 mg, 44%) of light yellow crystal.

mp 164-165° C.

IR (Nujol) 3173, 1633 cm$^{-1}$

APCI-MS m/z 364[M+H]$^+$ $^1$H-NMR (DMSO-d$_6$) δ 3.127 (6H, s) 3.61-3.67 (2H, m) 4.54-4.82 (3H, s) 5.06 (1H, t, J=5.7 Hz) 6.33 (1H, dd, J=15.75 Hz, J=0.54 Hz) 6.99 (1H, dd, J=8.8 Hz, J=2.4 Hz) 7.36 (1H, d, J=2.4 Hz) 7.53 (1H, d, J=8.6 Hz) 7.59 (1H, br, s) 7.75 (1H, dd, J=15.75 Hz, J=0.54 Hz) 7.53 (1H, d, J=8.6 Hz) 7.59 (1H, br, s) 7.75 (1H, dd, J=15.75 Hz, J=0.54 Hz)

THK-761 ((E)-6-[(1-fluoromethyl-2-hydroxy)ethoxy]-2-[2-[2-methylaminothiazole-5-yl-ethyl]benzoxazole: Production of (53)

[Formula 75]

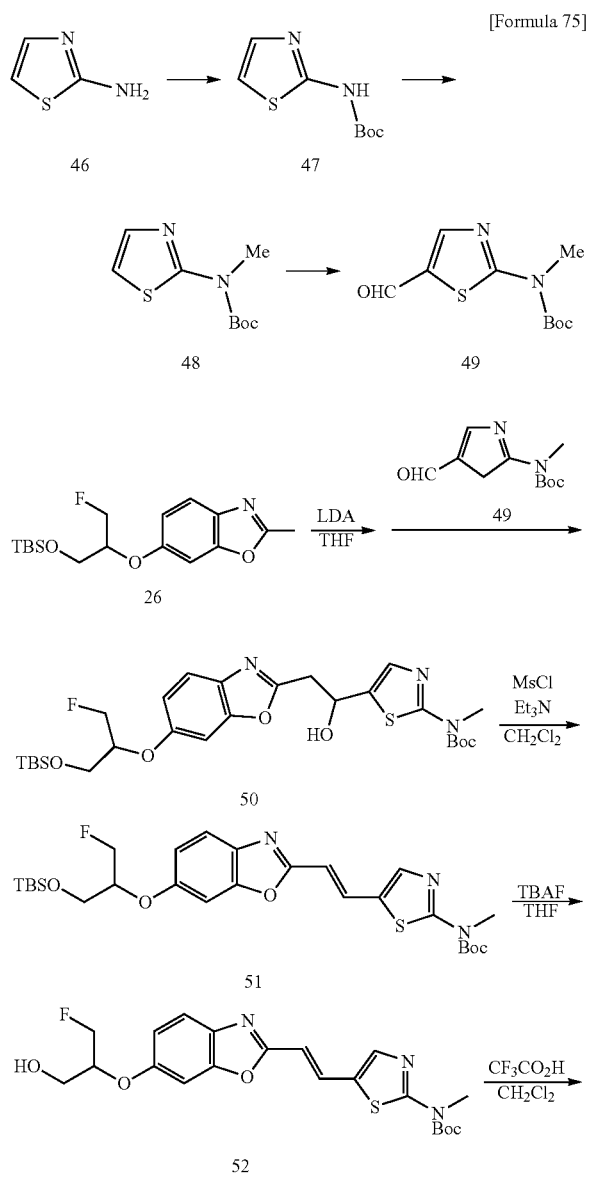

-continued

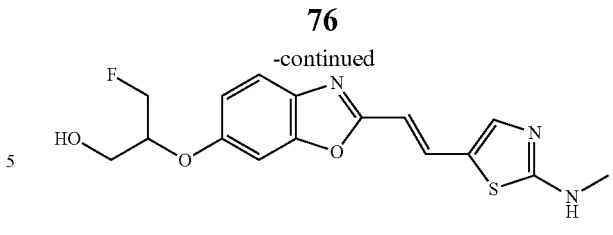

53

Production of 47

To tetrahydrofuran solution (20 ml) of 46 (10.0 g, 99.9 mmol), (Boc)2O (27.5 ml, 119.9 mmol) was added, and stirred at room temperature for 16 hours. The solvent of the reaction mixture was evaporated to dryness under reduced pressure, and the obtained crystal was pulverized in n-hexane, to obtain 47 (19.25 g, 96%) of colorless crystal.

mp 181.5~182.5° C., $^1$H NMR (300 MHz, CDCl$_3$) δ 1.60 (9H, s), 6.88 (1H, d, J=3.7 Hz), 7.38 (1H, d, J=3.7 Hz), 11.9 (1H, s)

IR (Nujol) 1713 cm$^{-1}$, APCI-MS m/z 201[M+H]$^+$

Production of 48

To tetrahydrofuran solution (100 ml) of 47 (10.0 g, 49.9 mmol), t-butoxy potassium (6.72 g, 59.9 mmol) was added at 0° C. while stirring, stirred for 10 min at the same temperature, added iodomethane (4.66 ml, 74.9 mmol), and stirred for 16 hours at room temperature. The insolubles were removed by filtering the reaction mixture, and the filtrate was evaporated to dryness under reduced pressure. The residue was purified by silica gel column chromatography (solvent: n-hexane/ethyl acetate=9/1), to obtain 48 (6.53 g, 61%) of colorless solid substance.

mp 51~52° C., $^1$H NMR (500 MHz, DMSO-D$_6$) δ 1.53 (9H, s), 3.47 (3H, s), 7.25 (1H, d, J=3.5 Hz), 7.45 (1H, d, J=3.51 Hz), IR (Neat) 1734 cm$^{-1}$, APCI-MS m/z 215[M+H]$^+$ Production of 49

To tetrahydrofuran solution (50 ml) of di-isopropylamine (5.12 ml, 36.4 mmol), 1.58 M n-butyllithium/n-hexane solution (23.0 ml, 36.4 mmol) was dropped at −60° C. or below in argon atmosphere, and then, the mixture was slowly warmed up to 0° C. Then, tetrahydrofuran solution (10 ml) of 48 (7.08 g, 33.1 mmol) was dropped at −70° C. or below, and the mixture was stirred at −78° C. for 1 hr. Then, tetrahydrofuran solution (10 ml) of N-formylmorpholine (4.98 ml, 49.6 mmol) was added all at once at the same temperature, and the mixture was stirred for 30 min at the same temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=4/1), to obtain 49 (6.40 g, 80%) of yellow solid substance.

mp 80~81° C., $^1$H NMR (500 MHz, DMSO-D$_6$) δ 1.55 (9H, s), 3.52 (3H, s), 8.38 (1H, s), 9.90 (1H, s) IR (Nujol) 1714, 1659 cm$^{-1}$, APCI-MS m/z 243[M+H]$^+$ Production of 50

To tetrahydrofuran solution (30 ml) of di-isopropylamine (0.90 ml, 6.36 mmol), 1.57 M n-butyllithium/n-hexane solution (4.05 ml, 6.36 mmol) was dropped at −60° C. or below in argon atmosphere while stirring, and then, the mixture was slowly warmed up to 0° C. Then, tetrahydrofuran solution (10 ml) of 26 (1.44 g, 4.24 mmol) was dropped at −70° C. or below, and the mixture was stirred at 78° C. for 1 hr. Then, tetrahydrofuran solution (20 ml) of 49 (1.23 ml, 5.09 mmol) was added all at once at the same temperature, and the mixture was stirred for 30 min at the same temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=2/1), to obtain 50 (2.06 g, 84%) of viscous light yellow substance.

APCI-MS m/z 582[M+H]+

Production of 51

To dichloromethane solution (20 ml) of 50 (2.06 g, 3.54 mmol), triethylamine (1.98 ml, 14.16 mmol) was added, and methane sulfonyl chloride (0.60 ml, 7.79 mmol) was dropped while cooling in ice with shaking, and stirred for 1 hr at room temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=4/1), to obtain 51 (1.85 g, 93%) of light yellow solid substance.

APCI-MS m/z 564[M+H]+

Production of 52

To tetrahydrofuran solution (20 ml) of 51 (1.85 g, 3.28 mmol), 1M tetrabutylammonium fluoride/tetrahydrofuran solution (3.28 ml, 3.28 mmol) was dropped while ice-cooling with shaking, and stirred for 1 hr at room temperature. The reaction mixture was added cold water, and extracted with ethyl acetate. The extract was washed with water, dried, and evaporated to dryness under reduced pressure, and the residue was purified by silica gel column chromatography (solvent: ethyl acetate/n-hexane 2/1 to 1/1), and recrystallized with ethyl acetate, to obtain 52 (1.02 g, 69%) of yellow crystal.

mp 181.0~181.5° C., IR (Nujol) 3352, 1700, 1631 cm$^{-1}$

APCI-MS m/z 450[M+H]+

Production of 53

To dichloromethane suspension (18 ml) of 52 (1.13 g, 2.51 mmol), trifluoroacetic acid (12 ml) was dropped while ice-cooling with shaking, and stirred at room temperature for 1 hr and 20 min. The reaction mixture was added cold water, diluted with ethyl acetate, and added potassium carbonate to adjust the pH to 9. The mixture was partitioned, and the extract was washed with water, dried, and evaporated to dryness under reduced pressure, and the residue was purified by silica gel column chromatography (solvent: ethyl acetate), to obtain 53 (0.72 g, 82%) of yellow crystal.

mp 178~179° C., $^1$H NMR (300 MHz, CDCl$_3$) δ 3.06 (3H, s), 3.89~4.01 (2H, m), 4.50~4.78 (3H, m), 5.53 (1H, m, D$_2$O, disappeared), 6.38 (1H, d, J=15.7 Hz), 6.99 (1H, dd, J=8.7, 2.4 Hz), 7.14 (1H, d, J=2.4 Hz), 7.32 (1H, s), 7.55 (1H, d, J=8.7 Hz), 7.69 (1H, d, J=15.7 Hz)

IR (Nujol) 3231, 1631 cm$^{-1}$, APCI-MS m/z 350[M+H]+

THK-760 ((E)-6-[(2-hydroxy-1-tosyloxymethyl) ethoxy]-2-[2-[2-methylaminothiazole-5-yl]ethenyl] benzoxazol: Production of (59)

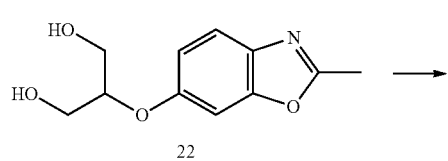

[Formula 76]

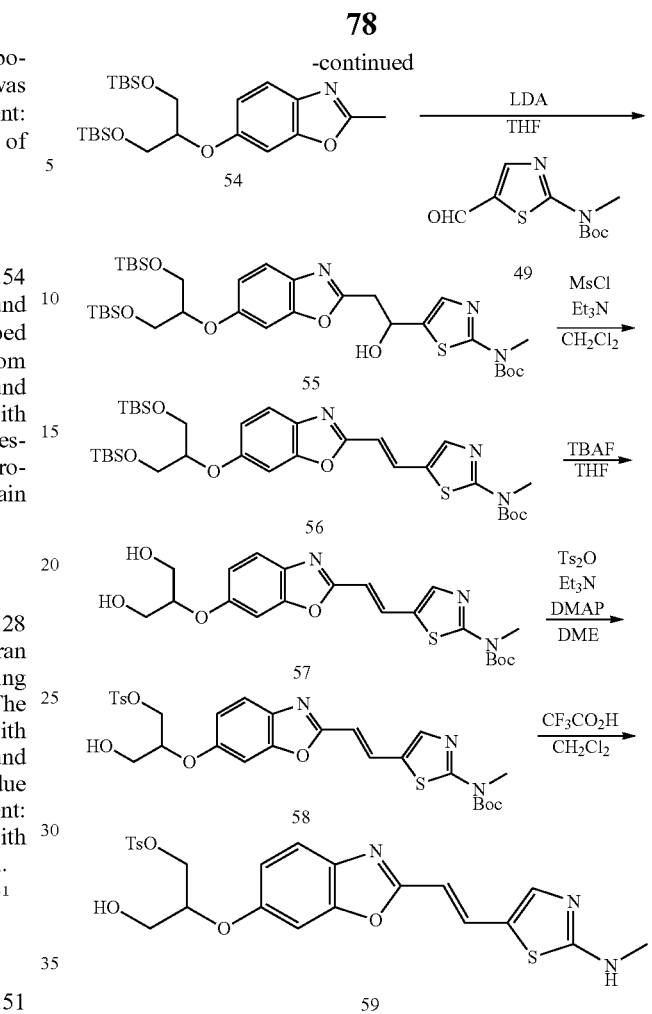

Production of 54

To dimethylformamide solution (50 ml) of 22 (5.51 g, 24.68 mmol), Imidazole (4.03 g, 59.24 mmol) was added, and t-butyl dimethylsilylchloride (8.93 g 59.24 mmol) was further added while shaking at room temperature, and stirred for 2 hours at room temperature. The reaction mixture was added water, and extracted with ethyl acetate. The extract was washed with water, dried, and evaporated to dryness under reduced pressure, and the residue was purified by silica gel column chromatography (solvent: ethyl acetate/n-hexane=50/1 to 20/1), to obtain 54 (11.2 g, 100%) of oily colorless substance.

Production of 55

To tetrahydrofuran solution (50 ml) of di-isopropylamine (2.38 ml, 16.91 mmol), 1.59 M n-butylithium/n-hexane solution (10.63 ml, 16.91 mmol) was dropped at −60° C. or below in argon atmosphere while stirring, and then, the mixture was slowly warmed up to 0° C. Then, tetrahydrofuran solution (30 ml) of 54 (5.09 g, 11.27 mmol) was dropped at −70° C. or below, and the mixture was stirred at −78° C. for 1 hr. Then, tetrahydrofuran solution (30 ml) of 49 (2.73 g, 11.27 mmol) was added all at once at the same temperature, and the mixture was stirred for 30 min at the same temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=4/1 to 3/1), to obtain 55 (6.90 g, 88%) of viscous yellow substance.

APCI-MS m/z 695[M+H]+

Production of 56

To dichloromethane solution (70 ml) of 55 (6.90 g, 9.94 mmol), triethylamine (5.55 ml, 39.8 mmol) was added, and methane sulfonyl chloride (1.69 ml, 21.9 mmol) was dropped while cooling in ice with shaking, and stirred for 50 min at room temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=9/1), to obtain 55 (6.20 g, 92%) of light yellow solid substance.

APCI-MS m/z 677 [M+H]$^+$

Production of 57

To tetrahydrofuran solution (600 ml) of 56 (6.20 g, 9.17 mmol), 1M tetrabutylammonium fluoride/tetrahydrofuran solution (18.34 ml, 18.34 mmol) was added while shaking at room temperature, and refluxed for 1 hr at room temperature. The reaction mixture was added water, and extracted with ethyl acetate. The extract was washed with water, dried, and evaporated to dryness under reduced pressure, and the residue was purified by silica gel column chromatography (solvent: ethyl acetate/n-hexane=1/1 to ethyl acetate), and recrystallized with ethyl acetate to obtain 57 (3.21 g, 78%) of yellow crystal.

mp 180 to 181° C., APCI-MS m/z 448 [M+H]$^+$

Production of 58

To ethylene glycol dimethyl ether suspension (200 ml) of 57 (3.21 g, 7.17 mmol), triethylamine (1.50 ml, 10.8 mmol), toluenesulfonate anhydride (2.34 g, 7.17 mmol), and dimethyl aminopyridine (0.088 g, 0.72 mmol) were added, and refluxed for 24 hours. The reaction mixture was allowed to stand to cool down, diluted with ethyl acetate, washed with water, dried, and evaporated to dryness under reduced pressure. The residue was purified by silica gel column chromatography (solvent: ethyl acetate/n-hexane=2/1 to ethyl acetate), and recrystallized with ethyl acetate, to obtain 58 (1.65 g, 38%) of yellow crystal.

mp 108 to 109° C., APCI-MS m/Z 602 [M+H]$^+$

Production of 59

To dichloromethane suspension (18 ml) of 58 (0.78 g, 1.30 mmol), trifluoroacetic acid (12 ml) was dropped while ice-cooling with shaking, and stirred at room temperature for 1 hr and 15 min. The reaction mixture was added cold water, diluted with ethyl acetate, and added potassium carbonate to adjust the pH to 9. The mixture was partitioned, and the extract was washed with water, dried, and evaporated to dryness under reduced pressure, and the residue was purified by silica gel column chromatography (solvent: ethyl acetate), and recrystallized with ethyl acetate, to obtain 59 (0.52 g, 79%) of yellow crystal.

mp 174.5~175.5° C., $^1$H NMR (300 MHz, CDCl$_3$) δ 2.36 (3H, s), 2.89 (3H, d, J=4.6 Hz, D$_2$O, s), 3.53~3.64 (2H, m), 4.19~4.33 (2H, m), 4.54 (1H, m), 5.06 (1H, t, J=5.6 Hz, D$_2$O, disappeared), 6.29 (1H, d, J=15.8 Hz), 6.84 (1H, dd, J=8.7, 2.3 Hz), 7.18 (1H, d, J=2.3 Hz), 7.39 (2H, d, J=8.1 Hz), 7.48 (1H, d, J=8.7 Hz), 7.52 (1H, s), 7.73 (2H, d, J=8.1 Hz) 7.75 (1H, d, J=15.8 Hz), 8.27 (1H, q, J=4.6 Hz, D$_2$O, disappeared), IR (Nujol) 3227, 1634, 1621 cm$^{-1}$ APCI-MS m/z 502[M+H]$^+$ THK-711 ((E)-6-[(2-fluoromethyl-3-hydroxy)propoxy]-2-[2-(2-piperidineothiazole-5-yl)ethenyl]benzoxazole: Production of (65)

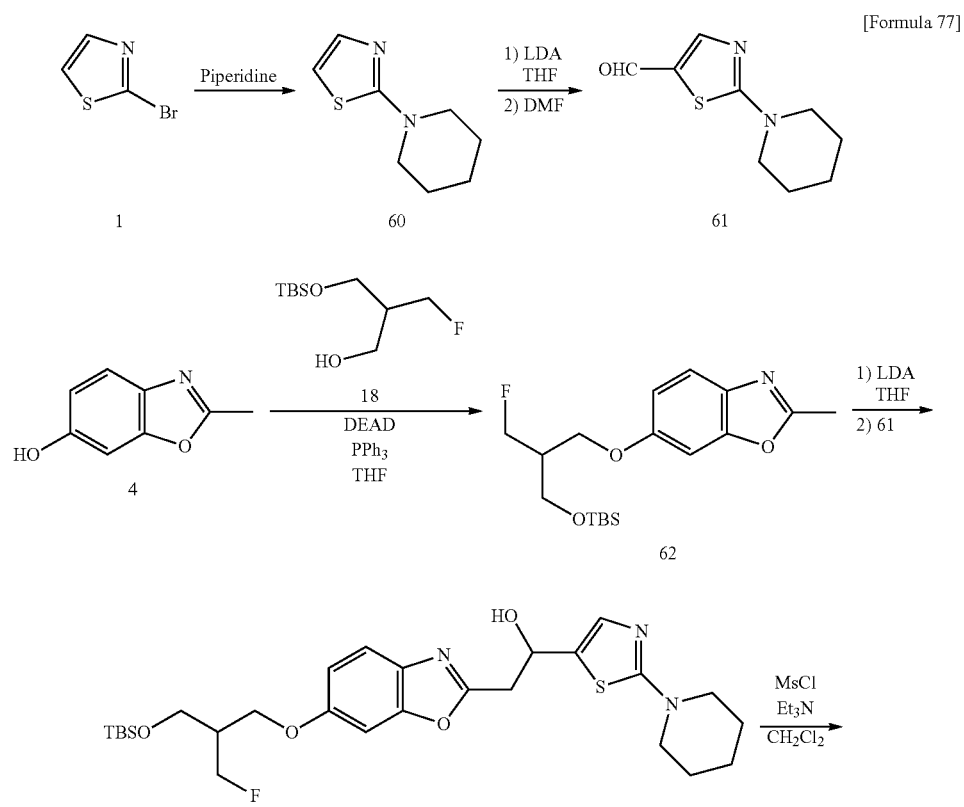

[Formula 77]

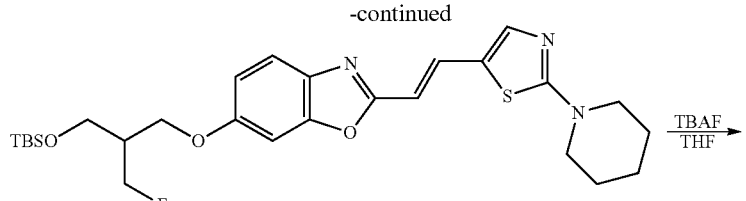

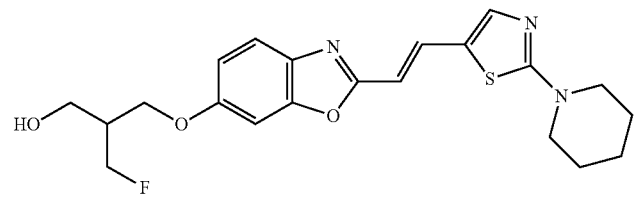

Production of 60

Piperidine solution (70 ml) of 1 (15.0 g 91.45 mmol) was stirred at 100° C. for 2.5 hours. The reaction solution was allowed to stand to cool down and filtered to remove the insolubles, and the filtrate was evaporated to dryness under reduced pressure. The residue was purified by silica gel column chromatography (solvent: n-hexane/ethyl acetate=9/1), to obtain 60 (15.39 g, 100%) of oily colorless substance.

APCI-MS m/z 169[M+H]$^+$

Production of 61

To tetrahydrofuran solution (200 ml) of di-isopropylamine (15.47 ml, 109.7 mmol), 1.59 M n-butylithium/n-hexane solution (69.0 ml, 109.7 mmol) was dropped at −60° C. or below in argon atmosphere while stirring, and then, the mixture was slowly warmed up to 0° C. Then, tetrahydrofuran solution (40 ml) of 60 (15.39 g, 91.45 mmol) was dropped at −70° C. or below, and the mixture was stirred at −78° C. for 1 hr. Then, dimethylformamide (14.15 ml, 182.9 mmol) was added all at once at the same temperature, and the mixture was stirred for 40 min at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate=4/1), to obtain 61 (17.55 g, 98%) of light yellow substance.

mp 58~59° C., APCI-MS m/z 197[M+H]$^+$

Production of 62

To tetrahydrofuran solution (20 ml) of 4 (0.53 g, 3.55 mmol), 18 (0.79 g, 3.55 mmol) and triphenylphosphine (0.93 g, 3.55 mmol) were added, and 40% diethyl azodicarboxylate/toluene solution (1.55 g, 3.55 mmol) was dropped while ice-cooling with shaking, and the mixture was stirred at room temperature for 3 days. The reaction mixture was evaporated to dryness under reduced pressure, and the residue was purified by silica gel column chromatography (solvent: n-hexane/ethyl acetate=4/1), to obtain 62 (1.12 g, 89%) of oily light yellow substance.

APCI-MS m/z 354[M+H]$^+$

Production of 63

To tetrahydrofuran solution (20 ml) of di-isopropylamine (0.67 ml, 4.75 mmol), 1.57 M n-butylithium/n-hexane solution (3.03 ml, 4.75 mmol) was dropped at −60° C. or below in argon atmosphere while stirring, and then, the mixture was slowly warmed up to 0° C. Then, tetrahydrofuran solution (10 ml) of 62 (1.12 g, 3.17 mmol) was dropped at −70° C. or below, and the mixture was stirred at −78° C. for 1 hr. Then, tetrahydrofuran solution (10 ml) of 61 (0.75 g, 3.80 mmol) was added all at once at the same temperature, and the mixture was stirred for 30 min at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate=1.5/1), to obtain 63 (1.50 g, 86%) of viscous yellow substance.

APCI-MS m/z 550[M+H]$^+$

Production of 64

To dichloromethane solution (30 ml) of 63 (1.50 g, 2.73 mmol), triethylamine (1.52 ml, 10.9 mmol) was added, and methane sulfonyl chloride (0.46 ml, 6.00 mmol) was dropped while cooling in ice with shaking, and stirred for 20 min at room temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=4/1), to obtain 68 (1.31 g, 90%) of yellow solid substance.

mp 96~98° C., IR (Nujol) 1628 cm$^{-1}$

APCI-MS m/z 532 [M+H]$^+$

Production of 65

To tetrahydrofuran solution (20 ml) of 64 (1.31 g, 2.46 mmol), 1M tetrabutylammonium fluoride/tetrahydrofuran solution (2.46 ml, 2.46 mmol) was added while shaking at room temperature, and refluxed for 40 min at room temperature. The reaction mixture was added water, and extracted with ethyl acetate. The extract was washed with water, dried, and evaporated to dryness under reduced pressure, and the residue was purified by silica gel column chromatography (solvent: ethyl acetate/n-hexane 2/1 to 1/1) and recrystallized with ethyl acetate, to obtain 65 (0.68 g, 66%) of yellow crystal.

mp 169~170° C., $^1$H NMR (300 MHz, CDCl$_3$) δ 1.72 (6H, s), 2.38~2.53 (1H, m), 3.62 (4H, s), 3.91 (2H, d, J=5.7 Hz), 4.16 (2H, dd, J=5.8, 0.5 Hz), 4.71 (2H, dd, J=47.0, 5.3 Hz), 6.35 (1H, d, J=15.7 Hz), 6.91 (1H, dd, J=8.7, 2.3 Hz), 7.03 (1H, d, J=2.3 Hz), 7.35 (1H, s), 7.52 (1H, d, J=8.7 Hz), 7.64 (1H, dd, J=15.7 Hz)

IR (Nujol) 3343, 1623 cm$^{-1}$, APCI-MS m/z 418[M+H]$^+$

THK-710 ((E)-6-[(3-hydroxy-2-tosyloxymethyl)propoxy]-2-[2-(2-piperidineothiazole-5-yl)ethenyl]benzoxazole: Production of (68)

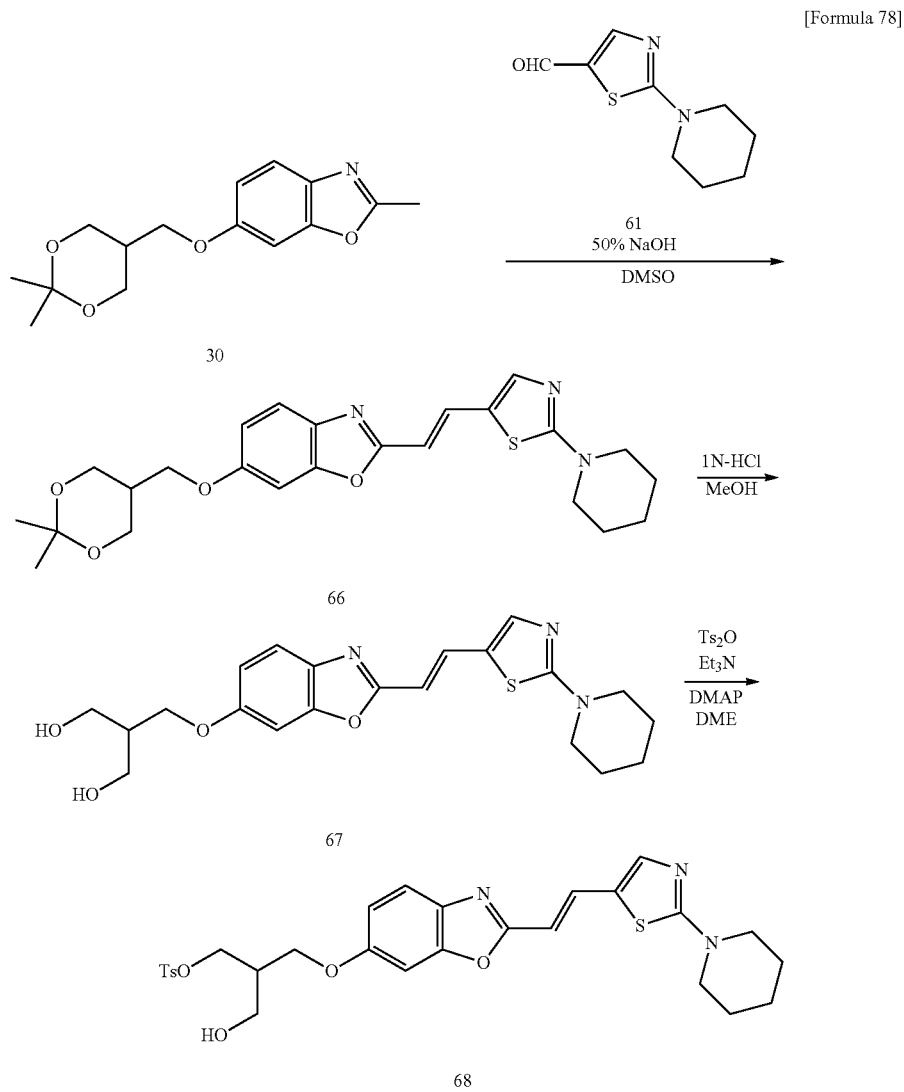

Production of 66

Dimethyl sulfoxide solution (14.2 ml) of 30 (1.50 g, 5.41 mmol) and 61 (1.06 g, 5.41 mmol) was added 50% (w/w) sodium hydroxide solution (2.03 ml) at room temperature while stirring, and further stirred for 1.5 hours at room temperature. The reaction mixture was added water and filtered, and the filtrate was washed with water, and dried. The crude crystal was recrystallized with ethyl acetate to obtain 66 (1.26 g, 51%) of yellow crystal.

mp 151.0~151.5° C., IR (Nujol) 1601 cm$^{-1}$
APCI-MS m/z 456[M+H]$^+$

Production of 67

To methanol suspension (30 ml) of 66 (1.26 g, 2.77 mmol), 1N hydrochloric acid (5.53 ml, 5.53 mmol) was added, and stirred for 1 hr at room temperature. The reaction mixture was evaporated to dryness under reduced pressure, and the residue was dissolved in water/ethyl acetate, and the pH was adjusted to 10 with potassium carbonate solution. The mixture was partitioned, and the organic layer was washed with water, dried, and evaporated to dryness under reduced pressure. The residue was recrystallized with ethyl acetate, to obtain 67 (1.09 g, 95%) of yellow crystal.

mp 170~171° C., APCI-MS m/z 416[M+H]$^+$

Production of 68

To ethylene glycol dimethyl ether suspension (100 ml) of 67 (1.09 go 2.62 mmol), triethylamine (0.55 ml, 3.93 mmol), toluenesulfonate anhydride (0.86 g, 2.62 mmol), and dimethyl aminopyridine (0.032 g, 0.26 mmol) were added, and stirred at 70° C. for 16 hours. The reaction mixture was allowed to stand to cool down, diluted with ethyl acetate, washed with water, dried, and evaporated to dryness under reduced pressure. The residue was purified by silica gel column chromatography (solvent: ethyl acetate/n-hexane=1/2 to ethyl acetate), and recrystallized with ethyl acetate, to obtain 68 (0.76 g, 51%) of yellow crystal.

mp 149~150° C., $^1$H NMR (300 MHz, CDCl$_3$) δ 1.72 (6H, m), 2.37 (3H, s), 2.41 (1H, m), 3.63 (4H, m), 3.83 (2H, d,

J=5.7 Hz), 4.02 (2H, dd, J=5.8, 4.3 Hz), 6.35 (1H, d, J=15.7 Hz), 6.77 (1H, dd, J=8.8, 2.4 Hz), 6.90 (1H, d, J=2.4 Hz), 7.24~7.28 (2H, m), 7.36 (1H, s), 7.49 (1H, d, J=8.8 Hz), 7.64 (1H, d, J=15.7 Hz), 7.66~7.79 (2H, m)

IR (Nujol) 3298, 1630 cm$^{-1}$, APCI-MS m/z 570[M+H]$^+$

THK-713 ((E)-6-[(1-fluoromethyl)-2-hydroxy)ethoxy]-2-[2-(2-piperidinothiazole-5-yl)ethenyl]benzoxazole: Production of (72), and THK-712 ((E)-6-[(2-hydroxy-1-tosyloxymethyl)ethoxy-2-[2-(2-piperidinothiazole-5-yl)ethenyl]benzoxazole: Production of (71)

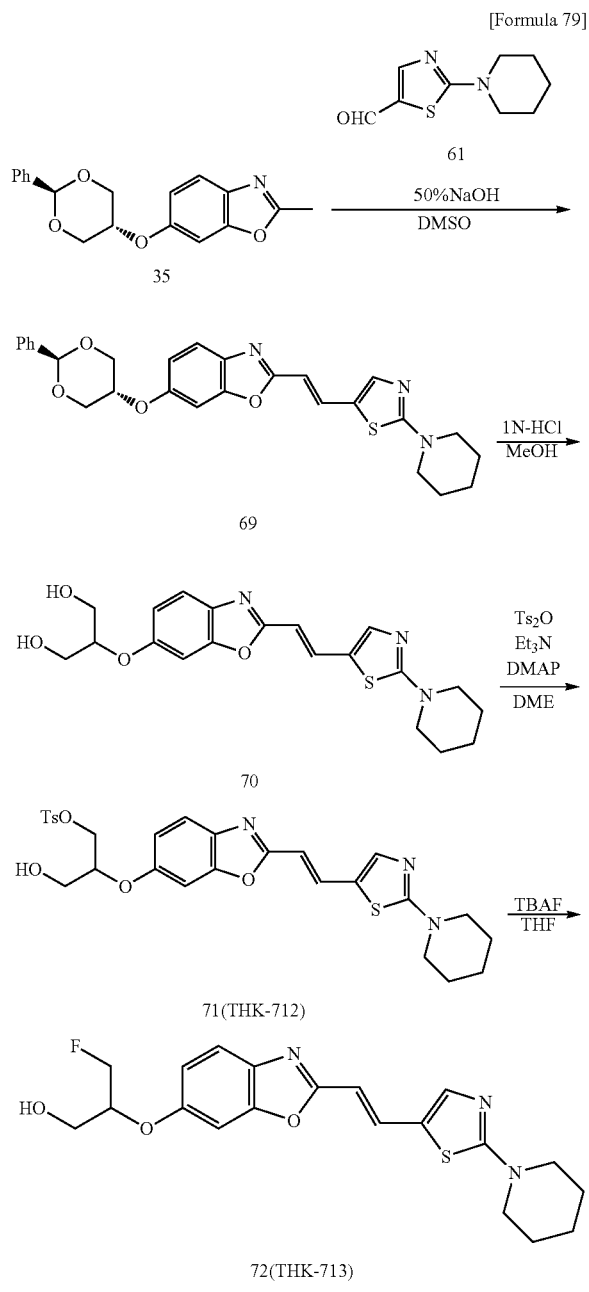

[Formula 79]

Production of 69

To dimethyl sulfoxide solution (36 ml) of 35 (3.00 g, 9.64 mmol) and 61 (3.28 g, 16.71 mmol), 50% (w/w) sodium hydroxide solution (5.23 ml) was added at room temperature while starring and stirred for 1.5 hours at room temperature. The reaction solution was added water and filtered. The filtrate was washed with water, and dried, and the crude crystal was recrystallized with ethyl acetate to obtain 69 (3.55 g, 75%) of yellow crystal.

mp 207~208° C., IR (Nujol) 1631 cm$^{-1}$

APCI-MS m/z 490[M+H]$^+$

Production of 70

To methanol suspension (60 ml) of 69 (3.55 g, 7.25 mmol), 1 N hydrochloric acid (14.5 ml, 14.5 mmol) was dropped and stirred at 70° C. for 1 hr while stirring. The reaction mixture was evaporated to dryness under reduced pressure, and the residue was dissolved in triethylamine (3 ml), water (5 ml), and ethyl acetate. The solution was purified by silica gel column chromatography (solvent: ethyl acetate) for purification and recrystallization was made with ethyl acetate, to obtain 70 (2.57 g, 88%) of yellow crystal.

mp 161.0~161.5° C., IR (Nujol) 3332, 1632 cm$^{-1}$

APCI-MS m/z 402[M+H]$^+$

Production of 71

To ethylene glycol dimethyl ether suspension (100 ml) of 70 (2.57 g, 6.40 mmol), triethylamine (1.34 ml, 9.60 mmol), toluenesulfonate anhydride (2.09 g, 6.40 mmol), and dimethyl aminopyridine (0.078 g, 0.64 mmol) were added, and stirred at 70° C. for 24 hours. The reaction solvent was evaporated to dryness under reduced pressure, and the residue was purified by silica gel column chromatography (solvent: ethyl acetate/n-hexane=1/1 to ethyl acetate), and recrystallized with ethyl acetate, to obtain 71 (1.47 g, 41%) of yellow crystal.

mp 170~172° C., $^1$H NMR (300 MHz, CDCl$_3$) δ 1.72 (6H, m), 2.15 (1H, m, D$_2$O, disappeared), 2.42 (3H, s), 3.62 (4H, m), 3.81~3.95 (2H, m), 4.28 (2H, d, J=5.1 Hz), 4.48~4.56 (1H, m), 6.34 (1H, d, J=15.7 Hz), 6.84 (1H, dd, J=8.7, 2.2 Hz), 7.00 (1H, d, J=2.2 Hz), 7.30 (1H, d, J=8.7 Hz), 7.36 (1H, s), 7.48 (2H, d, J=8.5 Hz), 7.66 (1H, d, J=15.7 Hz), 7.76 (2H, d, J=8.5 Hz)

IR (Nujol) 3332, 1632 cm$^{-1}$, APCI-MS m/z 556[M+H]$^+$

Production of 72

To tetrahydrofuran suspension (10 ml) of 71 (1.05 g 1.89 mmol), 1M tetrabutylammonium fluoride/tetrahydrofuran solution (9.45 ml, 9.45 mmol) was added, and refluxed for 7.5 hours. The reaction mixture was allowed to stand to cool down, added cold water, and extracted with ethyl acetate. The extract was washed with water, dried, and evaporated to dryness under reduced pressure, and the residue was purified by silica gel column chromatography (solvent: ethyl acetate/n-hexane=1/1), and recrystallized with ethyl acetate/n-hexane, to obtain 72 (0.35 g, 46%) of yellow crystal.

mp 146.5~147.5° C., $^1$H NMR (300 MHz, CDCl$_3$) δ 1.71 (6H, m), 2.35 (1H, m, D$_2$O, disappeared), 3.60 (4H, m), 3.95 (2H, m) 4.55 (1H, m), 4.68 (2H, ddd, J=47.7, 4.6, 2.6 Hz), 6.33 (1H, d, J=15.7 Hz), 6.98 (1H, dd, J=8.7, 2.3 Hz), 7.13 (1H, d, J=2.3 Hz), 7.34 (1H, s), 7.53 (1H, d, J=8.7 Hz), 7.66 (1H, d, J=15.7 Hz)

IR (Nujol) 3323, 1625 cm$^{-1}$, APCI-MS m/z 404[M+H]$^+$

THK-707 ((E)-6-[(1-fluoromethyl-2-hydroxy) ethoxy]-2-[2-[2-(4-methylpiperazine-1-yl)thiazole-5-yl]ethenyl]benzoxazole: Production of (77)

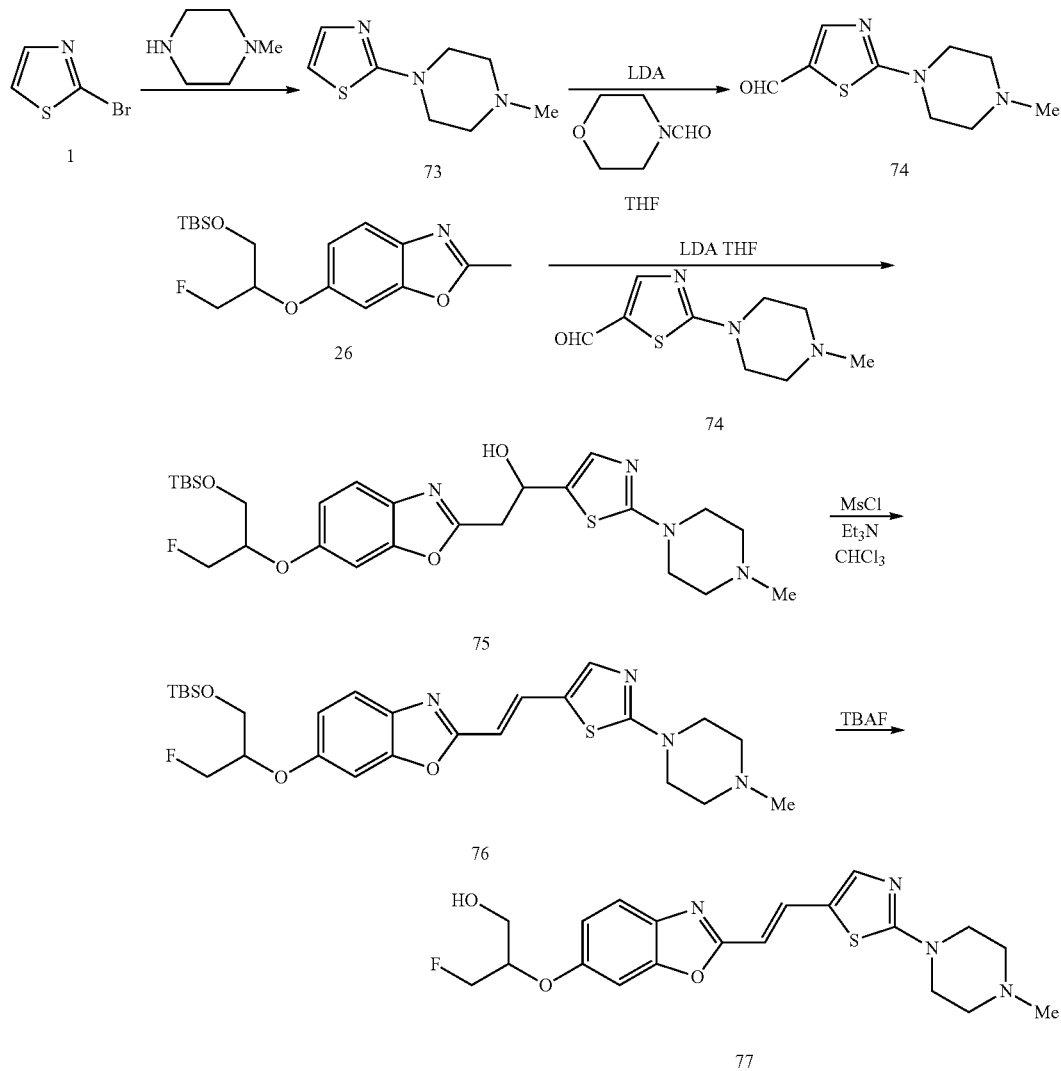

[Formula 80]

Production of 73

A mixture of 1 (10 g, 61.0 mmol) and N-methylpiperazine (40 ml) was stirred at 140° C. for 1 hr. The reaction mixture was allowed to stand to cool down, diluted with ice-10% sodium hydroxide solution, and extracted with ethyl acetate. The extract was dried and evaporated to dryness under reduced pressure, and the residue was purified by basic silica gel column chromatography (solvent: n-hexane/ethyl acetate=2/1), to obtain 73 (8.62 g, 77%) of oily yellow substance.

APCI-MS m/z 184[M+H]$^+$

Production of 74

To tetrahydrofuran solution (40 ml) of di-isopropylamine (3.39 g, 33.5 mmol), 1.59 M n-butyllithium/n-hexane solution (21.1 ml, 33.5 mmol) was dropped at −60° C. or below in argon atmosphere while stirring, and then, the mixture was slowly warmed up to 0° C. Then, tetrahydrofuran solution (40 ml) of 73 (5 g, 30.5 mmol) was dropped at −70° C. or below, and the mixture was stirred at −78° C. for 40 min. Then, tetrahydrofuran solution (40 ml) of 4-formylmorpholine (5.26 g, 45.7 mmol) was added at the same temperature, and the mixture was stirred for 30 min at the same temperature. The reaction mixture was added saturated ammonium chloride solution, and made alkaline with saturated sodium bicarbonate solution, and extracted with is ethyl acetate. The extract was washed with water and saturated sodium chloride solution in this order, dried, and evaporated to dryness under reduced pressure, and the residue was washed with n-hexane/diisopropyl ether, to obtain 74 (4.14 g, 65%) of light yellow solid substance.

APCI-MS m/z 212[M+H]$^+$

Production of 75

To tetrahydrofuran solution (20 ml) of di-isopropylamine (326 mg, 3.22 mmol), 1.59 M n-butyllithium/n hexane solution (2.03 ml, 3.22 mmol) was dropped at −60° C. or below in argon atmosphere while stirring, and then, the mixture was slowly warmed up to 0° C. Then, tetrahydrofuran solution (20 ml) of 26 (911 mg, 2.68 mmol) was dropped at −70° C. or below, and the mixture was stirred at −78° C. for 40 min. Then, tetrahydrofuran solution (20 ml) of 74 (680 mg, 3.22 mmol) was dropped at the same temperature, and the mixture was stirred for 30 min at the same temperature. The reaction mixture was added saturated ammonium chloride solution, and made alkaline with saturated sodium bicarbonate solution, and extracted with ethyl acetate. The extract was washed with water and saturated sodium chloride solution in this order, dried, and evaporated to dryness under reduced pressure. The residue was purified by basic silica gel column chromatography (solvent: n-hexane/ethyl acetate=1/1 and ethyl acetate), to obtain 75 (1.28 g, 87%) of yellow solid substance.

Production of 76

To chloroform solution (25 ml) of 75 (1.28 g, 2.32 mmol), triethylamine (1.94 ml, 13.9 mmol) was added, and methane sulfonyl chloride (0.36 ml, 4.65 mmol) was dropped while cooling in ice with shaking, and stirred for 30 min at room temperature. The reaction mixture was added ice-cold water, and extracted with ethyl acetate. The extract was washed with water and saturated sodium chloride solution in this order, dried, and evaporated to dryness under reduced pressure, and the residue was purified by basic silica gel column chromatography (solvent: n-hexane/ethyl acetate 1/3), to obtain 76 (1.07 g, 86%) of oily yellow substance.

APCI-MS m/z 533[M+H]$^+$

Production of 77

To tetrahydrofuran solution (25 ml) of 76 (1.07 g, 2.01 mmol), 1M tetrabutylammonium fluoride/tetrahydrofuran solution (2.21 ml, 2.21 mmol) was added while shaking at room temperature, and refluxed for 30 nm at room temperature. The reaction mixture was added ice-water, and extracted with ethyl acetate. The extract was washed with water and saturated sodium chloride solution in this order, dried, and evaporated to dryness under reduced pressure, and the residue was purified by basic silica gel column chromatography (solvent: chloroform and chloroform/methanol=5/1) and mashed with ethyl acetate, to obtain 77 (485 mg, 58%) of yellow solid substance.

mp 151~153° C.

IR (Nujol) 1629 cm$^{-1}$, APCI-MS m/z 419[M+H]$^+$

THK-708 ((E)-6-[(2-fluoromethyl-3-hydroxy)propoxy]-2-[2-[2(pyrrolidine-1-yl)thiazole-5-yl]ethenyl]benzoxazole: Production of (83)

[Formula 81]

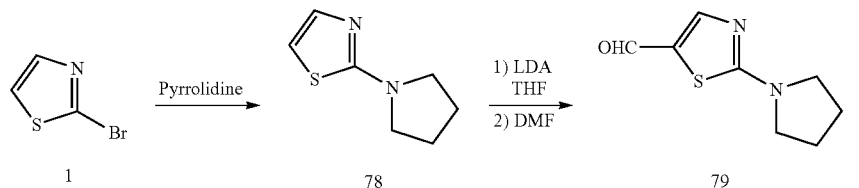

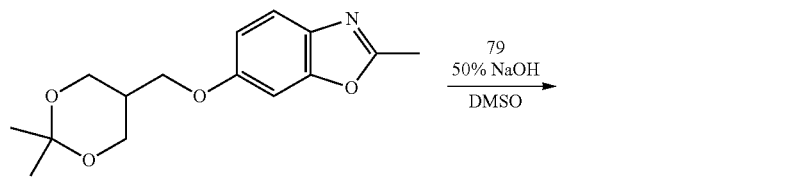

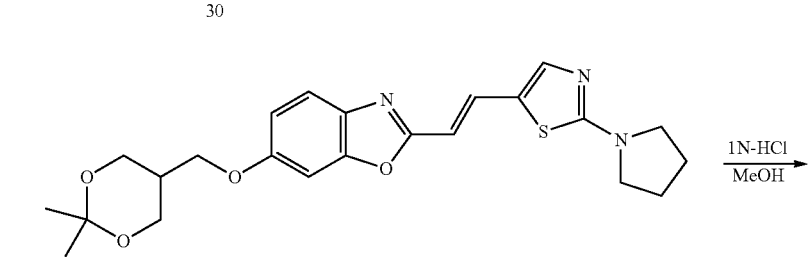

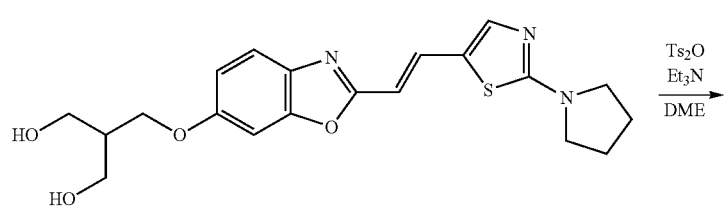

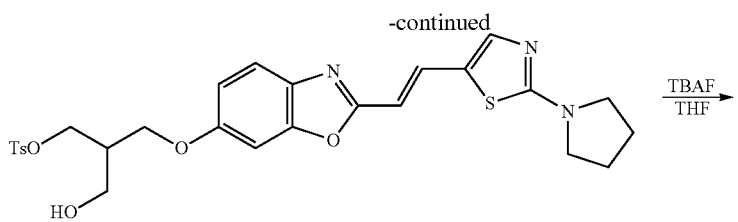

82

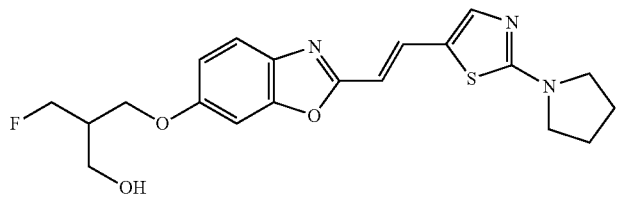

83 (THK-708)

Production of 78

Pyrrolidine solution (60 ml) of 1 (10.21 g, 62.25 mmol) was stirred at 90° C. for 1.3 hours. The reaction solvent was evaporated to dryness under reduced pressure, and the residue was purified by silica gel column chromatography (solvent: n-hexane/ethyl acetate=4/1), to obtain 78 (9.47 g, 99%) of colorless solid substance.

mp 45~46° C., APCI-MS m/z 155[M+H]$^+$

Production of 79

To tetrahydrofuran solution (150 ml) of di-isopropylamine (10.38 g, 73.68 mmol), 1.59 M n-butyllithium/n-hexane solution (46.34 ml, 73.68 mmol) was dropped at −60° C. or below in argon atmosphere while stirring, and then, the mixture was slowly warmed up to 0° C. Then, tetrahydrofuran solution (50 ml) of 78 (9.47 g, 6140 mmol) was dropped at −70° C. or below, and the mixture was stirred at −78° C. for 1 hr. Then, dimethylformamide (9.50 ml, 122.8 mmol) was added all at once at the same temperature, and the mixture was stirred for 40 min at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate 1/1), and recrystallized with ethyl acetate/n-hexane, to obtain 79 (10.41 g, 93%) of light yellow crystal.

mp 92.0~92.5° C., IR (Nujol) 1635 cm$^{-1}$

APCI-MS m/z 183[M+H]$^+$

Production of 80

Dimethyl sulfoxide solution (15.0 ml) of 30 (3.00 g, 10.82 mmol) and 79 (1.97 g, 82 mmol) was added 50% (w/w) sodium hydroxide solution (4.07 ml) at room temperature while stirring, and further stirred for 1 hr at room temperature. The reaction mixture was added water and filtered, and the filtrate was washed with water, dried, and the crude crystal was purified by silica gel column chromatography (solvent: n-hexane/ethyl acetate=1/1 to ethyl acetate), and recrystallized with ethyl acetate, to obtain 80 (2.10 g, 44%) of yellow crystal.

mp 175~176° C., IR (Nujol) 1633 cm$^{-1}$

APCI-MS m/z 442[M+H]$^+$

Production of 81

To methanol suspension (90 ml) of 80 (3.58 g, 7.99 mmol), 1N hydrochloric acid (16.0 ml, 16.0 mmol) was added, and stirred for 30 min at room temperature. The reaction mixture was evaporated to dryness under reduced pressure, and the residue was dissolved in water/ethyl acetate, and the pH was adjusted to 10 with potassium carbonate solution. The mixture was partitioned, and the organic layer was washed with water, dried, and evaporated to dryness under reduced pressure. The residue was recrystallized with ethyl acetate, to obtain 81 (3.10 g, 97%) of yellow crystal.

mp 196.0~196.5° C., IR (Nujol) 3330, 1624 cm$^{-1}$

APCI-MS m/z 402[M+H]$^+$

Production of 82

To ethylene glycol dimethyl ether suspension (200 ml) of 81 (3.10 g, 7.72 mmol), triethylamine (1.62 ml, 11.6 mmol), toluenesulfonate anhydride (2.52 g, 7.72 mmol), and dimethyl aminopyridine (0.094 g, 0.77 mmol) were added, and stirred at 70° C. for 16 hours. The reaction solution was evaporated to dryness under reduced pressure. The residue was purified by silica gel column chromatography (solvent: ethyl acetate/n-hexane=1/1 to ethyl acetate), and recrystallized with ethyl acetate, to obtain 82 (1.26 g, 29%) of yellow crystal.

mp 168~170° C., IR (Nujol) 3311, 1736, 1636 cm$^{-1}$

APCI-MS m/z 556[M+H]$^+$

Production of 83

To tetrahydrofuran suspension (10 ml) of 32 (1.26 g, 2.27 mmol), 1M tetrabutylammonium fluoride/tetrahydrofuran solution (11.3 ml, 11.3 mmol) was added and refluxed for 1 hr and 10 min. The reaction mixture was allowed to stand to cool down, added cold water, and extracted with ethyl acetate. The extract was washed with water, dried, and evaporated to dryness under reduced pressure, and the residue was purified by silica gel column chromatography (solvent: ethyl acetate/n-hexane=1/2), and recrystallized with ethyl acetate, to obtain 83 (0.59 g, 64%) of yellow crystal.

mp 175.5~176.5° C., $^1$H NMR (300 MHz, CDCl$_3$) δ 2.06~2.18 (4H, m), 2.35~2.53 (2H, m, D$_2$O, 1H), 3.58 (4H, t, J=6.4 Hz), 3.91 (2H, d, J=5.7 Hz), 4.16 (2H, d, J=6.0 Hz), 4.70 (2H, dd, J=47.0, 5.5 Hz), 6.35 (1H, dd, J=15.7, 0.6 Hz), 6.90 (1H, dd, J=8.7, 2.4 Hz), 7.03 (1H, d, J=2.4 Hz), 7.38 (1H, s), 7.52 (1H, d, J=8.7 Hz), 7.65 (1H, dd, J=15.7, 0.6 Hz)

IR (Nujol) 3218, 1625 cm$^{-1}$ APCI-MS m/z 404[M+H]$^+$

THK-751 ((E)-6-[(1-hydroxymethyl-2-tosyloxy) ethoxy]-2-[2-[2-(pyrrolidine-1-yl)-thiazole-5-yl] ethenyl]benzoxazole: Manufacturing of (86), and THK-752 ((E)-6-[(1-fluoromethyl-2-hydroxy) ethoxy]-2-[2-[2-(pyrrolidine-1-yl)]-thiazole-5-yl] ethenyl]benzoxazole: Production of (87)

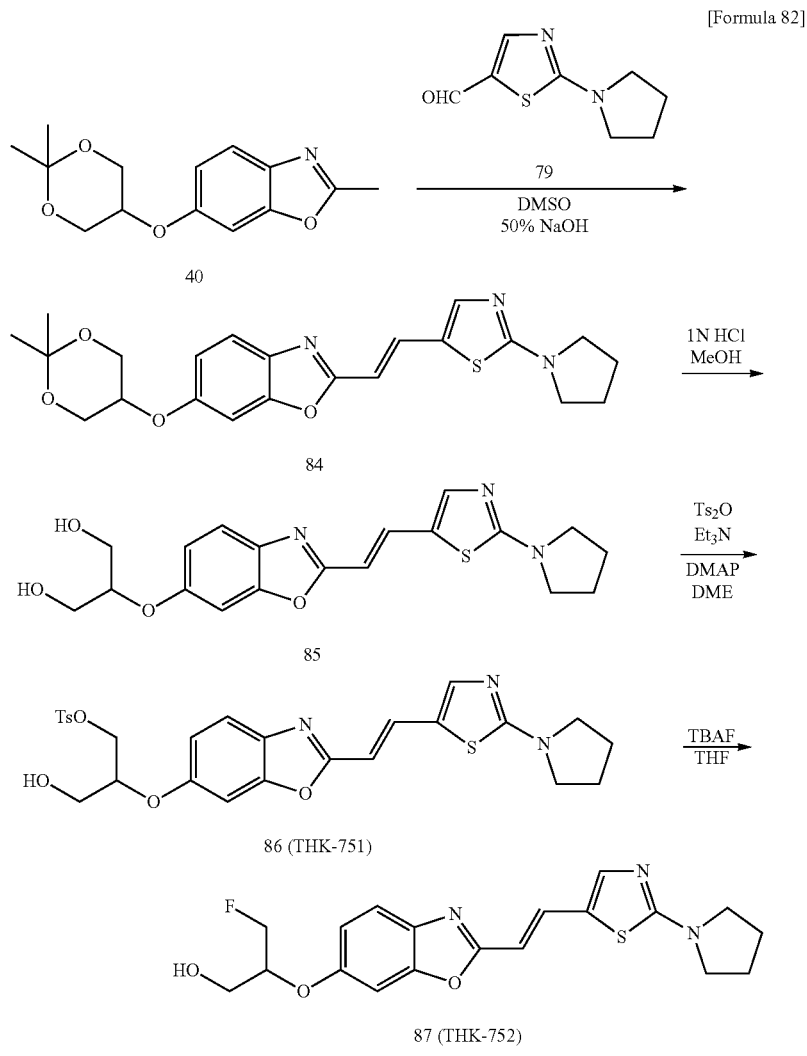

[Formula 82]

Production of 84

Dimethyl sulfoxide solution (37.5 ml) of aldehyde 79 (2.55 g, 14 mmol) and benzoxazole 40 (3.7 g, 14 mmol) was dropped 50% sodium hydroxide solution (5.4 ml) and stirred for 2 hours to react at room temperature. Yellow solid substance was precipitated out. The reaction solution was added 150 ml of water and stirred for 20 min. Then, the yellow precipitate was collected by filtering, washed with water, and dried under reduced pressure at 70° C., and further recrystallized with ethyl acetate to obtain 84 (2.85 g, 48%).

mp 193-194° C.
IR (Nujol) 1628, 1600 cm$^{-1}$
APCI-MS m/z 428[M+H]$^+$

Production of 85

To methanol 90 ml, 84 (2.65 g, 6.08 mmol) was added, and 1 N hydrochloric acid (12 ml) was dropped at room temperature while stirring. The reaction mixture soon became homogeneous and clear. After reaction for 4 hours, the solvent was evaporated to dryness under reduced pressure, and the residue was dissolved in water. Upon alkalization of the solution with potassium carbonate solution, yellow precipitate was formed. The precipitate was extracted with ethyl acetate, and the organic layer was washed with water and saturated sodium chloride solution, and dried with magnesium sulfate anhydride. The solvent was evaporated to dryness under reduced pressure, to obtain 85 (2.26 g, 96%).

mp 179-182° C.
APCI-MS m/z 388 [M+H]$^+$

Production of 86

Diol 85 (3.50 g, 9.68 mmol) was dissolved in dry dimethoxyethane (200 ml), and further added p-toluene sulfonic acid anhydride (3.16 g, 9.68 mmol), triethylamine (1.5 g, 14.85 mmol), and dimethyl aminopyrine (100 mg), mixed, and heated to 75° C. to react for 6.5 hours. Upon completion of the reaction, the reaction mixture was allowed to stand to cool down to room temperature, and filtered to remove the precipitates. The filtrate was evaporated to dryness under reduced pressure, to obtain the reaction mixture. The mixture was applied to silica gel column chromatography (solvent:

n-hexane/ethyl acetate=1/1 to 1/2 to ethyl acetate) for purification, to obtain 86 (2.10 g, 40%) and unreacted diol 85 (1.40 g, 37%).

mp 147-148° C.
IR (Nujol) 3231, 1629, 1613 cm$^{-1}$
APCI-MS m/z 542[M+H]$^+$
$^1$HNMR (DMSO-d$_6$) δ 1.98-2.05 (4H, m) 2.36 (3H, s) 3.42-3.50 (4H, m) 3.55-3.62 (2H, m)-4.26 (2H, m)-4.40-4.60 (1H, m) 5.06 (1H, t, J=5.7 Hz) 6.32 (1H, d, J=15.7 Hz) 6.48 (1H, dd, J=8.6 Hz, 2.4 Hz) 7.18 (1H, d, J=2.2 Hz) 7.39 (2H, d, J=7.9 Hz) 7.48 (1H, d, J=8.6 Hz) 7.61 (1H, s) 7.72 (2H, d, 8.0 Hz) 7.76 (1H, d, J=15.7 Hz)

Production of 87

Monotosylate 86 (1.27 g, 2.34 mmol) was dissolved in dry tetrahydrofuran solution (21 ml), and added 1M tetra-n-butylammonium fluoride/tetrahydrofuran solution (10 ml), and heated for reflux for 2.5 hours. Upon completion of the reaction, the reaction mixture was diluted with ethyl acetate, and partitioned with water. The organic layer was washed with water and saturated sodium chloride solution, and dried with magnesium sulfate anhydride. After evaporation of the solvent, the obtained crude product was purified by silica gel column chromatography (solvent: n-hexane/ethyl acetate=2/1), and recrystallized with ethyl acetate, to obtain 87 (520 mg, 57%).

mp 159-161° C.
IR (Nujol) 3192, 1630 cm$^{-1}$
APCI-MS m/z 390[M+H]
$^1$HNMR (DMSO-d$_6$) δ 1.97-2.04 (4H, m), 3.45 (4H, br t), 3.64 (2H, br t), 4.55-4.83 (3H, m), 5.06 (1H, t, J=5.7 Hz), 6.31 (1H, d, J=15.8 Hz), 6.99 (1H, dd, J=8.6 Hz, 2.4 Hz), 7.36 (1H, d, J=2.4 Hz), 7.53 (1H, d, J=8.6 Hz), 7.60 (1H, s), 7.75 (1H, d, J=15.7 Hz)

THK-757 ((E)-6-[(1-fluoromethyl-2-hydroxy)ethoxy]-2-[2-[2-([1,2]oxazinane-3-yl)-thiazole-5-yl]ethenyl]benzoxazole: Production of (97)

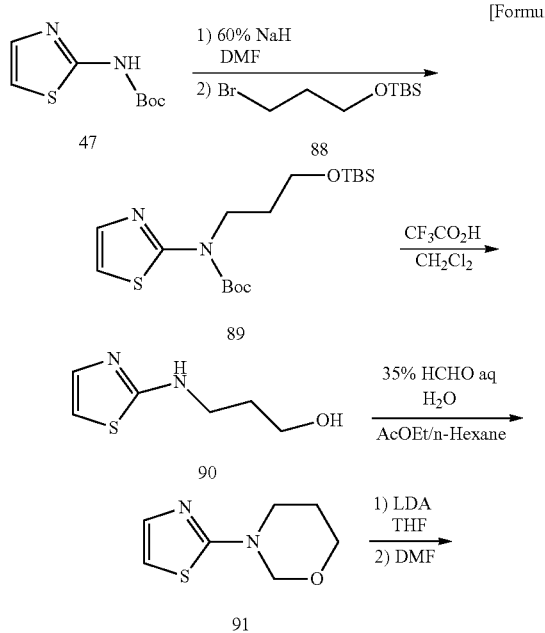

[Formula 83]

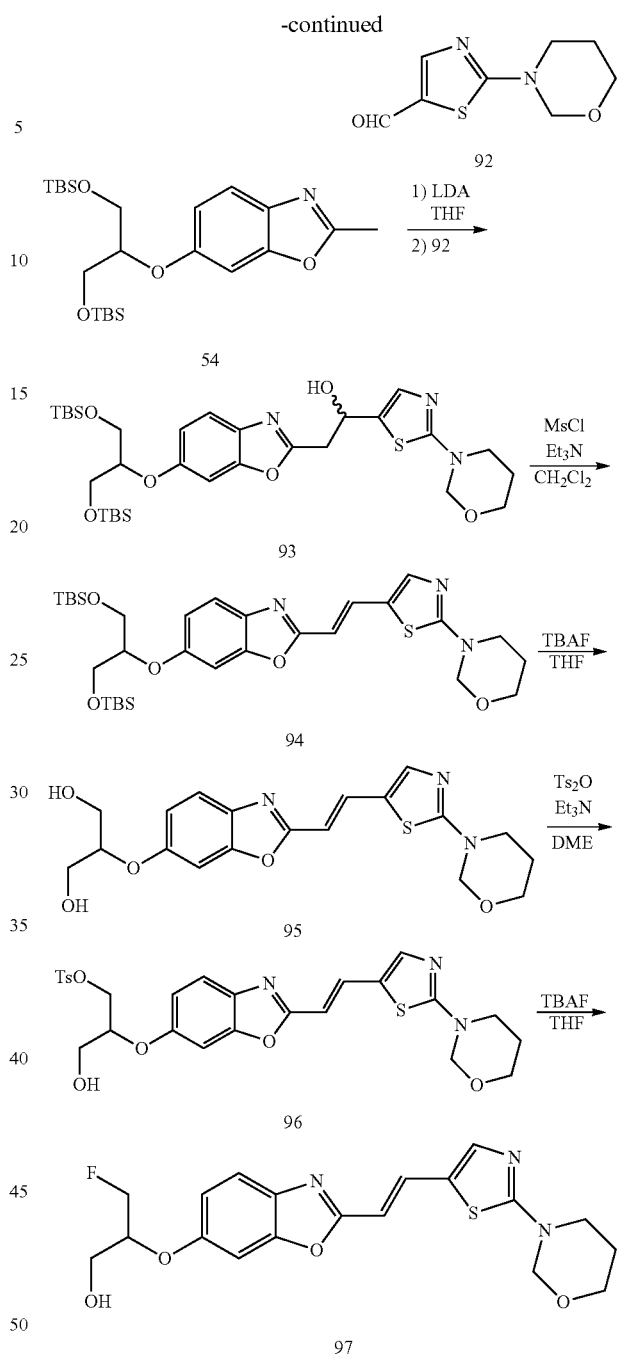

Production of 89

To dimethylformamide solution (50 ml) of 47 (5.00 g, 25.0 mmol), 60% sodium hydride (1.50 g, 37.5 mmol) was added in several portions in argon atmosphere with stirring at room temperature, and stirred for 20 min at room temperature. Then, 88 (12.65 g, 50.0 mmol) was further added, and stirred for 2 hours at room temperature. The reaction mixture was added ice chips, and extracted with ethyl acetate. The extract was washed with water, dried, and evaporated to dryness under reduced pressure. The residue was purified by silica gel column chromatography (solvent: ethyl acetate/n-hexane 30/1), to obtain 89 (7.89 g, 85%) of oily colorless substance.

APCI-MS m/z 373[M+H]$^+$

Production of 90

To dichloromethane solution (30 ml) of 89 (7.89 g, 21.18 mmol), trifluoroacetic acid (30 ml) was dropped while ice-cooling with shaking, and stirred at room temperature for 3 days. The reaction solvent was evaporated to dryness under reduced pressure, and the residue was diluted with ethyl acetate, and the pH was adjusted to pH 8 with potassium carbonate solution. After partition, the organic layer was washed with water, dried, and evaporated to dryness under reduced pressure, and the residue was purified by silica gel column chromatography (solvent: ethyl acetate/n-hexane=2/1 to ethyl acetate), to obtain 90 (3.35 g, 100%) of oily light yellow substance.

APCI-MS m/z 159[M+H]$^+$

Production of 91

To aqueous solution (73 ml) of 90 (2.95 g, 18.65 mmol), 36% formaldehyde solution (37 ml) was added while shaking at room temperature, and stirred for 5 min at room temperature. The reaction mixture was added a mixture (1100 ml) of ethyl acetate/n-hexane (2/1), and stirred for 16 hours at room temperature. After partition, the aqueous layer was extracted with ethyl acetate, and the organic layers were combined, dried, and evaporated to dryness under reduced pressure. The residue was purified by silica gel column chromatography (solvent: ethyl acetate/n-hexane=2/1), to obtain 91 (1.75 g, 55%) of oily light yellow substance.

APCI-MS m/z 171 [M+H]$^+$

Production of 92

To tetrahydrofuran solution (20 ml) of di-isopropylamine (2.51 ml, 17.80 mmol), 1.59 M n-butyllithium/n-hexane solution (11.19 ml, 17.80 mmol) was dropped at −60° C. or below in argon atmosphere while stirring, and then, the mixture was slowly warmed up to 0° C., Then, tetrahydrofuran solution (40 ml) of 91 (2.02 g, 11.87 mmol) was dropped at −70° C. or below, and the mixture was stirred at −78° C. for 1 hr. Then, dimethylformamide (1.84 ml, 23.74 mmol) was added all at once at the same temperature, and the mixture was stirred for 1 hr at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate=2/1), and recrystallized with n-hexane/ethyl acetate to obtain 92 (1.89 g, 80%) of colorless crystal.

mp 94.0~94.5° C., IR (Nujol) 1655 cm$^{-1}$

APCI-MS m/z 199[M+H]$^+$

Production of 93

To tetrahydrofuran solution (40 ml) of di-isopropylamine (2.02 ml, 14.3 mmol), 1.59 M n-butyllithium/n-hexane solution (8.99 ml, 14.3 mmol) was dropped at −60° C. or below in argon atmosphere while stirring, and then, the mixture was slowly warmed up to 0° C. Then, tetrahydrofuran solution (40 ml) of 54 (4.31 g, 9.54 mmol) was dropped at −70° C. or below, and the mixture was stirred at −78° C. for 1 hr. Then, tetrahydrofuran solution (30 ml) of 92 (1.89 g, 9.54 mmol) was added all at once at the same temperature, and the mixture was stirred for 1 hr at the same temperature. The reaction mixture was added water, and extracted with ethyl acetate. The extract was washed with water, dried, and evaporated to dryness under reduced pressure, and the residue was purified by silica gel column chromatography (solvent: n-hexane/ethyl acetate=2/1 to 1/1), to obtain 93 (4.60 g, 74%) of oily yellow substance.

APCI-MS m/z 650[M+H]$^+$

Production of 94

To dichloromethane solution (50 ml) of 93 (4.60 g, 7.08 mmol), triethylamine (3.95 ml, 28.3 mmol) was added, and methane sulfonyl chloride (1.21 ml, 15.6 mmol) was dropped while cooling in ice with shaking and stirred for 30 min at room temperature. The reaction mixture was added cold water, and extracted with ethyl acetate. The extract was washed with water, dried, and evaporated to dryness under reduced pressure, and the residue was purified by silica gel column chromatography (solvent: n-hexane/ethyl acetate=4/1), to obtain 94 (3.90 g, 87%) of yellow solid substance.

mp 131~132° C., APCI-MS m/z 632[M+H]$^+$

Production of 95

To tetrahydrofuran solution (40 ml) of 94 (3.90 g, 6.17 mmol), 1M tetrabutylammonium fluoride/tetrahydrofuran solution (12.34 ml, 12.34 mmol) was added while shaking at room temperature, and stirred for 1 hr at room temperature. The reaction mixture was added water, and extracted with ethyl acetate. The extract was washed with water, dried, and evaporated to dryness under reduced pressure, and the residue was purified by silica gel column chromatography (solvent: ethyl acetate), and recrystallized with ethyl acetate to obtain 95 (1.96 g, 79%) of yellow crystal.

mp 163~165° C., IR (Nujol) 3276, 1629 cm$^{-1}$

APCI-MS m/z 404[M+H]$^+$

Production of 96

To ethylene glycol dimethyl ether suspension (80 ml) of 95 (1.66 g, 4.11 mmol), triethylamine (0.86 ml, 6.17 mmol), toluenesulfonate anhydride (1.34 g, 4.11 mmol), and dimethyl aminopyridine (0.050 g, 0.41 mmol) were added, and stirred at 70° C. for 16 hours. The reaction mixture was allowed to stand to cool down, diluted with ethyl acetate, washed with water, dried, and evaporated to dryness under reduced pressure. The residue was purified by silica gel column chromatography (solvent: ethyl acetate/n-hexane=1/2 to ethyl acetate), and recrystallized with ethyl acetate/n-hexane, to obtain 96 (0.74 g, 32%) of yellow crystal.

mp 115~117° C., APCI-MS m/z 558[M+H]$^+$

Production of 97

To tetrahydrofuran suspension (20 ml) of 96 (1.92 g, 3.44 mmol), 1M tetrabutylammonium fluoride/tetrahydrofuran solution (17.22 ml, 17.22 mmol) was added and refluxed for 6 hours. The reaction mixture was allowed to stand to cool down, added cold water, and extracted with ethyl acetate. The extract was washed with water, dried, and evaporated to dryness under reduced pressure, and the residue was purified by silica gel column chromatography (solvent: ethyl acetate/n-hexane=1/1 to ethyl acetate), and recrystallized with ethyl acetate, to obtain 97 (0.29 g, 21%) of yellow crystal.

mp 162~163° C., $^1$H NMR (300 MHz, CDCl$_3$) δ 1.82~1.92 (2H, m), 1.97 (1H, t, J=6.3 Hz, D$_2$O, disappeared), 3.80 (2H, t, J=5.7 Hz), 3.91~4.00 (4H, m), 4.51~4.59 (1H, m), 4.68 (2H, ddd, J=46.7, 4.7, 2.3 Hz), 5.10 (2H, s), 6.40 (1H, dd, J=15.8, 0.6 Hz), 6.98 (1H, dd, J=8.8, 2.4 Hz), 7.14 (1H, d, J=2.4 Hz), 7.37 (1H, t, J=0.6 Hz), 7.54 (1H, dd, J=8.8, 0.4 Hz), 7.69 (1H, dd, J=15.8, 0.6 Hz)

IR (Nujol) 3265, 1634 cm$^{-1}$, APCI-MS m/z 406[M+H]$^+$

THK-765 ((E)-6-[(1-fluoromethyl-2-hydroxy) ethoxy]-2-[2-[2-homopiperidine-1-yl]thiazole-5-yl] ethenyl)benzoxazole): Production of 104

[Formula 84]

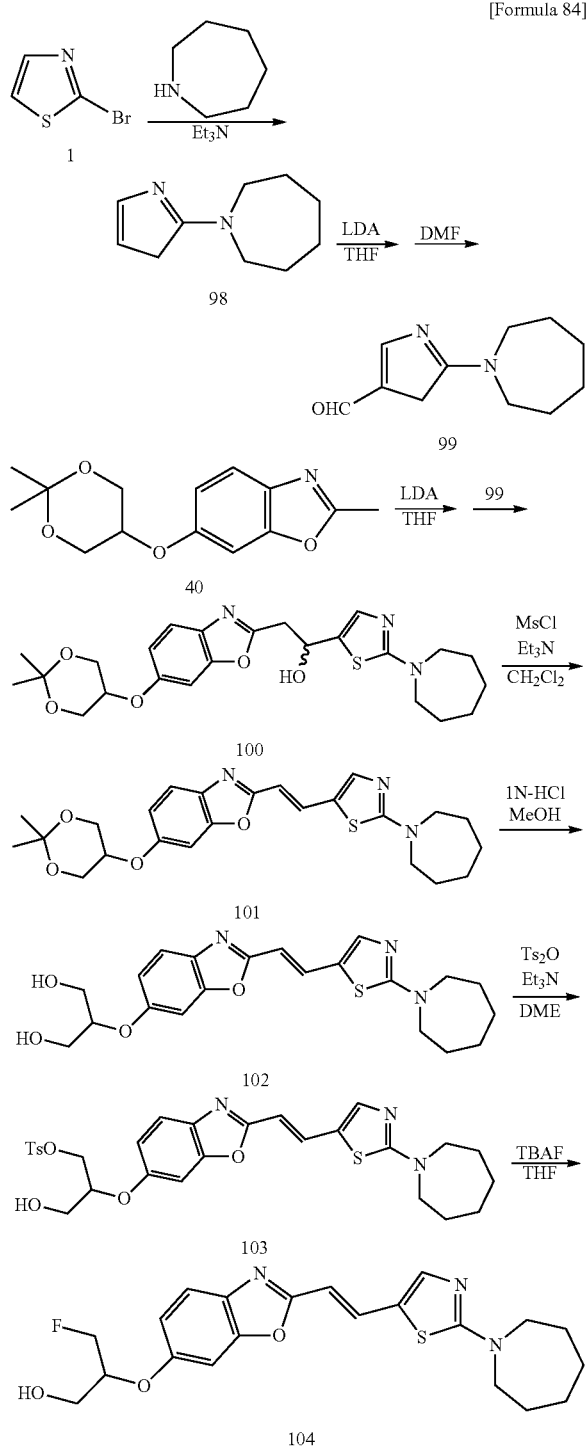

Production of 98

Homopiperidine solution (20.61 ml, 182.9 mmol) and triethylamine solution (42.55 ml, 304.8 mmol) of 1 (10.0 g, 60.97 mmol) were stirred at 95° C. for 16 hours and at 115° C. for 8 hours. The reaction mixture was allowed to stand to cool down and filtered to remove the insolubles. The filtrate was evaporated to dryness under reduced pressure, and the residue was purified by silica gel column chromatography (solvent: n-hexane/ethyl acetate=9/1 to 4/1), to obtain 98 (8.77 g, 79%) of oily colorless substance.

APCI-MS m/z 183[M+H]$^+$

Production of 99

A mixture of 1.59M n-butyllithium and n-hexane (45.39 ml, 72.17 mmol) was delivered by drops into a solution of di-isopropylamine (10.17 ml, 72.17 mmol) in tetrahydrofuran (130 ml) under argon atmosphere agitation at not more than −60° C. and gradually warmed up to 0° C. Next, a solution of 98 (8.77 g, 49.11 mmol) in tetrahydrofuran (50 ml) was delivered by drops at not more than −70° C. and stirred at −78° C. for 1 hour. Dimethylformamide (7.40 ml, 96.2 mmol) was added at one time at the same temperature and stirred at the same temperature for 30 minutes. To the reaction solution water was added and extracted with ethyl acetate. The extract solution was washed with water, dried, and solvent distilled in vacuum, and the residue was purified with silica gel column chromatography (dissolved solvent: n-hexane:ethyl acetate=3/1-2/1), yielding 99 (9.36 g, 93%) as yellow solid.

mp 32~34° C., APCI-MS m/z 211 [M+H]$^+$

Production of 100

A mixture of 1.57M n-butyllithium and n-hexane (7.26 ml, 11.4 mmol) was delivered by drops into a solution of di-isopropylamine (1.61 ml, 11.4 mmol) in tetrahydrofuran (60 ml) under argon atmosphere agitation at not more than −60° C. and gradually warmed up to 0° C. Next, 40 (2.00 g, 7.60 mmol) a solution of tetrahydrofuran (60 ml) was delivered by drops at not more than −70° C. and stirred at −78° C. for 1 hour. A solution of 99 (1.92 g, 9.12 mmol) in tetrahydrofuran (60 ml) was added at one time at the same temperature and stirred at the same temperature for 1 hour. To the reaction solution water was added and extracted with ethyl acetate. The extract solution was washed with water, dried, and solvent distilled in vacuum, and the residue was purified with silica gel column chromatography (dissolved solvent: n-hexane:ethyl acetate=1:1) and recrystallized with ethyl acetate and n-hexane, yielding 100 (2.80 g, 78%) as light yellow crystals.

mp 149~150° C., IR (Nujol) 3273 cm$^{-1}$

APCI-MS m/z 474[M+H]$^+$

Production of 101

To a solution of 100 (2.80 g, 5.91 mmol) in dichloromethane (30 ml) triethylamine (3.30 ml, 23.7 mmol) was added, and methanesulfonyl chloride (1.01 ml, 13.0 mmol) was delivered by drops under ice water agitation and stirred at room temperature for 30 minutes. To the reaction solution ice water was added and extracted with ethyl acetate. The extract solution was washed with water, dried, solvent distilled in vacuum, and the residue was purified with silica gel column chromatography (dissolved solvent: n-hexane:ethyl acetate: 1/1-1/2), and recrystallized with ethyl acetate/hexane, yielding 101 (2.35 g, 87%) as orange crystals.

mp 152~153° C., APCI-MS m/z 456[M+H]$^+$

Production of 102

To a suspension of 101 (2.35 g, 5.16 mmol) in methanol (60 ml) 1N hydrochloric acid (5.67 ml, 5.67 mmol) was added, and stirred at room temperature for 4 hours, and at 60° C. for 30 minutes. The reaction solution was solvent distilled in vacuum, and the residue was dissolved in a mixture of water and ethyl acetate, and adjusted to the pH 10 with potassium carbonate solution. After separation, the organic layer was washed with water, dried, solvent distilled in vacuum, and the residue was recrystallized with ethyl acetate, yielding 102 (2.11 g, 98%) as yellow crystals.

mp 161~162° C., IR (Nujol) 1624 cm$^{-1}$

APCI-MS m/z 416[M+H]$^+$

Production of 103

To a suspension of 102 (2.11 g, 5.08 mmol) in ethylene glycol dimethylether (100 ml), triethylamine (1.06 ml, 7.62 mmol) and toluenesulfonate anhydride (1.66 g, 5.08 mol) were added, and stirred at 80° C. for 16 hours. The reaction solution was diluted with ethyl acetate, washed with water, dried, solvent distilled in vacuum, and the residue was purified with silica gel column chromatography (dissolved solvent: ethyl acetate:n-hexane=1/2-ethyl acetate), and recrystallized with ethyl acetate, yielding 103 (1.35 g, 47%) as yellow foams.

APCI-MS m/z 570[M+H]$^+$

Production of 104

To a solution of 103 (1.35 g, 2.37 mmol) of tetrahydrofuran (10 ml), 1M tetrabutylammonium fluoride/tetrahydrofuran (11.85 ml, 11.85 mmol) was added and refluxed for 4 hours. The reaction solution was left to cool, ice water was added, and the solution was extracted with ethyl acetate. The extract solution was washed with water, dried, solvent distilled in vacuum, and the residue was purified with silica gel column chromatography (dissolved solvent: chloroform/methanol/25% ammonia water=1000/10/1), and recrystallized with ethyl acetate, yielding 104 (0.42 g, 42%) as yellow crystals.

mp 137~138° C., $^1$H NMR (300 MHz, CDCl$_3$) δ 1.54~1.68 (4H, m), 1.81~1.91 (4H, m), 2.00 (1H, t, J=6.2 Hz, D$_2$O, disappeared), 3.64 (4H, t, J=5.9 Hz), 3.88~4.02 (2H, m), 4.50~4.58 (1H, m), 4.68 (2H, ddd, J=46.8, 4.6, 2.3 Hz), 6.31 (1H, d, J=15.4 Hz), 6.97 (1H, dd, J=8.7, 2.4 Hz), 7.13 (1H, d, J=2.4 Hz), 7.36 (1H, s), 7.53 (1H, d, J=8.7 Hz), 7.69 (1H, d, J=15.4 Hz)

IR (Nujol) 3232, 1630 cm$^{-1}$, APCI-MS m/z 418[M+H]$^+$

Production of (109): THK-766 ((E)-6-[(1-fluoromethyl-2-hydroxy)ethoxy]-2-[2-(2-homomorpholinothiazole-5-yl)ethenyl]benzoxazole)

[Formula 85]

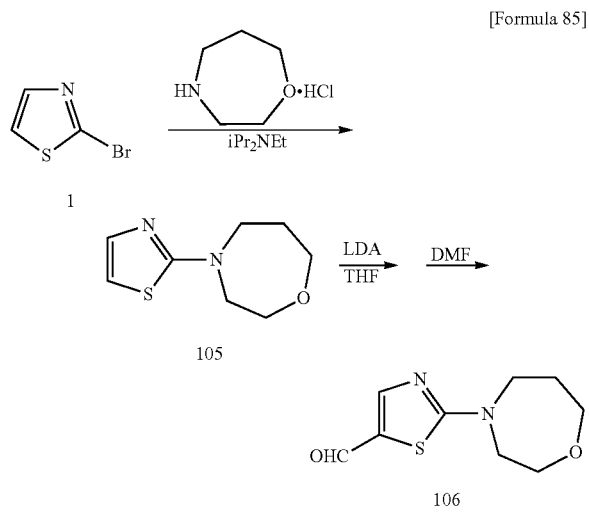

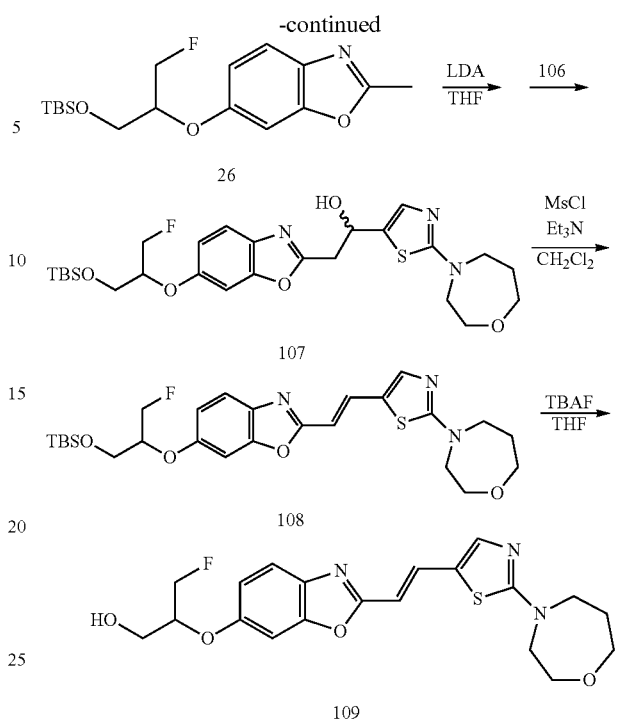

Production of 105

To a solution of 1 (6.06 g, 36.9 mmol) in diisopropylethylamine (64.5 ml, 369 mmol) homomorpholino hydrochloride (5.08 g, 36.9 mmol) was added, and stirred at 125° C. under argon atmosphere agitation for 24 hours. The reaction solution was left to cool, dissolved in methanol, silica gel (100 ml) was added, and solvent distilled in vacuum. The residue was purified with silica gel column chromatography (dissolved solvent: n-hexane/ethyl acetate=9/1-2/1, yielding 105 (2.10 g, 31%) as a light yellow oily substance.

APCI-MS m/z 185[M+H]$^+$

Production of 106

To a solution of diisopropylamine (2.41 ml, 17.1 mmol) in tetrahydrofuran (30 ml) 1.57M n-butyllithium/n-hexane solution (10.89 ml, 17.1 mmol) was delivered by drops at not more than −60° C. under argon atmosphere agitation and was gradually warmed up to 0° C. Next, a solution of 105 (2.10 g, 11.4 mmol) in tetrahydrofuran (30 ml) was delivered by drops at not more than 70° C. and stirred at −78° C. for 1 hour. Dimethylformamide (1.75 ml, 22.8 mmol) was added at one time at the same temperature, and stirred at the same temperature for 1 hour. Water was added to the reaction solution, which was extracted with ethyl acetate. The extract solution was washed with water, dried, solvent distilled in vacuum, and the residue was purified with silica gel column chromatography (dissolved solvent: n-hexane/ethyl acetate=1/1), yielding 106 (1.56 g, 65%) as a yellow solid.

mp 70~72° C., IR (Nujol) 1633 cm$^{-1}$

APCI-MS m/z 213[M+H]$^+$

Production of 107

To a solution of diisopropylamine (0.50 ml, 3.53 mmol) in tetrahydrofuran (20 ml) a mixture of 1.57M n-butyllithium/n-hexane solution (2.25 ml, 3.53 mmol) was delivered by drops at not more than −70° C. under argon atmosphere agitation, and was gradually warmed up to 0° C. Next, a solution of 26 (0.80 g, 2.36 mmol) in tetrahydrofuran (20 ml) was delivered by drops at not more than −70° C. and stirred at −78° C. for 1 hour. A solution of 106 (0.60 g, 2.83 mmol) in tetrahydrofuran (20 ml) was added at one time at the same temperature, and stirred at the same temperature for 40 minutes. Water was added to the reaction solution, which was extracted with ethyl acetate. The extract solution was washed with water, dried, solvent distilled in vacuum, and the residue was purified with silica gel column chromatography (dissolved solvent: ethyl acetate), yielding 107 (1.30 g, 100%) as a yellow viscous body.

APCI-MS m/z 552[M+H]+

Production of 108

To a solution of 107 (1.30 g, 2.36 mmol) in dichloromethane (20 ml) triethylamine (1.32 ml, 9.44 mmol) was added, and methanesulfonyl chloride (0.40 ml, 5.19 mmol) was delivered by drops under ice cooled agitation, and was stirred at room temperature for 30 minutes. Ice water was added to the reaction solution, which was extracted with ethyl acetate. The extract solution was washed with water, dried, solvent distilled in vacuum, and the residue was purified with silica gel column chromatography (dissolved solvent: n-hexane/ethyl acetate=1/1), yielding 108 (1.10 g, 87%) as a yellow viscous body.

APCI-MS m/z 534[M+H]+

Production of 109

To a solution of 108 (1.10 g, 2.06 mmol) in tetrahydrofuran (10 ml) a mixture of 1M tetrabutylammonium fluoride/tetrahydrofuran solution (2.06 ml, 2.06 mmol) was added under room temperature agitation, and was stirred at room temperature for 1 hour. Water was added to the reaction solution, which was extracted with ethyl acetate. The extract solution was washed with water, dried, solvent distilled in vacuum, and the residue was purified with silica gel column chromatography (dissolved solvent: n-hexane:ethyl acetate: 2/1-ethyl acetate), and recrystallized with ethyl acetate, yielding 109 (0.45 g, 53%) as yellow crystals.

mp 119~120° C., $^1$H NMR (300 MHz, CDCl$_3$) δ 1.99 (1H, t, J=6.3 Hz, D$_2$O, disappeared), 2.04~2.18 (2H, m), 3.77~3.98 (10H, m), 4.51~4.59 (1H, m), 4.68 (2H, ddd, J=46.7, 4.6, 2.2 Hz), 6.34 (1H, d, J=15.3 Hz), 6.98 (1H, dd, J=8.8, 2.4 Hz), 7.13 (1H, d, J=2.4 Hz), 7.35 (1H, s), 7.53 (1H, d, J=8.8 Hz), 7.69 (1H, d, J=15.3 Hz)

IR (Nujol) 3310, 1624 cm$^{-1}$, APCI-MS m/z 420[M+H]+

Production of (115): THK-767 ((E)-6-[(1-fluoromethyl-2-hydroxy)ethoxy]-2-[2-(2-thiormorpholino thiazole-5-yl)ethenyl]benzoxazole)

[Formula 86]

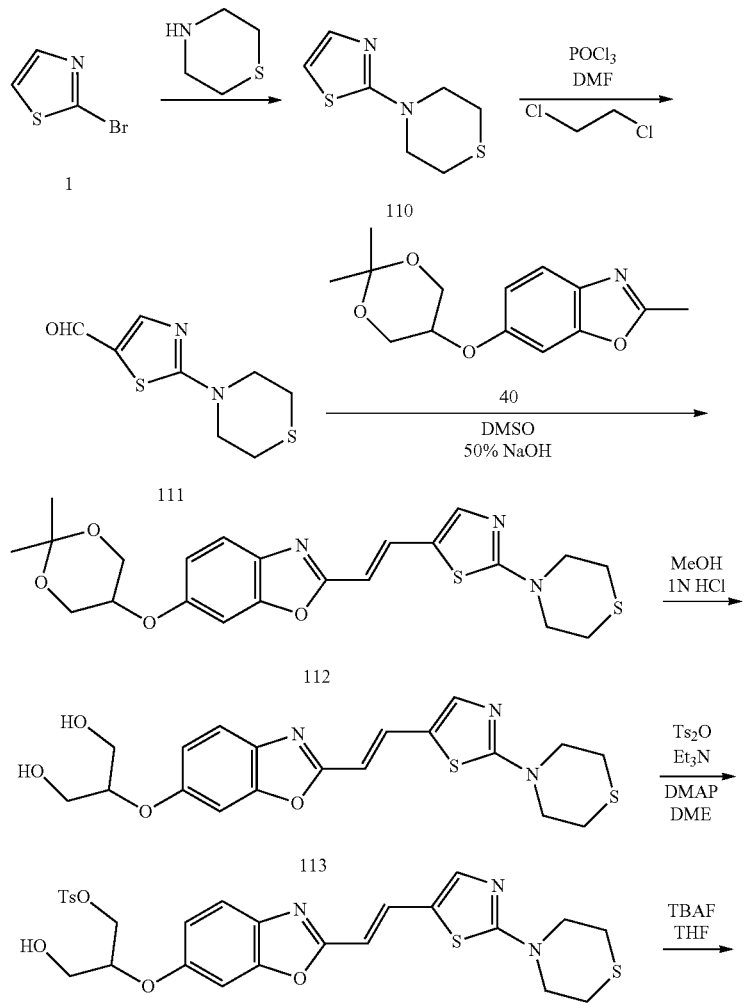

Production of 110

To bromothiazole 1 (8 g, 48.7 mmol) thiomorpholine (20 g, 194 mmol) was added, heated while stirring, and reacted over night at 85 to 90° C. After completion of reaction, the reaction was dissolved in ethyl acetate, insoluble substance was filtered out, and the filtrate was distilled in vacuum, yielding composition of crude product. This was purified with silica gel chromatography (dissolved solvent: n-hexane:ethyl acetate: 4:1), the composite 110 (8.80 g, 100%) as a brown oily substance.

APCI-MS m/z 187[M+H]$^+$

Production of 111

Phosphorous oxychloride (8.86 g, 57.8 mmol) was dropped into dried dimethylformamide (10.3 g, 0.14 mmol) cooled to 5° C. and stirred at 5° C. for 30 minutes. To this solution, thiazole derivative 110 (8.8 g, 47 mmol) and a solution of 1,2-dichloroethane solution (40 ml) containing dimethylformamide (35 g, 0.48 mol) was dropped, and reacted by raising the reaction temperature under reflux for 4 hours. After reaction ended, the reaction solution was cooled down to room temperature, and neutralized by adding in potassium carbonate solution containing ice, and the product was extracted with chloroform. The organic layer was segregated, washed with water, and washed with saturated saline solution, and dried with anhydrous magnesium sulfate. Crude product obtained from solvent distilled in vacuum was recrystallized from ethyl acetate, yielding 111 (8.92 g, 88%).

mp 137-138° C.
IR (Nujol) 1657 cm$^{-1}$
APCI-MS m/z 215[M+H]$^+$

Production of 112

50% aqueous sodium hydroxide (5.0 ml) was dropped into dimethyl sulfoxide dissolved aldehyde 111 (2.35 g, 11 mmol) and benzoxazole derivative 40 (2.9 q, 11 mmol) (30 ml) and stirred for reaction at room temperature for 3 hours and a half to react. Yellow solid was precipitated. To the reaction solution 50 ml of water was added and stirred for about 20 minutes, the yellow solid was filtered, washed with water, and dried in vacuum at 70° C., yielding 112 (4.06 g, 80%).

mp 173-175° C.
IR (Nujol) 1633 cm$^{-1}$
APCI-MS m/z 460[M+H]$^+$

Production of 113

To 120 ml of methanol 112 (4.56 g, 9.92 mmol) was added, and 1N hydrochloric acid (20 ml) was dropped while stirring at room temperature. Later, the reaction solution was heated, and reacted at 55° C. for 3 hours. After reaction ended, solvent was distilled in vacuum, and the residue was dissolved in water. Subsequently, potassium aqueous carbonate was alkalified, which precipitated yellow deposite. This was filtered out, and washed with water repeatedly, then washed with a mixture of ethyl acetate and methanol, and refiltered, and dried in vacuum, yielding 113 (3.77 g, 90%).

mp 177-178° C.
APCI-MS m/z 420[M+H]$^+$

Production of 114

Diol 113 (3.70 g, 8.82 mmol) was dissolved in dried dimethoxyethane (170 ml), and to this p-toluenesulfonate anhydride (2.87 g, 8.8 mmol), triethylamine (1.38 g, 13.7 mmol) and dimethilaminopyridine (95 mg) were added and stirred, heated to 75° C., and reacted for 5 hours. After reaction ended, the reaction solution was cooled down to is room temperature, the deposit was filtered out, the filtrate was diluted with ethyl acetate (200 ml), and water was added for separation. The organic layer was washed with water, washed with saturated saline solution, and dried with anhydrous magnesium sulfate. The solvent was distilled in vacuum, yielding crude product, which was separated and purified with silica gel column chromatography (dissolved solvent: chloroform:methanol=20:1), yielding 114 (1.85 g, 36.5%) and unreacted diol 113 (1.52 g, 41%).

mp 191-193° C.
APCI-MS m/z 574[M+H]$^+$

Production of 115

Monotosyl compound 114 (1.8 g, 3.13 mmol) was dissolved in dried tetrahydrofuran solution (16 ml), a tetra n-butylammonium fluoride in 1 mol tetrahydrofuran (16 ml) were added, heated and reacted under reflux for 1 hour and a half. After reaction ended, the reaction solution was diluted with ethyl acetate, water was added to separate, and the organic layer was washed with water, washed with saturated saline solution, and dried with anhydrous magnesium sulfate. Crude product obtained from solvent distilled in vacuum was purified with basic silica gel column chromatography (dissolved solvent: n-hexane/acetone=3:2), and further recrystallized with ethanol, yielding 115 (470 mg, 36%)

mp 137-138° C.
IR (Nujol) 3248, 1633 cm$^{-1}$
APCI-MS m/z 422[M+H]$^+$
$^1$HNMR (DMSO-d$_6$) δ 2.70-2.75 (4H, m), 3.62-3.64 (2H, br.t), 3.84-3.90 (4H, m) 4.58-4.79 (3H, m) 5.07 (1H, t, J=5.75 Hz) 6.37 (1H, d, J=15.7 Hz) 7.00 (1H, dd, J=8.7 Hz, 2.2 Hz) 7.37 Hz (1H, d, J=2.3 Hz) 7.55 (1H, d, J=8.7 Hz) 7.61 (1H, s) 7.77 (1H, d, J=15.7 Hz)

Production of (122): THK-775 ((E)-6-[(1-fluoromethyl-2-hydroxy)ethoxy]-2-[2-[2-(1,2,4-triazole-4-yl]-thiazole-5-yl)ethenyl]benzoxazole)

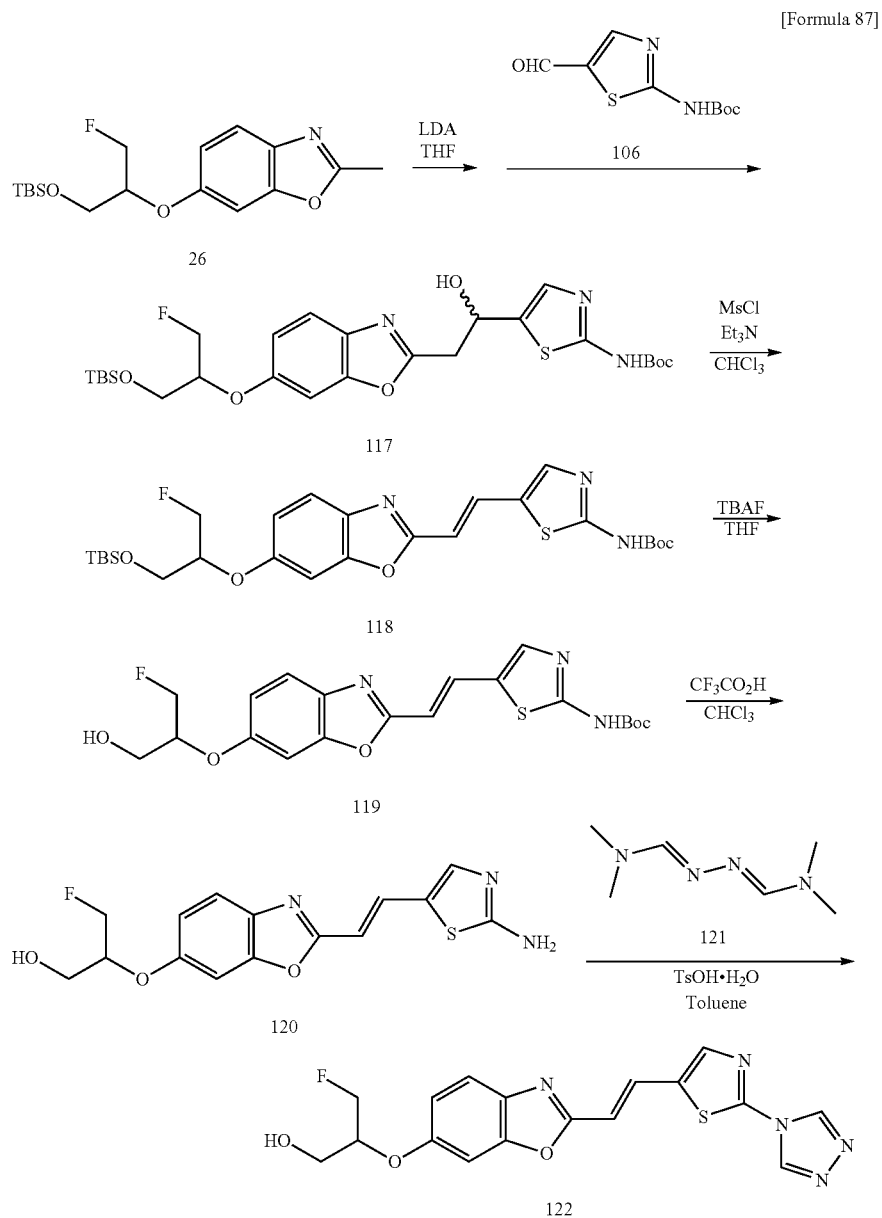

[Formula 87]

Production of 117

1.58M n-butyllithium/n-hexane solution (18.64 ml, 29.5 mmol) was dropped into a solution of diisopropylamine (4.15 ml, 29.5 mmol) in tetrahydrofuran (60 ml) under argon atmosphere stirring at −60° C. or below, and gradually warmed up to 0° C. Next, 26 (4.00 g, 11.78 mmol) a solution of tetrahydrofuran (60 ml) was dropped at not more than −70° C. or below and stirred at −78° C. for 1 hour. A solution of 116 (4.03 g, 17.7 mmol) in tetrahydrofuran (80 ml) was added at one time at the same temperature and stirred at the same temperature for 30 minutes. To the reaction solution water was added and extracted with ethyl acetate. The extract solution was washed with water, dried, and solvent distilled in vacuum, and the residue was purified with silica gel column chromatography (dissolved solvent: n-hexane/ethyl acetate=4/1 to 1/1), yielding 117 (5.20 g, 78%) as light yellow foams.

APCI-MS m/z 568[M+H]$^+$

Production of 118

To a solution of 117 (5.20 g, 9.16 mmol) in chloroform (80 ml) triethylamine (5.11 ml, 36.6 mmol) was added, and methanesulfonyl chloride (1.56 ml, 20.2 mmol) was dropped under ice cooled agitation, and stirred at room temperature for 1 hour. Further, triethylamine (2.56 ml, 18.3 mmol) was added, and methanesulfonyl chloride (0.78 ml, 10.1 mmol) was dropped and stirred under ice cooled agitation at room temperature for 20 minutes. To the reaction solution cold water was added and extracted with ethyl acetate. The extract solution was washed with water, dried, solvent distilled in vacuum, and the residue was purified with silica gel column chromatography (dissolved solvent: n-hexane:ethyl acetate: 4:1), yielding 118 (5.03 g, 100%) as light yellow solid.

APCI-MS m/z 550[M+H]$^+$

Production of 119

To a solution of 118 (5.03 g, 9.16 mmol) in tetrahydrofuran (60 ml) a mixture of 1M tetrabutylammonium fluoride and tetrahydrofuran (18.3 ml, 18.3 mmol) was added under room temperature agitation and stirred at room temperature for 40 minutes. To the reaction solution water was added and extracted with ethyl acetate. The extract solution was washed with water, dried, solvent distilled in vacuum, and the residue was purified with silica gel column chromatography (dissolved solvent: n-hexane/ethyl acetate: 2/1 to 1/1), yielding 119 (3.36 g, 84%) as yellow solid.

mp 218~219° C., APCI-MS m/z 436[M+H]$^+$

Production of 120

Trifluoroacetic acid (24 ml) was dropped into a solution of 119 (3.36 g, 7.72 mmol) in chloroform (36 ml) under ice cooled agitation, and stirred at room temperature for 2 hours and 40 minutes. The reaction solution was diluted with ethyl acetate, adjusted to the pH 9 with potassium carbonate solution, after separation the organic layer was washed with water, dried, solvent distilled in vacuum, and the residue was purified with silica gel column chromatography (dissolved solvent: ethyl acetate), and recrystallized with ethyl acetate/ n-hexane, yielding 120 (1.97 g, 76%) as yellow crystals.

mp 220~220° C., APCI-MS m/z 336[M+H]$^+$

Production of 122

Toluene suspension (200 ml) of 120 (1.97 g, 5.87 mmol), 121 (1.00 g, 7.04 mmol) and toluenesulfonate 1 hydrate (56 mg, 0.29 mmol) was refluxed for 16 hours. The reaction solution was left to cool, diluted with ethyl acetate, purified with silica gel column chromatography (dissolved solvent: ethyl acetate), and recrystallized with ethyl acetate, yielding 122 (0.77 g, 34%) as yellow crystals.

mp 205~207° C., $^1$H NMR (500 MHz, DMSO-D$_6$) δ 3.66 (2H, t, J=5.0 Hz), 4.59~4.79 (3H, m), 5.09 (1H, t, J=5.6 Hz, D$_2$O, disappeared), 7.08 (1H, d, J=16.3 Hz), 7.06 (1H, m), 7.44 (1H, d, J=2.1 Hz), 7.65 (1H, d, J=8.7 Hz), 7.96 (1H, d, J=16.3 Hz), 8.19 (1H, s), 9.31 (2H, s)

IR (Nujol) 3333, 1637, 1620 cm$^{-1}$

APCI-MS m/z 388[M+H]$^+$

Production of (131): THK-774 (6-[(1-fluoromethyl-2-hydroxy)ethoxy]2-[4-(1,2,4-triazole-4-yl)-phenyl]benzoxazole)

[Formula 88]

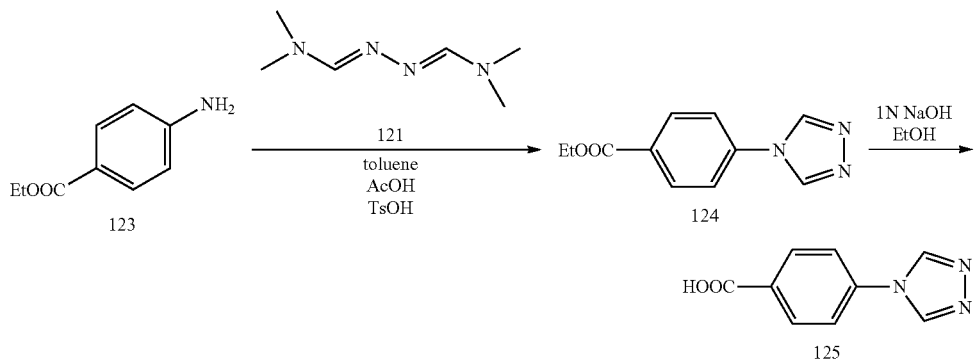

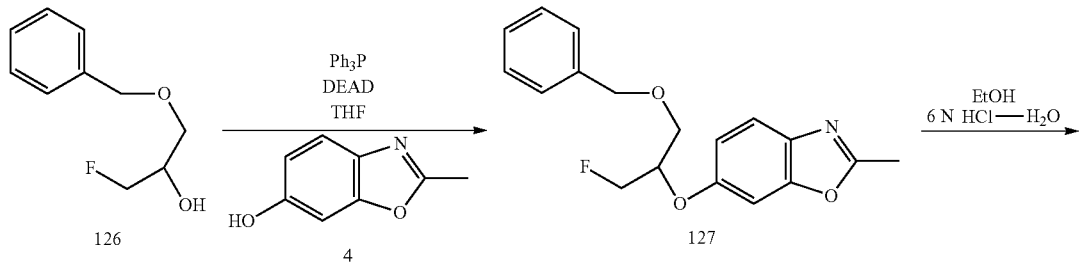

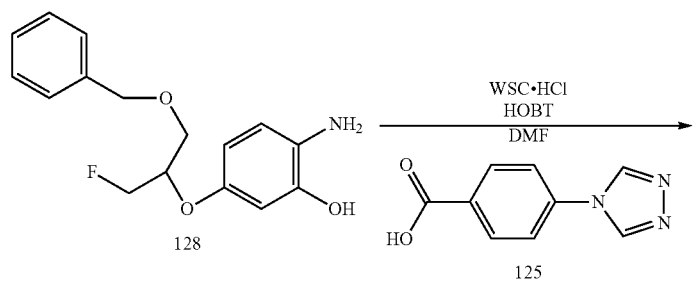

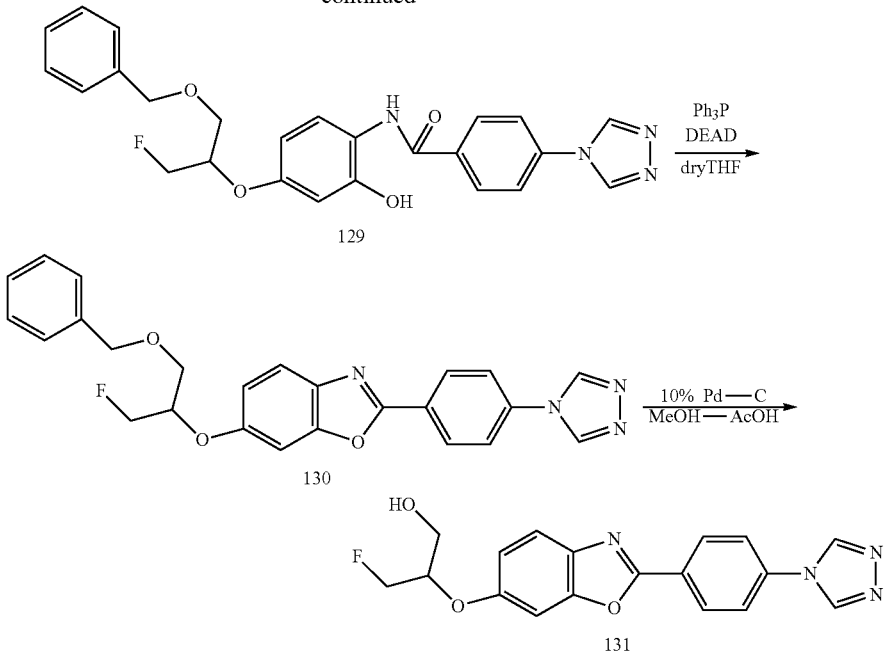

Production of 124

To 4-aminobenzoic acid ethyl ester 123 (20 g, 0.12 mol) dissolved in toluene (200 ml) 121 (13.2 g, 0.093 mol), p-toluensulfonic acid (300 mg) and acetic acid (20 ml) were added, heated and refluxed over night. The reaction solution was cooled down to 5° C., the precipitate was filtered out, and dried in vacuum, yielding 6.87 g (34%) of colorless crystals 124.

APCI-MS m/z 218[M+H]$^+$
IR (Nujol) 1700, 1630, 1611 cm$^{-1}$

Production of 125

Ester 124 (6.8 g, 31.3 mmol) was dispersed into ethanol (70 ml), 1N sodium hydroxide (70 ml) was added, heated and refluxed for 30 minutes. After reaction ended, the solvent was distilled in vacuum, and the residue obtained was dissolved in water. 1N hydrochloric acid (70 ml) was added, precipitated colorless solid was filtered out, washed with water and dried in vacuum, yielding 125 (5.88 g, 99%).

>mp 330° C.
APCI-MS m/z 190[M+H]$^+$
IR (Nujol) 1692, 1609 cm$^{-1}$

Production of 127

To a solution of dried tetrahydrofuran (500 ml) in which alcohol 126 (24 g, 0.13 mol), benzoxazole derivative 4 (19.4 g, 0.13 mol) were dissolved, triphenylphosphine (40.9 g, 0.16 mol) was added and dissolved, and a solution of 40% diethylazodicarboxylate (69.5 g, 0.16 mol) in toluene was dropped while this solution was cooled down to 5° C. Later, the reaction solution was stirred and reacted at room temperature throughout the night. Further, triphenylphosphine (8.18 g, 0.031 mol) and 40% diethylazodicarboxylate (13 g, 0.031 mol) were added to the reaction solution, and stirred at room temperature for 4 hours, and the reaction ended. The solvent was distilled in vacuum, and the residue was dissolved in isopropylether, cooled down with ice water, which precipitated triphenylphosphine oxide. This was filtered out, and the filtrate was adsorbed to silica gel, and crude product was obtained under column chromatography (silica gel BW300: eluate n-hexane and ethyl acetate=3:1). Further, the crude product was purified with column chromatography (silica gel BW300: eluate chloroform:methanol=50:1), yielding 127 (27.7 g, 68%) as colorless, clear, oily substance.

APCI-MS m/z 316[M+H]$^+$

Production of 128

Benzoxazole derivative 127 (10.0 g, 31.7 mmol) was dissolved in ethanol (50 ml) and water (30 ml) and 6N hydrochloric acid (20 ml) were added, stirred, and reacted under heated reflux for 4 hours. After reaction ended, the reaction was cooled down to room temperature, solvent distilled in vacuum, the crude product obtained was separated with ethyl acetate and saturated sodium bicarbonate water, and the organic layer was washed with saturated saline solution, and dried with anhydrous magnesium sulfate. After distillation of solvent, the obtained product was caked by processing with mixture of isopropyl ether and ethyl acetate, yielding 128 (6.5 g, 71%) as colorless solid.

mp 115~117° C.
APCI-MS m/z 292[M+H]$^+$

Production of 129

Carbonic acid 125 (1.89 g, 10 mmol) was dissolved in dried dimethylformamide (50 ml), and further 1-hydroxybenzotriazole (2.026 g, 15 mmol), water-soluble carbodiimide hydrochloride (WSC-HCl) (2.875 g, 15 mmol) and triethylamine (2.02 g, 20 mmol) were added, and stirred at room temperature for 2 hours to react. Next, 128 (2.92 g, 10 mmol) was added to the reaction solution, the temperature raised to 50° C., and it was further reacted for 3 hours. After cooling down, the reaction solution was poured into water, the product was extracted with ethyl acetate, washed with water and saturated saline solution, and dried with anhydrous magnesium sulfate. After solvent distilled, the obtained crude product was purified with column chromatography (silica gel BW300: eluate chloroform:methanol=20:1), yielding 129 (2.52 g, 54%).

mp 175-177° C.
IR (Nujol) 3312, 1652, 1610 cm$^{-1}$
APCI-MS m/z 463[M+H]$^+$

Production of 130

Amide 129 (2.52 g, 5.4 mol) was dissolved in dry tetrahydrofuran (80 ml). Into the resulting solution, triphenylphosphine (2.14 g, 8.17 mmol) and 40% diethylazodicarboxylate (3.52 g, 8.17 mmol) were added and reacted with stirring at room temperature overnight. After the reaction, the reaction solution was absorbed in NH-silica (FUJI SILYSIA), purified by column chromatography (NH-silica; solvent n-hexane-ethyl acetate=1:3) to obtain 130 (2.22 g, 92%) as a colorless solid.

mp 105-107° C.
APCI-MS m/z 445[M+H]$^+$

Production of 131

Compound 130 (2.22 g, 5 mmol) was melted in the mixture of methanol (100 ml) and acetic acid (10 ml) and 10% paradium carbon catalyst (1.0 g) was added therein. And the resulting solution was heated to 50° C. under hydrogen atmosphere and reacted with stirring for 7 hours. After the reaction, the catalyst was removed by filtration, and the filtrate was distilled away under reducing pressure to obtain 131 (1.25 g, 70%). Recrystallization was conducted using methanol and obtained 131 as a colorless crystal.

mp 219-220° C.
IR (Nujol) 3484, 1618 cm$^{-1}$
APCI-MS m/z 355[M+H]$^+$
$^1$H NMR (DMSO-d$_6$) δ 3.68 (2H, bt), 4.59-4.83 (3H, m), 5.11 (1H, t, J=5.6 Hz), 7.10 (1H, dd, J=8.8 Hz, 2.4 Hz), 7.55 (1H, d, J=2.4 Hz) 7.73 (1H, d, J=8.8 Hz), 7.98 (2H, bd, J=8.8 Hz), 8.30 (2H, bd, J=8.8 Hz), 9.29 (2H, s)

Production of THK-683 ((E)-2-[2-(2,2-dicyanoethenylthiazol-5-yl)ethenyl]-6-[(2-fluoromethyl-3-hydroxy)propoxy]benzoxazol): (152)

[Formula 89]

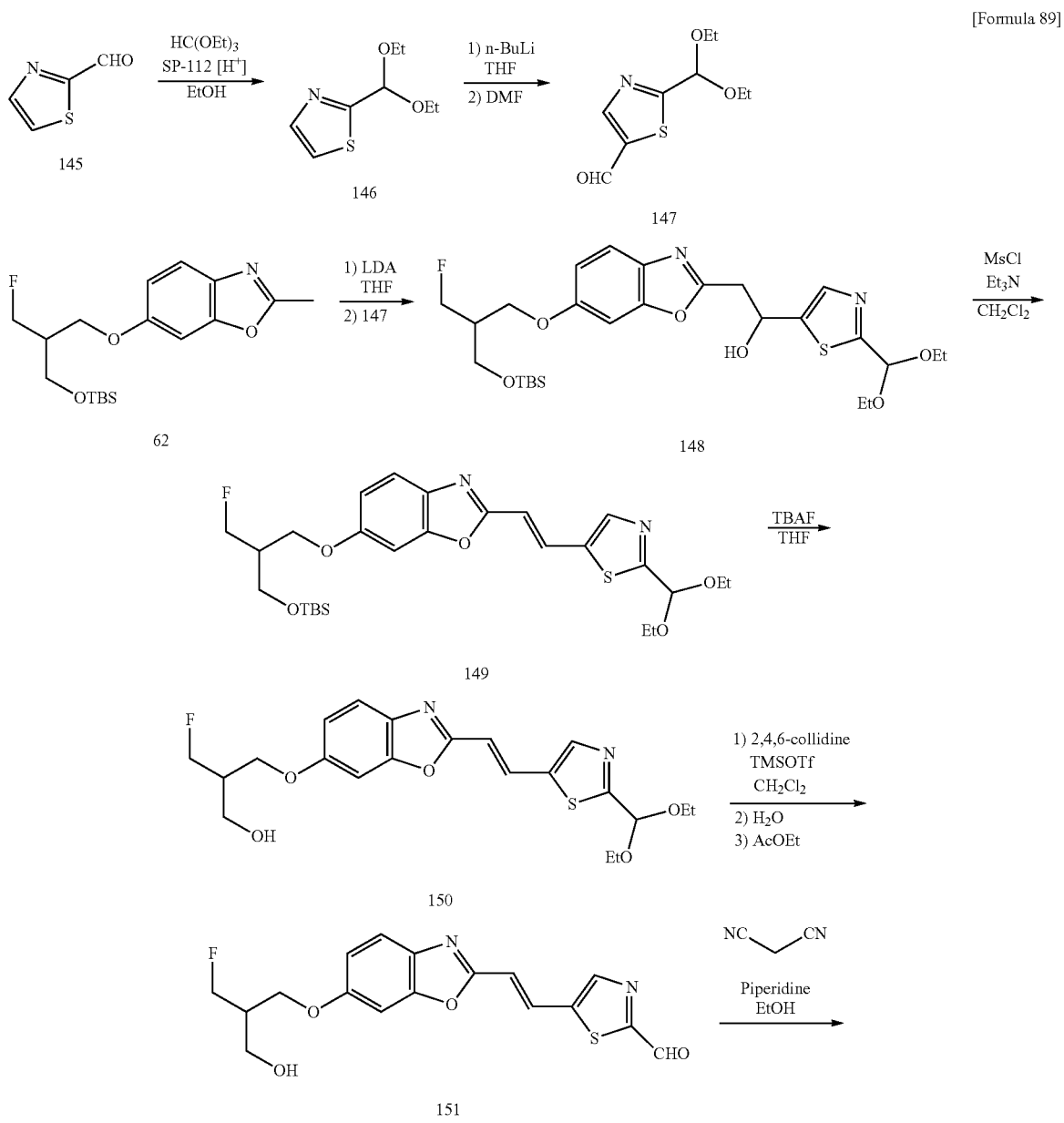

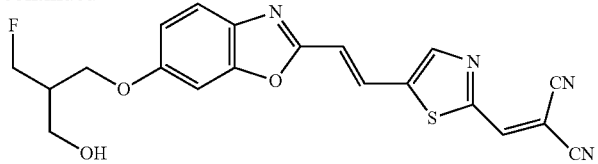

152

Production of 146

Ortho triethyl formate (10 ml) and SP-112 [H$^+$] (1.0 g) were added in ethanol (62 ml) solution of 145 (5.18 g, 45.78 mmol), and the resulting solution was refluxed for 5 hours. SP-112 [H$^+$] of the reaction solution was separated by filtration, and the filtrate was distilled away under reducing pressure to filtrate the solvent. The residue was purified by silica gel column chromatography (elution solvent: ethyl acetate/n-hexane=4/1) to obtain 146 (8.57 g, 100%) as a colorless oily substance. APCI-MS m/z 188[M+H]

Production of 147

1.60 M n-butyllithium/n-hexane solution (45.2 ml, 72.3 mmol) was dropped into tetrahydrofuran (100 ml) solution of 146 (9.02 g, 48.17 mmol) with stirring under argon atmosphere at −70° C. or less, and the resulting solution was stirred at −78° C. for 1 hour. At the same temperature, dimethyl formaldehyde (7.45 ml, 96.3 mmol) was added therein at a time, and stirred for 30 minutes. Water was added in the reaction solution and extracted with ethyl acetate. The extracted solution was washed, dried, and distilled away under reducing pressure to filtrate the solution. The residue was purified by silica gel column chromatography (elution solvent: n-hexane/ethyl acetate=9/1) to obtain 147 (5.55 g, 54%) as a faintly-yellow oily substance.

APCI-MS m/z 216[M+H]$^+$

Production of 148

1.60 M n-butyllithium/n-hexane solution (12.62 ml, 20.20 mmol) was dropped into tetrahydrofuran (60 ml) solution of diisopropylamine (2.85 ml, 20.20 mmol) with stirring under argon atmosphere at −60° C. or less and the resulting solution was heated gradually to 0° C. Then, tetrahydrofuran (20 ml) solution of 62 (4.76 g, 13.47 mmol) was dropped therein at −70° C. or less, the resulting solution was stirred at −78° C. for 1 hour. At the same temperature, tetrahydrofuran (20 ml) solution was added therein at a time, and stirred for 30 minutes. Water was added in the reaction solution and extracted with ethyl acetate. The extracted solution was washed, dried, and distilled away under reducing pressure to filtrate the solution. The residue was purified by column chromatography (elution solvent: n-hexane/ethyl acetate 4/1 to 1/1) to obtain 148 (5.25 g, 69%) as a faintly-yellow oily substance.

APCI-MS m/z 569[M+H]$^+$

Production of 149

Triethylamine (5.15 ml, 36.9 mmol) was added in dichloromethane (50 ml) solution of 148 (5.25 g, 9.23 mmol), and methanesulfonyl chloride (1.57 ml, 20.3 mmol) was dropped therein with stirring cooled on ice and stirred at room temperature for 2 hours. Cool water was added in the reaction solution and extracted with ethyl acetate. The extracted solution was washed, dried, and distilled away under reducing pressure to filtrate the solution. The residue was purified by column chromatography (elution solvent: n-hexane/ethyl acetate=4/1) to obtain 149 (4.24 g, 83%) as a faintly-yellow solid.

APCI-MS m/z 551[M+H]$^+$

Production of 150

1 M tetrabutylammoniumfluoride/tetrahydrofuran solution (1.82 ml, 1.82 mmol) was added to tetrahydrofuran (10 ml) solution of 149 (1.00 g, 1.82 mmol) with stirring at room temperature, and the resulting solution was stirred at room temperature for 1.5 hours. Water was added in the reaction solution and extracted with ethyl acetate. The extracted solution was washed, dried, and distilled away under reducing pressure to filtrate the solution. The residue was purified by silica gel column chromatography (elution solvent: ethyl acetate/n-hexane=2/1 to 1/1) to obtain 150 (0.65 g, 82%) as an yellow solid.

APCI-MS m/z 437[M+H]$^+$

Production of 151

2,4,6-collidine (1.18 ml, 8.94 mmol) was added in dichloromethane (20 ml) solution of 150 (0.65 g, 1.49 mmol), and trimethylsilyl trifluoromethanesulfonate (1.08 ml, 5.96 mmol) was dropped therein with stirring cooled on ice and stirred at the same temperature for 40 minutes. Water (20 ml) was added in the reaction solution and stirred at room temperature for 1 hour. Ethyl acetate (40 ml) was added therein and stirred at 70° C. for 12 hours. The reaction solution was allowed to cool and separated, and then the organic layer thereof was washed, dried, and distilled away under reducing pressure to filtrate the solution. The residue was purified by silica gel column chromatography (elution solvent: n-hexane/ethyl acetate=2/1 to 1/1) to obtain 151 (0.48 g, 89%) as a yellow solid.

mp 134~135° C., IR (Nujol) 1685 cm$^{-1}$

APCI-MS m/z 363[M+H]$^+$

Production of 152

Malononitrile (0.11 g, 1.58 mmol) and piperidine (0.004 ml, 0.04 mmol) were added in ethanol (27 ml) solution of 151 (0.48 g, 1.32 mmol) and the resulting solution was stirred at 60° C. for 40 minutes. The reaction solution was cooled on ice, filtrated and separated, washed by ethanol, and dried to obtain 152 (0.45 g, 83%) as a purple-red crystal.

mp 192~193° C. (dec), $^1$H NMR (300 MHz, CDCl$_3$) δ 2.39~2.55 (1H, m), 3.93 (2H, d, J=5.7 Hz), 4.19 (2H, d, J=5.9 Hz), 4.72 (2H, dd, J=47.1, 5.4 Hz), 6.97 (1H, dd, J=8.8, 2.3 Hz), 7.07 (1H, dd, J=16.1, 0.4 Hz), 7.08 (1H, d, J=2.3 Hz), 7.62 (1H, d, J=8.8 Hz), 7.82 (1H, dd, J=16.1, 0.6 Hz), 7.94 (1H, s), 8.25 (1H, s)

IR (Nujol) 2225, 1617 cm$^{-1}$, APCI-MS m/z 411[M+H]$^+$

EXAMPLE 2

Investigation of models with amyloid β protein deposition in their brain.

Investigation of transgenic (Tg) mice with amyloid deposition in their brain.

(1) Tg mice (Ta2576 or APPswe2576/Tau JPL3) were used. A test compound was administered to a Tg mouse via its tail vein. After 1 hour, the chest of the mouse was cut open under deep anesthesia with Na-pentobarbital, and 10% neutral buffer formalin was transcardially perfused through the mouse to fix it.

(2) The head was cut open, and its brain was taken out, and dipped in 30% sucrose for 12 hours or more. Next, the taken-out brain was immediately frozen in finely-ground dry ice, and using a cryostat (by Bright, Model-OT), a frozen section of the brain was formed on a poly-L-lysine-coated slide.

(3) Not entrapped, the thus-prepared brain section was microscopically observed with a fluorescence microscope (Nikon Eclipse 80i), and photographed with a digital camera (Nikon Dxm 1200F or Photometrics' Cool SNAP ES). The results are shown in FIGS. 1 to 3. THK-097, THK-525 and THK-727 intravenously administered to the animals passed through the blood-brain barrier, and bound to the Tg mouse intracerebral amyloid plaque.

The same section was immunostained as follows:

(1) About 150 µl of 90% formic acid was dropwise applied to the same section, and statically left as at room temperature for 5 minutes. This was washed with tap water for 5 minutes, and then dipped in cold PBS-Tween 20 for 2 minutes, and thereafter about 150 µl of 0.05% trypsin solution was dropwise applied to it and reacted at 37° C. for 15 minutes.

(2) in an ice bath, this was washed with cold PBS-Tween 20, twice for 5 minutes, and then 2 drops of blocking serum were applied to it and reacted at 37° C. for 30 minutes. Excess water was removed, and then about 150 µl of a specific antibody to amyloid β protein, 4G8 (by Chemicon, 1/100 dilution) was dropwise applied to it, and reacted at 37° C. for 1 hour.

(3) Further, this was washed with cold PBS-Tween 20, 5 times for 2 minutes, and then 2 drops of an anti-mouse IgG (H+L), goat, biotin-binding solution were applied to it and reacted at 37° C. for 1 hour. Then, this was washed with cold PBS-Tween 20, three times for 2 minutes, and 2 drops of an ABC solution (streptoavidin-biotin-peroxidase composite solution) were applied to it, and left statically as such for 30 minutes. Again this was washed with cold PBS-Tween 20, three times for 2 minutes, and then about 150 µl of a DAB solution (10 mg of DAB was dissolved in 20 ml of 0.05 mol/liter tris-HCl buffer, and just before use, 100 µl of 3% hydrogen peroxide water was added to it) was dropwise applied to it for sufficiently staining it. Then, this was washed with distilled water for 1 minute to stop the reaction, then entrapped and observed through microscopy.

The results are shown in FIG. 4 and FIG. 5. THK-702 passed through the blood-brain barrier, and bound to the amyloid plaque of the Tg mouse (FIG. 3, upper panel), and the binding site corresponded to the anti-Aβ antibody stained site of the same section (FIG. 3, lower panel). FIG. 4 shows enlarged images of FIG. 3. A, B and C correspond to A, B and C in FIG. 3, respectively. THK-702 bound to the amyloid plaque of the Tg mouse (FIG. 4, left panels), and the binding site completely corresponded to the anti-Aβ antibody-stained site of the same section (FIG. 4, right panels).

The protocol of a staining test with the compound of the invention on a brain section of an Alzheimer disease patient is described below.

(1) Brain specimens at the temporal lobe and the hippocampus of patients to which a definitive diagnosis of Alzheimer disease had been given, and those of normal senile persons were used. The specimens were given by our coworker, Fukushimura Hospital, Longevity Medicine Institute, and we were given their consent of use of the specimens for our study purpose by the bereaved of the patients (Fukushimura Hospital Ethical Review Board Approval No. 20).

(2) The paraffin-embedded brain tissue was cut Into slices having a thickness of 6 µm or 8 µm, and extended and dried on a slide. The paraffin brain section was steeped for paraffin removal in xylene twice for 10 minutes, 100% ethanol twice for 5 minutes, 90% ethanol for 5 minutes and running water for 10 minutes in that order.

(3) For pretreatment prior to the staining treatment with a compound of the invention, the sections were steeped for autofluorescence removal with lipofuscin. First, the paraffin-removed sections were dipped in 0.25% $KMnO_4$ solution for 20 minutes. These were washed with PBS, twice for 2 minutes, then dipped in 0.1% $K_2S_2O_5$/oxalic acid solution for about 5 seconds, and then further washed with PBS, three times for 2 minutes.

(4) About 150 µl of a 100 µM solution of a compound of the invention dissolved in 50% ethanol was dropwise applied to the section and reacted for 10 minutes. After dipped five times in tap water, the section was entrapped with Fluor Save Reagent (Calbiochem), and analyzed through microscopy with a fluorescence microscope (Nikon, Eclipse 80i). The images were taken with a digital camera (Nikon Dxm 1200F or Photometrics' Cool SNAP ES).

Immunostaining was attained as follows:

(a) Method of Immunostaining of Amyloid β Protein (1) After paraffin removal, the sections were washed in distilled water, twice for 2 minutes. Then, using ImmunoPen, the tissue was marked with a surrounding line; about 150 µl of formic acid was dropwise applied to the section and statically left at room temperature for 5 minutes. The section was washed with tap water for 5 minutes, then dipped in cold PBS-Tween 20 for 2 minutes, and thereafter about 150 µl of 0.05% trypsin solution was dropwise applied to it and reacted at 37° C. for 15 minutes.

(2) In an ice bath, this was washed with cold PBS-Tween 20, twice for 5 minutes, and then 2 drops of blocking serum were applied to it and reacted at 37° C. for 30 minutes. Excess water was removed, and then about 150 µl of a specific antibody to amyloid β protein, 6F/3D (by DAKO, 1/50 dilution) was dropwise applied to it, and reacted at 37° C. for 1 hour.

(3) Further, this was washed with cold PBS-Tween 20, 5 times for 2 minutes, and then 2 drops of an anti-mouse IgG (H+L), goat, biotin-binding solution were applied to it and reacted at 37° C. for 1 hour. Then, this was washed with cold PBS-Tween 20, three times for 2 minutes, and 2 drops of an ABC solution (streptoavidin-biotin-peroxidase composite solution) were applied to it, and left statically as such for 30 minutes. Again this was washed with cold PBS-Tween 20, three times for 2 minutes, and then about 150 µl of a DAB solution (10 mg of DAB was dissolved in 20 ml of 0.05 mol/liter tris-HCl buffer, and just before use, 100 µl of 3% hydrogen peroxide water was added to it) was dropwise applied to it for sufficiently staining it. Then, this was washed with distilled water for 1 minute to stop the reaction, then entrapped and observed through microscopy.

(b) Method of Immunostaining of Neurofibrillary Tangle (1) After paraffin removal treatment, the section was washed with cold PBS-Tween 20, twice for 5 minutes, and then 2 drops of blocking serum were applied to it and reacted at 37° C. for 30 minutes. Excess water was removed, and then 2 drops of an antibody specific to tau, AT-8 (by Mia Nobels, 1/100 dilution) were applied to it, and reacted overnight at 4° C.

(2) On the next day, this was washed with cold PBS-Tween 20, five times for 2 minutes, and then 2 drops of an anti-rabbit IgG, goat, biotin-binding solution were applied to it and reacted at 37° C. for 1 hour. Then, this was washed with cold PBS-Tween 20, three times for 2 minutes, and 2 drops of an ABC solution (streptoavidin-biotin-peroxidase composite solution) were applied to it, and left statically as such for 30 minutes.

(3) Again this was washed with cold PBS-Tween 20, three times for 2 minutes, and then about 150 µl of a DAB solution (10 mg of DAB was dissolved in 20 ml of 0.05 mol/liter tris-HCl buffer, and just before use, 100 µl of 3% hydrogen peroxide water was added to it) was dropwise applied to it for sufficiently staining it. Then, this was washed with distilled water for 1 minute to stop the reaction, then entrapped and observed through microscopy. The blocking serum, the anti-rabbit IgG, goat, biotin-binding solution and the ABC solution used herein were those in a phosphorylated tau immunohistostain kit (Wako 299-57301).

The results of the above-mentioned staining tests with the compounds of the invention are shown in FIG. 2 to FIG. 26. THK-097 bound to the amyloid β protein in the brain section of an Alzheimer disease patient (FIG. 2). THK-184 bound to the amyloid β protein in the brain section of an Alzheimer disease patient (FIG. 3). THK-185 bound to the amyloid β protein and the neurofibrillary tangle in the brain section of an Alzheimer disease patient (FIG. 4). THK-203 bound to the amyloid β protein in the brain section of an Alzheimer disease patient (FIG. 5). THK-207 bound to the amyloid β protein in the brain section of an Alzheimer disease patient (FIG. 6). THK-248 bound to the amyloid β protein in the brain section of an Alzheimer disease patient (FIG. 7). THK-254 bound to the neurofibrillary tangle in the brain section of an Alzheimer disease patient (FIG. 8). THK-258 bound to the amyloid β protein and the neurofibrillary tangle in the brain section of an Alzheimer disease patient (FIG. 9). THK-262 bound to the amyloid β protein in the brain section of an Alzheimer disease patient (FIG. 10). THK-276 bound to the amyloid β protein in the brain section of an Alzheimer disease patient (FIG. 11). THK-281 bound to the amyloid β protein in the brain section of an Alzheimer disease patient (FIG. 12). THK-308 bound to the amyloid β protein in the brain section of an Alzheimer disease patient (FIG. 13). THK-317 bound to the amyloid β protein and the neurofibrillary tangle in the brain section of an Alzheimer disease patient (FIG. 14). THK-383 bound to the amyloid β protein in the brain section of an Alzheimer disease patient (FIG. 15). THK-385 bound to the amyloid β protein in the brain section of an Alzheimer disease patient (FIG. 16). THK-386 bound to the amyloid β protein and the neurofibrillary tangle in the brain section of an Alzheimer disease patient (FIG. 17). THK-525 bound to the amyloid β protein in the brain section of an Alzheimer disease patient (FIG. 18). THK-556 bound to the amyloid β protein in the brain section of an Alzheimer disease patient (FIG. 19). THK-558 bound to the amyloid β protein in the brain section of an Alzheimer disease patient (FIG. 20). THK-559 bound to the amyloid β protein in the brain section of an Alzheimer disease patient (FIG. 21). THK-561 bound to the amyloid β protein in the brain section of an Alzheimer disease patient (FIG. 22). THK-562 bound to the amyloid β protein in the brain section of an Alzheimer disease patient (FIG. 23). THK-563 bound to the amyloid β protein in the brain section of an Alzheimer disease patient (FIG. 24). THK-565 bound to the amyloid β protein in the brain section of an Alzheimer disease patient (FIG. 25). THK-585 bound to the amyloid β protein in the brain section of an Alzheimer disease patient (FIG. 26). In that manner, it has been found that the compounds of the invention can specifically recognize the amyloid β protein and the neurofibrillary tangle in the brain sections of Alzheimer disease patients. In addition, it has also been found that the other compounds of the invention than those mentioned above can also specifically bind to amyloid β protein.

Test methods for the properties of the compounds of the invention are described below.

EXAMPLE 3

Acute Toxicity Test

The compounds of the invention were tested for their acute toxicity through intravenous administration thereof to mice. Four Crj:CD1 male mice formed one test group, and some test groups of those mice were used (the mean body weight of the mice of each group was from 31 to 32 g). A test compound was dissolved in a mixture of 1 N HCl, polyethylene glycol-400 and distilled water, or dissolved in DMSO, and then diluted with distilled water. This was administered to each mouse via its tail vein. After that, the mice were observed for 7 days. The results are shown in Table 2.

TABLE 2

Acute Toxicity Test of Compounds of the Invention

| | Maximum Permissible Dose (mg/kg, intravenous administration) |
|---|---|
| THK-525 | ≧10 |
| THK-702 | ≧10 |
| THK-707 | ≧10 |
| THK-708 | ≧10 |
| THK-713 | ≧10 |
| THK-727 | ≧10 |
| THK-752 | ≧10 |
| THK-757 | ≧10 |
| THK-761 | ≧10 |
| THK-763 | ≧10 |
| THK-765 | ≧10 |
| THK-766 | ≧10 |

EXAMPLE 4

Brain Permeability Test

I. Brain Permeability Test Through HPLC

A compound of the invention was intravenously administered to mice, and tested for its in-vivo brain permeability in the mice.

(1) Slc:ICR mice (by Nippon SLC) (body weight, 30 to 40 g; n=3) were used.

(2) A test compound was dissolved in a mixture of 5% Tween 80-5% ethyl alcohol-5% 1 N HCl-physiological saline water, and injected into the test mouse via its tail vein. Two minutes after the administration, the blood was collected from the test mouse under ether anesthesia via its abdominal aorta using a heparin-steeped syringe, and the brain material was collected from it.

(3) After collected, the blood was centrifuged at 4° C. and 14,000 rpm for 10 minutes, and the supernatant was stored at −80° C. as plasma. After collected, the brain material (including the cerebellum) was stored at −80° C.

(4) 0.3 ml of acetonitrile was added to 0.1 ml of the plasma, then vortexed, and centrifuged at 4° C. and under 10,000 G for 5 minutes. After centrifuged, 0.2 ml of the resulting supernatant was transferred into Mini-Uniprep (Whatman), then 0.2 ml of 20 mM phosphate buffer was added to it and filtered. 0.2 ml of the resulting filtrate was analyzed through HPLC (Shiseido Nanospace SI-2; pump, 3001; UV-VIS detector, 3002; column thermostat, 3004; fluorescence detector, 3013).

(5) 2 ml of methanol was added to the brain, homogenized, and centrifuged at 4° C. and 3000 or 4000 rpm for 10 minutes. After centrifuged, 500 μl of the resulting supernatant was diluted 10-fold with 20 mM phosphate buffer. (i) 2 to 3 ml of acetonitrile, (ii) 2 to 5 ml of methanol and (iii) 4 to 6 ml of ultra-pure water were led through a cartridge for solid-phase extraction (J. T. Baker Speedisk) in that order, and the 10-fold diluted supernatant solution was led through it. Via an empty syringe, air was applied to the cartridge for solid-phase extraction, two or three times to remove water, and then this was eluted with about 500 μl of acetonitrile or methanol, and the eluate was diluted 2-fold with 20 mM phosphate buffer. 0.2 ml of the resulting solution was analyzed through HPLC.

(6) The test compound content in the plasma and in the brain was determined relative to the dose of the compound (% ID (injected dose)/g or ml).

Table 3 shows the brain permeability of the test compound in mice in 2 minutes after intravenous administration of the compound. It is considered that the brain permeability of a compound necessary for PET or SPECT directed to a central nervous system will be at least 0.5% ID/g. To that effect, the compounds tested herein have an extremely high brain permeability.

TABLE 3

Brain Permeability of Compound of the Invention
in 2 minutes after intravenous administration (mice)

| | % ID/g or ml | |
| --- | --- | --- |
| | Brain | Plasma |
| THK-525 | 7.9 | 3.1 |
| THK-702 | 5.1 | 2.7 |
| THK-707 | 4.4 | 0.58 |
| THK-713 | 5.9 | 3.29 |
| THK-752 | 6.7 | 1.9 |

EXAMPLE 5

II. Investigation with [$^{18}$F]-Labeled Compounds

The compounds according to the present invention can be labeled by use of known methods in the art. Examples of synthesis of [$^{18}$F]-labeled compounds according to the present invention are shown below.
Synthesis of [$^{18}$F]THK525

A positron beam of 12 MeV, accelerated with a cyclotron HM12 (by Sumitomo Heavy Industries), was applied to [$^{18}$O] H$_2$O having an isotope purity of at least 95%, for 30 minutes, thereby producing $^{18}$F$^-$. Next, the solution was led through an anion exchange resin (AG1-X8) whereby $^{18}$F$^-$ was trapped by the resin, and then this was eluted with 33 mM K$_2$CO$_3$ solution. 300 μL (3.28 GBq) of the aqueous $^{18}$F$^-$-containing K$_2$CO$_3$ solution was put into a brown vial (capacity 10 mL), and Kryptofix 222 (16 mg) and acetonitrile (2 mL) were added to it. Then, with heating in an oil bath (110° C.), He gas was jetted to it, and acetonitrile was completely removed while azeotroped with water. Further, acetonitrile (3 mL) was added to it, and acetonitrile was removed under the same heating condition. This operation was repeated three times, whereby the vial was made to contain no water. A DMSO solution (0.8 mL) with a labeling precursor THK575 (1.9 mg) dissolved therein was added to it, and stirred under heat in an oil bath (110° C.) for 10 minutes. Next, the DMSO solution was led through a Sep-Pak™ alumina cartridge (by Waters) and a filter (0.5 μm), and the resulting filtrate was steeped through semi-partitioning HPLC (column, Inertsil™ ODS-3 (10×250 mm); mobile phase, EtOH/MeCN/20 mM NaH$_2$PO$_4$=15/45/40; flow rate, 5.0 mL/min)$_1$ in which the [$^{18}$F]THK525-derived radioactive peak that was eluted in about 11 to 12 minutes was collected. The radiochemical yield after attenuation correction, obtained from the radioactivity of the fraction, was 42%; and the radiochemical purity was 99% or more.
Synthesis of [$^{18}$F]THK702

A positron beam of 12 MeV, accelerated with a cyclotron HM12 (by Sumitomo Heavy Industries), was applied to [$^{18}$O] H$_2$O having an isotope purity of at least 95%, for 30 minutes, thereby producing $^{18}$F$^-$. Next, the solution was led through an anion exchange resin (AG1-X8) whereby $^{18}$F$^-$ was trapped by the resin, and then this was eluted with 33 mM K$_2$CO$_3$ solution. 200 μL (3.24 GBq) of the aqueous $^{18}$F$^-$-containing K$_2$CO$_3$ solution was put into a brown vial (capacity 10 mL), and Kryptofix 222 (16 mg) and acetonitrile (3 mL) were added to it. Then, with heating in an oil bath (110° C.), He gas was jetted to it, and acetonitrile was completely removed while azeotroped with water. Further, acetonitrile (3 mL) was added to it, and acetonitrile was removed under the same heating condition. This operation was repeated three times, whereby the vial was made to contain no water. A DMSO solution (0.8 mL) with a labeling precursor THK703 (2.2 mg) dissolved therein was added to it, and stirred under heat in an oil bath (110° C.) for 10 minutes. Next, the reaction solution was diluted with distilled water (8 mL), and loaded in Sep-Pak tC18 cartridge (by Waters). Then, the cartridge was washed with distilled water, and eluted with EtOH, and the resulting eluate was steeped through semi-partitioning HPLC (column, Inertsil™ ODS-3 (10×250=m); mobile phase, MeCN/20 mM NaH PO$_4$=40/60; flow rate, 7.0 mL/min), in which the [$^{18}$F]THK702-derived radioactive peak that was eluted in about 11 minutes was collected. The radiochemical yield after attenuation correction, obtained from the radioactivity of the fraction, was 21%; and the radiochemical purity was 99% or more.
Synthesis of [$^{18}$F]THK727

A positron beam of 12 MeV, accelerated with a cyclotron HM12 (by Sumitomo Heavy Industries), was applied to [$^{18}$O] H$_2$O having an isotope purity of at least 95%, for 30 minutes, thereby producing $^{18}$F$^-$. Next, the solution was led through an anion exchange resin (AG1-X8) whereby is $^{18}$F$^-$ was trapped by the resin, and then this was eluted with 33 mM K$_2$CO$_3$ solution. 100 μL (1.27 GBq) of the aqueous $^{18}$F$^-$-containing K$_2$CO$_3$ solution was put into a brown vial (capacity 10 mL), and Kryptofix 222 (10 mg) and acetonitrile (3 mL) were added to it. Then, with heating in an oil bath (110° C.), He gas was jetted to it, and acetonitrile was completely removed while azeotroped with water. Further, acetonitrile (3 mL) was added to it, and acetonitrile was removed under the same heating condition. This operation was repeated three times, whereby the vial was made to contain no water. A DMSO solution (0.4 mL) with a labeling precursor THK726 (1.9 mg) dissolved therein was added to it, and stirred under heat in an oil bath (110° C.) for 10 minutes. Next, the DMSO reaction solution was led through a Sep-Pak™ alumina cartridge (by Waters) and a filter (0.5 μm), then DMSO (0.2 mL) was additionally given to it. The resulting filtrate was steeped through semi-partitioning HPLC (column, Inertsil™ ODS-3 (10×250 mm); mobile phase, MeCN/20 mM NaH$_2$PO$_4$=40/60; flow rate, 5.0 mL/min), in which the [$^{18}$F]THK727-derived radioactive peak that was eluted in about 23 minutes was collected. The radiochemical yield after attenuation correction, obtained from the radioactivity of the fraction, was 44%; and the radiochemical purity was 99% or more.

Synthesis of [$^{18}$F] THK-761

$^{18}$F$^-$ was synthesized by passing 12 MeV proton-beam accelerated in Cyclotron HM12 (produced Sumitomo Heavy Industries, Ltd.) through [$^{18}$O] H$_2$O having 95% or more of isotopic purity for 30 minutes. And then, the resulting solution was passed through an anion-exchange resin (AG1-X8), captured $^{18}$F$^-$ on the resin, and eluted by 33 mM K$_2$CO$_3$ solution. The 400 µL (3.73 GBq) of K$_2$CO$_3$ aqueous solution containing $^{18}$F$^-$ was poured into a brown vial (volume: 10 mL), and then Kryptofix 222 (16 mg) and acetonitrile (2 mL) were added therein. He gas was sprayed to the vial with heated on oil bath (110° C.), and acetonitrile was removed completely being subjected to azeotropy with water. Furthermore, acetonitrile (2 mL) was added therein, and the process of removing acetonitrile under heating condition was repeated 3 times same as above manner to be contained no water in the vial. DMSO solution (0.7 mL) dissolved in THK-760 (4.0 mg) as a label precursor was added therein and heated and stirred with oil bath (110° C.) for 10 minutes. And then, the reaction solution was diluted by distilled water (7 mL) and loaded on Sep-Pak tC18 cartridge (produced by Waters Corporation). Next, the cartridge was washed by distilled water and MeCN/20 mM NaH$_2$PO$_4$ (v/v=3/7.2 mL) sequentially, and then the solution of crude product eluted by EtOH was passed through semi-separated HPLC (column: Inertsil (registered mark) ODS-3 (10×250 mm), mobile-phase: MeCN/20 mM MaH$_2$PO$_4$=30/70, flow rate: 5.5 mL/min) and separated radioactive peaks derived from [$^{18}$F] THK-761 eluted at about 15.5 to 16.0 minutes. The radiochemical yield after decay compensation calculated from the radioactivity of this fraction was 11%.

Synthesis of [$^{18}$F]THK763

A positron beam of 12 MeV, accelerated with a cyclotron HM12 (by Sumitomo Heavy Industries), was applied to [$^{18}$O] H$_2$O having an isotope purity of at least 95%, for 30 minutes, thereby producing $^{18}$F$^-$. Next, the solution was led through an anion exchange resin (AG1-X8) whereby $^{18}$F$^-$ was trapped by the resin, and then this was eluted with 33 mM K$_2$CO$_3$ solution. 200 µL (3.02 GBq) of the aqueous $^{18}$F$^-$-containing K$_2$CO$_3$ solution was put into a brown vial (capacity 10 mL), and Kryptofix 222 (16 mg) and acetonitrile (3 mL) were added to it. Then, with heating in an oil bath (110° C.), He gas was jetted to it, and acetonitrile was completely removed while azeotroped with water. Further, acetonitrile (3 mL) was added to it, and acetonitrile was removed under the same heating condition. This operation was repeated three times, whereby the vial was made to contain no water. A DMSO solution (0.7 mL) with a labeling precursor THK762 (3.1 mg) dissolved therein was added to it, and stirred under heat in an oil bath (110° C.) for 10 minutes. Next, the reaction solution was diluted with distilled water (7 mL), and loaded in Sep-Pak tC18 cartridge (by Waters). Then, the cartridge was washed with distilled water and MeCN/20 mM NaH$_2$PO$_4$ (v/v=3/7, 5 mL) in that order, and eluted with EtOH, and the resulting eluate was steeped through semi-partitioning HPLC (column, Inertsil™ ODS-3 (10×250 mm); mobile phase, MeCN/20 mM NaH$_2$PO$_4$=35/65; flow rate, 6.0 mL/min), in which the [$^{18}$F]THK763-derived radioactive peak that was eluted in about 24 to 25 minutes was collected. The radiochemical yield after attenuation correction, obtained from the radioactivity of the fraction, was 38%.

PREPARATION EXAMPLES

Synthesis of [$^{18}$F] BF-227

$^{18}$F$^-$ was synthesized by passing 12 MeV proton-beam accelerated in Cyclotron HM12 (produced Sumitomo Heavy Industries, Ltd.) through [$^{18}$O] H$_2$O having 95% or more of isotopic purity for 30 minutes. And then, the resulting solution was passed through an anion-exchange resin (AG1-X8), captured $^{18}$F$^-$ on the resin, and eluted by 33 mM K$_2$CO$_3$ solution. The 200 µL (1.58 GBq) of K$_2$CO$_3$ solution containing $^{18}$F$^-$ was poured into a brown vial (volume: 10 mL), and then Kryptofix 222 (16 mg) and acetonitrile (2 mL) were added therein. He gas was sprayed to the vial with heated on the oil bath (110° C.), and acetonitrile was removed completely with being subjected to azeotropy with water. Furthermore, acetonitrile (2 mL) was added therein, and the process of removing acetonitrile under heating condition was repeated 3 times same as above manner to be contained no water in the vial. DMSO solution (0.7 mL) dissolved a label precursor (TsO, 2.0 mg) was added therein and heated and stirred with oil bath (110° C.) for 10 minutes. And then, the reaction solution was diluted by distilled water (8 mL) and loaded on Sep-Pak tC18 cartridge (produced by Waters Corporation). Next, the cartridge was washed by distilled water and MeCN/H$_2$O (v/v=1/1, 1.5 mL) sequentially, and then the solution of crude product eluted by EtOH was passed through semi-separated HPLC (column: YMC-Pack Pro C18 RS (10× 250 mm), mobile-phase: EtOH/MeCN/20 mM NaH$_2$PO$_4$=15/40/45, flow rate: 5.0 mL/min) and separated radioactive peaks derived from [$^{18}$F] BF-227 eluted at about 12 to 13 minutes. The radiochemical yield after the decay compensation calculated from the radioactivity of this fraction was 42%.

Preparation of Labeled Compound-Containing Saline

Separated HPLC fractions containing [$^{18}$F] THK-702, [$^{18}$F] THK-761, [$^{18}$F] THK-763 or [$^{18}$F] BF-227 obtained by above mentioned synthesis of label were diluted with distilled water (about 20 mL), loaded thereon Sep-PaktC18 cartridge (produced by Waters Corporation). And the cartridge was washed by distilled water (5 to 10 mL), and labeled compound by EtOH (3 to 5 mL). A proper amount of 5% polysorbate 80-ethanol solution was added in the EtOH eluate and solvent was distilled away by a rotary evaporator with heating at 80° C. Obtained residue (mixture of the label compound and polysorbate 80) was dissolved in saline to prepare the labeled compound-containing saline. The radiochemical purity of chemical after the preparation was 95% or more.

Evaluation of Brain-Penetration and Bone-Seeking Properties of the Labeled Compound in Mouse Saline containing [$^{18}$F] BF-227, [$^{18}$F] THK-702, [$^{18}$F] THK-761 or [$^{18}$F] THK-763 was administered by intravenous injection through the tail vein of male ICR mouse (6 to 7 week), and brain-penetration and bone-seeking properties of each labeled compound was evaluated in the terms of seeking property of radioactivity in brain-tissue and bone tissue at 2, 30, 60 minutes after the injection.

And, BF-227 (2-[2-(2-dimethylaminothiazol-5-yl)ethenyl]-6-(2-fluoroethoxy)benzoxazol) comparatively has a similarity in chemical structure to that of the present invention. Moreover, BF-227 has been used as a [$^{11}$C] label and has F in the chemical structure thereof (Kudo et al., Journal of Nuclear Medicine, vol. 48, pp. 553 to 561, 2007), therefore, the difference between the property of [$^{18}$F] BF-227 as a PET probe for diagnosis of Alzheimer's disease and that of [$^{18}$F] labeled compound of the present invention was examined.

The radiochemical purity of the saline containing the labeled compound used in the present invention was 95% or more, and the specific radioactivity was 18.5 to 148 GBq/ µmol. 1.11 to 2.22 Mbq of the labeled compound per mouse was administrated. In evaluation of seeking property of radioactivity, the proportion of radioactivity in unit weight of evaluated tissue to all dosed radioactivity (% Injected Dose/g of tissue; % ID/g) was used as an index. Gamma counter (1480 WIZARD, produced by PerkinElmer, Inc.) was used in the measurement of radioactivity. Experimental procedures will be explained as follows. The labeled compound was administered by intravenous injection through the tail vein, 2, 30 and 60 minutes after the injection, cervical dislocation of the mouse was conducted under ether anesthesia, and blood was collected from heart rapidly. And then, whole brain (containing cerebellum and brain-stem) and thighbone of mouse were extracted. Moreover, radioactivity and the tissue weight of each sample were measured, the resulting data was used for calculating % ID/g.

Table 4 summarizes the results of the evaluation experiment. FIG. 38 shows the evaluation results of bone-seeking property.

TABLE 4

Evaluation results of brain-penetration and bone-seeking properties of [$^{18}$F] label compound of the present invention (mouse)

| | | % ID/g | | |
|---|---|---|---|---|
| | | Brain | bone | blood |
| [$^{18}$F]BF-227 | 2 min | 6.05 | 1.59 | 2.93 |
| | 30 min | 1.91 | 4.38 | 2.14 |
| | 60 min | 1.67 | 7.04 | 2.09 |
| [$^{18}$F]THK-702 | 2 min | 4.15 | 1.95 | 3.34 |
| | 30 min | 0.53 | 0.92 | 1.06 |
| | 60 min | 0.35 | 1.16 | 0.67 |
| [$^{18}$F]THK-761 | 2 min | 1.67 | 1.36 | 3.16 |
| | 30 min | 0.22 | 0.88 | 0.78 |
| | 60 min | 0.13 | 0.95 | 0.34 |
| [$^{18}$F]THK-763 | 2 min | 4.64 | 1.84 | 3.65 |
| | 30 min | 0.53 | 0.88 | 1.19 |
| | 60 min | 0.28 | 1.38 | 0.64 |

Brain-penetration of the labeled compound for PET or SPECT being aimed at central nerve system has been considered sufficient to be 0.5% ID/g or more. [$^{18}$F] labeled compound of the present invention has extremely high brain-penetration property in that way.

Sometimes, bone-seeking of $^{18}$F ion based on defluorination of [$^{18}$F] label compound in vivo may results in problems (Tipre et al., Journal of Nuclear Medicine, vol. 47, pp. 345 to 353, 2006). In view of high bone-seeking property of $^{18}$F ion, obtained PET image at using [$^{18}$F] label compound for a diagnosis probe of Alzheimer's disease will be like a bone (skull) image. However, the labeled compound being less subjected to defluorination sufficiently has not been obtained at present (See Cai et al., Journal of Medicinal Chemistry, vol. 47, pp. 2208 to 2218, 2004; Zhang et al., Journal of Medicinal Chemistry, vol. 48, pp. 5980 to 5988, 2005; Chang et al., Nuclear Medicine and Biology, vol. 33, pp. 811 to 820, 2006; and Stephenson et al., Bioconjugate Chemistry, vol. 18, pp. 238 to 246, 2007).

The results of bone-seeking properties of [$^{18}$F] THK-702, [$^{18}$F] THK-761, [$^{18}$F] THK-763 and [$^{18}$F] BF-227 measured at same time in investigation of brain-penetration property of that were as Table 4. Bone-seeking of [$^{18}$F] THK-702, [$^{18}$F] THK-761, [$^{18}$F] THK-763 have not found. By the way, in [$^{18}$F] BF-227, significant time-dependent bone-seeking property after the injection has been found. For this reason, it was suggested that [$^{18}$F] THK-702, [$^{18}$F] THK-761, [$^{18}$F] THK-763 were not subjected to defluorination, but [$^{18}$F] BF-227 was easily subjected to that easily and seek $^{18}$F ions on bone.

To sum up the experimental results above mentioned, [$^{18}$F] labeled compound, specifically [$^{18}$F] THK-702, [$^{18}$F] THK-761, [$^{18}$F] THK-763 of the present invention were excellent characteristics in washout from brain more than [$^{18}$F] BF-227 clearly (Table 4). Moreover, the bone-seeking of $^{18}$F ions based on defluorination observed in [$^{18}$F] BF-227 was hardly observed in [$^{18}$F] labeled compound, specifically [$^{18}$F] THK-702, [$^{18}$F] THK-761, [$^{18}$F] THK-763 of the present invention. Therefore, it was found that defluorination was suppressed on desired level (Table 4).

Therefore, [$^{18}$F] labeled compound, specifically [$^{18}$F] THK-702, [$^{18}$F] THK-761, [$^{18}$F] THK-763 of the present invention are extremely useful as a PET probe for diagnosis of Alzheimer's disease compared with BF-227 not having the structure of compound of the present invention.

EXAMPLE 6

Mutagenicity Test

In view of their use, it is desirable that the compounds of the invention have no mutagenicity or have little mutagenicity to a level causing no problem. For investigating the gene mutagenesis of the compounds of the invention, herein carried out was a reverse mutation test with histidine-requiring *Salmonella typhimurium* TA100 and TA98 strains. Two tests were carried out. One is a test for dose determination test; and the other is for mutagenicity.

The test methods and the mutagenicity of the compounds of the invention are mentioned below. In the dose determination test, six doses of 0.160, 0.800, 4.00, 20.0, 100 and 500 μg/plate (common ratio 5) were tried.

As a result of the dose determination test, when the mutagenicity of the test compound was admitted, then the actual test for mutagenicity was carried out, using the dose capable of giving an accurate dose-reaction curve. When no mutagenicity of the test compound was admitted in the dose determination test and when the growth inhibition of the test cells was admitted therein, then the dose to present the growth inhibition was taken as the maximum dose; and when the growth inhibition was not admitted, then a dose of 5000 μg/plate was taken as the maximum dose. With that, the actual test for mutagenicity was carried out on the level of 6 doses (common ratio 2).

First, a test compound was dissolved or suspended in DMSO, then diluted in order to prepare test compound liquids having a varying concentration.

100 μl of a test compound liquid or a negative control (DMSO) solution was put into a sterilized test tube. Then, for the case in the absence of a metabolic activation system (−S9mix), 500 μl of 0.1 mol/liter sodium-phosphate buffer (pH 7.4) was added to it; and for the case in the presence of a metabolic activation system (+S9mix), 500 μl of S9mix was added to it.

Next, 100 μl of the test strain suspension that had been cultivated with shaking at 37° C. for 8 hours was added to it, and preincubated in a shaking thermostat at 37° C. for 20 minutes. After shaken, 2 ml of top agar was added to it, and the contents were mixed.

Next, the mixture was poured onto a minimal glucose agar plate medium (plate) and spread uniformly thereon, then the top agar was solidified, and the plate was transferred into a thermostat and incubated at 37° C. for 48 hours.

After the incubation, the growing condition or the test cells on the plate was observed with a stereoscopic microscope, and the deposition condition of the test substance was observed with the naked eye. Then, the number of the colonies grown through reverse mutation was counted.

For counting it, used as a colony analyzer. After area correction and miss-counting correction, the number of the colonies was computed. When the colony analyzer could not be used owing to the deposition of the test compound or the cell growth inhibition, then the number of the colonies was counted with the naked eye.

In case where the number of the colonies through reverse mutation increased two times or more that of the negative control and where the dose dependency or the reproducibility of the increase was admitted, then the tested sample was decided as positive. When the sample was is decided as positive, then the relative activity that indicates the relative comparative value of the intensity of the mutagenicity of the test compound was obtained according to the following formula:

Relative Activity={(number of colonies per plate having the concentration)−(number of colonies per negative control plate)}/the value of concentration (mg/plate).

According to the step mentioned above, the reverse mutation test was carried out. The following Table 5 shows the relative activity value that indicates the relative comparative value of the intensity of the mutagenicity of the test compound.

Irrespective of the absence or presence of S9mix, THK-097, THK-336, THK-525, THK-683, THK-702, THK-708, THK-711, THK-713, THK-727 and THK-752 did not increase the number of the colonies after reverse mutation, at least two times that of the negative control, and their relative activity was minus. In the presence of S9mix, the relative activity of THK-707, THK-761 and THK-763 was weak; but on the other hand, in the presence of S9mix, the relative activity of FDDNP (Agdeppa et al., Journal of Neuroscience, Vol. 21, page RC189, 2001) and IMPY (Kung et al., Brain Research, Vol. 956, page 202, 2002) was extremely high. The results in Table 5 confirm that the compounds of the invention tested in this experiment did not have mutagenicity or, even though they had it, their relative activity was extremely weak as compared with that of FDDNP and IMPY.

TABLE 5

Mutagenicity Test of Compounds of the Invention

| | Relative Activity | |
|---|---|---|
| | in the presence of S9Mix | in the absence of S9Mix |
| THK-097 | minus[1] | minus |
| THK-336 | minus | minus |
| THK-525 | minus | minus |
| THK-683 | minus | minus |
| THK-702 | minus | minus |
| THK-707 | minus | 264 |
| THK-708 | minus | minus |
| THK-711 | minus | minus |
| THK-713 | minus | minus |
| THK-727 | minus | minus |
| THK-752 | minus | minus |
| THK-761 | minus | 11995 |
| THK-763 | minus | 3058 |
| FDDNP[2] | minus | 3,564,960 |
| IMPY[2] | minus | 3,326,100 |

[1] The number of colonies after reverse mutation did not increase at least two times that of the negative control,
[2] The data of FDDNP and IMPY were from PCT/JP03/07183 (WO03/106439).

EXAMPLE 7

Fluorescence Congo Red Method

Next described is a screening method for the compounds of the invention. Some of the compounds of the invention could not be screened according to a Thioflavin T method, since their fluorescence wavelength overlaps with that of Thioflavin T. For such compounds, the following novel screening method was introduced.

(1) Amyloid β protein 1-40 (bought from Peptide Laboratory) was dissolved in a phosphate buffer (pH 7.4) and left at 37° C. for 4 days.

(2) 50 μl of Congo red dissolved in the buffer was applied to a 96-well microplate (final concentration, 0.1, 0.3, 1 μM).

(3) 100 μl of amyloid β protein was added to it (final concentration 5 μM), and left as such for 30 minutes.

(4) 100 μl of a test compound dissolved in the buffer was added to it (final concentration, 10 μM, and left as such for 60 minutes.

(5) Using a fluorescence microplate reader (Spectra Max 190 by Molecular Device), the sample was analyzed at the optimum exciting wavelength and the test wavelength that had been previously determined.

(6) The fluorescence intensity in the presence of the test compound, amyloid β protein and Congo red is represented by A; that in the presence of the test compound and Congo red is by B; that in the presence of the test compound and amyloid β protein is by C; and that in the presence of only the test compound is by D. The β structure recognition of the test compound is computed according to the following formula:

$$\beta \text{ structure recognition (\%) of test compound} = \{(A-B)/(C-D)\} \times 100.$$

(7) It may be said that the test compound having a higher β structure recognition percentage may have higher binding specificity to amyloid β protein.

Table 6 shows the results. The binding of the test compound to Aβ was concentration-dependently inhibited by Congo red that specifically binds to Aβ. The above clarifies that the test compounds recognized the β structure of Aβ.

TABLE 6

Binding of Compound of the Invention to Aβ (fluorescence Congo red method)

| | Binding Percentage of Compound in the presence of Congo red (CR) | | |
|---|---|---|---|
| Compound (10 μM) | in the presence of 0.1 μM CR | in the presence of 0.3 μM CR | in the presence of 1 μM CR |
| THK-525 | 61.4 | 24.1 | −6.4 |
| THK-702 | 74.9 | 37.3 | 0.8 |
| THK-707 | 66.8 | 36.4 | 29.7 |
| THK-708 | 66.5 | 29.1 | 11.0 |
| THK-711 | 60.4 | 29.1 | 10.3 |
| THK-713 | 58.2 | 21.2 | 3.0 |
| THK-727 | 73.6 | 35.0 | 3.1 |
| THK-752 | 50.4 | 20.6 | 11.3 |
| THK-757 | 52.4 | 24.8 | 10.3 |
| THK-761 | 55.2 | 21.6 | 7.0 |
| THK-763 | 54.7 | 22.9 | 7.5 |
| THK-765 | 71.2 | 41.3 | 23.0 |
| THK-766 | 61.0 | 21.5 | 11.2 |
| THK-767 | 60.0 | 29.9 | 15.9 |
| Thioflavin T | 49.4 | 22.3 | 9.3 |

INDUSTRIAL APPLICABILITY

The compounds of the invention for diagnostic probe for conformation disease, especially those for imaging diagnostic probe, as well as the pharmaceutical composition for treatment and/or prevention of conformation disease comprising the compound are extremely useful for early detection, treatment and prevention of conformation disease such as Alzheimer disease that is at present considered as a most intractable disease; and they are applicable to the field of production of diagnostic drugs and kits for conformation disease, to the field of production of remedial medicines and preventive medicines for conformation disease, and to studies of conformation disease.

The invention claimed is:

1. A compound, pharmaceutically acceptable salt or solvate thereof represented by formula (I):

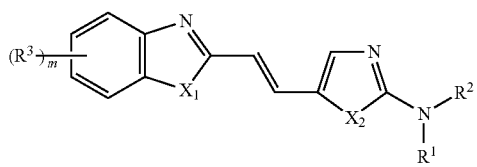

wherein $R^1$ and $R^2$ are independently hydrogen atom, lower alkyl group respectively, or cycloalkyl group, or 3- to 8-membered nitrogen-containing aliphatic ring formed by $R^1$, $R^2$ and a nitrogen atom bonded thereto, together (carbon atoms which constitute the nitrogen-containing aliphatic ring may be substituted with nitrogen atom, sulfur atom or oxygen atom, and when the carbon atom is substituted with nitrogen atom, the nitrogen atom may be substituted with lower alkyl group), $X_1$ and $X_2$ are each independently denotes nitrogen atom, sulfur atom, or oxygen atom, $R^3$ is —O— lower alkyl group (the alkyl group is substituted with halogen atom, and furthermore may be optionally substituted hydoxy group), and m is an integer of 1 to 3 provided that the compounds are excluded wherein $R^3$ is a —O— lower alkyl group substituted with only halogen atom, and $R^1$ and $R^2$ are each independently hydrogen atom or lower alkyl group.

2. The compound, pharmaceutically acceptable salt or solvate thereof according to claim 1, wherein $X_1$ is an oxygen atom.

3. The compound, pharmaceutically acceptable salt or solvate thereof according to claim 1, wherein $X_1$ is an oxygen atom, and $X_2$ is a sulfur atom.

4. The compound, pharmaceutically acceptable salt or solvate thereof according to claim 1, wherein $R^3$ is —O— lower alkyl group substituted with hydroxy group and halogen atom.

5. The compound, pharmaceutically acceptable salt or solvate thereof according to claim 1, wherein the group in formula (I) represented by:

wherein each variable is a morpholino group or dimethylamino group.

6. The compound, pharmaceutically acceptable salt or solvate thereof according to claim 1, wherein $R^3$ is a group represented by:

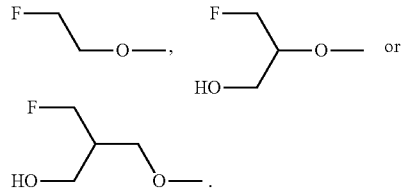

7. The compound, pharmaceutically acceptable salt or solvate thereof according to claim 1, wherein the compound represented by formula (I) is selected from the group consisting of:
  6-(2-fluoro-etoxy)-2-[2-(2-morpholin-4-yl-thiazole-5-yl)-vinyl]benzoxazol;
  toluene-4-sulfonic acid 2-[2-[2-(2-morpholin-4-yl- thiazole-5-yl) -vinyl- benzoxazol-6-yloxy]ethyl ester;
  2-fluoromethyl-3-[2-[2-(2-morpholin-4-yl-thiazole-5-yl)-vinyl]benzoxazol-6-yloxy]-propane-1-ole;
  (E)-2-[2-(2-morpholinothiazole-5-yl)ethenyl]-6-[(1-fluoromethyl-2-hydoxy)ethoxy]benzoxazol;
  (E)-6-[(1-fluoromethyl-2-hydroxy)ethoxy]-2-[2-[2-methylaminothiazole-5-yl]ethenyl]benzoxazol;
  (E)-6-[(1-fluoromethyl-2-hydroxy)ethoxy]-2-[2-[2-dimethylamino-thiazole-5-yl]ethenyl]benzoxazol;
  (E)-6-[(2-fluoromethyl-3-hydroxy)propoxy]-2-[2-(2-piperidinothiazole-5-yl]ethenyl]benzoxazol;
  (E)-6-[(1-fluoromethyl-2-hydroxy)ethoxy]-2-[2-(2-piperidinothiazole-5-yl)ethenyl]benzoxazol;
  (E)-6-[(1-fluoromethyl-2-hydroxy)ethoxy]-2-[2-(4-methylpiperidine-1-yl)thiazole-5-yl)ethenyl]benzoxazol;
  (E)-6- [(2-fluoromethyl-3-hydroxy)propoxy]-2- [2-[2-(pyrrolidine-1-yl]thiazole-5-yl)ethenyl]benzoxazol;
  (E)-6-[(1-fluoromethyl-2-hydroxy)ethoxy]-2-[2-[2-(pyrrolidine-1-yl)-thiazole-5-yl]ethenyl]benzoxazol;
  (E)-6-[(1-fluoromethyl-2-hydroxy)ethoxy]-2-[2-[2-([1,3]oxazine-3-yl)-thiazole-5-yl)ethenyl]benzoxazol;
  (E)-6-[(1-fluoromethyl-2-hydroxy)ethoxy]-2-[2-[2-homopiperidine-1-yl)-thiazole-5-yl)ethenyl]benzoxazol;
  (E)-6-[(1-fluoromethyl-2-hydroxy)ethoxy]-2-[2-(2-homomorpholinothiazole-5-yl)ethenyl]benzoxazol; and
  (E)-6-[(1-fluoromethyl-2-hydroxy)ethoxy]-2-[2-(2-thiomorpholinothiazole-5-yl)ethenyl]benzoxazol.

8. The compound, pharmaceutically acceptable salt or solvate thereof according to claim 1, which is labeled.

9. The compound, pharmaceutically acceptable salt or solvate thereof according to claim 8, which is labeled with a radionuclide.

10. The compound, pharmaceutically acceptable salt or solvate thereof according to claim 9, wherein the radionuclide is a gamma-ray emitting radionuclide.

11. The compound, pharmaceutically acceptable salt or solvate thereof according to claim 8, wherein the label is a positron emitter.

12. The compound, pharmaceutically acceptable salt or solvate thereof according to claim 11, wherein the positron emitter is selected from the group consisting of $^{11}$C, $^{13}$N, $^{15}$O, $^{18}$F, $^{35}$mCl, $^{76}$Br, $^{45}$Ti, $^{48}$V, $^{60}$Cu, $^{61}$Cu, $^{62}$C, $^{66}$Ga, $^{89}$Zr, $^{94}$mTc and $^{124}$I.

13. The compound, pharmaceutically acceptable salt or solvate thereof according to claim 11, wherein the positron emitter is $^{11}$C or $^{18}$F.

14. A pharmaceutical composition containing the compound, pharmaceutically acceptable salt or solvate thereof according to claim 1.

15. A pharmaceutical composition containing the compound, pharmaceutically acceptable salt or solvate thereof according to claim 1 and a solubilizing agent.

16. The pharmaceutical composition according to claim 15, wherein the solubilizing agent is selected from the group consisting of polysolvate 80, polyethylene glycol, ethanol, and propylene glycol.

17. The pharmaceutical composition according to claim 14, wherein the pharmaceutical composition is an injection drug.

18. A composition for diagnosis of Alzheimer's disease containing the compound, pharmaceutically acceptable salt or solvate thereof according to claim 1.

19. A pharmaceutical composition containing the compound, pharmaceutically acceptable salt or solvate thereof according to claim 1; wherein said compound binds to amyloid β protein.

20. A kit for diagnosis of Alzheimer's disease, containing the compound, pharmaceutically acceptable salt or solvate thereof according to claim 1 as a essential component; wherein said compound binds to amyloid β protein.

21. A composition or kit for detecting or staining proteins with beta sheet structure or neurofibrillary tangle, containing the compound, pharmaceutically acceptable salt or solvate thereof according to claim 1 as a essential component.

22. The kit according to claim 20, wherein the kit is intended for diagnostic imaging.

23. A method for irradiating an intracerebral amyloid plaque, which comprises administering an irradiated compound, pharmaceutically acceptable salt or solvate thereof according to claim 1 to a subject.

24. A method for diagnosis of a Alzheimer's disease in a subject, which comprises administering the compound, pharmaceutically acceptable salt or solvate thereof according to claim 1 to the subject.

25. A method of detecting or staining proteins with beta sheet structure in a sample or neurofibrillary tangle, which comprises using the compound, pharmaceutically acceptable salt or solvate thereof according to claim 1 to stain the sample.

26. The composition or the kit according to claim 21, wherein the compound is 6-(2-fluoro-etoxy)-2-[2-(2-morpholin-4-yl-thiazole-5-yl)-vinyl]benzoxazol;
2-fluoromethyl-3-[2-[2-(2-morpholin-4-yl-thiazole-5-yl)-vinyl]benzoxazol-6-yloxy]-propane-1-ole; (E)-2-[2-(2-morpholinothiazole-5-yl)ethenyl]-6-[(1-fluoromethyl-2-hydoxy)ethoxy]benzoxazol; or (E)-6-[(1-fluoromethyl-2-hydroxy)ethoxy]-2-[2-[2-dimethylamino-thiazole-5-yl]ethenyl]benzoxazol.

27. A compound, pharmaceutically acceptable salt or solvate thereof represented by formula (I')

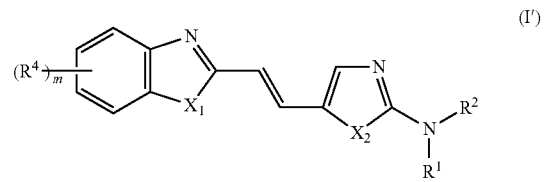

(I')

wherein
R$^1$ and R$^2$ are independently hydrogen atom, lower alkyl group respectively, or cycloalkyl group, or 3- to 8-membered nitrogen-containing aliphatic ring formed by R$^1$, R$^2$ and a nitrogen atom bonded thereto, together (carbon atoms which constitute the nitrogen-containing aliphatic ring may be substituted with nitrogen atom, sulfur atom or oxygen atom, and when the carbon atom is substituted nitrogen atom, the nitrogen atom may be substituted with lower alkyl group),
X$_1$ and X$_2$ are each independently nitrogen atom, sulfur atom, or oxygen atom,
R$^4$ is —O— lower alkyl group (the alkyl group may be substituted with tosyl group, and furthermore may be substituted with hydoxy group), and
m is an integer of 1 to 3]
provided that the compounds are excluded wherein R$^3$ is a —O— lower alkyl group substituted with only halogen atom, and R$^1$ and R$^2$ are each independently denotes hydrogen atom or lower alkyl group.

28. The compound according to claim 27, wherein R$^4$ is a group represented by:

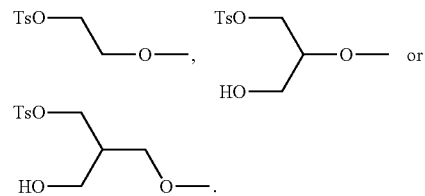

29. The compound according to claim 27, wherein the compound represented by formula (I') is
toluene-4-sulfonic acid 2-[2-[2-(2-morpholin-4-yl-thiazole-5-yl)-vinyl-benzoxazol-6-yloxy]ethyl ester;
(E)-6-[(3-hydroxy-2-tosyloxymethyl)propoxy]-2-[2-(2-morpholinothiazole-5-yl)ethenyl]benzoxazol;
(E)-6-[2-hydroxy-1-tosyloxymethyl)ethoxy]-2-[2-[2-dimethylamino-thiazole-5-yl]ethenyl]benzoxazol;
(E)-6-[(2-hydroxy-1-tosyloxymethyl)ethoxy]-2-[2-[2-methylaminothiazole-5-yl]ethenyl]benzoxazol;
(E)-6-[(3-hydroxy-2-tosyloxymethyl)propoxy]-2-[2-(2-piperidinothiazole-5-yl)ethenyl]benzoxazol;
(E)-6-[(2-hydroxy-1-tosyloxymethyl)ethoxy]-2-[2-(2-piperidinothiazole-5-yl)ethenyl]benzoxazol; or (E)-6-[(1-hydroxymethyl-2-tosyloxy)ethoxy]-2-[2-[2-(pyrrolidine-1-yl)-thiazole-5-yl]ethenyl]benzoxazol.

* * * * *